(12) United States Patent
Cid-Nunez et al.

(10) Patent No.: US 11,071,729 B2
(45) Date of Patent: Jul. 27, 2021

(54) 1',3'-DISUBSTITUTED-4-PHENYL-3,4,5,6-TETRAHYDRO-2H,1'H-[1,4']BIPYRIDINYL-2'-ONES

(71) Applicants: Janssen Pharmaceuticals, Inc., Titusville, NJ (US); Addex Pharma SA, Geneva (CH)

(72) Inventors: Jose Maria Cid-Nunez, Toledo (ES); Andres Avelino Trabanco-Suarez, Toledo (ES); Gregor James MacDonald, Beerse (BE); Guillaume Albert Jacques Duvey, Geneva (CH); Terry Patrick Finn, Geneva (CH)

(73) Assignees: Addex Pharmaceuticals S.A., Geneva (CH); Janssen Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 16/601,431

(22) Filed: Oct. 14, 2019

(65) Prior Publication Data
US 2020/0038391 A1    Feb. 6, 2020

Related U.S. Application Data

(63) Continuation of application No. 14/817,676, filed on Aug. 4, 2015, now abandoned, which is a
(Continued)

(30) Foreign Application Priority Data

Sep. 14, 2007    (EP) .................................. 07116390

(51) Int. Cl.
| | |
|---|---|
| A61K 31/4545 | (2006.01) |
| C07D 401/04 | (2006.01) |
| C07D 493/10 | (2006.01) |
| A61K 9/20 | (2006.01) |
| A61K 9/00 | (2006.01) |
| A61K 47/10 | (2017.01) |
| A61K 9/08 | (2006.01) |
| A61K 9/10 | (2006.01) |
| A61K 47/44 | (2017.01) |
| A61K 31/5377 | (2006.01) |
| A61K 45/06 | (2006.01) |

(Continued)

(52) U.S. Cl.
CPC ........ *A61K 31/4545* (2013.01); *A61K 9/0014* (2013.01); *A61K 9/0019* (2013.01); *A61K 9/08* (2013.01); *A61K 9/10* (2013.01); *A61K 9/2009* (2013.01); *A61K 9/2013* (2013.01); *A61K 9/2018* (2013.01); *A61K 9/2059* (2013.01); *A61K 31/444* (2013.01); *A61K 31/5377* (2013.01); *A61K 45/06* (2013.01); *A61K 47/10* (2013.01); *A61K 47/44* (2013.01); *C07D 211/86* (2013.01); *C07D 401/04* (2013.01); *C07D 491/107* (2013.01); *C07D 493/10* (2013.01)

(58) Field of Classification Search
CPC .................................................. A61K 31/4545
See application file for complete search history.

(56) References Cited

U.S. PATENT DOCUMENTS

| | | |
|---|---|---|
| 2,976,146 A | 3/1961 | Salminen et al. |
| 3,906,953 A | 9/1975 | Wallace et al. |

(Continued)

FOREIGN PATENT DOCUMENTS

| | | |
|---|---|---|
| BE | 841390 | 11/1976 |
| CA | 1019323 A | 10/1977 |

(Continued)

OTHER PUBLICATIONS

Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2003, 74, 76-78.*
Shah "The role of fluorine in medicinal chemistry", Journal of Enzyme Inhibition and Medicinal Chemistry, 2007, 22:5, 527-540.*
Cartmell "The metabotropic glutamate 2/3 receptor agonists LY354740 and LY379268 selectively attenuate phencyclidine versus d-amphetamine motor behaviors in rats." J. Pharmacol. Exp. Ther. 1999, 291, 161-170.*

(Continued)

*Primary Examiner* — David K O'Dell
(74) *Attorney, Agent, or Firm* — BakerHostetler

(57) ABSTRACT

The present invention relates to novel compounds, in particular novel pyridinone derivatives according to Formula (I)

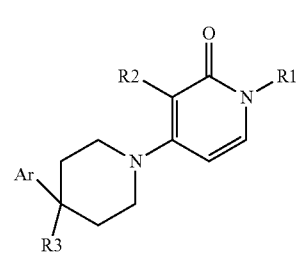

wherein all radicals are as defined in the application and claims. The compounds according to the invention are positive allosteric modulators of metabotropic receptors—subtype 2 ("mGluR2") which are useful for the treatment or prevention of neurological and psychiatric disorders associated with glutamate dysfunction and diseases in which the mGluR2 subtype of metabotropic receptors is involved. In particular, such diseases are central nervous system disorders selected from the group of anxiety, schizophrenia, migraine, depression, and epilepsy. The invention is also directed to pharmaceutical compositions and processes to prepare such compounds and compositions, as well as to the use of such compounds for the prevention and treatment of such diseases in which mGluR2 is involved.

20 Claims, No Drawings

Related U.S. Application Data continuation of application No. 13/803,267, filed on Mar. 14, 2013, now Pat. No. 9,132,122, which is a continuation of application No. 12/677,618, filed as application No. PCT/EP2008/007551 on Sep. 12, 2008, now Pat. No. 9,114,138.

(51) Int. Cl.
   *C07D 211/86* (2006.01)
   *C07D 491/107* (2006.01)
   *A61K 31/444* (2006.01)

(56) References Cited

U.S. PATENT DOCUMENTS

| | | | |
|---|---|---|---|
| 4,051,244 A | 9/1977 | Mattioda et al. |
| 4,066,651 A | 1/1978 | Brittain et al. |
| 4,146,716 A | 3/1979 | Cox et al. |
| 4,196,207 A | 4/1980 | Webber |
| 4,256,738 A | 3/1981 | Woitun et al. |
| 4,358,453 A | 11/1982 | Bristol et al. |
| 4,550,166 A | 10/1985 | Moran et al. |
| 4,866,074 A | 9/1989 | Spada et al. |
| 4,898,654 A | 2/1990 | Toda et al. |
| 4,978,663 A | 12/1990 | Effland et al. |
| 5,032,602 A | 7/1991 | Fey et al. |
| 5,130,442 A | 7/1992 | Meisel et al. |
| 5,175,157 A | 12/1992 | Psiorz et al. |
| 5,204,198 A | 4/1993 | Bugner et al. |
| 5,236,917 A | 8/1993 | Dunlap et al. |
| 5,254,543 A | 10/1993 | Hanko et al. |
| 5,260,293 A | 11/1993 | Baker et al. |
| 5,280,026 A | 1/1994 | Brown et al. |
| 5,332,750 A | 7/1994 | Mederski et al. |
| 5,356,911 A | 10/1994 | Mueller-Gliemann et al. |
| 5,366,981 A | 11/1994 | Vecchietti et al. |
| 5,371,074 A | 12/1994 | Dunlap et al. |
| 5,374,513 A | 12/1994 | Ohzeki et al. |
| 5,378,720 A | 1/1995 | Hlasta et al. |
| 5,407,948 A | 4/1995 | Fey et al. |
| 5,418,243 A | 5/1995 | Angerbauer et al. |
| 5,424,435 A | 6/1995 | Hani et al. |
| 5,473,077 A | 12/1995 | Monn et al. |
| 5,498,774 A | 3/1996 | Mitsudera et al. |
| 5,500,420 A | 3/1996 | Maiese |
| 5,512,576 A | 4/1996 | Desai et al. |
| 5,532,242 A | 7/1996 | Cliffe |
| 5,596,012 A | 1/1997 | Dunlap et al. |
| 5,602,145 A | 2/1997 | Samanen |
| 5,650,422 A | 7/1997 | Dunlap et al. |
| 5,654,307 A | 8/1997 | Bridges et al. |
| 5,675,013 A | 10/1997 | Hani et al. |
| 5,710,274 A | 1/1998 | Yuan et al. |
| 5,723,463 A | 3/1998 | Hoefgen et al. |
| 5,741,798 A | 4/1998 | Lazer et al. |
| 5,801,179 A | 9/1998 | Van et al. |
| 5,814,645 A | 9/1998 | Kanellakopulos et al. |
| 5,855,654 A | 1/1999 | Willingham et al. |
| 5,859,020 A | 1/1999 | Preuss et al. |
| 5,869,428 A | 2/1999 | Morishima et al. |
| 5,874,432 A | 2/1999 | Dunlap et al. |
| 5,922,773 A | 7/1999 | Lipton et al. |
| 5,948,911 A | 9/1999 | Pamukcu et al. |
| 5,958,931 A | 9/1999 | Adam et al. |
| 6,013,672 A | 1/2000 | Ye et al. |
| 6,022,869 A | 2/2000 | Faull |
| 6,054,588 A | 4/2000 | Adam et al. |
| 6,093,718 A | 7/2000 | Waterson et al. |
| 6,100,268 A | 8/2000 | Van et al. |
| 6,103,475 A | 8/2000 | Burnett et al. |
| 6,107,342 A | 8/2000 | Adam et al. |
| 6,110,920 A | 8/2000 | Rochus et al. |
| 6,121,278 A | 9/2000 | Jackson et al. |
| 6,130,217 A | 10/2000 | Arnold et al. |
| 6,133,271 A | 10/2000 | Pamukcu et al. |
| 6,136,861 A | 10/2000 | Chenard |
| 6,143,783 A | 11/2000 | Monn et al. |
| 6,162,804 A | 12/2000 | Bilodeau et al. |
| 6,169,091 B1 | 1/2001 | Cockerill et al. |
| 6,172,058 B1 | 1/2001 | Pedregal et al. |
| 6,204,292 B1 | 3/2001 | Kozikowski et al. |
| 6,262,068 B1 | 7/2001 | Atwal et al. |
| 6,262,074 B1 | 7/2001 | Otten et al. |
| 6,284,759 B1 | 9/2001 | He |
| 6,313,127 B1 | 11/2001 | Waterson et al. |
| 6,316,498 B1 | 11/2001 | Nakazato et al. |
| 6,333,428 B1 | 12/2001 | Nakazato et al. |
| 6,358,975 B1 | 3/2002 | Eliasson et al. |
| 6,361,571 B1 | 3/2002 | Goettel et al. |
| 6,403,588 B1 | 6/2002 | Hayakawa et al. |
| 6,407,094 B1 | 6/2002 | Adam et al. |
| 6,432,958 B1 | 8/2002 | He |
| 6,433,014 B1 | 8/2002 | Acher et al. |
| 6,455,528 B1 | 9/2002 | Adachi et al. |
| 6,465,484 B1 | 10/2002 | Bilodeau et al. |
| 6,472,392 B1 | 10/2002 | Starck et al. |
| 6,479,436 B1 | 11/2002 | Otten et al. |
| 6,498,180 B1 | 12/2002 | Collado et al. |
| 6,509,328 B1 | 1/2003 | Adam et al. |
| 6,569,863 B1 | 5/2003 | Gerritsma et al. |
| 6,586,441 B2 | 7/2003 | Borroni et al. |
| 6,607,563 B2 | 8/2003 | Ohashi et al. |
| 6,664,250 B2 | 12/2003 | Atwal et al. |
| 6,670,307 B2 | 12/2003 | Schnatterer et al. |
| 6,835,726 B2 | 12/2004 | Cushing et al. |
| 6,977,266 B2 | 12/2005 | Tada et al. |
| 7,393,549 B2 | 7/2008 | Ebinuma |
| 7,456,289 B2 | 11/2008 | Hsieh et al. |
| 7,572,807 B2 | 8/2009 | Li et al. |
| 7,579,360 B2 | 8/2009 | Li et al. |
| 7,700,593 B2 | 4/2010 | Zhang et al. |
| 7,879,837 B2 | 2/2011 | Hayashi et al. |
| 7,939,549 B2 | 5/2011 | Nagato et al. |
| 7,960,563 B2 | 6/2011 | Johnson et al. |
| 7,977,325 B2 | 7/2011 | Schwede et al. |
| 8,252,937 B2 | 8/2012 | Cid-Nunez et al. |
| 8,299,101 B2 | 10/2012 | Cid-Nunez et al. |
| 8,399,493 B2 | 3/2013 | Imogai et al. |
| 8,937,060 B2 | 1/2015 | Cid-Nunez et al. |
| 9,012,448 B2 | 4/2015 | Cid-Nunez et al. |
| 9,226,930 B2 | 1/2016 | Cid-Nunez et al. |
| 9,737,533 B2 | 8/2017 | Cid-Nunez et al. |
| 2002/0009713 A1 | 1/2002 | Miller et al. |
| 2002/0022636 A1 | 2/2002 | Li et al. |
| 2002/0028813 A1 | 3/2002 | Jackson et al. |
| 2002/0041880 A1 | 4/2002 | DeFeo-Jones et al. |
| 2002/0137770 A1 | 9/2002 | Nara et al. |
| 2002/0147362 A1 | 10/2002 | Kozikowski |
| 2002/0188128 A1 | 12/2002 | Mutel et al. |
| 2002/0193367 A1 | 12/2002 | Adam et al. |
| 2002/0198197 A1 | 12/2002 | Adam et al. |
| 2003/0055085 A1 | 3/2003 | Wagenen et al. |
| 2003/0109504 A1 | 6/2003 | Brotchie et al. |
| 2003/0130264 A1 | 7/2003 | Jaen |
| 2003/0134902 A1 | 7/2003 | Nakazato et al. |
| 2003/0158155 A1 | 8/2003 | Hori et al. |
| 2003/0162802 A1 | 8/2003 | Guo et al. |
| 2003/0166639 A1 | 9/2003 | Adam et al. |
| 2003/0171380 A1 | 9/2003 | Arvanitis et al. |
| 2003/0199692 A1 | 10/2003 | Biediger et al. |
| 2003/0207882 A1 | 11/2003 | Stocker et al. |
| 2003/0207916 A1 | 11/2003 | Cheng et al. |
| 2004/0006114 A1 | 1/2004 | Coleman et al. |
| 2004/0034040 A1 | 2/2004 | Eggenweiler et al. |
| 2004/0043388 A1 | 3/2004 | Come et al. |
| 2004/0049032 A1 | 3/2004 | Charrier et al. |
| 2004/0053914 A1 | 3/2004 | Gharagozloo et al. |
| 2004/0063955 A1 | 4/2004 | Biediger et al. |
| 2004/0077599 A1 | 4/2004 | Curry |
| 2004/0097562 A1 | 5/2004 | Olesen et al. |
| 2004/0101833 A1 | 5/2004 | Lazdunski et al. |
| 2004/0102521 A1 | 5/2004 | Collado-Cano et al. |
| 2004/0106791 A1 | 6/2004 | Yoakim et al. |
| 2004/0116489 A1 | 6/2004 | Massey et al. |

(56) References Cited

U.S. PATENT DOCUMENTS

| | | | |
|---|---|---|---|
| 2004/0127936 A1 | 7/2004 | Salahieh et al. | |
| 2004/0132723 A1 | 7/2004 | Yoakim et al. | |
| 2004/0138204 A1 | 7/2004 | Harrington | |
| 2004/0138238 A1 | 7/2004 | Dhanoa et al. | |
| 2004/0167123 A1 | 8/2004 | Pratt et al. | |
| 2004/0176385 A1 | 9/2004 | Nuss et al. | |
| 2004/0204448 A1 | 10/2004 | Muller et al. | |
| 2004/0220222 A1 | 11/2004 | Galley et al. | |
| 2005/0004142 A1 | 1/2005 | Adams et al. | |
| 2005/0026935 A1 | 2/2005 | Ford et al. | |
| 2005/0054819 A1 | 3/2005 | Catalano et al. | |
| 2005/0070538 A1 | 3/2005 | Cheng et al. | |
| 2005/0113283 A1 | 5/2005 | Solow-Cordero et al. | |
| 2005/0187227 A1 | 8/2005 | Himmelsbach et al. | |
| 2005/0245530 A1 | 11/2005 | Borzilleri et al. | |
| 2006/0083676 A1 | 4/2006 | Lesage et al. | |
| 2006/0240501 A1 | 10/2006 | Ebinuma | |
| 2007/0032469 A1 | 2/2007 | Isaac et al. | |
| 2007/0066582 A1 | 3/2007 | Herold et al. | |
| 2007/0213323 A1 | 9/2007 | Imogai et al. | |
| 2007/0275984 A1 | 11/2007 | Imogai et al. | |
| 2008/0097210 A1 | 4/2008 | Salgo et al. | |
| 2008/0221179 A1 | 9/2008 | Gaul et al. | |
| 2008/0286265 A1 | 11/2008 | Gaul et al. | |
| 2008/0306077 A1 | 12/2008 | Clayton et al. | |
| 2009/0031422 A1 | 1/2009 | Aaron et al. | |
| 2009/0111855 A1 | 4/2009 | Gaul et al. | |
| 2009/0124609 A1 | 5/2009 | Albrecht et al. | |
| 2009/0124612 A1 | 5/2009 | Albrecht et al. | |
| 2009/0203668 A1 | 8/2009 | Li et al. | |
| 2009/0275751 A1 | 11/2009 | Nagato et al. | |
| 2009/0318436 A1 | 12/2009 | Albrecht et al. | |
| 2010/0037487 A1 | 2/2010 | Connett | |
| 2010/0063054 A1 | 3/2010 | Bressi et al. | |
| 2010/0063092 A1 | 3/2010 | Cid-Nunez et al. | |
| 2010/0087487 A1 | 4/2010 | Cid-Nunez et al. | |
| 2010/0099715 A1 | 4/2010 | Cid-Nunez et al. | |
| 2010/0166655 A1 * | 7/2010 | Imogai .................... | A61P 25/00 424/9.1 |
| 2010/0240688 A1 | 9/2010 | Cid-Nunez et al. | |
| 2010/0240706 A1 | 9/2010 | Cid-Nunez et al. | |
| 2010/0286206 A1 | 11/2010 | Cid-Nunez et al. | |
| 2010/0292241 A1 | 11/2010 | Brnardic et al. | |
| 2011/0009441 A1 | 1/2011 | Trabanco-Suarez et al. | |
| 2011/0245232 A1 | 10/2011 | Braje et al. | |
| 2011/0245247 A1 | 10/2011 | Braje et al. | |
| 2011/0275624 A1 | 11/2011 | Cid-Nunez et al. | |
| 2011/0306642 A1 | 12/2011 | Cid-Nunez | |
| 2012/0035167 A1 | 2/2012 | Cid-Nunez et al. | |
| 2012/0135977 A1 | 5/2012 | Beshore et al. | |
| 2012/0184525 A1 | 7/2012 | Cid-Nunez et al. | |
| 2012/0184527 A1 | 7/2012 | Cic-Nunez et al. | |
| 2012/0184528 A1 | 7/2012 | Cic-Nunez et al. | |
| 2012/0309793 A1 | 12/2012 | Duvey et al. | |
| 2013/0109052 A1 | 5/2013 | Yan et al. | |
| 2013/0150412 A1 | 6/2013 | Cid-Nunez et al. | |
| 2013/0196992 A1 | 8/2013 | Cid-Nunez et al. | |
| 2013/0197019 A1 | 8/2013 | Cid-Nunez et al. | |

FOREIGN PATENT DOCUMENTS

| | | |
|---|---|---|
| CA | 2035144 A1 | 7/1991 |
| CA | 2360648 A1 | 8/2000 |
| CA | 2390948 A1 | 12/2000 |
| CA | 2390348 A1 | 12/2003 |
| CN | 2390948 Y | 8/2000 |
| CN | 1842532 | 10/2006 |
| CN | 102002040 A | 4/2011 |
| DE | 19507522 A1 | 9/1996 |
| EP | 0082023 | 6/1983 |
| EP | 0154190 | 9/1985 |
| EP | 0292840 | 11/1988 |
| EP | 0308020 | 3/1989 |
| EP | 0365486 | 4/1990 |
| EP | 0373423 A1 | 6/1990 |
| EP | 0379806 | 8/1990 |
| EP | 0430385 A2 | 6/1991 |
| EP | 0441718 | 8/1991 |
| EP | 0447118 | 9/1991 |
| EP | 0447891 | 9/1991 |
| EP | 0452002 A2 | 10/1991 |
| EP | 0478195 | 4/1992 |
| EP | 0482939 A1 | 4/1992 |
| EP | 0530702 | 3/1993 |
| EP | 0542059 A1 | 5/1993 |
| EP | 0547708 | 6/1993 |
| EP | 0548934 | 6/1993 |
| EP | 0557016 | 8/1993 |
| EP | 0612746 | 8/1994 |
| EP | 0626378 | 11/1994 |
| EP | 0728759 | 8/1996 |
| EP | 0799826 | 10/1997 |
| EP | 0838458 | 4/1998 |
| EP | 0856255 | 8/1998 |
| EP | 0903343 | 3/1999 |
| EP | 0955301 | 11/1999 |
| EP | 1006112 A1 | 6/2000 |
| EP | 1203766 A2 | 5/2002 |
| EP | 1277726 A1 | 1/2003 |
| EP | 1459765 A1 | 9/2004 |
| EP | 1764099 A2 | 3/2007 |
| EP | 1764367 A1 | 3/2007 |
| EP | 2039687 A1 | 3/2009 |
| GB | 1392849 A | 4/1975 |
| GB | 1502312 A | 3/1978 |
| JP | 50-106981 | 8/1975 |
| JP | 53-082783 A | 7/1978 |
| JP | 57-052334 | 3/1982 |
| JP | 61-010557 | 1/1986 |
| JP | 02-124871 | 5/1990 |
| JP | 02-503317 | 10/1990 |
| JP | 02-277044 | 11/1990 |
| JP | 05-204071 | 8/1993 |
| JP | 06-211797 | 8/1994 |
| JP | 06-211798 | 8/1994 |
| JP | 07-070018 | 3/1995 |
| JP | 07-101861 | 4/1995 |
| JP | 10-029979 | 2/1998 |
| JP | 10-045750 A | 2/1998 |
| JP | 2000-072731 | 3/2000 |
| JP | 2001-089367 A | 4/2001 |
| JP | 2002-003401 A | 1/2002 |
| JP | 2002-105085 A | 4/2002 |
| JP | 2002-308882 A | 10/2002 |
| JP | 2003-012653 A | 1/2003 |
| JP | 2004-525192 | 8/2004 |
| JP | 2004-339080 A | 12/2004 |
| JP | 2005-531501 | 10/2005 |
| JP | 2008-509714 | 4/2008 |
| JP | 2008-513414 A | 5/2008 |
| RU | 1796625 | 2/1993 |
| RU | 2143433 C1 | 12/1999 |
| WO | 84/00544 A1 | 2/1984 |
| WO | 84/00685 A1 | 3/1984 |
| WO | 91/09848 A1 | 7/1991 |
| WO | 92/18115 A1 | 10/1992 |
| WO | 93/01195 A1 | 1/1993 |
| WO | 93/15056 A1 | 8/1993 |
| WO | 94/19315 A1 | 9/1994 |
| WO | 95/04733 | 2/1995 |
| WO | 95/06032 A1 | 3/1995 |
| WO | 95/11233 | 4/1995 |
| WO | 95/17397 A1 | 6/1995 |
| WO | 95/24393 A1 | 9/1995 |
| WO | 95/35293 A1 | 12/1995 |
| WO | 96/05828 A1 | 2/1996 |
| WO | 96/06167 A1 | 2/1996 |
| WO | 96/15108 A1 | 5/1996 |
| WO | 96/22021 A1 | 7/1996 |
| WO | 96/33974 A1 | 10/1996 |
| WO | 96/37481 A1 | 11/1996 |
| WO | 96/41639 A1 | 12/1996 |
| WO | 97/10229 A1 | 3/1997 |

(56) References Cited

FOREIGN PATENT DOCUMENTS

| | | |
|---|---|---|
| WO | 97/10238 | 3/1997 |
| WO | 97/21701 | 6/1997 |
| WO | 97/46532 A1 | 12/1997 |
| WO | 97/48724 A2 | 12/1997 |
| WO | 98/01075 A1 | 1/1998 |
| WO | 98/06724 A1 | 2/1998 |
| WO | 98/11075 | 3/1998 |
| WO | 98/17668 | 4/1998 |
| WO | 98/24780 | 6/1998 |
| WO | 98/32762 | 7/1998 |
| WO | 98/38168 A1 | 9/1998 |
| WO | 98/50384 A1 | 11/1998 |
| WO | 99/06041 A1 | 2/1999 |
| WO | 99/11622 A1 | 3/1999 |
| WO | 99/11628 A1 | 3/1999 |
| WO | 99/11649 A2 | 3/1999 |
| WO | 99/12532 A2 | 3/1999 |
| WO | 99/16755 A1 | 4/1999 |
| WO | 99/18096 A1 | 4/1999 |
| WO | 99/21992 A2 | 5/1999 |
| WO | 99/31062 A1 | 6/1999 |
| WO | 99/31066 A1 | 6/1999 |
| WO | 99/32448 A1 | 7/1999 |
| WO | 99/33829 A1 | 7/1999 |
| WO | 99/36072 A1 | 7/1999 |
| WO | 99/52893 A1 | 10/1999 |
| WO | 99/53956 A1 | 10/1999 |
| WO | 99/62908 | 12/1999 |
| WO | 00/03990 | 1/2000 |
| WO | 00/12089 | 3/2000 |
| WO | 00/21934 | 4/2000 |
| WO | 00/34244 | 6/2000 |
| WO | 00/51849 A1 | 9/2000 |
| WO | 00/53605 | 9/2000 |
| WO | 00/61126 | 10/2000 |
| WO | 00/69816 | 11/2000 |
| WO | 00/73283 | 12/2000 |
| WO | 2000/072751 | 12/2000 |
| WO | 01/10846 | 2/2001 |
| WO | 01/29025 | 4/2001 |
| WO | 01/32632 | 5/2001 |
| WO | 01/32644 | 5/2001 |
| WO | 01/46190 | 6/2001 |
| WO | 01/53288 A1 | 7/2001 |
| WO | 01/55132 | 8/2001 |
| WO | 01/56990 | 8/2001 |
| WO | 01/68097 | 9/2001 |
| WO | 01/70731 | 9/2001 |
| WO | 01/72712 | 10/2001 |
| WO | 01/83421 A1 | 11/2001 |
| WO | 01/83431 | 11/2001 |
| WO | 01/83481 A1 | 11/2001 |
| WO | 01/85716 | 11/2001 |
| WO | 01/96308 | 12/2001 |
| WO | 02/02568 | 1/2002 |
| WO | 02/10807 | 2/2002 |
| WO | 02/12236 | 2/2002 |
| WO | 02/14282 A1 | 2/2002 |
| WO | 02/22598 | 3/2002 |
| WO | 02/28837 A1 | 4/2002 |
| WO | 02/40025 A1 | 5/2002 |
| WO | 02/51849 | 7/2002 |
| WO | 02/74025 | 9/2002 |
| WO | 02/79498 | 10/2002 |
| WO | 02/94264 | 11/2002 |
| WO | 2002/090333 | 11/2002 |
| WO | 02/96318 | 12/2002 |
| WO | 02/96363 | 12/2002 |
| WO | 02/98869 | 12/2002 |
| WO | 2002/102807 | 12/2002 |
| WO | 03/11293 | 2/2003 |
| WO | 03/29209 | 4/2003 |
| WO | 03/35639 | 5/2003 |
| WO | 03/42989 | 5/2003 |
| WO | 03/44021 | 5/2003 |
| WO | 03/47577 | 6/2003 |
| WO | 03/51841 | 6/2003 |
| WO | 03/51842 | 6/2003 |
| WO | 2003/051481 | 6/2003 |
| WO | 03/55878 | 7/2003 |
| WO | 03/59871 | 7/2003 |
| WO | 03/59884 | 7/2003 |
| WO | 03/62392 | 7/2003 |
| WO | 03/64428 | 8/2003 |
| WO | 03/65994 | 8/2003 |
| WO | 03/68230 | 8/2003 |
| WO | 03/68750 | 8/2003 |
| WO | 03/70712 | 8/2003 |
| WO | 03/76405 | 9/2003 |
| WO | 03/82191 | 10/2003 |
| WO | 03/84610 | 10/2003 |
| WO | 03/92595 | 11/2003 |
| WO | 03/99808 | 12/2003 |
| WO | 2003/104217 | 12/2003 |
| WO | 2003/105846 | 12/2003 |
| WO | 2004/000846 A1 | 12/2003 |
| WO | 2004/004720 A1 | 1/2004 |
| WO | 2004/011441 A1 | 2/2004 |
| WO | 2004/014859 A2 | 2/2004 |
| WO | 2004/014920 A1 | 2/2004 |
| WO | 2004/017950 A2 | 3/2004 |
| WO | 2004/018386 A2 | 3/2004 |
| WO | 2004/019863 A2 | 3/2004 |
| WO | 2004/021984 A2 | 3/2004 |
| WO | 2004/024150 A2 | 3/2004 |
| WO | 2004/024936 A2 | 3/2004 |
| WO | 2004/029060 A1 | 4/2004 |
| WO | 2004/031189 A1 | 4/2004 |
| WO | 2004/041818 A1 | 5/2004 |
| WO | 2004/043927 A1 | 5/2004 |
| WO | 2004/054979 A1 | 7/2004 |
| WO | 2004/065380 A1 | 8/2004 |
| WO | 2004/067002 A2 | 8/2004 |
| WO | 2004/072025 A2 | 8/2004 |
| WO | 2004/076413 A2 | 9/2004 |
| WO | 2004/078175 A2 | 9/2004 |
| WO | 2004/078176 A1 | 9/2004 |
| WO | 2004/080891 A1 | 9/2004 |
| WO | 2004/080981 A1 | 9/2004 |
| WO | 2004/092123 A2 | 10/2004 |
| WO | 2004/092135 A2 | 10/2004 |
| WO | 2005/002585 A1 | 1/2005 |
| WO | 2005/007144 A2 | 1/2005 |
| WO | 2005/021552 A1 | 3/2005 |
| WO | 2005/028445 A2 | 3/2005 |
| WO | 2005/040337 A2 | 5/2005 |
| WO | 2005/080356 A1 | 9/2005 |
| WO | 2005/097052 A1 | 10/2005 |
| WO | 2005/100365 A1 | 10/2005 |
| WO | 2005/123703 A2 | 12/2005 |
| WO | 2006/012622 A2 | 2/2006 |
| WO | 2006/014918 A2 | 2/2006 |
| WO | 2006/015158 A1 | 2/2006 |
| WO | 2006/015737 A1 | 2/2006 |
| WO | 2006/018727 A2 | 2/2006 |
| WO | 2006/020879 A1 | 2/2006 |
| WO | 2006/029980 A1 | 3/2006 |
| WO | 2006/030031 A1 | 3/2006 |
| WO | 2006/030032 A1 | 3/2006 |
| WO | 2006/047237 A2 | 5/2006 |
| WO | 2006/057860 A1 | 6/2006 |
| WO | 2006/057869 A1 | 6/2006 |
| WO | 2006/071730 A1 | 7/2006 |
| WO | 2006/074041 A2 | 7/2006 |
| WO | 2006/091496 A2 | 8/2006 |
| WO | 2006/099972 A1 | 9/2006 |
| WO | 2006/109876 A1 | 10/2006 |
| WO | 2006/137350 A1 | 12/2006 |
| WO | 2007/021308 A1 | 2/2007 |
| WO | 2007/021309 A1 | 2/2007 |
| WO | 2007/027669 A1 | 3/2007 |
| WO | 2007/031558 A1 | 3/2007 |
| WO | 2007/039439 A1 | 4/2007 |
| WO | 2007/059257 A2 | 5/2007 |

(56) References Cited

FOREIGN PATENT DOCUMENTS

| WO | 2007/078523 | A2 | 7/2007 |
|---|---|---|---|
| WO | 2007/095024 | A1 | 8/2007 |
| WO | 2007/103760 | A2 | 9/2007 |
| WO | 2007/104783 | A2 | 9/2007 |
| WO | WO-2007104783 | A2 * | 9/2007 ............ A61P 25/28 |
| WO | 2007/113276 | A1 | 10/2007 |
| WO | 2007/122258 | A1 | 11/2007 |
| WO | 2007/135527 | A2 | 11/2007 |
| WO | 2007/135529 | A2 | 11/2007 |
| WO | 2008/006540 | A1 | 1/2008 |
| WO | 2008/008539 | A2 | 1/2008 |
| WO | 2008/012622 | A2 | 1/2008 |
| WO | 2008/012623 | A1 | 1/2008 |
| WO | 2008/032191 | A2 | 3/2008 |
| WO | 2008/045393 | A2 | 4/2008 |
| WO | 2008/051197 | A2 | 5/2008 |
| WO | 2008/057855 | A2 | 5/2008 |
| WO | 2008/076225 | A2 | 6/2008 |
| WO | 2008/078091 | A1 | 7/2008 |
| WO | 2008/078100 | A2 | 7/2008 |
| WO | 2008/100715 | A1 | 8/2008 |
| WO | 2008/107081 | A1 | 9/2008 |
| WO | 2008/107125 | A1 | 9/2008 |
| WO | 2008/107479 | A1 | 9/2008 |
| WO | 2008/107480 | A1 | 9/2008 |
| WO | 2008/107481 | A1 | 9/2008 |
| WO | 2008/112483 | A2 | 9/2008 |
| WO | 2008/124085 | A2 | 10/2008 |
| WO | 2008/130853 | A1 | 10/2008 |
| WO | 2008/145616 | A1 | 12/2008 |
| WO | 2008/150232 | A1 | 12/2008 |
| WO | 2008/150233 | A1 | 12/2008 |
| WO | 2009/004430 | A1 | 1/2009 |
| WO | 2009/033702 | A1 | 3/2009 |
| WO | 2009/033703 | A1 | 3/2009 |
| WO | 2009/033704 | A1 | 3/2009 |
| WO | 2009/041567 | A1 | 4/2009 |
| WO | 2009/045753 | A1 | 4/2009 |
| WO | 2009/062676 | A2 | 5/2009 |
| WO | 2009/091374 | A2 | 7/2009 |
| WO | 2009/094265 | A1 | 7/2009 |
| WO | 2009/110901 | A1 | 9/2009 |
| WO | 2009/123703 | A2 | 10/2009 |
| WO | 2009/124609 | A1 | 10/2009 |
| WO | 2009/140163 | A1 | 11/2009 |
| WO | 2009/140166 | A2 | 11/2009 |
| WO | 2009/148403 | A1 | 12/2009 |
| WO | 2010/009062 | A1 | 1/2010 |
| WO | 2010/022076 | A1 | 2/2010 |
| WO | 2010/022081 | A1 | 2/2010 |
| WO | 2010/025890 | A1 | 3/2010 |
| WO | 2010/043396 | A1 | 4/2010 |
| WO | 2010/060589 | A1 | 6/2010 |
| WO | 2010/063054 | A1 | 6/2010 |
| WO | 2010/089303 | A1 | 8/2010 |
| WO | 2010/114726 | A1 | 10/2010 |
| WO | 2010/117926 | A1 | 10/2010 |
| WO | 2010/123424 | A1 | 10/2010 |
| WO | 2010/130425 | A1 | 11/2010 |
| WO | 2010/130423 | A1 | 11/2010 |
| WO | 2010/130424 | A1 | 11/2010 |
| WO | 2010/141360 | A1 | 12/2010 |
| WO | 2011/022312 | A1 | 2/2011 |
| WO | 2011/034741 | A1 | 3/2011 |
| WO | 2011/034828 | A1 | 3/2011 |
| WO | 2011/034830 | A1 | 3/2011 |
| WO | 2011/034832 | A1 | 3/2011 |
| WO | 2011/051490 | A1 | 5/2011 |
| WO | 2011/109277 | A1 | 9/2011 |
| WO | 2011/116356 | A2 | 9/2011 |
| WO | 2011/136723 | A1 | 11/2011 |
| WO | 2011/137048 | A1 | 11/2011 |
| WO | 2011/156245 | A2 | 12/2011 |
| WO | 2012/021382 | A1 | 2/2012 |
| WO | 2012/062750 | A1 | 5/2012 |
| WO | 2012/062751 | A1 | 5/2012 |
| WO | 2012/062752 | A1 | 5/2012 |
| WO | 2012/062759 | A1 | 5/2012 |
| WO | 2012/151136 | A1 | 11/2012 |
| WO | 2012/151139 | A1 | 11/2012 |
| WO | 2012/151140 | A1 | 11/2012 |

OTHER PUBLICATIONS

Khilevich, "Discovery of LY2607540: A novel and selective mGluR2 positive allosteric modulator (PAM) demostrates activity in animal models of anxiety and depression." Abstracts of Papers, 246th ACS National Meeting & Exposition, Indianapolis, IN, United States, Sep. 8-12, 2013 (2013), MEDI-87.*

Layton "Development of benzothiadiazole-diones as positive allosteric modulators of mGluR2 for the treatment of schizophrenia" Abstracts of Papers, 248th ACS National Meeting & Exposition, San Francisco, CA, United States, Aug. 10-14, 2014 (2014), MEDI-292.*

Prager et al., "The Synthesis fo Perloline, 6-(3,4-Dimethoxyphenyl)5-hydroxy-5,6-dihydro-benzo[c][2,7]naphthyridin-4(3HO)-one", Aust. J. Chem, 1983, 36, 1441-53.

Pralong et al. "Cellular perspectives on the glutamate-monoamine interactions in limbic lobe structures and their relevance for some psychiatric disorders" Progress in Neurobiology 2002, vol. 67, pp. 173-202.

Prezeau et al. Pharmacological characterization of metabotropic glutamate receptors in several types of brain cells in primary cultures. Mol Pharmacol 1994,45 (4), 570-577.

Prezeau et al., "Functional Crosstalk Between Gpers: With or Without Oligomerization", Current Opinion in Pharmacology, 2010, 10, 6-13.

Prina et al. "Cooccurrence of anxiety and depression amongst older adults in low and middle income countries: findings from the 10/66 study" Psychological Medicine/vol. 41/Issue 10/Oct. 2011, pp. 2047-2056.

Priolo et al. "Panic-like attack induced by microinfusion into the locus coeruleus of antagonists and inverse agonists at GABAA-receptors in rodents" Funct neurol 1991, vol. 6, pp. 393-403.

Profaci et al. "Group II mGluR agonist LY354740 and NAAG peptidase inhibitor effects on prepulse inhibition in PCP and D-amphetamine models of schizophrenia" Psychopharmacology 2011, vol. 216, pp. 235-243.

Prous Science Integrity 2007—Chemical structure LY-2140023.
Prous Science Integrity 2007—Chemical Synthesis LY-404039.

Pszczolkowski et al. "Effect of metabotropic glutamate receptor agonists and signal transduction modulators on feeding by a caterpillar" Pharmacology, Biochemistry and Behavior 2005, vol. 82, pp. 678-685.

Putt et al. "An enzymatic assay for poly(ADP-ribose) polymerase-1 (PARP-1) via the chemical quantitation of NAD+: application to the high-throughput screening of small molecules as potential inhibitors." Analytical Biochemistry. vol. 326. 2004. 78-86.

Quitkin et al. "Placebo run-in period in studies of depressive disorders: Clinical, heuristic and research implications" British Journal of psychiatry 1998, vol. 173, pp. 242-248.

Raffray et al. Apoptosis and necrosis in toxicology: a continuum or distinct modes of cell death?. [Review] [181 refs]. Pharmacology & Therapeutics 1997, 75 (3), 153-177.

Rani et al. "Thiazoline Analogues of Epiderstatin, New Inhibitiors of Cell Cycle of TsFT-210 Cells", Journal of Antibiotics, 1995, 48(10), 1179-1181.

Rao et al., "Anxious Depression: Clinical Features and Treatment", Current Psychiatry Reports, 2009, 11, 429-436.

Raskin et al. "Differential response to chlorpromazine, imipramine, and placebo. A study of subgroups of hospitalized depressed patients" Arch Gen Psychiat 1970, vol. 23, 164-173.

Ravaris et al. "Phenelzine and Amitriptyline in the Treatment of Depression: A Comparison of Present and Past Studies" Arch Gen Psychiatry 1980, vol. 37, pp. 1075-1080.

Recasens et al. "Metabotropic Glutamate Receptors as Drug Targets" Current Drug Targets 2007, vol. 8(5), pp. 651-681.

Redondo et al. "Selective Heteronuclear NOE Enhancements in Benzoheterocycles. Effect of Ring Size on Indirect Three-Spin Effects." Magnetic Resonance in Chemistry. vol. 26. 1988. 511-7.

(56) References Cited

OTHER PUBLICATIONS

Regier et al. "Comorbidity of mental disorders with alcohol and other drug abuse. Results from the epidemiologic catchment area (ECA) study" JAMA 1990, vol. 264, pp. 2511-2518.
Rehwald et al. "3-Amino-2(1 H)-Quinolones by Cyclization of N-Acylated Anthranilic Acid Derivatives." Heterocycles. vol. 45 (3). 1997. 483-92.
Reiner et al. "BDNF may play a differential role in the protective effect of the mGluR2/3 agonist LY379258 on striatal projection neurons in R6/2 Huntington's disease mice" Brain Research 2012, vol. 1473, 161-172.
Renslo et al., "Synthesis of Aza-, Oxa-, and Thiabicyclo[3.1.0]hexane Heterocycles from a Common Synthetic Intermediate", Organic Letters, 2005, vol. 7, No. 13, pp. 2627-2630, American Chemical Society.
Reynolds et al . "Sleep research in affective illness: state of the art circa" Sleep 1987, vol. 10, pp. 199-215.
Reynolds et al., "New Approaches to the Drug Treatment of Schizophrenia", Adv. Pharmacol., 1995, 32, 461-503.
Rhebergen et al. "The 7-year course of depression and anxiety in the general population" Acta Psychiatr Scand 2011, vol. 123, pp. 297-306.
Ribeiro et al. "Group I metabotropic glutamate receptor signaling and its implication in neurological disease" CNS & Neurological Disorders—Drug Targets 2010, vol. 9, pp. 574-595.
Ribeiro et al. Metabotropic glutamate receptor-mediated cell signaling pathways are altered in a mouse model of Huntington's disease. Journal of Neuroscience. 30(1):316-24, 2010.
Richards et al. "Distribution and abundance of metabotropic glutamate receptor subtype 2 in rat brain revealed by [3H]LY354740 binding in vitro and quantitative radioautography: correlation with the sites of synthesis, expression, and agonist stimulation of [35S]GTPS binding" J Comp Neurology 2005, vol. 487, pp. 15-27.
Richardson-Burns et al., Metabotropic Glutamate Receptor Mrna Expression in the Schizophrenic Thalamus, Biol. Psychiatry, 2000, 47(1), 22-28.
Rickels et al. "Efficacy of Extended-Release Venlafaxine in Nondepressed Outpatients With Generalized Anxiety Disorder" Am J Psychiatry 2000; 157:968-974.
Rickels et al. "Long-term Diazepam Therapy and Clinical Outcome" JAMA 1983, vol. 250, pp. 767-771.
Ried et al. "Reactions with Cyclobutenediones, IX. 3-Hydroxypyridones-(2) from Phenylcyclobutenedione and Enamines." Liebigs Ann. Chem. vol. 725. 1969. 230-3.
Riedel et al. "Glutamate receptor function in learning and memory" Behavioural Brain Research Article in press 2002, 1-47.
Riederer et al. "Pharmacotoxic psychosis after memantine in Parkinson's disease" The Lancet 1991, vol. 338, pp. 1022-1023.
Ritzen et al. "Molecular pharmacology and therapeutic prospects of metabotropic glutamate receptor allosteric modulators" Basic Clin Pharmacol Toxicol 2005, vol. 97, pp. 202-213.
Robbe et al., "Role of P/Q-Ca2+ Channels in Metabotropic Glutamate Receptor 2/3Dependent Presynaptic Long-Term Depression at Nucleus Accumbens Synapses", J Neurosci., 2002, 22(11), 4346-4356.
Robber et al. Metabotropic glutamate receptor 2 3-dependent long-term depression in the nucleus accumbens is blocked in morphine withdrawn mice. Eur. J Neurosci. 2002, 16 (11), 2231-2235.
Robbins et al . "The Neuropsychopharmacology of Fronto-Executive Function: Monoaminergic Modulation" Annu Rev Neurosci 2009, vol. 32, pp. 267-287.
Roberts et al. Pharmacological tools for the investigation of metabotropic glutamate receptors (mGluRs): phenylglycine derivatives and other selective antagonists—an update. [Review] [38 refs]. Neuropharmacology. 1995, 34 (8), 813-819.
Robins et al . "Establishment of Diagnostic Validity in Psychiatric Illness: Its Application to Schizophrenia" Amer J Psychiat 1970, vol. 126(7), pp. 107-111.
Robison et al. "The Rearrangement of Isoquinoline-n-oxides" J Org Chem 1957, vol. 21, 1337-1341.

Rodd et al. "The metabotropic glutamate 2/3 receptor agonist LY404039 reduces alcohol-seeking but not alcohol self-administration in alcohol-preferring (P) rats" Behavioural Brain Research 2006, vol. 171, pp. 207-215.
Rodriguez et al. "Attenuation of ketamine-induced hyperactivity responses in rats following administration of a novel metabotropic glutamate receptor 2 selective positive modulator" [abstract], in Proceedings of the Annual Meeting of the Society for Neuroscience; Oct. 23-27, 2004; Abstract No. 798.8,San Diego, CA, Society for Neuroscience, Washington, DC.
Rodriguez et al. "Relationships among psychosocial functioning, diagnostic comorbidity, and the recurrence of generalized anxiety disorder, panic disorder, and major depression" Anxiety Disorders 2005, vol. 19, 752-766.
Rodriguez-Moreno et al., "Kainate Receptors with a Metabotropic Modus Operandi", Trends Neurosci., 2007, 30(12), 630-637.
Roma et al., "1,8-Naphthyridines VII. New substituted 5-amino[I,2,4]triazolo[4,3-a] [1 ,8]naphthyridine-6-carboxamides and their isosteric analogues, exhibiting notable anti-inflammatory and/or analgesic activities, but no acute gastrolesivity",Eouropean Journal of Medical Chemistry. 2008, 43, 1665-1680, Elsevier.
Rondard et al., "Coupling of Agonist Binding to Effector Domain Activation in Metabotropic Glutamate-Like Receptors" J Biol. Chem., 2006, 281(34), 24653-24661.
Rorick-Kehn et al. "Improved Bioavailability of the mGlu2/3 Receptor Agonist LY354740 Using a Prodrug Strategy: In Vivo Pharmacology of LY544344" J. Pharmacol. Exper. Therapeut. 2006, vol. 316, pp. 905-913.
Rorick-Kehn et al. "In vivo pharmacological characterization of the structurally novel, potent, selective mGlu2/3 receptor agonist LY404039 in animal models of psychiatric disorders" Psychopharmacology 2007, vol. 193, pp. 121-136.
Wheeler et al. "(2S,1,S,2'R,3'R)-2(2'-Carboxy-3,-hydroxymethyl-cyclopropyl)glycine-[3H], a potent and selective radioligand for labeling group 2 and 3 metabotropic glutamate receptors" Bioorganic & Medicinal Chemistry Letters 2005, vol. 15, pp. 349-351.
Wieronska et al. "Metabotropic glutamate receptor 4 novel agonist LSP1-2111 with anxiolytic, but not antidepressant-like activity, mediated by serotonergic and GABAergic systems" Neuropharmacology 2010, vol. 59, pp. 627-634.
Wieronska et al. "On the mechanism of anti-hyperthermic effects of LY379268 and LY487379, group II mGlu receptors activators, in the stress-induced hyperthermia in singly housed mice" Neuropharmacology 2012, vol. 62, pp. 322-331.
Wieronska et al. "Opposing efficacy of group III mGlu receptor activators, LSP1-2111 and AMN082, in animal models of positive symptoms of schizophrenia" Psychopharmacology, 2011, EPUB, No Page Numbers, DOI 10.1007/S00213-011-2502-2, Published online Sep. 28, 2011.
Wieronska et al. Anxiolytic action of group II and III metabotropic glutamate receptors agonists involves neuropeptide Y in the amygdala. Pharmacol. Rep. 2005, 57 (6), 734-743.
Wieronska et al. Metabotropic glutamate receptors in the tripartite synapse as a target for new psychotropic drugs. Neurochem. Int2009, 55(1-3), 85-97.
Wiethoff et al. "Prevalence and Treatment Outcome in Anxious Versus Nonanxious Depression: Results From the German Algorithm Project" J Clin Psychiatry 2010, vol. 71(8), pp. 1047-1054.
Wikipedia, "Allosteric Regulation", 2010, 1-4.
Wiley et al. "2-Pyrones. XVIII. 5-Aroyl-2-pyridones." vol. 78. Jun. 1956. 2393-98.
Williams et al. Characterization of polyamines having agonist, antagonist, and inverse agonist effects at the polyamine recognition site of the NMDA receptor. Neuron. 1990, 5 (2), 199-208.
Wischhof et al . "Pre-treatment with the mGlu213 receptor agonist LY379268 attenuates DOI-induced impulsive responding and regional c-Fos protein expression" Psychopharmacology 2011, EPUB, No Page Numbers, DOI 10.1007/s00213-011-2441-y, published online Aug. 24, 2011.
Witkin et al. "Metabotropic Glutamate Receptors in the Control of Mood Disorders" CNS & Neurological Disorders—Drug Targets, 2007, vol. 6, pp. 87-100.

(56) References Cited

OTHER PUBLICATIONS

Wittchen et al. "DSM-III-R Generalized Anxiety Disorder in the National Comorbidity Survey" Arch Gen Psychiatry 1994, vol. 51, pp. 355-364.
Woolley et al. "The mGlu2 but not the mGlu3 receptor mediates the actions of the mGluR2/3 agonist, LY379268, in mouse models predictive of antipsychotic activity" Psychopharmacology 2007, EPUB, No Page Numbers, DOI 10.1007/S00213-007-0974-x.
Xi, Neuropsychopharmacology (2011), 36, pp. 1260-1274.
Xu et al. "Neurotransmitter receptors and cognitive dysfunction in Alzheimer's disease and Parkinson's disease" Progress in Neurobiology 2012, vol. 97, pp. 1-13.
Yakovidis et al. Copper(II) Complexes ofThieno[2,3-d] pyrimidine Derivatives. Inorganica Chimica Acta. vol. 151. 1988. 165-7.
Yalyaheva et al., Chemical Abstract, Heterocycles, p. 687, vol. 107, 1987.
Yasuhara et al. "Metabotropic Glutamate Receptors: Potential Drug Targets for Psychiatric Disorders" The Open Medicinal Chemistry Journal 2010, vol. 4, pp. 20-36.
Yokoi et al. "Impairment of Hippocampal Mossy Fiber LTD in Mice Lacking mGluR2" Science, 1996, vol. 273, pp. 645-647.
Yousif et al. "Studies on Tertiary Amine Oxides. LXXV. Reactions of Aromatic N-oxides with Meldrum's Acid in the Presence of Acetic Anhydride." Chem. Pharm. Bull. vol. 30 (5). 1982. 1680-91.
Yucel et al. "Anterior Cingulate Volumes in Never-Treated Patients with Major Depressive Disorder" Neuropsychopharmacology 2008, vol. 33, pp. 3157-3163.
Yui et al. "Studies of Amphetamine or Methamphetamine Psychosis in Japan: Relation of Methamphetamine Psychosis to Schizophrenia." Annals New York Academy of Sciences. 2000; p. 1-12.
Yuzwa "O-GlcNAc and neurodegeneration: biochemical mechanisms and potential roles in Alzheimer's disease and beyond" Chem. Soc. Rev., 2014, 43, 6839.
Zhang et al. "Neuroprotective Effects of Poly(ADP-ribose) Polymerase Inhibition on Focal Cerebral lschemia." 125.
Zhang et al."1-[(1-Methyl-1H-imidazol-2-yl)methyl]-4-phenylpiperidines as mGluR2 Positive Allosteric Modulators for the Treatment of Psychosis" J Med Chem 2011, vol. 54, pp. 1724-1739.
Zhang et al. "3-(Imidazolyl methyl)-3-aza-bicyclo[3.1,0]hexan-6-yl)methyl ethers: a novel series of mGluR2 positive allosteric modulators" Bioorg Med Chem Lett 2008, vol. 18, pp. 5493-5496.
Zhang, Jie et al. "Neuroprotective Effects of Poly(ADP-ribose) Polymerase Inhibition on Focal Cerebral Ischemia" Portland Press Proceedings, 1998, vol. 15 (Biology of Nitric Oxide, Part 6), pp. 125.
Zusso et al. "Cerebellar Granular Cell Cultures as an in vitro model for antidepressant drug-induced meurogenesis" Critical ReviewsTM in neurobiology 2004, vol. 16(1&2), pp. 59-65.
Basan et al. Valproate for schizophrenia. Cochrane Database Syst Rev. 2008; (1):CD004028.
Batchelor et al., "Novel Synaptic Potentials in Cerebellar Purkinje Cells: Probable Mediation by Metabotropic Glutamate Receptors", Neuropharmacology, 1993, 32(1), 11-20.
Battaglia et al., "Selective Activation of Group-II Metabotropic Glutamate Receptors Is Protective Against Excitotoxic Neuronal Death," European Journal of Pharmacology, 1998, 356(2-3), 271-274.
Bauer et al. "Extended Release Quetiapine as Adjunct to an Antidepressant in Patients With Major Depressive. Disorder: Results of a Randomized, Placebo-Controlled, Double-Blind Study" J Clin Psychiatry 2009, vol. 70(4), pp. 540-549.
Bauzo et al. Interactions between the mGluR2/3 agonist, LY379268, and cocaine on in vivo neurochemistry and behavior in squirrel monkeys. Pharmacol. Biochem. Behav. 2009, 94 (1), 204-210.
Bech "Dose-response Relationship of Pregabalin in Patients with Generalized Anxiety Disorder. A Pooled Analysis of Four Placebo-controlled Trials" Pharmacopsychiatry 2007, vol. 40, pp. 163-168.
Bech et al., Quantitative rating of depressive states. Acta Psychiatr Scand Mar. 1975; 51(3): 161-170 (abstract).

Bech, The Bech-Rafaelsen Melancholia Scale (MES) in clinical trials of therapies in depressive disorders: a 20-year review of its use as outcome measure. Acta Psychiatr Scand Oct. 2002; 106(4): 252-264.
Beesdo "Incidence and Risk Patterns of Anxiety and Depressive Disorders and Categorization of Generalized Anxiety Disorder" Arch Gen Psychiatry 2010, vol. 67(1), 47-57.
Behrens et al. "Ketamine-induced loss of phenotype of fast-spiking interneurons is mediated by NADPH-oxidase" Science 2007, vol. 318, pp. 1645-1647.
Belenikin et al. Comparative analysis of the ligand-binding sites of the metabotropic glutamate receptors mGluR1-mGluR8. Doklady Biochemistry & Biophysics. 386:251-6, Oct. 2002.
Bell et al. Altered synaptic function in Alzheimer's disease. [Review] [146 refs]. European Journal of Pharmacology 2006, 545 (1), 11-21.
Bellani et al. "Brain anatomy of major depression II. Focus on amygdala" Epidemiology and Psychiatric Sciences 2011, vol. 20(1), pp. 33-36.
Bellesi et al. "The mGluR2/3 agonist LY379268 blocks the effects of GLT-I upregulation on prepulse inhibition of the startle reflex in adult rats" Neuropsychopharmacology 2010, pp. 1-8 (epub ahead of print).
Belousov et al. Non-cholinergic excitation in neurons after a chronic glutamate receptor blockade. Neuroreport. 15 (1):113-7, 2004.
Benarroch, "Metabotropic Glutamate Receptors: Synaptic Modulators and Therapeutic Targets for Neurologic Disease", Neurology, 2008, 70(12), 964-968.
Benca et al. "Sleep and psychiatric disorders. A meta-analysis" Arch Gen Psychiatry 1992, vol. 49, pp. 651-670.
Beneyto et al., "Abnormal Glutamate Receptor Expression in the Medial Temporal Lobe in Schizophemia and Mood Disorders", Neuropsychopharmacology, 2007, 32(9), 1888-1902.
Benilova et al. "The toxic A.beta. oligomer and Alzheimer's disease: an emperor in need of clothes" Nature Neuroscience 2012, vol. 15(3), pp. 349-357.
Benneyworth et al., ""A Selective Positive Allosteric Modulator of Metabotropic Glutamate Receptor Subtype 2 Blocks a Hallucinogenic Drug Model of Psychosis,"" Mol. Pharmacol., 2007, 72, 477-484.
Benneyworth et al., "Chronic Phenethylamine Hallucinogen Treatment Alters Behavioral Sensitivity to a Metabotropic Glutamate 2/3 Receptor Agonist", Neuropsychopharmacology, 2008, 33(9), 2206-2216.
Bennyworth et al. "A Selective Positive Allosteric Modulator of Metabotropic Glutamate Receptor Subtype 2 Blocks a Hallucinogenic Drug Model of Psychosis", Molecualr Pharmocology, 2007, 72, 477-484, The American Soc. for Phamacology and Experimental Therapeutics, USA.
Benquet et al. Two distinct signaling pathways upregulate NMDA receptor responses via two distinct metabotropic glutamate receptor subtypes. Journal of Neuroscience. 22(22):9679-86, 2002.
Benson et al., "A Comparison of Observational Studies and Randomized, Controlled Studies", N Engl J Med., 2000, 342(25), 1878-1886.
Bergink et al. "Metabotropic glutamate II receptor agonists in panic disorder: a double blind clinical trial with LY354740" International Clinical Psychopharmacology 2005, vol. 20, pp. 291-293.
Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, 68, 843-853.
Bermudo-Soriano, "New Perspectives in Glutamate and Anxiety", Pharmacol Biochem Behav, 2011, Epub, No Page Numbers, Doi:10. 1016/J.Pbb.2011.04.010.
Berthele et al. Distribution and developmental changes in metabotropic glutamate receptor messenger RNA expression in the rat lumbar spinal cord. Developmental Brain Research 1999, 112 (1), 39-53.
Berthele et al. Expression of metabotropic glutamate receptor subtype mRNA (mGluR1-8) in human cerebellum. Neuroreport 1999, 10 (18), 3861-3867.
Bertrand et al. Common and selective molecular determinants involved in metabotopic glutamate receptor agonist activity. J. Med. Chem. 2002, 45 (15), 3171-3183.

(56) References Cited

OTHER PUBLICATIONS

Bespalov et al. "Behavioral characterization of the mGlu group II/III receptor antagonist, LY-341495, in animal models of anxiety and depression" European Journal of Pharmacology (2008), epub, no page numbers, doi: 10.1016/j.ejphar.2008.06.089.

Bespalov et al. Habituation deficits induced by metabotropic glutamate receptors 2/3 receptor blockade in mice: reversal by antipsychotic drugs. Journal of Pharmacology & Experimental Therapeutics 2007, 320 (2), 944-950.

Bessho et al. Glutamate and quisqualate regulate expression of metabotropic glutamate receptor mRNA in cultured cerebellar granule cells. Journal of Neurochemistry 1993, 60 (1), 253-259.

Bessis et al. Metabotropic glutamate receptors: exciting possibilities in excitatory transmission. Celltransmissions 2000, 17, 3-10.

Bick et al. "Photo-oxidative cleavage: an alternative method for degrading bisbenzylisoquinoline alkaloids." Journal of Natural Products. vol. 49 (3). May-Jun. 1986. 373-85.

Bijl et al. "Current and residual functional disability associated with psychopathology: findings from the Netherlands Mental Health Survey and Incidence Study (NEMESIS)" Psychological Medicine / vol. null / Issue 03 / May 2000, pp. 657-668.

Bilkei-Gorzo et al. mCPP-induced anxiety in the light-dark box in rats—a new method for screening anxiolytic activity. Psychopharmacology (Berl) 1998, 136 (3), 291-298.

Binder et al., "Association of Polymorphisms in Genes Regulating the Corticotropin-Releasing Factor System With Antidepressant Treatment Response", Arc Gen Psychiatry, 2010, vol. 67(4), 369-379.

Black et al. Compound A, a novel, potent and selective mGluR2 positive allosteric modulator: II. Effects in models predictive of therapeutic activity against cognitive impairment associated with schizophrenia Poster 767.7 Presented at the 40th annual meeting of Society for Neuroscience 2010, Nov. 12-17, 2010, San Diego, CA, USA.

Blaha et al. Stimulation of the ventral subiculum of the hippocampus evokes glutamate receptor-mediated changes in dopamine efflux in the rat nucleus accumbens. European Journal of Neuroscience 1997, 9 (5), 902-911.

Blanco et al. "Changes in the prevalence of non-medical prescription drug use and drug use disorders in the United States: 1991-1992 and 2001-2002" Drug and Alcohol Dependence 90 (2007) 252-260.

Boatman et al., "Alkylations at the Methyl or alpha-Methylene Group of 6- or 4-Alkyl-3-cyano-2(1 )-pyridones through Dianions", Journal of Organic Chemistry, 1965, vol. 30 Pt 11, pp. 3593-3597.

Boatman et al., Journal of Organic Chemistry, 1965, 30, 3593-3597.

Bockaert et al. "Molecular tinkering of G protein-coupled receptors: an evolutionary success" The EMBO Journal 1999, vol. 18(7), pp. 1723-1729.

Bockaert et al. Metabotropic glutamate receptors: an original family of G protein-coupled receptors. [Review] [81 refs]. Fundamental & Clinical Pharmacology 1993, 7 (9), 473-485.

Bodick et al. "Protocols to demonstrate slowing of Alzheimer disease Progression. Position Paper on the International working Group on Harmonization of Dementia Drug Guidelines" Alzheimer Disease and Associated Disorders 1997, vol. 11, Suppl 3, pp. 50-53.

Bohm et al. "Thieno Compounds Part 5: Basically Substituted Thieno[2,3-d]pyrimidines." Pharmazie. vol. 41. 1986. 23-25.

Bohme et al., "Darstellng and Umsetzungen von 3-Arylamino-2-halogencrotononitilen", Chem. Ber., 1976, 109, 2908-2913.

Boldyrev et al. Homocysteine and its derivatives as possible modulators of neuronal and non-neuronal cell glutamate receptors in Alzheimer's disease. J Alzheimer. Dis 2007, 11 (2), 219-228.

Bolton et al. "Exploring the Correlates of Suicide Attempts Among Individuals With Major Depressive Disorder: Findings From the National Epidemiologic Survey on Alcohol and Related Conditions" J Clin Psychiatry 2008, vol. 69, pp. 1139-1149.

Rorick-Kehn et al. "Pharmacological and Pharmacokinetic Properties of a Structurally Novel, Potent, and Selective Metabotropic Glutamate 2/3 Receptor Agonist: In Vitro Characterization of Agonist (−)-(1R,4S,5S,6S)-4-Amino-2-sulfonylbicyclo[3.1.0]-hexane-4,6-dicarboxyli-c Acid (LY404039)" J. Pharmacol. Exper. Therapeut. 2007, vol. 321, pp. 308-317.

Rorick-Kehn et al. "Pharmacological and Pharmacokinetic Properties of a Structurally-Novel, Potent, Selective mGlu2/3 Receptor Agonist: In Vitro Characterization of LY404039" JPET 2007, EPUB, No Page Numbers, DOI:10.1124/jpet.106.110809.

Rorick-Kehn et al. "Pharmacological characterization of stress-induced hyperthermia in DBA/2 mice using metabotropic and ionotropic glutamate receptor ligands" Psychopharmacology (Berl). 2005, vol. 183(2), pp. 226-240.

Rosowsky et al., "2,4-Oiaminothieno[2,3-dJpyrimidines as Antifolates and Antimalarials. 3. Synthesis of S,6-Disubstituted Derivatives and Related Tetracyclic Analogs", Journal of Medicinal Chemistry, 1973, vol. 16, No. 3 191-194.

Ross et al., "Expression of Functional Metabotropic and Ionotropic Glutamate Receptors in Baculovirus-Infected Insect Cells", Neuroscience Letters, 1994, 173(1-2), 139-142.

Roth et al. G protein-coupled receptor (GPCR) trafficking in the central nervous system: relevance for drugs of abuse. [Review] [152 refs]. Drug & Alcohol Dependence 1998, 51 (1-2), 73-85.

Roth et al., "Synthesis of Small Molecule Inhibitors of the Orphan Nuclear Receptor Steroidogenic Factor-1 (Nr5a1) Based on Isoquinolinone Scaffolds", Bioorg Med Chem Lett, 2008, 18, 2628-2632.

Rothman et al., "Excitatory and the NMDA Receptor", Trends in Neurosciences, 1987, 10(7), 299-302.

Rovira et al. "Modeling the Binding and Function of Metabotropic Glutamate Receptors" JPET 2008, vol. 325, pp. 443-456.

Rowe et al. "Transposition of Three Amino Acids Transforms the Human Metabotropic Glutamate Receptor (mGluR)-3 Positive Allosteric Modulation Site to mGluR2, and additional Characterization of the mGluR2 Positive Allosteric Modulation Site" JPET Fast Forward. (2008) EPUB, No Page Numbers, DOI:10.1124/jpet.108.138271.

Roy et al. "A twin study of generalized anxiety disorder and major depression" Psychological Medicine 1995, vol. 5, pp. 1037-1049.

Roychowdhury et al. G protein beta1gamma2 subunits promote microtubule assembly. J. Biol. Chem. 1997, 272 (50), 31576-31581.

Roychowdhury et al., "G Protein Alpha Subunits Activate Tubulin Gtpase and Modulate Microtubule Polymerization Dynamics", J. Biol. Chem., 1999, 274(19), 13485-13490.

Rozenfeld et al. "Receptor heteromerization and drug discovery" Trends in Pharmacological Sciences, 2010, vol. 31(3), pp. 124-130.

Rudd et al. "Positive Allosteric Modulators of the Metabotropic Glutamate Receptor Subtype 2 (mGluR2)" Current Topics in Medicinal Chemistry 2005, vol. 5, pp. 869-884.

Rush et al. "Sequenced treatment alternatives to relieve depression (Star*D): rationale and design" Controlled Clinical Trials 2004, vol. 25, pp. 119-142.

Rush et al., "Comorbid Psychiatric Disorders in Depressed Outpatients: Demographic and Clinical Features", Journal of Affective Disorders, 2005, 87, 43-55.

Rush et al., "Response in Relation to Baseline Anxiety Levels in Major Depressive Disorder Treated with Bupropion Sustained Release or Sertraline", Neuropsychopharmacology, 2001, 25(1), 131-138.

Rush et al.: The Inventory for Depressive Symptomatology (IDS): preliminary findings. Psychiatry Res May 1986; 18 (1):65-87.

Rush et al.: The Inventory of Depressive Symptomatology (Ids)—Preliminary Findings. Psychopharmacology Bulletin 1986; 22(3): 985-990.

Rush et al.: The Inventory of Depressive Symptomatology (IDS): Psychometric properties. Psychol Med May 1996 ; 26(3):477-486.

Ryndina et al., "Torp-Ziegler Cyclization in the Synthesis of 3-Ami No-4Cyanopyrole Derivatives", 2000, 36, 1409-1420, Plenum Publishing Corp.

Sackheim et al. The impact of medication resistance and continuation pharmacotherapy on relapse following response to electroconvulsive therapy in major depression. J Clin Psychpharmacol Apr. 1990; 10(2): 96-104.

Sahara et al. Cellular localization of metabotropic glutamate receptors mGluRI, 2/3, 5 and 7 in the main and accessory olfactory bulb of the rat. Neuroscience Letters. 2001, 312 (2), 59-62.

(56) References Cited

OTHER PUBLICATIONS

Sahni et al. "Compound A, a novel, potent and selective metabotropic glutamate receptor 2 (mGluR2) positive allosteric modulator: I. Pharmacological characterization" Poster 767.6 Presented at the 40th annual meeting of Society for Neuroscience 2010, Nov. 12-17, 2010, San Diego, CA, USA.

Sakamoto et al. "Condensed Heteroaromatic Ring Systems. VIII. Synthesis 3-Substituted Isocoumarins from o-Halobenzoic Acid Derivatives." Chem. Pharm. Bull. vol. 34 (7). 1986. 2754-9.

Sanacora et al. "Subtype-specific alterations of gamma-aminobutyric acid and glutamate in patients with major depression" Arch Gen Psychiatry 2004, vol. 61, pp. 705-713.

Sanacora et al. Targeting the glutamatergic system to develop novel, improved therapeutics for mood disorders. Nat Rev Drug Discov May 2008; 7(5): 426-437.

Sanderson et al. Syndrome comorbidity in patients with major depression or dysthymia: prevalence and temporal relationships. Am J Psychiatry Aug. 1990; 147(8): 1025-1028.

Sanger et al. "Pharmacological profiling of native group II metabotropic glutamate receptors in primary cortical neuronal cultures using a FLIPR" Neuropharmacology 2012, epub, no page numbers, doi:10.1016/j.neuropharm.2012.05.023.

Satow et al. "Pharmacological Effects of the Metabotropic Glutamate Receptor 1 Antagonist Compared with Those of the Metabotropic Glutamate Receptor 5 Antagonist and Metabotropic Glutamate Receptor 2/3 Agonist in Rodents: Detailed Investigations with a Selective Allosteric Metabotropic Glutamate Receptor 1 Antagonist, FTIDC [4-[1-(2-Fluoropyridine-3-yl)-5-methyl-1 H-1,2,3-triazol-4-yl]-Nisopropyl-N-methyl-3,6-dihydropyridine-1 (2H)-carboxamide]" J. Pharmacol. Exper. Therapeut. 2008, vol. 326, pp. 577-586.

Sawamoto et al., 2002. Cognitive slowing in Parkinson's disease: a behavioral evaluation independent of motor slowing. J.Neurosci. 22, 5198-5203.

Scaccianoce et al. "Endogenous activation of group-II metabotropic glutamate receptors inhibits the hypothalamic-pituitary-adrenocortical axis" Neuropharmacology 2003, vol. 44, pp. 555-561.

Schaffhauser et al. Multiple pathways for regulation of the KCl-induced [3H]-GABA release by metabotropic glutamate receptors, in primary rat cortical cultures. Brain Res. 1998, 782 (1-2), 91-104.

Schaffhauser et al. Pharmacological characterization of metabotropic glutamate receptors linked to the inhibition of adenylate cyclase activity in rat striatal slices. Neuropharmacology 1997, 36 (7), 933-940.

Schaffhauser et al., "In Vitro Binding Characteristics of a New Selective Group II Metabotropic Glutamate Receptor Radioligand, [3H]LY354740, in Rat Brain," Mol Pharmacology, 53, 228-233, 1998.

Schaffhauser et al., "Pharmacological Characterization and Identification of Amino Acids Involved in the Positive Modulation of Metabotropic Glutamate Receptor Subtype 2," Mol. Pharmacol 64:798-810, 2003, vol. 64, No. 4.

Scheer et al. Constitutively active G protein-coupled receptors: potential mechanisms of receptor activation. [Review [46 refs]. Journal of Receptor & Signal Transduction Research 1997, 17 (1-3), 57-73.

Schlumberger et al. "Comparison of the mGlu5 receptor positive allosteric modulator ADX47273 and the 3 mGlu2/3 receptor agonist LY354740 in tests for antipsychotic-like activity" Eur. J. Pharmacol. 2009, epub, no page numbers, doi:10.1016/j.ejphar.2009.09.006.

Schmidt, D. "Drug treatment of epilepsy: Options and limitations" Epilepsy & Behavior 2009, 15, 56-65.

Schoepp "Unveiling the functions of presynaptic metabotropic glutamate receptors in the central nervous system" J Pharmacol Exp Ther 2001, vol. 299, pp. 12-20.

Schoepp et al, "Pharmacological agents acting at subtypes of metabotropic glutamate receptors," Neuropharmacology 38 (1999) 1431-1476.

Schoepp et al. "LY354740, an mGlu2/3 Receptor Agonist as a Novel Approach to Treat Anxiety/Stress" Stress 2003 6(3), 189-197.

Schoepp et al. LY354740 Is a Potent and Highly Selective Group II Metabotropic Glutamate Receptor Agonist in Cells Expressing Human Glutamate Receptors. Neuropharmacology 1997, vol. 36, pp. 1-11.

Schoepp, Darryle D. and Marek, Gerard J. "Preclinical Pharmacology of mGlu2/3 Receptor Agonists: Novel Agents for Schizophrenia?" Current Drug Targets 2002, vol. 1, pp. 215-225.

Schreiber et al.; De Vry, J. LY354740 affects startle responding but not sensorimotor gating or discriminative effects of phencyclidine. Eur. J Pharmacol. 2000, 388 (2), R3-R4.

Schweitzer et al. Characterization of [(3)H]-LY354740 binding to rat mGlu2 and mGlu3 receptors expressed in CHO cells using semliki forest virus vectors. Neuropharmacology 2000, 39 (10), 1700-1706.

Seddon "Psudopolymorph" Crystal growth & design 4(6) p. 1087 (2004) (two pages from internet).

Seebahn et al. RanBPM is expressed in synaptic layers of the mammalian retina and binds to metabotropic glutamate receptors. FEBS Lett. 2008, 582 (16), 2453-2457.

Seedat et al. Measuring anxiety in patients with schizophrenia. J Nery Ment Dis. Apr. 2007; 195(4):320-324.

Andres et al. "2-(Dimethylaminomethyl)-tetrahydroisoxazolopyridobenzazepine Derivatives. Synthesis of a New 5-HT2C Antagonist with Potential Anxiolytic Properties" Bioorganic & Medicinal Chemistry Letters 2002, vol. 12, pp. 3573-3577.

Andres et al. "Synthesis, evaluation, and radiolabeling of new potent positive allosteric modulators of the metabotropic glutamate receptor 2 as potential tracers for positron emission tomography imaging" J Med Chem 2012, vol. 55, pp. 8685-8699.

Angenstein et al., Activation of metabotropic glutamate receptors increases endogenous protein kinase C substrate phosphorylation in adult hippocampal slices. Brain Research 1997, 745 (1-2), 46-54.

Angers et al., Dimerization: an emerging concept for G protein-coupled receptor ontogeny and function. Annu. Rev. Pharmacol. Toxicol. 2002, 42, 409-435.

Antuono, "Decreased glutamate 1 glutamine in Alzheimer's disease detected in vivo with 1H-MRS at 0.5 T", Neurology, 2001, 56:737-742.

Anwyl "Metabotropic glutamate receptor-dependent long-term potentiation" Neuropharmacology 2009, vol. 56, pp. 735-740.

Anwyl "Metabotropic glutamate receptors: electrophysiological properties and role in plasticity" Brain Res. Brain Res. Rev. 1999, vol. 29, pp. 83-120.

Aparicio-Legarza et al., Deficits of [3H]D-aspartate binding to glutamate uptake sites in striatal and accumbens tissue in patients with schizophrenia. Neuroscience Letters 1997, 232 (1), 13-16.

Aparicio-Legarza et al., Increased density of glutamate/N-methyl-D-aspartate receptors in putamen from schizophrenic patients. Neuroscience Letters 1998, 241 (2-3), 143-146.

Armstrong et al. "Characterization of Competitive Inhibitors for the Transferase Activity of Pseudomonas aeruginosa Exotoxin A." Journal of Enzyme Inhibition and Medicinal Chemistry. vol. 17 (4). 2002. 235-46.

Arnt. "Differential effects of classical and newer antipsychotics on the hypermotility induced by two dose levels of D-amphetamine." European Journal of Pharmacology. vol. 283. 1995. 55-62.

Arnt: Pharmacological specificity of conditioned avoidance response inhibition in rats: inhibition by neuroleptics and correlation to dopamine receptor blockade. Acta Pharmacol. Toxicol. 51: 321-329 (1982).

Aronica et al., Metabotropic glutamate receptors in cultured cerebellar granule cells: developmental profile. Journal of Neurochemistry 1993, 60 (2), 559-565.

Aronica et al., Pharmacological characterization of metabotropic glutamate receptors in cultured cerebellar granule cells. Neurochemical Research 1993, 18 (5), 605-612.

Aronica et al., Status epilepticus-induced alterations in metabotropic glutamate receptor expression in young and adult rats. J. Neurosci. 1997, 17 (21), 8588-8595.

Aronson et al. "Triiodothyronine Augmentation in the Treatment of Refractory Depression. A Meta-analysis" Arch Gen Psychiatry 1996, vol. 53, pp. 842-848.

(56) References Cited

OTHER PUBLICATIONS

Arriza et al., Functional comparisons of three glutamate transporter subtypes cloned from human motor cortex. J. Neurosci. 1994, 14 (9), 5559-5569.
Arundine, "Molecular mechanisms of glutamate-dependent neurodegeneration in ischemia and traumatic brain injury", Cellular and Molecular Life Sciences, 61, 2004, pp. 657-668.
Atlante, "Glutamate neurotoxicity, oxidative stress and mitochondria", FEBS Letters 497, 2001, 1-5.
Attwell et al., "Anticonvulsant and Glutamate Release-Inhibiting Properties of the Highly Potent Metabotropic Glutamate Receptor Agonist (2s,2'r, 3'r)-2-(2',3'-Dicarboxycyclopropyl)Glycine (Dcg-lv)", Brain Res., 1998, 805(1-2), 138-143.
Auer et al., "Reduced glutamate in the anterior cingulate cortex in depression: an in vivo proton magnetic resonance spectroscopy study" Biol Psychiatry Feb. 2000; 47(4): 305-313.
Auerbach et al. "Mutations causing syndromic autism define an axis of synaptic pathophysiology" Nature 2011, vol. 480, pp. 63-68.
Aultman et al., "Distinct Contributions of Glutamate and Dopamine Receptors to Temporal Aspects of Rodent Working Memory Using a Clinically Relevant Task", Psychopharmacology (Berl), 2001, 153(3), 353-364.
Austin et al. "Symptomatic and neuroprotective effects following activation of nigral group III metabotropic glutamate receptors in rodent models of Parkinson's disease" British Journal of Pharmacology 2010, vol. 160, 1741-1753.
Australian Patent Application No. 2005/284098: Office Action dated Oct. 11, 2010, 2 pages.
Australian Patent Application No. 2007/224431: Office Action dated Mar. 19, 2010, 6 pages.
Australian Patent Application No. 2008/223795: Office Action dated May 29, 2012, 2 pages.
Australian Patent Application No. 2008/223796: Examiner's Report dated Nov. 3, 2010, 2 pages.
Australian Patent Application No. 2008/297877: Examiner's Report dated Oct. 31, 2012, 3 pages.
Awouters et al. Astemizole: effects on general behavior and interactions with the central nervous system, Jap. Pharmacol. & Therapeutics, 19:73-89 (1991).
Ayalew et al., "Convergent Functional Genomics of Schizophrenia: From Comprehensive Understanding to Genetic Risk Prediction", Molecular Psychiatry 2012, 1-19.
Ayan-Oshodi et al. "Adverse events in healthy subjects exposed to single and multiple doses of Ly2140023 monohydrate" J Clin Psychopharmacol 2012, vol. 32, pp. 408-411.
Azimov et al., "Chemical Abstracts", Abstract No. 78798, 1986, 105(10), 1 page.
Azuma et al., "Synthesis and reactions of 4-choloro-1,2-dihydro-6-methyl-2-oxo-3-pyridinecarbonitrile,\CA139:197340", 2003, 1 page.
Backstrom, "Suppression of alcohol self-administration and cue-induced reinstatement of alcohol seeking by the mGlu 2/3 receptor agonist LY379268 and the mGlu8 receptor agonist (S)-3,4-DCPG" Eur. J. Pharmacol. 528:110-118 (2005).
Badawy et al. "Epilepsy: Ever-changing states of cortical excitability" Neuroscience 2012, vol. 22, pp. 89-99.
Baffa et al., "Norepinephrine and Serotonin Transporter Genes: Impact on Treatment Response in Depression", Neuropsychobiology, 2010, 62, 121-131.
Bagby et al. "Psychosocial and clinical predictors of response to pharmacotherapy for depression" J Psychiatry Neurosci 2002; 27(4):250-7.
Bakker et al. "Activation of the metabotropic glutamate receptor 2 (mGlu2) by orthosteric and allosteric ligands" Poster 642.6/E30 Presented at the 40th annual meeting of Society for Neuroscience 2010, Nov. 12-17, 2010, San Diego, CA, USA.
Bakker et al., "Reduction of Hippocampal Hyperactivity Improves Cognition in Amnestic Mild Cognitive Impairment", Neuron, 2012, 74(3), 467-474.
Balastrieri et al. "Assessing mixed anxiety-depressive disorder. A national primary care survey" Psychiatry Research 2010, vol. 176, 197-201.
Balazs et al., "Metabotropic Glutamate Receptor Agonists Potentiate Cyclic Amp Formation Induced by Forskolin or Beta-Adrenergic Receptor Activation in Cerebral Cortical Astrocytes in Culture", Journal of Neurochemistry, 1998, 70(6), 2446-2458.
Bandelow et al. "Adjunct Quetiapine XR in Patients with Major Depressive Disorder: A Pooled Analysis of Data from Patients with Anxious Depression" P02-11 Abstracts of the 19th European Congress of Psychiatry, Mar. 12-15, 2011, Vienna, Austria.
Bar-Peled et al., "Distribution of Glutamate Transporter Subtypes During Human Brain Development", J Neurochem., 1997, 69(6), 2571-2580.
Barda et al. "SAR study of a subtype selective allosteric potentiator of metabotropic glutamate 2 receptor, N-(4phenoxyphenyl)-N-(3-pyridinylmethyl)ethanesulfonamide" Bioorganic & Medicinal Chemistry Letters 2004, vol. 14, pp. 3099-3102.
Barker et al., "A Temporally Distinct Role for Group I and Group II Metabotropic Glutamate Receptors in Object Recognition Memory", Learn. Mem., 2006, 13(2), 178-186.
Barnes et al., "A review of central 5-HT receptors and their function" Neuropharmacology 1999, vol. 38, pp. 1083-1152.
Barrett "mGluR2-Positive Allosteric Modulators: Therapeutic Potential for Treating Cocaine Abuse?" Neuropsychopharmacology 2010, vol. 35, pp. 2007-2008.
Bartha et al., "Measurement of Glutamate and Glutamine in the Medial Prefrontal Cortex of Never-Treated Schizophrenic Patients and Healthy Controls by Proton Magnetic Resonance Spectroscopy", Archives of General Psychiatry, 1997, 54(10), 959-965.
Barton et al., "Comparison of the Effect of Glutamate Receptor Modulators in the 6 Hz and Maximal Electroshock Seizure Models", Epilepsy Research, 2003, 56, 17-26.
Muly et al., "Group II Metabotropic Glutamate Receptors in Anxiety Circuitry: Correspondence of Physiological Response and Subcellular Distribution", J Comp Neurol., 2007, 505(6), 682-700.
Muntasir et al., "Inverse Agonist Activity of Sarpogrelate, A Selective 5-Ht2a-Receptor Antagonist, at the Constitutively Active Human 5-Ht2a Receptor", Journal of Pharmacological Sciences, 2006, 102(2), 189-195.
Murck et al. "State markers of depression in sleep EEG: dependency on drug and gender in patients treated with tianepine or paroxetine" Neuropsychopharmacology 2003, vol. 28, pp. 348-358.
Mutel et al., "Characterization of (2S,2,R,3,R)-2-(2,,3'-[3H]-Dicarboxycyclopropyl)glycine Binding in Rat Brain," J Neurochemistry, 71(6), 1998, 2558-2564.
Mutel, V. Therapeutic potential of non-competitive, subtype-selective metabotropic glutamate receptor ligands,Expert Opin. Ther. Patents (2002), 12 (12) p. 1845-1852.
Muto et al. Structures of the extracellular regions of the group II/III metabotropic glutamate receptors. Proc. Natl. Acad. Sci. U. S. A 2007, 104 (10), 3759-3764.
Nabeshima et al. "Animal Model of Schizophrenia. Dysfunction of NMDA Receptor-Signaling in Mice following Withdrawal from Repeated Administration of Phencyclidine" Ann. N. Y. Acad. Sci. 2006, vol. 1086, pp. 160-168.
Nadin et al. "Synthesis of Tricyclic Pyridones by Radical Cyclization." Tetrahedron Letters. vol. 40. 1999. 4073-76.
Naimoli et al. "Compound A, a novel potent and selective mGluR2 positive allosteric modulator: III. Effects in clinically relevant translational cognition models that could be used as biomarkers" Poster 767.1 Presented at the 40th annual meeting of Society for Neuroscience 2010, Nov. 12-17, 2010, San Diego, CA, USA.
Nakano et al. "1-Alkyl-3-phenylpyridinium 1-Alkyl-2(1 H)-pyridone 3-Phenyl 5-Phenyl", Annual Report of Tohoku College of Pharmacy, 1998, 45, 145-148.
Nasca et al. "L-acetylcarnitine causes rapid antidepressant effects through the epigenetic induction of mGlu2 receptors" PNAS Early Edition 2013, epub, no page numbers, doi:10.1073/pnas.1216100110.
Neale "The neurotransmitter N-acetylaspartylglutamate in models of pain, ALS, diabetic neuropathy, CNS injury and schizophrenia" Trends in Pharmacological Sciences 2005, vol. 26(9), 477-484.

(56) References Cited

OTHER PUBLICATIONS

Neki et al. Metabotropic glutamate receptors mGluR2 and mGluR5 are expressed in two non-overlapping populations of Golgi cells in the rat cerebellum. Neuroscience 1996, 75 (3), 815-826.

Neki et al., "Pre- and Postsynaptic Localization of a Metabotropic Glutamate Receptor, Mglur2, in the Rat Brain: An Immunohistochemical Study with a Monoclonal Antibody", Neurosci. Lett., 1996, 202(3), 197-200.

Nell et al., "Preparation of 4-amino-3,5-dicyano-2-thiopyridines as cardiovascular agents", CA149:32326 (2008).

Nelson et al. "Anxiety does not predict response to antidepressant treatment in late life depression: results of a meta-analysis" Int J Geriatr Psychiatry 2009, vol. 24, pp. 539-544.

Nelson et al. "Species differences in the pharmacology of the 5-Hydroxytrayptamine2 receptor: structurally specific differentiation by ergolines and tryptamines" JPET 1993, vol. 265, pp. 1272-1279.

Nelson, "Anxiety Does Not Predict Response to Duloxetine in Major Depression: Results of a Pooled Analysis of Individual Patient Data From 11 Placebo-Controlled Trials", Depression and Anxiety, 2010, 27, 12-18.

Nelson, "Anxious Depression and Response to Treatment", Am J Psychiatry, 2008, 165(3), 297-299.

Neubig et al., "Specificity of Receptor-G Protein Coupling: Protein Structure and Cellular Determinants", Seminars in Neuroscience, 1998, 9, 189-197.

Neugebauer "Metabotropic glutamate receptors—important modulators of nociception and pain behavior" Pain 2002, vol. 98, pp. 1-8.

Neugebauer et al. "Groups II and III Metabotropic Glutamate Receptors Differentially Modulate Brief and Prolonged Nociception in Primate STT Cells" J Neurophysiol 2000, vol. 84, pp. 2998-3009.

Neugebauer et al. Peripheral metabotropic glutamate receptors as drug targets for pain relief. [Review] [142 refs]. Expert Opinion on Therapeutic Targets. 6(3):349-61, 2002.

Neugebauer et al., "Requirement of Metabotropic Glutamate Receptors for the Generation of Inflammation-Evoked Hyperexcitability in Rat Spinal Cord Neurons", European Journal of Neuroscience, 1994, 6(7), 1179-1186.

Ngomba et al. "Metabotropic glutamate receptors in the thalamocortical network: Strategic targets for the treatment of absence epilepsy" Epilepsia, 2011, vol. 52(7), pp. 1211-1222.

Ngomba et al. The Preferential mGlu2/3 receptor antagonist, LY341495, reduces the frequency of spike-wave discharges in the WAG/Rij rat model of absence epilepsy, Neuropharmacology, 49:89-103 (2005).

Nguyen et al., "An in Vivo Biosensor for Neurotransmitter Release and in Situ Receptor Activity", Nature Neuroscience, 2010, 13(1), 127-132.

Nicholls et al. "mGluR2 acts through inhibitory G? subunits to regulate transmission and long-term plasticity at hippocampal mossy fiber-CA3 synapses" Proc. Natl. Acad. Sci. USA, 2006, vol. 103(16), pp. 6380-6385.

Nicholls et al. The release and uptake of excitatory amino acids. [Review]. Trends in Pharmacological Sciences 1990, 11 (11), 462-468.

Nicolas et al. A combined marble buyring-locomotor activity test in mice: a practical screening test with sensitivity to different classes of anxiolytics and antidepressants. Eur J Pharmacol. Oct. 10, 2006;547(1-3):106-15. Epub Jul. 25, 2006.

Nicoletti et al. "Metabotropic glutamate receptors: From the workbench to the bedside" Neuropharmacology 2011, vol. 60, pp. 1017-1041.

Nicoletti et al., "Lesions of Putative Glutamatergic Pathways Potentiate the Increase of Inositol Phospholipid Hydrolysis Elicited by Excitatory Amino Acids", Brain Research, 1987, 436(1), 103-112.

Nicoletti et al., "Metabotropic Glutamate Receptors: Beyond the Regulation of Synaptic Transmission", Psychoneuroendocrinology, 2007, 32(Suppl 1), S40-S45.

Nicoletti et al., "Metabotropic Glutamate Receptors: New Targets for the Control of Tumor Growth", Trends in Pharmacological Sciences, 2007, 206-213.

Nicoletti et al., "Pertussis Toxin Inhibits Signal Transduction at a Specific Metabolotropic Glutamate Receptor in Primary Cultures of Cerebellar Granule Cells", Neuropharmacology, 1988, 27(6), 551-556.

Nielson et al. "Phosphoramides XIV. Phosphorus pentozide and amine hydrochlorides as reagents in the synthesis of thieno(2,3-d]pyrimidin-4(3H)-ones." Chemica Scripta. vol. 18. 1981. 135-8.

Niemegeers et al. Interaction of Drugs with Apomorphine, Tryptamine, and Norepinephrine. A New 'in vivo' Approach: the ATN-Test in Rats, Arch. int. Pharmacodyn., 227:238-253 (1977).

Niemegeers et al. Protection of Rats from Compound 48/80-Induced Lethality. A Simple Test for Inhibitors of Mast Cell-Mediated Shock, Arch. int. Pharmacodyn., 234:164-176 (1978).

Nierenberg et al. "Lithium augmentation of nortriptyline for subject resistant to multiple antidepressants" J Clin Psychopharmacol 2003, vol. 23, pp. 92-95.

Nijholt et al. "Neuronal AKAP150 coordinates PKA and Epac-mediated PKB/Akt phosphorylation" Cellular signaling 2008, vol. 20, pp. 1715-1724.

Nikiforuk et al. "Effects of a positive allosteric modulator of mGlu2 receptors LY487379 on cognitive flexibility and impulsive-like responding in rats" JPET Fast Forward. Published on Aug. 25, 2010 as EPUB, No Page Numbers, DOI:10.1124/jpet.110.170506.

Ninomiya et al. "Photocyclisation of Enamides. Part 14. Substituent Effects in the Photocyclisation of N-a,B-Unsaturated Acylanilides." 1980. 197-202.

Nishi et al. "Pharmacological characterization of metabotropic glutamate receptor-mediated high-affinity GTPase activity in rat cerebral cortical membranes." British Journal of Pharmacology. vol. 130. 2000. 1664-70.

Nishi et al., "Glutamatergic system abnormalities in posttraumatic stress disorder", Psychopharmacology, 2015, 232, 4261-4268.

Niswender et al. "Metabotropic Glutamate Receptors: Physiology, Pharmacology, and Disease" Annu Rev Pharmacol Toxicol 2010, vol. 50, pp. 295-322.

Nofzinger et al. "Changes in forebrain function from waking to REM sleep in depression: preliminary analyses of [18F]FDG PET studies" Psychiatry Res 1999, vol. 91, pp. 59-78.

Noguchi et al. "Quantum Chemical Study on Conformational Properties of Bipyridine Cardiotonics." Chem. Pharm. Bull. vol. 41 (8). 1993. 1331-6.

Nordquist "Metabotropic glutamate receptor modulation, translational methods, and biomarkers: relationships with anxiety" Psychopharmacology 2008, vol. 199, pp. 389-402.

Norman et al. "Structure-Activity Relationships of a Series of Pyrrolo[3,2-d]pyrimidine Derivatives and Related Compounds as Neuropeptide Y5 receptor Antagonists." J. Med. Chem. vol. 43. 2000. 4288-312.

O'Brien et al. Molecular mechanisms of glutamate receptor clustering at excitatory synapses. [Review] [59 refs]. Current Opinion in Neurobiology 1998, 8 (3), 364-369.

Japanese Patent Application No. 2007-531759: Office Action dated Jun. 27, 2011, 12 pages.

Japanese Patent Application No. 2008-558820: Office Action dated Aug. 28, 2012, 14 pages.

Japanese Patent Application No. 2009-552215: Office Action dated Dec. 18, 2012, 3 pages.

Japanese Patent Application No. 2010-553485: Office Action dated Jul. 11, 2013, 3 pages.

Javitt "Glutamatergic Theories of Schizophrenia" Isr J Psychiatry Relat Sci 2010, vol. 47(1), pp. 4-16.

Javitt et al. "Recent advances in the phenylcyclidine model of schizophrenia" Am J Psychiatry 1991, vol. 148, pp. 1301-1308.

Jenkins et al., "Disturbances in Social Interaction Occur Along with Pathophysiological Deficits Following Sub-Chronic Phencyclidine Administration in the Rat", Behavioural Brain Research, 2008, 194, 230-235.

Jensen et al., "Allosteric Modulation of the Calcium-Sensing Receptor", Current Neuropharmacology, 2007, 5, 180-186.

Jhee et. al. "B-amyloid therapies in Alzheimer's disease" Expert Opinion on Investigational Drugs 2001, 10, 593-605.

Jin et al. The mGluR2 positive allosteric modulator BINA decreases cocaine self-administration and cue-induced cocaine-seeking and

(56) References Cited

OTHER PUBLICATIONS counteracts cocaine-induced enhancement of brain reward function in rats. Neuropsychopharmacology. 35(10):2021-36, 2010.
Jingami et al. Structure of the metabotropic glutamate receptor. [Review] [49 refs]. Current Opinion in Neurobiology. 13(3):271-8, 2003.
Joffe et al. "Anxious and Nonanxious Depression" Am J Psychiatry 1993, vol. 150, pp. 1257-1258.
Joffe et al. "Lifetime History of Depression and Anxiety Disorders as a Predictor of Quality of Life in Midlife Women in the Absence of Current Illness Episodes" Arch Gen Psychiatry 2012, vol. 69(5), pp. 484-492.
Johansen et al. Excitatory amino acid receptor ligands: resolution, absolute stereochemistry, and enantiopharmacology of 2-amino-3-(4-butyl-3-hydroxyisoxazol-5-yl)propionic acid. Journal of Medicinal Chemistry 1998, 41 (6), 930-939.
John et al. Rapid changes in glutamate levels in the posterior hypothalamus across sleep-wake states in freely behaving rats. American Journal of Physiology—Regulatory Integrative & Comparative Physiology. 295(6):R2041-9, 2008.
Johnson et al. "Activation of group II metabotropic glutamate receptors induces long-term depression of excitatory synaptic transmission in the substantia nigra pars reticulata" Neuroscience Letters 2011, vol. 504, pp. 102-106.
Johnson et al. "Disruption of GABAergic tone in the dorsomedial hypothalamus attenuates responses in a subset of serotonergic neurons in the dorsal raphe nucleus following lactate-induced panic" J Psychopharmacol 2008, vol. 22, pp. 642-652.
Johnson et al. "Glutamate receptors as therapeutic targets for Parkinson's disease" CNS Neurol Disord Drug Targets 2009, vol. 8, pp. 475-491.
Johnson et al. "Group II metabotropic glutamate receptor type 2 allosteric potentiators prevent sodium lactate-induced panic like response in panic-vulnerable rats" J Psychopharmacol 2013, vol. 27, pp. 152-161.
Johnson et al. "Species variations in transmembrane region V of the 5-hydroxytryptamine type 2A receptor alter the structure-activity relationship of certain ergolines and tryptamines" Molecular Pharmacology 1994, vol. 45, pp. 277-286.
Johnson et al., "Allosteric modulators of metabotropic glutamate receptors: lessons learnt from mGlu1, mGlu2 and mGlu5 potentiators and antagonists", Biochemical Society Transactions, 2004, vol. 32, part 5, 881-887.
Johnson et al., "Discovery of Allosteric Potentiators for the Metabotropic Glutamate 2 Receptor: Synthesis and Subtype Selectivity of N-(4-(2-Methoxyphenoxy)phenyl)-N-(2,2,2-trifluorethylsulfonyl)pyrid-3-ylm-ethyl-amine", J. Med. Chem., 2003, 46, 3189-3192.
Johnson et al., "Metabotropic glutamate 2 receptor potentiators: receptor modulation, frequency-dependent synaptic activity, and efficacy in preclinical anxiety and psychosis model(s)", Psychopharmacology, 2005, 179, 271-283.
Jones et al. "Analgesic effects of the selective group II (mGlu2/3) metabotropic glutamate receptor agonists LY379268 and LY389795 in persistent and inflammatory pain models after acute and repeated dosing" Neuropharmacology 2005, vol. 49, 206-218.
Jones et al. "Discovery, Synthesis, and Structure-Activity Relationship Development of a Series of N-4-(2,5-Dioxopyrrolidin-1-yl)phenylpicolinamides (VU0400195, ML182): Characterization of a Novel Positive Allosteric Modulator of the Metabotropic Glutamate Receptor 4 (mGlu4) with Oral Efficacy in an Antiparkinsonian Animal Model" J Med Chem 2011, vol. 54, pp. 7639-7647.
Jones et al. "The mGluR2/3 agonist LY379268 reverses post-weaning social isolation-induced recognition memory deficits in the rat" Psychopharmacology 2011, vol. 214, pp. 269-283.
Jones et al. A Rotarod Suitable for Quantitative Measurements of Motor Incoordination in Naive Mice, Naunyn Schmiedebergs Arch. Exper. Pathol. Pharmacol., 259:211 (1968).
Julio-Pieper et al. "Exciting Times beyond the Brain: Metabotropic Glutamate Receptors in Peripheral and Non-Neural Tissues" Pharmacological Review 2011, vol. 63, pp. 35-58.

Kagaya et al. Heterologous supersensitization between serotonin2 and alpha 2-adrenergic receptor-mediated intracellular calcium mobilization in human platelets. Journal of Neural Transmission—General Section 1992, 88 (1), 25-36.
Kahn et al., "Group 2 Metabotropic Glutamate Receptors Induced Long Term Depression in Mouse Striatal Slices", Neurosci. Lett., 2001, 316(3), 178-182.
Kalivas et al., "Repeated Cocaine Administration Alters Extracellular Glutamate in the Ventral Tegmental Area", Journal of Neurochemistry, 1998, 70(4), 1497-1502.
Kambe et al., "A convenient method for the preparation of 2-pyridone derivatives", Synthesis, 1977, 12, 841-842.
Kappe et al. "Aktive Malonester als Synthons fur Heterocyclen: Eine Methode zur Herstellung von 4-Hydroxy-2(1 H)-pyridonen." Journal of Heterocyclic Chemistry. vol. 25. Mar./Apr. 1988. 463-8.
Kapur et al., "From Dopamine to Salience to Psychosis-Linking Biology, Pharmacology and Phenomenology of Psychosis", Schizophr. Res., 2005, 79, 59-68.
Karlsson et al., "Loss of Glial Glutamate and Aspartate Transporter (Excitatory Amino Acid Transporter 1) Causes Locomotor Hyperactivity and Exaggerated Responses to Psychotomimetics: Rescue by Haloperidol and Metabotropic Glutamate 2/3 Agonist", Biol. Psychiatry, 2008, 64(9), 810-814.
Kato "Molecular Genetics of Bipolar Disorder and Depression" Psychiatry and Clinical Neurosciences 2007, 61, 3-19.
Katon et al., "Major Depression: The Importance of Clinical Characteristics and Treatment Response to Prognosis", Depression and Anxiety, 2010, 27, 19-26.
Kaupmann et al., "Expression Cloning of Gaba(B) Receptors Uncovers Similarity to Metabotropic Glutamate Receptors", Nature, 1997, 386(6622), 239-246.
Kawabata et al., "Diversity of Calcium Signaling by Metabotropic Glutamate Receptors", J. Biol. Chem., 1998, 273(28), 17381-17385.
Kearney et al. Intrasubthalamic nucleus metabotropic glutamate receptor activation: a behavioral, Fos immunohistochemical and [14C] 2-deoxyglucose autoradiographic study. Neuroscience 2000, 95 (2), 409-416.
Kearney et al., "Metabotropic Glutamate Agonist-Induced Rotation: A Pharmacological, FOS Immunohistochemical, and [14c]-2-Deoxyglucose Autoradiographic Study", J Neurosci., 1997, 17(11), 4415-4425.
Kehne et al. Anxiolytic effects of buspirone and gepirone in the fear-potentiated startle paradigm, Psychopharmacology, 94:8-13 (1988).
Keller et al. "Anxiety Symptom Relief in Depression Treatment Outcomes" J Clin Psychiatry 1995, vol. 56 (suppl 6), pp. 22-29.
Kellner et al., "Effects of metabotropic glutamate2/3 receptor agonist (LY544344/LY354740) on panic anxiety induced by cholecystokinin tetrapeptide in health humans: preliminary results", Psychopharmacology, 2005, 179, 310-315.
Kenakin "A holistic view of GPCR signaling" nature Biotechnology 2010, vol. 28, pp. 928-929.
Kenakin "Seven transmembrane receptors as nature's prototype allosteric protein: de-emphasizing the geography of binding" Molecular Pharmacology 2008, vol. 74, pp. 541-543.
Kenakin et al. Seven transmembrane receptors as shapeshifting proteins: the impact of allosteric modulation and functional selectivity on new drug discovery. [Review] [459 refs]. Pharmacological Reviews. 62(2):265-304, 2010.
Kenakin et al., "Signalling Bias in New Drug Discovery: Detection, Quantification and Therapeutic Impact", Nature Reviews Drug Discovery, 2013, 12, 205-216.
Kenakin, "Allosteric Agonist Modulators", Journal of Receptors and Signal Transduction, 2007, 27(4), 247-259.
Kenakin, "Allosteric Modulators: The New Generation of Receptor Antagonist", Molecular Interventions, Aug. 2004, 4(4), 222-229.
Dhonnchadha et al. "Anxiolytic-like effects of 5-HT2 ligands on three mouse models of anxiety" Behavioural Brain Research 2003, vol. 140, pp. 203-214.
Di Liberto et al. "Group II Metabotropic Glutamate Receptor Activation by Agonist LY379268 Treatment Increases The Expres-

(56) References Cited

OTHER PUBLICATIONS sion of Brain Derived Neurotrophic Factor in the Mouse Brain" Neuroscience 2010, vol. 165, pp. 863-873.
DiMichele et al., Psychopathology, (Mar.-Apr. 2004), 37(2), pp. 98-104 (Abstract).
Dingledine et al "Peripheral glutamate receptors: molecular biology and role in taste sensation" J Nutr 2000, 130(4S Suppl):1039S-1042S.
Dingledine et al Excitatory amino acid receptors in epilepsy. [Review] [35 refs]. Trends in Pharmacological Sciences 1990, 11 (8), 334-338.
Doherty et al Functional interactions between cannabinoid and metabotropic glutamate receptors in the central nervous system. Current Opinion in Pharmacology. 3(1):46-53, 2003.
Doherty et al. Rapid internalization and surface expression of a functional, fluorescently tagged G-protein-coupled glutamate receptor. Biochemical Journal 1999, 341 (Pt 2), 415-422.
Domschke et al. "Anxious versus non-anxious depression: difference in treatment outcome" J Psychopharmacol 2010, vol. 24, 621-622.
Doreulee et al. The role of the mGluR allosteric modulation in the NMDA-hypofunction model of schizophrenia. Georgian Medical News. (177):59-65, 2009.
Doumazene "Illuminating the activation mechanisms and allosteric properties of metabotropic glutamate receptors" PNAS Early Edition 2013 epub, no page numbers, doi:10.1073/pnas.1215615110.
Doumazene et al. "A new approach to analyze cell surface protein complexes reveals specific heterodimeric metabotropic glutamate receptors" FASEB 2011, vol. 25, pp. 66-77.
Doung et al., "A Biogenic Like Synthesis of Perloline, 6-(3,4-Dimethoxyphenyl)5-hydroxy-5,6-dihydro-benzo[c][2,7]naphthyridin-4(3HO)-one", Aust. J. Chem, 1983, 36, 1431-1440.
Downey et al. "Ecdysone-Based System for Controlled Inducible Expression of Metabotropic Glutamate Receptor Subtypes 2,5, and 8" Journal of Biomolecular Screening 2005, vol. 10(8), pp. 841-848.
Doyle et al. "Quantifying the attenuation of the ketamine phMRI response in humans: a validation using antipsychotic and glutamatergic agents" JPET Fast Forward. Published on Jan. 31, 2013 as Epub, No Page Numbers, DOI:10.1124/jpet.112.201665.
Drevets et al. "Functional anatomical correlates of antidepressant drug treatment assessed using PET measures of regional glucose metabolism" European Neuropsychopharmacology 2002, vol. 12, pp. 527-544.
Drew et al. Multiple metabotropic glutamate receptor subtypes modulate GABAergic neurotransmission in rat periaqueductal grey neurons in vitro. Neuropharmacology. 46(7):927-34, 2004.
Dunayevich, "Efficacy and tolerability of an mGlu2/3 agonist in the treatment of generalized anxiety disorder," Neuropsychopharmacol. 33: 1603-1610 (2008).
Duncan et al. "Comparison of the Effects of Clozapine, Risperidone, and Olanzapine on Ketamine-Induced Alterations in Regional Brain Metabolism" JPET 2000, vol. 293, pp. 8-14.
Duncan et al. "Differential effects of clozapine and haloperidol on ketamine-induced brain metabolic activation" Brain Res 1998, vol. 812, pp. 65-75.
Duncan et al. "Metabolic mapping of the rat brain after subanesthetic doses of ketamine: potential relevance to schizophrenia" Brain Research 1998, vol. 787, pp. 181-190.
Duncan et al. "Topographic patterns of brain activity in response to swim stress: assessment by 2-deoxyglucose uptake and expression of Fos-like immunoreactivity" J Neurosci 1993, vol. 13, pp. 3932-3943.
Dunlop Glutamate-based therapeutic approaches: targeting the glutamate transport system. [Review] [60 refs]. Current Opinion in Pharmacology 2006, 6 (1), 103-107.
Duong et al. "A Biogenetic Like Synthesis of Perloline, 6-(3,4-Dimethoxyphenyl)-5-hydroxy-5,6-dihydrobenzo[c][2,7]naphthyridin-4(3H)-one", Aust. J. Chem., 1983, 36, 1431-1440.

Duplantier et al. "3-Benzyl-1,3-oxazolidin-2-ones as mGluR2 positive allosteric modulators: hit to lead and lead optimization" Bioorg Med Chem Lett 2009, vol. 19, pp. 2524-2529.
Durand et al. Role of metabotropic glutamate receptors in the control of neuroendocrine function. Neuropharmacology 2008, 55 (4), 577-583.
During, "Extracellular hippocampal glutamate and spontaneous seizure in the conscious human brain" Lancet 341:1607-1610(1993).
Dutar et al. Pharmacological characterization of an unusual mGluR-evoked neuronal hyperpolarization mediated by activation of GIRK channels. Neuropharmacology 1999, 38 (4), 467-475.
Dwyer, J Molecular Psychiatry, vol. 1(15), 2013, p. 1-4.
Egan et al. Neurobiology of schizophrenia. [Review] [52 refs]. Current Opinion in Neurobiology 1997, 7 (5), 701-707.
Egashira et al. "Impaired social interaction and reduced anxiety-related behavior in vasopressin V1a receptor knockout mice" Behav Brain Res (2007), epub, no page numbers, doi:10.1016/j.bbr.2006.12.009.
Ehlert, F. J. Analysis of allosterism in functional assays. J Pharmacol. Exp. Ther. 2005, 315 (2), 740-754.
Eintrei et al. "Effects of diazepam and ketamine administered individually or in combination on regional rates of glucose utilization in rat brain" Br J Anaesth 1999, vol. 82, pp. 596-602.
Eisa et al., "Synthesis of Some Novel Tetrazole Derivatives as Potential Antimicrobial Agents", Pak. J. Sci. Res, 1990, vol. 33, 417-420.
Eiger, C. E. "Modern management of epilepsy: A practical approach" Epilepsy & Behavior 2008, 12, 501-539.
Elia et al. "Genome-wide copy number variation study associates metabotropic glutamate receptor gene networks with attention deficit hyperactivity disorder" Nature Genetics Advance Online publication 2011, epub, no page numbers, doi:10.1038/ng.1013.
Ellenbroek et al. Animal models with construct validity for schizophrenia, Behavioural Pharmacology, 1:469-490 (1990).
Elokdah, Hassan, et al., "Design, synthesis, and biological evaluation of thio-containing compounds with serum HDL-cholesterol-elevating properties", J. Med. Chem. 47:681-695 (2004).
Emmitte "Recent Advances in the Design and Development of Novel Negative Allosteric Modulators of mGlu5" Chem. Neurosci. 2011, vol. 2, pp. 411-432.
Engin et al. "The effects of intra-cerebral drug infusions on animals' unconditioned fear reactions: a systematic review" Prog Neuropsychopharmacol Biol Psychiatry 2008, vol. 32, pp. 1399-1419.
Enomoto et al., "Phencyclidine and Genetic Animal Models of Schizophrenia Developed in Relation to the Glutamate Hypothesis", Methods Find. Exp. Clin Pharmacol., 2007, 29(4), 291-301.
Erlenmeyer et al., "Uber einige Derivate des 2-Aminothiazols", Helvetica Chim Acta, 1949, 35-38.
Ermolinsky et al., "Differential Changes in Mglu2 and Mglu3 Gene Expression Following Pilocarpine-Induced Status Epilepticus: a Comparative Real-Time Pcr Analysis", Brain Research, 2008, 1226, 173-180.
Ershov et al., Chemical Abstracts, 1985, vol. 103, Pt 21, pp. 678.
Esposito et al. Patterns of benzodiazepine use in a Canadian population sample. Epidemiol Psichiatr Soc. Jul.-Sep. 2009, 18(3): 248-254.
Etkin "Neurobiology of Anxiety: From neural Circuits to Novel Solutions?" Depression and Anxiety 2012, vol. 29, 355-358.
Etkin et al. "Common Abnormalities and Disorder-Specific Compensation During Implicit Regulation of Emotional Processing in Generalized Anxiety and Major Depressive Disorders" Am J Psychiatry 2011; 168: 968-978.
Euraisian Notification on the necessity to present additional matters from the Eurasian Patent Organization dated Dec. 17, 2008.
Eurasian Patent Application No. 200801934/28: Office Action dated May 13, 2010, 4 pages.
Eurasian Patent Application No. 200901162/28: Office Action dated Apr. 18, 2011, 7 pages.
European Patent Application No. 05787278.0: Office Action dated May 11, 2012, 4 pages.

(56) References Cited

OTHER PUBLICATIONS

Teitler et al. "4-[125I]Iodo-(2,5-dimethoxy)phenylisopropylamine and [3H]Ketanserin Labeling of 5-Hydroxytryptamine2 (5HT2) Receptors in Mammalian Cells Transfected with a Rat 5HT2 cDNA: Evidence for Multiple States and Not Multiple 5HT2 Receptor Subtypes" Molecular Pharmacology 1990, vol. 38, pp. 594-598.
Teran et al. "Regioselective Oxidation of 3-Substituted Pyridinium Salts." Molecules. vol. 5. 2000. 1175-81.
Testa et al., "Immunohistochemical Localization of Metabotropic Glutamate Receptors Mglur1a and Mglur2/3 in the Rat Basal Ganglia", Journal of Comparative Neurology, 1998, 390(1), 5-19.
Testa et al., "Metabotropic Glutamate Receptor Mma Expression in the Basal Ganglia of the Rat", Journal of Neuroscience, 1994, 14(5), 3005-3018.
Thase "Augmentation strategies for depression: History and concepts" CNS Spectr 2007, 12:12 (Supp) 22), pp. 3-5.
Thase "Depression and sleep: pathophysiology and treatment" Dialogues Clin Neurosci 2006, vol. 8, pp. 217-226.
Thase et al. "Remission Rates Following Antidepressant Therapy With Bupropion or Selective Serotonin Reuptake Inhibitors: A meta-Analysis of Original Data From 7 Randomized Controlled Trials" J Clin Psychiatry 2005, vol. 66(8), pp. 974-981.
Thase et al., "Extended Release Quetiapine Fumarate in Major Depressive Disorder: Analysis in Patients with Anxious Depression", Depression and Anxiety, 2012, 29, 574-586.
Thase, "Augmentation Strategies for Depression: History and Concepts", CNS Spectr, 2007, 12(12), (Supp) 22), 3-5.
Thathiah et al. "The role of G protein-coupled receptors in the pathology of Alzheimer's disease" Nature Reviews Neuroscience 2011, vol. 12, pp. 73-87.
Thompson et al., "Activation of Group II and Group III Metabotropic Glutamate Receptors by Endogenous Ligand(S) and the Modulation of Synaptic Transmission in the Superficial Superior Colliculus", Neuropharmacology, 2004, 47(6), 822-832.
Thomsen et al., "Actions of Phenylglycine Analogs at Subtypes of the Metabotropic Glutamate Receptor Family", European Journal of Pharmacology, 1994, 267(1), 77-84.
Thomsen et al., "Roles of Metabotropic Glutamate Receptor Subtypes in Modulation of Pentylenetetrazole-Induced Seizure Activity in Mice", Neuropharmacology, 1998, 37(12), 1465-1473.
Tiihonen et al. The efficacy of lamotrigine in clozapine-resistant schizophrenia: a systematic review and meta-analysis. Schizophr Res. 2009; 109(1-3):10-14.
Tilakaratne et al., "Chronic Fluoxetine or Desmethylimipramine Treatment Alters 5-Ht2 Receptor Mediated C-Fos Gene Expression", European Journal of Pharmacology, 1995, 290(3), 263-266.
Tizzano et al. "The anxiolytic action of mGlu2/3 receptor agonist, LY354740, in the fear-potentiated startle model in rats is machanistically distinct from diazepam" Pharmacology, Biochemistry and Behavior 2002, vol. 73, pp. 367-374.
Tizzano et al., "Induction or Protection of Limbic Seizures in Mice by Mglur Subtype Selective Agonists", Neuropharmacology, 1995, 34(8), 1063-1067.
Tokita et al., "Roles of Glutamate Signaling in Preclinical and/or Mechanistic Models of Depression", Pharmacology, Biochemistry and Behavior, 2012, 100, 688-704.
Tokunaga et al. "Neuroimaging and Physiological Evidence for Involvement of Glutamatergic Transmission in Regulation of the Striatal Dopaminergic System" The Journal of Neuroscience, 2009, vol. 29(6), pp. 1887-1896.
Tolchard et al., "Modulation of Synaptic Transmission in the Rat Ventral Septal Area by the Pharmacological Activation of Metabotropic Glutamate Receptors", European Journal of Neuroscience, 2000, 12(5), 1843-1847.
Tollefson et al. "Fluoxetine, Placebo, and Tricyclic Antidepressants in Major Depression With and Without Anxious Features" J Clin Psychiatry 1994, vol. 55(2), pp. 50-59.
Toms et al., "Latest Eruptions in Metabotropic Glutamate Receptors", Trends in Pharmacological Sciences, 1996, 17(12), 429-435.

Tong et al. Signal transduction in neuronal death. [Review] [185 refs]. Journal of Neurochemistry 1998, 71 (2), 447-459.
Trabanco et al. "Discovery of 5- and 6-Substituted Isoquinolones: A New Class of Positive Allosteric Modulators of the Metabotropic Glutamate 2 Receptor" XXI'st International Symposium on Medicinal Chemistry, Sep. 5-9, 2010, Brussels, Belgium (Poster).
Trabanco et al. "mGluR2 positive allosteric modulators (PAMs): a patent review (2009-present)" Expert Opin Ther Patents (Early Online) 2013, epub, no page numbers, doi: 10.1517/13543776.2013. 777043.
Trabanco et al. "New positive allosteric modulators of the metabotropic glutamate receptor 2 (mGluR2). Identification and synthesis of N-propyl-5-substituted isoquinolones" Med Chem Commun 2011, vol. 2, pp. 132-139.
Trabanco et al. "New positive allosteric modulators of the metabotropic glutamate receptor 2 (mGluR2): Identification and synthesis of N-propyl-8-chloro-6-substituted Isoquinolones" Bioorganic & Medicinal Chemistry Letters 2011, vol. 21, pp. 971-976.
Trabanco et al. "Progress in the Developement of Positive Allosteric Modulators of the Metabotropic Glutamate Receptor 2" Current Medicinal Chemistry 2011, vol. 18, pp. 47-68.
Trabanco et al., "Discovery of 5- and 6-Substituted Isoquinolones: A New Class of Positive Allosteric Modulators of the Metabotropic Glutamate 2 Receptor", XXI'st International Symposium on Medicinal Chemistry, Sep. 2010, 1 page.
Trabanco et al., "Imidazo[1,2-A]Pyridines: Orally Active Positive Allosteric Modulators of the Metabotropic Glutamate 2 Receptor", J Med Chem, 2012, 55, 2688-2701.
Trabanco et al., "Mglur2 Positive Allosteric Modulators (Pams): A Patent Review (2009-Present)", Expert Opin, 2013, 19 pages.
Trabanco et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8689.
Tresadern et al. "Scaffold hopping from pyridones to imidazo[1,2-a]pyridines. New positive allosteric modulators of metabotropic glutamate 2 receptor" Bioorganic & Medicinal Chemistry Letters 2010, vol. 20, pp. 175-179.
Trettel et al., "Endocannabinoid Signalling Selectively Targets Perisomatic Inhibitory Inputs to Pyramidal Neurones in Juvenile Mouse Neocortex", Journal of Physiology, 2004, 556(Pt 1), 95-107.
Treutlein et al., "Dissection of Phenotype Reveals Possible Association Between Schizophrenia and Glutamate Receptor Delta 1 (Grid1) Gene Promoter", Schizophr. Res., 2009, 111(1-3), 123-130.
Trivedi et al. "Adjunctive Aripiprazole in Major Depressive Disorder: Analysis of Efficacy and Safety in Patients With Anxious and Atypical Features" J Clin Psychiatry 2008, vol. 69, pp. 1928-1936.
Trivedi et al., "Evaluation of Outcomes with Citalopram for Depression Using Measurement-Based Care in Star D: Implications for Clinical Practice", Am J Psychiatry, 2006; 163, 28-40.
Trofimova et al., "The Lability of Behavior as a Marker of Comorbid Depression and Anxiety", Advances in Bioscience and Biotechnology, 2010, 1, 190-199.
Trullas et al. Functional antagonists at the NMDA receptor complex exhibit antidepressant actions. Eur J Pharmacol Aug. 1990; 185(1): 1-10.
Tsai et al., "Immunocytochemical Distribution of N-Acetylaspartylglutamate in the Rat Forebrain and Glutamatergic Pathways", Journal of Chemical Neuroanatomy, 1993, 6(5), 277-292.
Tsai, "Central N-Acetyl Aspartylglutamate Deficit: A Possible Pathogenesis of Schizophrenia", Med Sci. Monit., 2005, 11(9), Hy39-Hy45.
Tsiveriotis et al. "Nickel(II) and cobalt(II) complexes of 2,4-diaminothieno[2,3-d]pyrimidines." Transition Metal Chemistry. vol. 19. 1994. 335-9.
Tsunoka et al. Association analysis of GRM2 and HTR2A with methamphetamine-induced psychosis and schizophrenia in the Japanese population. Progress in Neuro-Psychopharmacology & Biological Psychiatry. 34(4):639-44, 2010.
Tsunoka et al. Association analysis of group II metabotropic glutamate receptor genes (GRM2 and GRM3) with mood disorders and

(56) References Cited

OTHER PUBLICATIONS fluvoxamine response in a Japanese population. Progress in Neuro-Psychopharmacology & Biological Psychiatry. 33(5):875-9, 2009.
Tuominen et al. "Glutamatergic drugs for schizophrenia" Cochrane Database Syst Rev. Apr. 19, 2006;(2):CD003730.
Turck et al. "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines", Tetrahedron, 2001, 57(21), 4489-4505.
Tutonda et al., "Diels-Alder Reactions of the Heterodiene System in 2(1H)-Pyrazinones", Tetrahedron Letters, 1986, vol. 27, No. 22, 2509-2512.
Tutonda et al., "Diels-Alder Reactions of the Heterodiene System in 2(1H)-Pyraziones" Tetrahedron Letters, 1986, vol. 27, No. 22. pp. 2509-2512, Pergamon Journals Ltd.
Tyrer "The case for cothymia: mixed anxiety and depression as a single diagnosis" The British Journal of Psychiatry 2001, vol. 179, pp. 191-193.
Uher et al. "Differential efficacy of escitalopram and nortriptyline on dimensional measures of depression" The British Journal of Psychiatry 2009, vol. 194, pp. 252-259.
Steckler et al. "Pharmacological treatment of PTSD—Established and new approaches" Neuropharmacology 2012, vol. 62, 617-627.
Steckler et al., "Effects of Mglu1 Receptor Blockade on Anxiety-Related Behavior in the Rat Lick Suppression Test", Psychopharmacology, 2005, 179, 198-206.
Steckler et al.—Chapter 7—Neuroimaging as a Translational Tool in Animal and Human Models of Schizophrenia, Translational Neuroimaging, Academic Press, 2013, pp. 195-220, ISBN 9780123869456, http://dx.doi.org/10.1016/B978-0-12-386945-6.00007-X. (http://www.sciencedirect.com/science/article/pii/B978012386945600007X).
Stefani et al. "Activation of type 5 metabotropic glutamate receptors attenuates deficits in cognitive flexibility induced by NMDA receptor blockade" European Journal of Pharmacology 2010, vol. 639, pp. 26-32.
Stefani et al. The modulation of calcium currents by the activation of mGluRs. Functional implications. [Review] [81 refs]. Molecular Neurobiology 1996, 13 (1), 81-95.
Steinpreis. "The behavioral and neurochemical effects of phencyclidine in humans and animals: some implications for modeling psychosis." Behavioral Brain Research. vol. 74. 1996. 45-55.
Stella et al. "4. Prodrugs: the contrul of drug delivery via bioreversible chemical modification." Drug Delivery Systems: Characteristics and Biomedical Applications. New York: Oxford University Press, 1980. 67 pgs.
Stella et al. "Prodrugs: Do They Have Advantages in Clinical Practice?" Drugs. vol. 29. 1985. 455-73.
Stepulak et al. Expression of glutamate receptor subunits in human cancers. Histochem. Cell Biol. 2009, EPUB, No Page Numbers, DOI 10.1007/s00418-009-0613-1.
Stewart et al., "Discovery of Inhibitors of Cell Adhesion, Molecule Expression in Human, Endothelial Cells. 1. Selective Inhibiton of ICAM-1 and E-Selection Expression", Journal of the Medical Society, 2001, 44, 988-1002, The British Library.
Stogryn et al. "5-Hetarylmethylene-2,4-diaminopyrimidines (1)." vol. 11. Apr. 1974. 251-3.
Stone et al., "Glutamate and Dopamine Dysregulation in Schizophrenia—A Synthesis and Selective Review", J Psychopharmacol., 2007, 21(4), 440-452.
Stone, "Imaging the Glutamate System in Humans: Relevance to Drug Discovery for Schizophrenia", Curr. Pharm. Des, 2009, 15(22), 2594-2602.
Stout et al., "High-Affinity Calcium Indicators Underestimate Increases in Intracellular Calcium Concentrations Associated with Excitotoxic Glutamate Stimulations", Neuroscience, 1999, 89(1), 91-100.
Stowell et al. Axon/dendrite targeting of metabotropic glutamate receptors by their cytoplasmic carboxy-terminal domains [see comments] [published erratum appears in Neuron Nov. 1999; 24(3):following 762]. Neuron 1999, 22 (3), 525-536.
Straiker et al., "Metabotropic Suppression of Excitation in Murine Autaptic Hippocampal Neurons", J Physiol, 2007, 578(Pt 3), 773-785.
Strange, "Use of the Gtpgs ([35s]Gtpgs and Eu-Gtpgs) Binding Assay for Analysis of Ligand Potency and Efficacy at G Protein-Coupled Receptors", British Journal of Pharmacology, 2010, 161, 1238-1249.
Stroup et al. Results of phase 3 of the CATIE schizophrenia trial. Schizophr Res. 2009; 107(1):1-12.
Stulz et al. Distinguishing Anxiety and Depression in Self-Report: Purification of the Beck Anxiety Inventory and Beck Depression Inventory—II J Clin Psychol 2010, vol. 66, pp. 927-940.
Suh et al. "Hypoglycemic Neuronal Death and Cognitive Impairment Are Prevented by Poly(ADP-Ribose) Polymerase Inhibitors Administered after Hypoglycemia." The Journal of Neuroscience. vol. 23 (33). Nov. 2003. 10681-90.
Sun et al. "Mechanism of glutamate receptor desensitization" Nature 2002, vol. 417, pp. 245-253.
Sutton et al. "Regulation of Akt and Wnt signaling by the group II metabotropic glutamate receptor antagonist LY341495 and agonist LY379268" Journal of Neurochemistry 2011, vol. 117, 973-983.
Suzuki et al. "Synthesis of the Selective 5-Hydroxytryptamine 4 (5-HT4) Receptor Agonist (+)-(S)-2-Chloro-5-methoxy-4-[5-(2-piperidylmethyl)-1,2,4-oxadiazol-3-yl]aniline." Chem. Pharm. Bull. vol. 47 (1). 1999. 120-2.
Svensson et al. "LY2607540 (THIIC), a novel mGlu2 receptor potentiator with potential anxiolytic/antidepressant properties: In vivo profiling suggests a link between behavioral and CNS neurochemical changes" Poster 642.4 Presented at the 40th annual meeting of Society for Neuroscience 2010, Nov. 12-17, 2010, San Diego, CA, USA.
Swanson et al. "Metabotropic glutamate receptors as novel targets for anxiety and stress disorders" Nature Reviews Drug Discovery 2005, vol. 4, 131-144.
Swanson et al. A role for noradrenergic transmission in the actions of phencyclidine and the antipsychotic and antistress effects of mGlu213 receptor agonists. [Review] [40 refs]. Annals of the New York Academy of Sciences. 1003:309-17, 2003.
Swanson et al., "The Group II Metabotropic Glutamate Receptor Agonist (−)-2-Oxa-4-Aminobicyclo[3.1.01]Hexane-4,6-Dicarboxylate (Ly379268) and Clozapine Reverse Phencyclidine-Induced Behaviors in Monoamine-Depleted Rats", Journal of Pharmacology & Experimental Therapeutics, 2002, 303(3), 919-927.
Swerdlow et al. Strain differences in the disruption of prepulse inhibition of startle after systemic and intraaccumbens amphetamine administration. Pharmacol. Biochem. Behay. 2007, 87 (1), 1-10.
Szapiro et al., "Facilitation and Inhibition of Retrieval in Two Aversive Tasks in Rats by Intrahippocampal Infusion of Agonists of Specific Glutamate Metabotropic Receptor Subtypes", Psychopharmacology, 2001, 156(4), 397-401.
Taiwanese Patent Application No. 094132375: Office Action dated Aug. 25, 2011, 10 pages.
Taiwanese Patent Application No. 096108666: Office Action, dated 2007, 3 pages.
Takahashi et al. "Post-treatment with an inhibitor of poly(ADP-ribose) polymerase attenuates cerebral damage in focal ischemia." Brain Research. vol. 829.1999. 46-54.
Takahashi et al. In vitro systems for the study of apoptosis. [Review] [77 refs]. Advances in Pharmacology 1997, 41, 89-106.
Takahashi et al., "Role of the Large Extracellular Domain of Metabotropic Glutamate Receptors in Agonist Selectivity Determination", J. Biol. Chem., 1993, 268(26), 19341-19345.
Takamori et al., "Antipsychotic Action of Selective Group II Metabotropic Glutamate Receptor Agonist Mgs0008 and Mgs0028 on Conditioned Avoidance Responses in the Rat", Life Sci., 2003, 73, 1721-1728.
Takamori VGLUTs: 'exciting' times for glutamatergic research?. [Review] [49 refs]. Neuroscience Research 2006, 55(4), 343-351.

(56) References Cited

OTHER PUBLICATIONS

Takumi et al., "The Arrangement of Glutamate Receptors in Excitatory Synapses", Annals of the New York Academy of Sciences, 1999, 868, 474-482.
Tamminga et al. Glutamate pharmacology and the treatment of schizophrenia: current status and future directions. International Clinical Psychopharmacology 1995, 10, Suppl 3, 29-37.
Tamminga Schizophrenia and glutamatergic transmission. [Review] [122 refs]. Critical Reviews in Neurobiology 1998, 12 (1-2), 21-36.
Tanabe et al., "A Family of Metabotropic Glutamate Receptors", Neuron, 1992, 8(1), 169-179.
Tandon et al. Schizophrenia, "Just the Facts" 5.Treatment and prevention Past, present, and future. Schizophr Res. Jul. 22, 2010 (in press).
Tang et al. (2009) Metabotropic glutamate receptors in the control of neuronal activity and as targets for development of anti-epileptogenic drugs. Curr. Med. Chem; 16 (17): 2189-2204.
Tang et al., "Prolonged Anticonvulsant Action of Glutamate Metabotropic Receptor Agonists in Inferior Colliculus of Genetically Epilepsy-Prone Rats", European Journal of Pharmacology, 1997, 327(2-3), 109-115.
Targum et al. "The Relevance of Anxious Depression as a Distinct Entity for Psychopharmacology and Drug Development" US Psychiatry, 2009; 2(1):29-31.
Targum et al., "Redefining Affective Disorders: Relevance for Drug Development", CNS Neuroscience and Therapeutics, 2008, 14, 2-9.
Tarrier et al. A trial of two cognitive behavioural methods of treating drug-resistant residual psychotic symptoms in schizophrenic patients: I. outcome. Br J Psychiatry 1993; 162:524-532.
Tatarczyska et al. "The Antianxiety-Like Effects of Antagonists of Group I and Agonists of Group II and III Metabotropic Glutamate Receptors After Intrahippocampal Administration" Psychopharmacology 2001, vol. 158, pp. 94-99.
Taylor et al. "Stimulation of Microglial Metabotropic Glutamate Receptor mGlu2 Triggers Tumor Necrosis Factor ?-Induced Neurotoxicity in Concert with Microglial-Derived Fas Ligand" The Journal of Neuroscience, 2005, vol. 25(11), pp. 2952-2964.
Taylor et al., "The Efficacy of Nefazodone Augmentation for Treatment-Resistant Depression with Anxiety Symptoms or Anxiety Disorder", Depression and Anxiety, 2003, 18, 83-88.
Malatynska et al., "Reduction of Dominant or Submissive Behaviors as Models for Antimanic or Antidepressant Drug Testing: Technical Considerations", J Neurosci Methods, 2007, 165(2), 175-182.
Malatynska et al., "Submissive Behavior in Mice as a Test for Antidepressant Drug Activity", Pharmacol Biochem Behavior, 2005, 82, 306-313.
Malenka et al. "LTP and LTD: an embarrassment of Riches" Neuron 2004, vol. 44, pp. 5-21.
Malherbe et al., "Identification of Essential Residues Involved in the Glutamate Binding Pocket of the Group I Metabotropic Glutamate Receptor", Molecular Pharmacology., 2001, 60 (5), 944-954.
Malherbe et al., "Opposite Effects of Zn on the In Vitro Binding of [3h]Ly354740 to Recombinant and Native Metabotropic Glutamate 2 and 3 Receptors", J Neurochem., 2005, 94(1), 150-160.
Malhi et al. "Recognizing the Anxious Face of Depression" The Journal of nervous and mental disease 2002, vol. 190 (6), pp. 366-373.
Malhotra et al. NMDA receptor function and human cognition: the effects of ketamine in healthy volunteers. Neuropsychopharmacology. May 1996; 14(5):301-7.
Mansbach et al. Blockade of potentiated startle responding in rats by 5-hydroxytryptamine1A receptor ligands, Eur. J. Pharmacology, 156:375-383 (1988).
Marcotte, "Animal models of schizophrenia: a critical review", Psychiatry Neurosci 2001, 26(5), 395-410.
Marcus et al. "The Efficacy and Safety of Aripiprazole as Adjunctive Therapy in Major Depressive Disorder: A Second Multicenter, Randomized, Double-Blind, Placebo-Controlled Study" Journal of Clinical Psychopharmacology 2008, vol. 28, No. 2, pp. 156-165.

Marek "Metabotropic glutamate213 (mGlu2/3) receptors, schizophrenia and cognition" European Journal of Pharmacology 2010, vol. 639, pp. 81-90.
Marek et al. "Glutamategic (N-methyl-D-aspartate receptor) hypofrontality in schizophrenia: Too little juice or miswired brain" Molecular Pharmacology Fast Forward. Published on Nov. 23, 2009 as epub, no page numbers, doi:10.1124/mol.109.059865.
Marek et al. "Physiological Antagonism between 5-Hydroxytryptamine2A and Group II Metabotropic Glutamate Receptors in Prefrontal Cortex" J. Pharm. Exper. Therapeut. 2000, vol. 292, pp. 76-87.
Marek et al. "The electrophysiology of prefrontal serotonin systems: therapeutic implications for mood and psychosis" Biol Psychiatry 1998, vol. 44, pp. 1118-1127.
Marek et al. 5-Hydroxytryptamine2A (5-HT2A) receptor regulation in rat prefrontal cortex: interaction of a phenethylamine hallucinogen and the metabotropic glutamate2/3 receptor agonist LY354740. Neuroscience Letters. 403(3):256-60, 2006.
Marek et al. Glutamatergic (N-methyl-D-aspartate receptor) hypofrontality in schizophrenia: too little juice or a miswired brain?. [Review] [100 refs]. Molecular Pharmacology. 77(3):317-26, 2010.
Marek, "Metabotropic Glutamate 2/3 Receptors as Drug Targets", Curr. Opin. Pharmacol., 2004, 4, 18-22.
Marino et al. "Glutamate-based therapeutic approaches: allosteric modulators of metabotropic glutamate receptors." Current Opinion in Pharmacology. vol. 6. 2006. 98-102.
Markou "The Role of Metabotropic Glutamate Receptors in Drug Reward, Motivation and Dependence" Drug News Perspect 2007, vol. 20(2), pp. 103-108.
Marquet et al. "VIII. Nouvelle methode de synthese des furo[2,3-d]pyrimidines sustituees en position 4 et de certains thieno[2,3-d]pyrimidines." Bulletin de la Societe Chimique de France. (12). 1969. 4344-8.
Martella et al., "Enhanced Sensitivity to Group II Mglu Receptor Activation at Corticostriatal Synapses in Mice Lacking the Familial Parkinsonism-Linked Genes Pink1 or Parkin.", Exp. Neurol., 2009, 215(2), 388-396.
Martin et al., "Cellular Localization of a Metabotropic Glutamate Receptor in Rat Brain", Neuron, 1992, 9(2), 259-270.
Martin et al., "Cross-Talk Between Beta-Adrenergic and Metabotropic Glutamate Receptors in Rat C6 Glioma Cells", Biochimica Et Biophysica Acta, 1998, 1393(1), 186-192.
Mason, "Acamprosate in the treatment of alcohol dependence," Expert Opin. Pharmacother. 6(12):2103-2115. (2005).
Masu et al., "Sequence and Expression of a Metabotropic Glutamate Receptor", Nature, 1991, 349(6312), 760-765.
Matrisciano et al. "Defective group-II metaboropic glutamate receptors in the hippocampus of spontaneously depressed rats" Neuropharmacology (2008), epub, no page numbers, doi:10.1016/j.neuropharm.2008.05.014.
Matrisciano et al., "Activation of Group-II Metabotropic Glutamate Receptors Promotes DNA Demethylation in the Mouse Brain", Molecular Pharmacology, Apr. 2011, 52 pages.
Matrisciano et al., "Group-II Metabotropic Glutamate Receptor Ligands as Adjunctive Drugs in the Treatment of Depression: A New Strategy to Shorten the Latency of Antidepressant Medication?", Molecular Psychiatry, 2007, 12, 704-706.
Matrisciano et al., "Imipramine Treatment Up-Regulates the Expression and Function of Mglu2/3 Metabotropic Glutamate Receptors in the Rat Hippocampus", Neuropharmacology, 2002, 42(8), 1008-1015.
Matrisciano, "Metabotropic glutamate receptors and neuroadaptation to antidepressants: imipramine-induced down-regulation of b-adrenergic receptors in mice treated with metabotropic glutamate 2/3 receptor ligands", Journal of Neurochemistry, 2005, 93, pp. 1345-1352.
Matrisciano, "Synergism between fluoxetine and the mGlu2/3 receptor agonist, LY379268, in an in vitro model for antidepressant drug-induced neurogenesis", Neuropharmacology, 54, 2008, pp. 428-437.
Maurel et al. "Cell-surface protein-protein interaction analysis with time-resolved FRET and snap-tag technologies: application to GPCR oligomerization" Nat Methods 2008 vol. 5(6), pp. 561-567.

(56) References Cited

OTHER PUBLICATIONS

Maxwell et al. "Ketamine produces lasting disruptions in encoding of sensory stimuli" J Pharmacol Exp Ther 2006, vol. 316, pp. 315-324.
May et al. "Allosteric Modulation of G Protein-Coupled Receptors" Annu Rev Pharmacol Toxicol 2007, vol. 47, pp. 14.1-14.51.
May et al., "Regional Serotonin Receptor Studies: Chronic Methysergide Treatment Induces a Selective and Dose-Dependent Decrease in Serotonin-2 Receptors in Mouse Cerebral Cortex", Life Sciences, 1986, 38(19), 1741-1747.
Mayers et al. "Antidepressants and their effect on sleep" Hum Psychopharmacol. 2005, vol. 20, pp. 5333-5559.
McClintock et al., "Assessing Anxious Features in Depressed Outpatients" Int. J. Methods Psychiatr. Res. 20(4): E69-E82 (2011).
McDermott et al. "Design and analysis of two-period studies of potentially disease-modifying treatments" Controlled Clinical Trials 2002, vol. 23, pp. 635-649.
McElvain et al. "Piperidine Derivatives. XXX. 1,4-Dialkyl-4-arylpiperidines", J. Am. Chem. Soc, 1958, 80, 3915-3923.
McEvoy et al. Effectiveness of clozapine versus olanzapine, quetiapine, and risperidone in patients with chronic schizophrenia who did not respond to prior atypical antipsychotic treatment. Am J Psychiatry. 2006;163(4):600-610.
McIntyre et al., "Quetiapine Adjunct to Selective Serotonin Reuptake Inhibitors or Venlafaxine in Patients with Major Depression, Comorbid Anxiety, and Residual Depressive Symptoms: A Randomized, Placebo-Controlled Pilot Study", Depression and Anxiety, 2007, 24, 487-494.
Meador-Woodruff et al. Glutamate receptor expression in schizophrenic brain. Brain Res. Brain Res. Rev 2000, 31 (2-3), 288-294.
Medical dictionary, "treatment" p. 1-6 (2015).
MedicineNet.com "risk factor" p. 1 (2015).
Melancon et al. "Allosteric Modulation of 7 Transmembrane Spanning Receptors: Theory, Practice and Opportunities for CNS Drug Discovery" J. Med. Chem., Just Accepted Manuscript .cndot. EPUB, No Page Numbers, DOI: 10.1021/jm201139r .cndot. Publication Date (Web): Dec. 9, 2011.
Melartin et al. "Current Comorbidity of Psychiatric Disorders Among Dsm-Iv Major Depressive Disorder Patients in Psychiatric Care in the Vantaa Depression Study" J Clin Psychiatry 2002, vol. 63, pp. 126-134.
Meldrum et al. "Glutamate receptors and trasnporters in genetic and acquired models of epilepsy" Epilepsy Res 1999, vol. 36, pp. 189-204.
Meldrum et al. Excitatory amino acid neurotoxicity and neurodegenerative disease. [Review] [49 refs]. Trends in Pharmacological Sciences 1990, 11 (9), 379-387.
Meltzer et al., "Serotonin Receptors: Their Key Role in Drugs to Treat Schizophrenia", Prog. Neuropsychopharmacol. Biol. Psychiatry, 2003, 27(7), 1159-1172.
Meltzer Illuminating the molecular basis for some antipsychotic drug-induced metabolic burden. Proc. Natl. Acad. Sci. U. S. A 2007, 104 (9), 3019-3020.
Honer et al. Clozapine alone versus clozapine and risperidone with refractory schizophrenia. N Engl J Med. 2006;354(5):472-482.
Hook, V.Y.H. "Neuroproteases in Peptide Neurotramission and Neurodegenerative Diseases Applications to Drug Discovery Research" Biodrugs. 2006, 20, 105-119.
Hopkins "Is There a Path Forward for mGlu2 Positive Allosteric Modulators for the Treatment of Schizophrenia?" ACS Chem. Neurosci. 2013, vol. 4, pp. 211-213.
Horiguchi et al. "Interaction of mGlu2/3 agonism with clozapine and lurasidone to restore novel object recognition in subchronic phencyclidine-treated rats" Psychopharmacology 2011, vol. 217, pp. 13-24.
Horiguchi et al. "Interactions among the atypical antipsychotic drug (APD), lurasidone, 5-HT1A and metabotropic glutamate receptor 2/3 (mGluR2/3) agonism, and 5-HT2A antagonism, to attenuate phencyclidine (PCP)-induced deficit in rat novel object recognition (NOR)" Poster 610.12 Presented at the 40th annual meeting of Society for Neuroscience 2010, Nov. 12-17, 2010, San Diego, CA, USA.
Hostetler "Pet tracer discovery for subtype-specific mGluR allosteric modulators: challenges and insights" presentation slides 7th International Meeting on Metabotropic Glutamate Receptors, Taormina, Sicily, in Oct. 2-7, 2011.
Houamed et al., "Cloning, Expression, and Gene Structure of a G Protein-Coupled Glutamate Receptor from Rat Brain", Science, 1991, 252(5010), 1318-1321.
Hovelso, "Therapeutic Potential of Metabotropic Glutamate Receptor Modulators", Current Neuropharmacology, 2012, 10, pp. 12-48.
Hsia et al. "Evidence against a role for metabotropic glutamate receptors in mossy fiber LTP: the use of mutant mice and pharmacological antagonists" Neuropharmacology 1995, vol. 34, pp. 1567-1572.
Hu et al. "Emotion Enhances Learning via Norepinephrine Regulation of AMPA-Receptor Trafficking" Cells 2007, vol. 131, pp. 160-173.
Hu et al. "Pyrimidine methyl anilines: selective potentiators for the metabotropic glutamate 2 receptor" Bioorganic & Medicinal Chemistry Letters 2004, vol. 14, pp. 5071-5074.
Hu et al., "Altered Profile of Gene Expression in Rat Hearts Induced by Chronic Nicotine Consumption", Biochemical and Biophysical Research Communications, 2002, 297, 729-736.
Hu et al., "Glutamate Receptors in Preclinical Research on Alzheimer's Disease: Update on Recent Advances", Pharmacology, Biochemistry and Behavior, 2012, 100, 855-862.
Hu et al., "Identification of Glutamate Receptors and Transporters in Mouse and Human Sperm", Journal of Andrology, 2004, 25(1), 140-6.
Hu et al., "The Regulation of Dopamine Transmission by Metabotropic Glutamate Receptors", J. Pharmacol. Exp. Ther., 1999, 289(1), 412-416.
Huang et al. "Alzheimer Mechanisms and Therapeutic Strategies" Cell 2012, vol. 148, pp. 1204-1222.
Huang et al. "Interdomain movements in metabotropic glutamate receptor activation" Proc Nati Acad Sci USA 2011, vol. 108, pp. 15480-15485.
Huang et al. "Potentiation of the Novel Atypical Antipsychotic Drug Lurasidone-induced Dopamine Efflux in Rat Medial Prefrontal Cortex and Hippocampus by Da D1 and mGluR2/3 Agonism but not D3 Receptor antagonism" Poster 610.13 Presented at the 40th annual meeting of Society for Neuroscience 2010, Nov. 12-17, 2010, San Diego, CA, USA.
Huang et al. "Prevalence, Correlates, and Comorbidity of Nonmedical Prescription Drug Use and Drug Use Disorders in the United States: Results of the National Epidemiologic Survey on Alcohol and Related Conditions" J Clin Psychiatry 2006, vol. 67, pp. 1062-1073.
Huang et al., "Inhibition of Microtubule Formation by Metabotropic Glutamate Receptors", Journal of Neurochemistry, 2000, 74(1), 104-113.
Hucho et al. "Epac Mediates a cAMP-to-PKC Signaling in Inflammatory Pain: An Isolectin B4(+) Neuron-Specific Mechanism" The Journal of Neuroscience, 2005, vol. 25(26), pp. 6119-6126.
Hucho et al. "Estrogen controls PKCe-dependent mechanical hyperalgesia through direct action on nociceptive neurons" European Journal of Neuroscience, 2006, vol. 24, pp. 527-534.
Huey et al., "Development of Subtle Psychotic Symptoms with Memantine: A Case Report", J Clin Psychiatry, 2005, 66, 658-659.
Hughes et al., "Progress in the Mitsunobu Reaction. A Review", Organic Preparations and Procedures Int, 1996, 28, 127-164.
Hughes et al., "The Mitsunobu Reaction", Organic Reactions, 1992, vol. 42, Part 1, 335-418, John Wiley & sons, Inc.
Huntington Study Group, "Dosage effects of riluzole in Huntington's disease: A multicenter placebo-controlled study", Neurology, 2003, 61, pp. 1551-1556.
Iacovelli et al. "Regulation of group II metabotropic glutamate receptors by G protein-coupled receptor kinases: mGlu2 receptors are resistant to homologous desensitization" Molecular Pharmacology Fast Forward. Published on Jan. 22, 2009 as epub, no page numbers, doi:10.1124/mol.108.052316.

(56) References Cited

OTHER PUBLICATIONS

Iglesias et al., "Metabotropic Glutamate Receptor/Phospholipase C System in Female Rat Heart", Brain Res., 2007, 1153, 1-11.

Imogai et al. "cis-Disubstituted Cyclopropanes via Asymmetric Catalytic Cyclopropenation: Synthesis of Cyclopropyl-dehydroamino Acids and of DictyoptereneC." Helvetica Chimica Acta. vol. 81.1998. 1754-64.

Imre et al. "Effects of the mGluR2/3 agonist LY379268 on ketamine-evoked behaviours and neurochemical changes in the dentate gyrus of the rat" Pharmacology, Biochemistry and Behavior 2006, vol. 84, pp. 392-399.

Imre et al., "Dose-Response Characteristics of Ketamine Effect on Locomotion, Cognitive Function and Central Neuronal Activity", Brain Res. Bull, 2006, 69(3), 338-345.

Imre et al., "Subchronic Administration of Ly354740 Does Not Modify Ketamine-Evoked Behavior and Neuronal Activity in Rats", Eur. J Pharmacol., 2006, 544(1-3), 77-81.

Imre, "The Preclinical Properties of a Novel Group II Metabotropic Glutamate Receptor Agonist Ly379268", CNS Drug Reviews, 2007, 13(4), 444-464.

Insel, et al., "Research Domain Criteria (Rdoc): Toward a New Classification Framework for Research on Mental Disorders", Am. J. Psychiatry, Jul. 2010, 167(7), 748-751.

Inta et al. Mice with genetically altered glutamate receptors as models of schizophrenia: a comprehensive review. [Review] [144 refs]. Neuroscience & Biobehavioral Reviews. 34(3):285-94, 2010.

International Search Report dated Jul. 2, 2008 for application No. PCT/EP08/52767.

International Search Report dated Jun. 10, 2008 for application No. PCT/EP08/52766.

International Search Report dated Jun. 10, 2008 for application No. PCT/EP08/52768.

International Search Report dated Oct. 26, 2009 for international application No. PCT/EP2009/006326.

International Search Report for International Application No. PCT/EP2007/052442 dated Sep. 7, 2007.

Investigation of the Safety, Tolerability and Potential Therapeutic Effects of JNJ-40411813 in Patients With Schizophrenia—Available from: http://clinic.altrials.gov/show/NCT01323205, retrieved on Aug. 1, 2013.

Ionescu et al. "Defining anxious depression: a review of the literature" CNS Spectrums 2013, pp. 1-9.

Iovieno et al. Does the Presence of an Open-Label Antidepressant Treatment Period Influence Study Outcome in Clinical Trials Examining Augmentation/Combination Strategies in Treatment Partial Responders/Nonresponders With Major Depressive Disorder? J Clin Psychiatry Online ahead of print: Apr. 3, 2012 (epub, no page numbers, doi: 10.4088/JCP.11r06978).

Irifune et al. "Riluzole, a Glutamate Release Inhibitor, Induces Loss of Righting Reflex, Antinociception, and Immobility in Response to Noxious Stimulation in Mice" Anesthesia & analgesia 2007, vol. 104(6), pp. 1415-1421.

Israeli Patent Application No. 192868: Office Action dated Dec. 21, 2011, 2 pages.

Itaya et al. "Purines. LXXV. Dimroth Rearrangement, Hydrolytic Deamination, and Pyrimidine-Ring Breakdown of 7-Allcylated 1-Alkoxyadenines: N{1}-C(2) versus N(1)-C(6) Bond Fission." Chem. Pharm. Bull. vol. 45 (5). 1997. 832-41.

Jablenski et al. "Polymorphisms associated with normal memory variation also affect memory impairment in schizophrenia" Genes, Brain and Behavior 2011, vol. 10, pp. 410-417.

Jain et al. "A One-Step Preparation of Functionalized 3-Cyano-2-Pryidones", Tetrahedron Letters, 1995, vol. 36, pp. 3307-3310, Pergamon.

Jane et al., "Potent Antagonists at the L-AP4- and (1s,3s)-ACPD-Sensitive Presynaptic Metabotropic Glutamate Receptors in the Neonatal Rat Spinal Cord", Neuropharmacology, 1996, 35(8), 1029-1035.

Janssens et al. "Glutamate receptor subunit expression in primary neuronal and secondary glial cultures" J Neurochem 2001, vol. 77, pp. 1457-1474.

Papakostas et al., "Severe and Anxious Depression: Combining Definitions of Clinical Sub-Types to Identify Patients Differentially Responsive to Selective Serotonin Reuptake Inhibitors", European Neuropsychopharmacology, 2012, 22, 347-355.

Papakostas et al., "Testing Anxious Depression as a Predictor and Moderator of Symptom Improvement in Major Depressive Disorder During Treatment with Escitalopram", Eur Arch Psychiatry Clin Neurosci, 2011, 261, 147-156.

Parmentier et al., "A Model for the Functioning of Family 3 Gpers", Trends in Pharmacological Sciences, 2002, 23(6), 268-274.

Parnot et al., "Toward Understanding Gpcr Dimers", Nature Structural & Molecular Biology, 2004, 11(8), 691-692.

Parry et al. "Functionalized Pyridylboronic Acids and Their Suzuki Cross-Coupling Reactions to Yield Novel Heteroarylpyridines." J. Org. Chem. vol. 67. 2002. 7541-3.

Parsons et al. "Memantine: a NMDA receptor antagonist that improves memory by restoration of homeostasis in the glutamatergic system—too little activation is bad, too much is even worse" Neuropharmacology 2007, vol. 53, pp. 699-723.

Passchier et al. "Measuring drug-related receptor occupancy with positron emission tomography" Methods 2002, vol. 27, pp. 278-286.

Pastorino et al. "Pin1 Protects Against Alzheimer's Disease: One Goal, Multiple Mechanisms" Intech 2013, http://dx.doi.org/10.5772/55085.

Patil et al. (2007) "Activation of mGlu2/3 receptors as a new approach to treat schizophrenia: a randomized Phase 2 clinical trial" Nature Medicine Advance Online Publication (epub, no page numbers, doi:10.1038/nm1632).

Patkar et al. "A Randomized, Double-blind, Placebo-controlled Trial of Augmentation With an Extended Release Formulation of Methylphenidate in Outpatients With Treatment-Resistant Depression" J Clin Psychopharmacol 2006, vol. 26, pp. 653-656.

Paykel et al. "Response to Phenelzine and Amitriptyline in Subtypes of Outpatient Depression" Arch Gen Psychiatry 1982, vol. 39, 1041-1049.

Pehrson et al. "Activation of mGlu2/3 receptors as a new approach to treat schizophrenia: a randomized Phase 2 clinical trial" Psychopharmacology 2010, vol. 211, pp. 443-455.

Pehrson et al., "Impact of Metabotropic Glutamate 2/3 Receptor Stimulation on Activated Dopamine Release and Locomotion", Psychopharmacology, 2010, 211, 443-455.

Pellicciari et al. Metabotropic G-protein-coupled glutamate receptors as therapeutic targets. [Review] [50 refs]. Current Opinion in Chemical Biology. 1999, 3 (4), 433-440.

Pellicciari et al. Modulation of glutamate receptor pathways in the search for new neuroprotective agents. [Review] [45 refs]. Farmaco 1998, 53 (4), 255-261.

Pellicciari et al., "Metabotropic Glutamate Receptors: Structure and New Subtype-Selective Ligands", Il Farmaco, 2001, 56(1-2), 91-94.

Penninx et al., "Two-Year Course of Depressive and Anxiety Disorders: Results from the Netherlands Study of Depression and Anxiety (Nesda)", Journal of Affective Disorders, 2011, 133, 76-85.

Pereira et al. "Study pharmacologic of the GABAergic and glutamatergic drugs on seizures and status epilepticus induced by pilocarpine in adult Wistar rats" Neuroscience letters 2007, vol. 419, pp. 253-257.

Perkins et al. "Pharmacokinetics, Metabolism, and Excretion of the Intestinal Peptide Transporter 1 (SLC15A1)-Targeted Prodrug (1S,2S,5R,6S)-2-[(2'S)-(2-Amino)propionyl]aminobicyclo[3.1.0.]hexen-2,6-d-icarboxylic acid (LY544344) in Rats and Dogs: Assessment of First-Pass Bioactivation and Dose Linearity" Drug Metabolism and Disposition 2007, vol. 35, pp. 1903-1909.

Perroy et al., "The C Terminus of the Metabotropic Glutamate Receptor Subtypes 2 and 7 Specifies the Receptor Signaling Pathways", Journal of Biological Chemistry, 2001, 276(49), 45800-45805.

Pettmann et al. Neuronal cell death. [Review] [177 refs]. Neuron 1998, 20 (4), 633-647.

(56) References Cited

OTHER PUBLICATIONS

Pfeiffer et al. "Benzodiazepines and Adequacy of Initial Antidepressant Treatment for Depression" J Clin Psychopharmacol 2011; 31: 360-364.
Piccinin et al. "Interaction between Ephrins and mGlu5 Metabotropic Glutamate Receptors in the Induction of Long-Term Synaptic Depression in the Hippocampus" The Journal of Neuroscience, 2010, vol. 30(8), pp. 2835-2843.
Pietraszek et al. "The role of group I metabotropic glutamate receptors in schizophrenia" Amino Acids (2006) EPUB, No Page Numbers, DOI 10.1007/s00726-006-0319-9.
PIKE PET radiotracers: Crossing the blood-brain barrier and surviving metabolism. Trends Pharmacol Sci 2009, vol. 30, pp. 431-440.
Pilc et al., "Mood Disorders: Regulation by Metabotropic Glutamate Receptors", Biochemical Pharmacology, 2008, 75, 997-1006.
Pin et al. Alternative splicing generates metabotropic glutamate receptors inducing different patterns of calcium release in Xenopus oocytes. Proceedings of the National Academy of Sciences of the United States of America 1992, 89 (21), 10331-10335.
Pin et al. The metabotropic glutamate receptors: structure and functions. [Review] [298 refs]. Neuropharmacology 1995, 34 (1), 1-26.
Pin et al., "Evolution, Structure, and Activation Mechanism of Family 3/C G-Protein-Coupled Receptors", Pharmacology & Therapeutics, 2003, 98, 325-354.
Pin et al., "Get Receptive to Metabotropic Glutamate Receptors", Current Opinion in Neurobiology, 1995, 5(3), 342-349.
Pin et al., "Positive Allosteric Modulators for-Aminobutyric Acidb Receptors Open New Routes for the Development of Drugs Targeting Family 3 G-Protein-Coupled Receptors" Mol Pharmacol 2001, 60, 881-884.
Pin et al., "Release of Endogenous Amino Acids From Striatal Neurons in Primary Culture", Journal of Neurochemistry, 1986, 47(2), 594-603.
Pinhasov et al., "Reduction of Submissive Behavior Model for Antidepressant Drug Activity Testing: Study Using a Video-Tracking System", Behav Pharmacol, 2005, 16, 657-664.
Pinheiro et al., "Presynaptic Glutamate Receptors: Physiological Functions and Mechanisms of Action", Nat. Rev Neurosci., 2008, 9(6), 423-436.
Pinkerton et al. "Allosteric potentiators of the metabotropic glutamate receptor 2 (mGlu2). Part 1: Identification and synthesis of phenyl-tetrazolyl acetophenones" bioorganic & Medicinal Chemistry Letters 2004, vol. 14, pp. 5329-5332.
Pinkerton et al. "Substituted Acetophenones as Selective and Potent Allosteric Potentiators of the Metabotropic Glutamate Receptor 2 (mGluR2)" 229th ACS National Meeting, San Diego, CA, United States, Mar. 13-17, 2005 (2005), MEDI-038.
Pinkerton et al., "Allosteric Potentiators of the Metabotropic Glutamate Receptor 2 (Mglu2). Part 2: 4-Thiopyridyl Acetophenones as Non-Tetrazole Containing Mglu2 Receptor Potentiators", Bioorganic & Medicinal Chemistry Letters, 2004, 14, 5867-5872.
Pinkerton et al., "Phenyl-tetrazolyl Acetophenones: Discovery of Positive Allosteric Potentiatiors for the Metabotropic Glutamate 2 Receptor", J. Med. Chem., 2004, 47, 4595-4599, American Chemical Society.
Pittenger et al. Stress, depression, and neuroplasticity: a convergence of mechanisms. Neuropsychopharmacology Jan. 2008; 33(1): 88-109.
Pills et al. "Lactate metabolism in anxiety neurosis" The New England Journal of Medicine 1967, vol. 277, pp. 1329-1336.
Pizzi et al., "Activation of Multiple Metabotropic Glutamate Receptor Subtypes Prevents NMDA-Induced Excitotoxicity in Rat Hippocampal Slices", European Journal of Neuroscience, 1996, 8(7), 1516-1521.
Popik et al. "Selective agonist of group II glutamate metabotropic receptors, LY354740, inhibits tolerance to analgesic effects of morphine in mice" British Journal of Pharmacology 2000, vol. 130, pp. 1425-1431.

Porter et al., "(S)-Homoquisqualate: A Potent Agonist at the Glutamate Metabotropic Receptor", British Journal of Pharmacology, 1992, 106(3), 509-510.
Posluns, "An Analysis of Chlorpromazine-Induced Suppression of the Avoidance Response.", Psychopharmacol. 3: 361-373 (1962).
Posner et al. Columbia Classification Algorithm of Suicide Assessment (C-CASA): Classification of suicidal events in the FDA's pediatric suicidal risk analysis of antidepressants. American Journal of Psychiatry. 2007; 164:1035-1043.
Potts et al. "1,2,4-Triazoles. XII. Derivatives of the s-Triazolo[4,3-a]pyridine Ring System", Journal of Organic Chemistry, 1966, 251-260.
Potts et al. "1,2,4-Trizoles. XXV. The Effect of Pyridine Substitution on the Isomerization of s-Triazolo [4,3-a] pyridines into s-Triazolo [1,5-a] pyridines (1)", J. Heterocycl. Chem., 1970, 7, 1019-1027.
Poyurovsky et al. Lamotrigine augmentation in schizophrenia and schizoaffective patients with obsessive-compulsive symptoms. J Psychopharmacol. 2010; 24(6):861-866.
Prabakaran et al. "2-D DIGE Analysis of Liver and Red Blood Cells Provides Further Evidence for Oxidative Stress in Schizophrenia" Journal of Proteome Research 2007, vol. 6, pp. 141-149.
Langmead "Ligand properties and behaviours in an allosteric age" Trends Pharmacol Sci 2012, vol. 33, pp. 621-622.
Langmead "Screening for Positive Allosteric Modulators: Assessment of Modulator Concentration-Response Curves as a Screening Paradigm" Journal of Biomolecular Screening 2007, pp. 668-676.
Large "Do NMDA receptor antagonist models of schizophrenia predict the clinical efficacy of antipsychotic drugs?" J Psychopharmacol 2007, vol. 21, pp. 283-301.
Large, "The potential role of lamotrigine in schizophrenia," Psychopharmacol., 181: 415-436 (2005).
Larock, "Comprehensive Organic Transformations", VCH Publishers, 1989, 595-596.
Larsson et al. "Neurochemical and behavioral studies on ethanol and nicotine interactions" Neuroscience and Biobehavioral Reviews 2004, vol. 27, 713-720.
Laruelle et al. "Glutamate, dopamine, and schizophrenia: From Pathophysiology to treatment" Ann NY Acad Sci 2003, vol. 1003, pp. 138-158.
Laruelle et al. "Relationships between radiotracer properties and image quality in molecular imaging of the brain with positron emission tomography" Mol Imaging Biol 2003, vol. 5, pp. 363-375.
Larzabal et al. "Distribution of the grlup II metabotropic glutamate receptors (mGluR2/3) in the enteric nervous system of the rat" Neuroscience Letters 1999, vol. 276, pp. 91-94.
Laughren "The scientific and ethical basis for placebo-controlled trials in depression and schizophrenia: an FDA perspective" Eur Psychiatry 2001, vol. 16, pp. 418-423.
Laughren et al. Food and Drug Administration perspective on negative symptoms in schizophrenia as a target for a drug treatment claim. Schizophr Bulk 2006; 32(2): 220-222.
Laurie et al. "Cloning, Distribution and Functional Expression of the Human mGlu6 Metabotropic Glutamate Receptor." Neuropharmacology. vol. 36 (2). 1997. 145-52.
Lavreysen "The development of mGlu2 PAMs: Identification of JNJ-40068782 as a novel tool compound" Allosteric Modulator Drug Discovery Congress, San Diego Nov. 11-12, 2010 (presentation slides).
Lavreysen et al. "[3H]R214127: A Novel High-Affinity Radioligand for the mGlu1 Receptor Reveals a Common Binding Site Shared by Multiple Allosteric Antagonists" Mol Pharmacol 2003, vol. 63, pp. 1082-1093.
Lavreysen et al. "A study on the molecular interaction between mGlu2 receptor agonists and positive allosteric modulators" International Meeting on Metabotropic Glutamate Receptors, Abstract, Taormina, Sicily—Italy, Sep. 14-19, 2008.
Lavreysen et al. "A study on the molecular interaction between mGlu2 receptor agonists and positive allosteric modulators" Poster 2009 Society for Neuroscience Annual Meeting, Chicago.
Lavreysen et al. "JNJ-40068782: a novel potent, selective and systemically active positive allosteric modulator of the mGlu2 receptor" Poster, 2010 Society for Neuroscience Annual Meeting, San Diego.

(56) References Cited

OTHER PUBLICATIONS

Lavreysen et al. "JNJ16259685, a highly potent, selective and systemically active mGlu1 receptor antagonist" Neuropharmacology 2004, vol. 47, pp. 961-972.
Lavreysen et al. "Pharmacological Characterization of JNJ-40068782, a New Potent, Selective, and Systemically Active Positive Allosteric Modulator of the mGlu2 Receptor and Its Radioligand [3H]JNJ-40068782" J Pharmacol Exp Ther 346:514-527, Sep. 2013.
Lavreysen et al. "Therapeutic Potential of Group III Metabotropic Glutamate Receptors" Current Medicinal Chemistry 2008, vol. 15, pp. 671-684.
Leach et al. "Allosteric GPCR modulators: taking advantage of permissive receptor pharmacology" Trends in Pharmacological Sciences 2007, vol. 28(8), pp. 382-389.
Leach et al. "Quantification of Allosteric Interactions UNIT 1.22 at G Protein-Coupled Receptors Using Radioligand Binding Assays" Current Protocols in Pharmacology 1.22.1-1.22.41, Mar. 2011.
Leber "Observations and Suggestions on antidementia drug development" Alzheimer disease and associated disorders 1996, vol. 10, Suppl 1, pp. 31-35.
Lebois Neither typical nor atypical: LY404039 provides proof of concept that selective targeting of mGluR213 receptors is a valid mechanism for obtaining antipsychotic efficacy. Curt Top. Med. Chem. 2008, 8 (16), 1480-1481.
Lecci et al. Pharmacological validation of a novel animal model of anticipatory anxiety in mice. Psychopharmacology, 101, 255-261, 1990.
Lee et al. "Glutamategic afferent projections to the dorsal raphe nucleus of the rat" Brain Res 2003, vol. 963, pp. 57-71.
Lee et al. "The mGlu2/3 receptor agonist LY354740 suppresses immobilization stress-induced increase in rat prefrontal cortical BDNF mRNA expression" Neuroscience Letters 2006, vol. 398, pp. 328-332.
Lee et al. Amyloid precursor protein processing is stimulated by metabotropic glutamate receptors. Proceedings of the National Academy of Sciences of the United States of America 1995, 92 (17), 8083-8087.
Lee et al. Characterization of the inward current induced by metabotropic glutamate receptor stimulation in rat ventromedial hypothalamic neurones. Journal of Physiology 1997, 504 (Pt 3), 649-663.
Lee et al. Low doses of cannabinoids enhance the antinociceptive effects of intracisternally administered mGluRs groups II and III agonists in formalin-induced TMJ nociception in rats. Pain 2008, 139 (2), 367-375.
Lee et al. The effect of mGluR2 activation on signal transduction pathways and neuronal cell survival. Brain Res. 2009, 1249, 244-250.
Lee et al., "Benzylic Bromination of Alkylbenzenes with Sodium Bromate-Bromotrimethylsilane", Bull. Korean Chem. Soc, 1995, vol. 16, pp. 371-374.
Lee, "The role of metabotropic glutamate receptors in Alzheimer's disease", Acta Neurobiol Exp, 2004, 64: 89-98.
Leeson et al. "The influence of drug-like concepts on decision-making in medicinal chemistry" Nat Rev Drug Discovery 2007, vol. 6, pp. 881-890.
Leever et al. Identification of a Site in GluR1 and GluR2 That Is Important for Modulation of Deactivation and Desensitization. Mol Pharmacol 2003, 64 (1), 5.
Lennon et al. "Metabotropic glutamate receptor mGlu2 is resistant to homologous agonist-induced desensitilization but undergoes protein kinase C-mediated heterologous desensitization" Eur J Phamacol 2010, vol. 649, pp. 29-37.
Lenox et al. "Mechanism of action of antidepressants and mood stabilizers" Neuropsychopharmacology: The Fifth Generation of Progress. Edited by Kenneth L. Davis, Dennis Charney, Joseph T. Coyle, and Charles Nemeroff. American College of Neuropsychopharmacology 2002, pp. 1139-1163.

Leo et al. "The application of nuclear magnetic resonance-based metabonomics to the dominant-submissive rat behavioral model" Analytical biochemistry 2005, vol. 339, pp. 174-178.
Lerner et al. The Work Limitations Questionnaire. Med Care Jan. 2001; 39(1): 72-85.
Leucht et al. Second-generation versus first-generation antipsychotic drugs for schizophrenia: a meta-analysis. Lancet. 2009;373(9657):31-41.
Levitz et al. Optical control of metabotropic glutamate receptors. Nature Neuroscience 2013, 16 (4), 507-516.
Lewis "The molecular choreography of a store-operated calcium channel" Nature (London, United Kingdom) 2007, vol. 446, pp. 284-287.
Lewis et al. Cognitive dysfunction in schizophrenia: convergence of gamma-aminobutyric acid and glutamate alterations. Arch. Neurol. 2006, 63 (10), 1372-1376.
Leysen et al. "Receptor interactions of new antipsychotics: relation to pharmacodynamics and clinical effects" International Journal of Psychiatry in Clinical Practice 1998, vol. 2, pp. S3-S17 Symposium on "Evidence from Experience", Lisbon, Portugal, Mar. 21-22, 1997.
Leysen et al. [3H]Ketanserin (R 41 468), a selective 3H-ligand for serotonin2 receptor binding sites. Binding properties, brain distribution, and functional role. Molecular Pharmacology. 1982, 21 (2), 301-314.
Li et al. "Design and synthesis of 4-arylpiperidinyl amide and N-arylpiperdin-3-yl-cyclopropane carboxamide derivatives as novel melatonin receptor ligands" Bioorganic & Medicinal Chemistry Letters 2011, vol. 21, pp. 1236-1242.
Li et al., 2004. Evaluation of the motor initiation hypothesis of APD-induced conditioned avoidance decreases. Pharmacol.Biochem. Behav. 78, 811-819.
Lieberman et al. "A Randomized, Placebo-Controlled Study of Memantine as Adjunctive Treatment in Patients with Schizophrenia" Neuropsychopharmacology 2009, vol. 34, pp. 1322-1329.
Lieberman et al. Antipsychotic drugs: comparison in animal models of efficacy, neurotransmitter regulation, and neuroprotection. Pharmacol. Rev 2008, 60 (3), 358-403.
Lieberman et al. Effectiveness of antipsychotic drugs in patients with chronic schizophrenia. N Engl J Med. 2005;353 (12):1209-1223.
O'Connor et al "Metabotropic glutamate receptor 7: At the interface of cognition and emotion" European Journal of Pharmacology 2010, vol. 639, pp. 123-131.
O'Neill et al. "Recent developments in metabotropic glutamate receptors as novel drug targets" Drugs of the Future 2010, vol. 35, pp. 307-324.
O'Neill et al., "Cingulate and thalamic metabolites in obsessive-compulsive disorder", Psychiatry Research: Neuroimaging, 2016, 254, 34-40.
O'Neill et al., "Effects of Ischaemic Conditions on Uptake of Glutamate, Aspartate, and Noradrenaline by Cell Lines Derived from the Human Nervous System", Journal of Neurochemistry, 1994, 63(2), 603-611.
Odagaki et al. "Functional Coupling between Metabotropic Glutamate Receptors and G-proteins in Rat Cerebral Cortex Assessed by Guanosine-5'-O-(3-[35S] thio)triphosphate ([35S]GTPyS) Binding Assay" Basic & Clinical Pharmacology & Toxicology 2011 "Accepted Article"; epub, no page numbers, doi: 10.1111/j.1742-7843.2011.00705.x.
Odagaki et al. "Group II metabotropic glutamate receptor-mediated activation of G-proteins in rat hippocampal and striatal membranes" Neuroscience Letters 2010, epub, no page numbers, doi:10.1016/j.neulet.2013.01.033.
Oehlrich "Positive Allosteric Modulation of mGluR2 Receptors in the treatment of CNS Disorders" Oct. 19, 2012 Leuven University, Belgium.
Office Action for Chilean application No. 2745-2008 dated Apr. 15, 2011.
Office Action for Chinese application No. 200880107135.0 dated Jul. 4, 2012.
Office Action for Japanese application No. 2010-524405 dated Jun. 5, 2012.

(56) References Cited

OTHER PUBLICATIONS

Office Action for U.S. Appl. No. 12/282,663 dated Aug. 9, 2012.
Office Action for U.S. Appl. No. 12/282,663 dated Jan. 13, 2012.
Office Action for U.S. Appl. No. 12/529,632 dated Dec. 16, 2011.
Office Action for U.S. Appl. No. 12/529,632 dated May 18, 2012.
Ohishi et al. "Distribution of the messenger RNA for metabotropic glutamate receptor, mGlu2, in the central nervous system of the rat" Neuroscience 1993, vol. 53, pp. 1009-1018.
Ohishi et al., "Distribution of a metabotropic glutamate receptor, mGluR2, in the central nervous system of the rat and mouse: an immunohistochemical study with a monoclonal antibody", Neuroscience Research, 1998, 30, 65-82.
Ojima et al., "Hydroformation of Fluoro Olefins, RfCH=CH2, Catalyzed by Group VIII Transition-Metal Catalysts. Crucial Factors for Extremly High Regioselectivity", Journal of American Chemical Society, 1987, 109, 7714-7720.
Olbrich et al. Frontolimbic glutamate alterations in first episode schizophrenia: evidence from a magnetic resonance spectroscopy study. World J Biol Psychiatry. 2008; 9(1):59-63.
Oldenziel et al., "In Vivo Monitoring of Extracellular Glutamate in the Brain with a Microsensor", Brain Res., 2006, 1118(1), 34-42.
Olive "Cognitive effects of Group I metabotropic glutamate receptor ligands in the context of drug addiction" European Journal of Pharmacology 2010, vol. 639, pp. 47-58.
Olive "Metabotropic glutamate receptor ligands as potential therapeutics for addiction" Curr Drug Abuse Rev. 2009, vol. 2(1), pp. 83-989 (manuscript).
Olivier et al. "Stress-induced hyperthermia and anxiety: pharmacological validation" Eur J Pharmacol 2003, vol. 463, pp. 117-132.
Olney et al. "NMDA receptor hypofunction model of schizophrenia" Journal of Psychiatric Research 1999, vol. 33, pp. 523-533.
Olszewski et al., "Naag Peptidase Inhibition Reduces Locomotor Activity and Some Stereotypes in the Pcp Model of Schizophrenia via Group II Mglur", J. Neurochem., 2004, 89(4), 876-885.
Olszewski et al., "Phencyclidine and Dizocilpine Induced Behaviors Reduced by NAcetylaspartylglutamate Peptidase Inhibition via Metabotropic Glutamate Receptors", Biol. Psychiatry, 2008, 63(1), 86-91.
Ong et al., "Localisation of Glutamate Receptors in the Substantia Nigra Pars Compacta of the Monkey", Journal Fur Himforschung, 1997, 38(3), 291-298.
Oquendo et al. "A Computer Algorithm for Calculating the Adequacy of Antidepressant Treatment in Unipolar and Bipolar Depression" J Clin Psychiatry 2003, vol. 64(7), pp. 825-833.
Orrenius et al. Calcium ions and oxidative cell injury. [Review] [73 refs]. Annals of Neurology 1992, 32, Suppl-42.
Osikowicz et al., "Glutamate Receptor Ligands Attenuate Allodynia and Hyperalgesia and Potentiate Morphine Effects in a Mouse Model of Neuropathic Pain", Pain, 2008, 139, 117-126.
Ossowska et al. The striatum as a target for anti-rigor effects of an antagonist of mGluR1, but not an agonist of group II metabotropic glutamate receptors. Jolanta Konieczny, Andrzej Pilc, and Stanislaw Wolfarth. Brain Research 2002, vol. 950, pp. 88-94.
Ossowska et al., "The Role of Glutamate Receptors in Antipsychotic Drug Action", Amino. Acids, 2000, 19(1), 87-94.
Othmer et al. "Brain functions and psychiatric disorders: a clinical view" Diagnostic Dilemmas, Part I, The Psychiatryc Clinics of North America, Sep. 1998, vol. 21(3), 517-566.
Ottersen et al. Organization of glutamate receptors at the synapse. [Review] [41 refs]. European Journal of Neuroscience 1997, 9 (11), 2219-2224.
Overstreet et al. "A 5-HT1A agonist and a 5-HT2C antagonist reduce social interaction deficit induced by multiple ethanol withdrawals in rats" Psychopharmacology 2003, vol. 167, pp. 344-352.
Ozawa et al. Glutamate receptors in the mammalian central nervous system. [Review] [406 refs]. Progress in Neurobiology 1998, 54 (5), 581-618.
Page et al., "Metabotropic Glutamate Receptors Inhibit Mechanosensitivity in Vagal Sensory Neurons", Gastroenterology, 2005, 128(2), 402-410.
Pajer et al. "Discovery of blood transcriptomic markers for depression in animal models and pilot validation in subjects with early-onset major depression" Transl Psychiatry (2012) 2, e101 (epub only, no page numbers).
Pajonk et al., "Comparing the Efficacy of Atypical Antipsychotics in Open Uncontrolled Versus Double-Blind Controlled Trials in Schizophrenia", Psychopharmacology (Berl.), 2002, 162(1), 29-36.
Palazzo et al. Metabotropic and NMDA glutamate receptors participate in the cannabinoid-induced antinociception. Neuropharmacology. 40(3):319-26, 2001.
Palop et al. "Amyloid-.beta.-induced neuronal dysfunction in Alzheimer's disease: from synapses toward neural networks" Nature Neuroscience 2010, vol. 13(7), pp. 812-818.
Palucha et al., "Chronic Imipramine Treatment Reduces Inhibitory Properties of Group II Mglu Receptors Without Affecting Their Density or Affinity", Pharmacol. Rep., 2007, 59(5), 525-530.
Palucha et al., "Metabotropic Glutamate Receptor Ligands as Possible Anxiolytic and Antidepressant Drugs", Pharmacology & Therapeutics, 2007, 115, 116-147.
Palucha et al., "The Involvement of Glutamate in the Pathophysiology of Depression", Drug News Perspect, 2005, 18(4), 262-268.
Palucha, "Are Compounds Acting at Metabotropic Glutamate Receptors the Answer to Treating Depression?", Expert Opin. Investig. Drugs, 2006, 15(12), 1545-1553.
Palucha-Poniewiera et al. "On the mechanism of the antidepressant-like action of group li mGlu receptor antagonist, MGS0039" Psychopharmacology 2010, vol. 212, pp. 523-535.
Panzer "Are SSRIs Really More Effective for Anxious Depression?" Annals of Clinical Psychiatry 2005, vol. 17(1), pp. 23-29.
Papakostas et al. "Predictors, moderators, and mediators (correlates) of treatment outcome in major depressive disorder" Dialogues Clin Neurosci. 2008; 10:439-451.
Papakostas et al., "Augmentation of Antidepressants with Atypical Antipsychotic Medications for Treatment-Resistant Major Depressive Disorder: A Meta-Analysis", J Clin Psychiatry 2007, 68(6), 826-831.
Papakostas et al., "Efficacy of Bupropion and the Selective Serotonin Reuptake Inhibitors in the Treatment of Major Depressive Disorder with High Levels of Anxiety (Anxious Depression): A Pooled Analysis of 10 Studies", J Clin Psychiatry, 2008, 69(8), 1287-1292.
Papakostas et al., "Fluxetine-Clonazepam Cotherapy for Anxious Depression: An Exploratory, Post-Hoc Analysis of a Randomized, Double Blind Study", International Clinical Psychopharmacology, 2010, 25, 17-21.
Seeman "An agonist at glutamate and dopamine D2 receptors, LY404039" Neuropharmacology 2012, epub, no page numbers, doi: 10.1016/tneuropharm.2012.07.001.
Seeman et al. Dopamine partial agonist actions of the glutamate receptor agonists LY354740 and LY379268. Synapse 2008, vol. 62, pp. 154-158.
Seeman et al. Glutamate receptor mGlu2 and mGlu3 knockout striata are dopamine supersensitive, with elevated D2 (High) receptors and marked supersensitivity to the dopamine agonist (+)PHNO. Synapse 2009, 63 (3), 247-251.
Semba et al. Regional differences in the effects of glutamate uptake inhibitor L-trans-pyrrolidine-2,4-dicarboxylic acid on extracellular amino acids and dopamine in rat brain: an in vivo microdialysis study. General Pharmacology 1998, 31 (3), 399-404.
Semple et al. "3-Aryl Pyridone Derivatives. Potent and Selective Kappa Opioid Receptor Agonists." Bioorganic and Medicinal Chemistry Letters. vol. 12. 2002. 197-200.
Seroquel XR (Registered) Highlights of Prescribing Information (2013).
Shear et al.. Multicenter Collaborative Panic Disorder Severity Scale, Am J Psychiatry Nov. 1997; 154(11): 1571-1575.
Shekhar et al. Dorsomedial hypothalamic GABA dysfunction produces physiological arousal following sodium lactate infusions. Pharmacol Biochem Behav. Oct. 1996, vol. 55(2), pp. 249-256.
Shekhar et al. "Dorsomedial hypothalamic GABA regulates anxiety in the social interaction test." Pharmacology, Biochemistry and Behavior (1995), 50(2), 253-8.

(56) References Cited

OTHER PUBLICATIONS

Shekhar et al. "The circumventricular organs form a potential neural pathway for lactate sensitivity: implications for panic disorder" The Journal of Neuroscience 1997, vol. 17(24), pp. 9726-9735.
Sheldon Margen Public Health Library, "Preventing disease" p. 1-3 (2015).
Shepherd et al. Behavioural and pharmacological characterisation of the elevated "zero-maze" as an animal model of anxiety, Psychopharmacology, 116:56-64 (1994).
Shiba et al. Synthesis and binding affinities of methylvesamicol analogs for the acetylcholine transporter and sigma receptor, Bioorganic and Medicinal Chemistry, 2006, 14, 2620-2626.
Shimazaki et al. "Blockade of the metabotropic glutamate 2/3 receptors enhances social memory via the AMPA receptor in rats" Eur. J. Pharmacol. (2007), epub, no page numbers, doi:10.1016/j.ejphar.2007.08.006.
Shin et al. "Metabotropic glutamate receptors (mGlus) and cellular transformation" Neuropharmacology (2008), epub, no page numbers, doi 10.1016/j.neuropharm.2008.04.021.
Simmons et al., "Group II mGluR receptor agonists are effective in persistent and neuropathic pain models in rats", Pharmacology, Biochemistry and Behavior, 2002, 73, 419-427.
Simon et al. "Advances in the Treatment of Anxiety: Targeting Glutamate" The Journal of the American Society for Experimental NeuroTherapeutics vol. 3, 57-68, Jan. 2006.
SIPO Office Action dated Jun. 30, 2010.
Smalley et al. "Pyrolysis of Aryle Azides in Acetic Anhydride." 1963. 5571-2.
Smith et al. "Short-Term Augmentation of Fluoxetine With Clonazepam in the Treatment of Depression: A Double-Blind Study" Am J Psychiatry 1998, vol. 155, pp. 1339-1345.
Smith et al. Ionotropic and metabotropic GABA and glutamate receptors in primate basal ganglia. [Review] [232 refs]. Journal of Chemical Neuroanatomy. 2001, 22 (1-2), 13-42.
Smith et al. Is extended clonazepam cotherapy of fluoxetine effective for outpatients with major depression? Journal of Affective Disorders 2002, vol. 70, pp. 251-259.
Smith et al. Schizophrenia (maintenance treatment). Clin Evid (Online). 2009; pii:1007.
Smith et al., "Schizophrenia (Maintenance Treatment)", Clin Evid (Online), 2009, 1007.
Smith, "Regulation of Glutamate Uptake in Astrocytes Continuously Exposed to Ethanol", Life Sciences, 1997, 61(25), 2499-2505.
Smits et al. "Outcomes of Acute Phase Cognitive Therapy in Outpatients with Anxious versus Nonaxious Depression" Psychother Psychosom 2012; 81:153-160.
Smolders et al. In vivo modulation of extracellular hippocampal glutamate and GABA levels and limbic seizures by group I and II metabotropic glutamate receptor ligands. Journal of Neurochemistry. 88(5):1068-77, 2004.
Snipe et al. Recent advances in positive allosteric modulators of metabotropic glutamate receptors. [Review] [32 refs]. Current Opinion in Drug Discovery & Development. 8(4):449-57, 2005.
Sodhi et al. "Role of glutamate in schizophrenia: integrating excitatory avenues of research" Expert Rev Neurother 2008, vol. 8(9), pp. 1389-1406.
Sokoloff et al. "The [14C]deoxyglucose method for the measurement of local cerebral glucose utilization: theory, procedure, and normal values in the conscious and anesthetized albino rat" J Neurochem 1977, vol. 28, pp. 897-916.
Sokolowski et al. "The behavioral effects of sertraline, fluoxetine, and paroxetine differ on the differentialreinforcement-of-low-rate 72-second operant schedule in the rat" Psychopharmacology 1999, vol. 147, pp. 153-161.
Sortino et al., "Immortalized Hypothalamic Neurons Express Metabotropic Glutamate Receptors Positively Coupled to Cyclic Amp Formation", Eur. J Neurosci., 1996, 8(11), 2407-2415.
Souery et al. Group for the Study of Resistant Depression. Clinical factors associated with treatment resistance in major depressive disorder: results from a European multicenter study. J. Clin. Psychiatry Jul. 2007; 68(7): 1062-1070.
South Korean Patent Application No. 2010-053694958: Office Action dated Nov. 25, 2010, 9 pages.
Spencer et al. "Novel strategies for Alzheimer's disease treatment" Expert Opin. Biol. Ther. 2007, vol. 7(12), pp. 1853-1867.
Spiegel et al. "Psychosis Induced by the Interaction of Memantine and Amantadine: Lending Evidence to the Glutamatergic Theory of Schizophrenia" Clinical Schizophrenia & Related Psychoses 2007, vol. 1(3), pp. 273-276.
Spiegel et al. Defects in G protein-coupled signal transduction in human disease. [Review] [90 refs]. Annual Review of Physiology 1996, 58, 143-170.
Spijker "The Course of anxiety and depression in NEMESIS and NESDA" Abstract AS36-04 of the 20th European Congress of Psychiatry, Mar. 3-6, 2012, Pargue, Czech Republic.
Spooren et al. "Lack of effect of LY314582 (a group 2 metabotropic glutamate receptor agonist) on phencyclidine-induced locomotor activity in metabotropic glutamate receptor 2 knockout mice" Eur J Pharmacol. 2000, vol. 397, pp. R1-R2.
Spooren et al. "Pharmacological and endocrinological characterization of stress-induced hypethermia in singly housed mice using classical and candidate anxiolytics (LY314582, MPEP and NKP608)" Eur J Pharmacol 2002, vol. 435, pp. 161-170.
Spooren et al., "Anxiolytic-Like Effects of the Prototypical Metabotropic Glutamate Receptor 5 Antagonist 2-Methyl-6-(Phenylethynyl)Pyridine in Rodents", Journal of Pharmacology & Experimental Therapeutics, 2000, 295(3), 1267-1275.
Spooren et al., "Insight Into the Function of Group I and Group II Metabotropic Glutamate (Mglu) Receptors: Behavioural Characterization and Implications for the Treatment of CNS Disorders", Behavioural Pharmacology, 2003, 14(4), 257-277.
Spooren et al., "Metabotropic Glutamate Receptors: Their Therapeutic Potential in Anxiety", Current Topics in Behavioral Neurosciences, 2010, 2, 391-413.
Srivastava et al., "Novel Anchorage of Glur2/3 to the Postsynaptic Density by the Ampa Receptor-Binding Protein Abp", Neuron, 1998, 21(3), 581-591.
Stachowicz et al. "Anxiolytic-like activity of MGS0039, a selective group II mGlu receptor antagonist, is serotonin-and GABA-dependent" Pharmacological reports 2011, vol. 63, pp. 880-887.
Stahl et al., "Negative Symptoms of Schizophrenia: A Problem That Will Not Go Away", Acta Psychiatr. Scand., 2007, 115(1), 4-11.
Star D Research Methods Section (2001), Available from Http:/Www.Edc.Gsph.Pitt.Edu/Stard/Public/Protocol/Star-D%20III%2Oresearc- h%20design%20methods.Pdf 2001, 50 pages.
Steckler "Glutamatergic Anxiolytics Are They Any Better?" ECNP Targeted Expert meeting 2009 (presentation slides), European College of Neuropsychopharmacology meeting, Istanbul, Turkey.
Steckler et al. "Effects of mGlu1 receptor blockade on anxiety-related behavior in the rat lick suppression test" Psychopharmacology 2005, vol. 179, pp. 198-206.
Merikangas et al. "Longitudinal Trajectories of Depression and Anxiety in a Prospective Community Study" Arch Gen Psychiatry 2003, vol. 60, pp. 993-1000.
Metman et al., "Huntington's disease a randomized, controlled trial using the NMDA-antagonist amantadine", Neurology, 2002; 59:694-699.
Mexican Patent Application No. MX/a/2009/009422: Office Action dated Jun. 28, 2011, 5 pages.
Mezler et al. "LY2140023, a prodrug of the group II metabotropic glutamate receptor agonist Ly-404039 for the potential treatment of schizophrenia" Current Opinion in Investigational Drugs 2010, vol. 11(7), 833-845.
Michael et al. Metabolic changes within the left dorsolateral prefrontal cortex occurring with electroconvulsive therapy in patients with treatment resistant unipolar depression. Psychol Med Oct. 2003; 33(7): 1277-1284.
Michael et al. Neurotrophic effects of eletroconvulsive therapy: a proton magnetic resonance study of the left amygdalar region in patients with treatment-resistant depression. Neuropsychopharmacology Apr. 2003; 28(4): 720-725.

(56) References Cited

OTHER PUBLICATIONS

Michelson, "Clinical studies with mGluR2/3 agonists: LY354740 compared with placebo in patients with generalized anxiety disorder," Abstracts Neuropharmacol. 49: 257 (2005).

Miller "Mechanisms of action of antipsychotic drugs of different classes, refractoriness to therapeutic effects of classical neuroleptics, and individual variation in sensitivity to their actions: part I" Current Neuropharmacology 2009, vol. 7, pp. 302-314.

Miller et al. Roles of metabotropic glutamate receptors in brain plasticity and pathology. [Review] [55 refs]. Annals of the New York Academy of Sciences 1995, 757, 460-474.

Mills et al. "Epidemiology and reporting of randomized trials employing re-randomization of patient groups: A systematic survey" Contemporary Clinical Trials 2007, vol. 28, pp. 268-275.

Mitchell et al., "An Update on the Role of Glutamate in the Pathophysiology of Depression", Acta Psychiatrica Scandinavica, 2010, 122(3), 192-210.

Mitri et al. Divergent evolution in metabotropic glutamate receptors. A new receptor activated by an endogenous ligand different from glutamate in insects. Journal of Biological Chemistry. 279(10):9313-20, 2004.

Mittal et al. "Impact of Comorbid Anxiety Disorders on Health-Related Quality of Live Among Patients With Major Depressive Disorder" Psychiatric services (Washington, D.C.) 2006, vol. 57(12), pp. 1731-1737.

Miuller et al. The immunological basis of glutamatergic disturbance in schizophrenia: towards an integrated view. J Neural Transm. Suppl 2007, (72), 269-280 (abstract).

Miyamoto et al. "Effects of Ketamine, MK-801, and Amphetamine on Regional Brain 2-Deoxyglucose Uptake in Freely Moving Mice" Neuropsychopharmacology 2000, vol. 22, pp. 400-412.

Miyamoto et al., "Treatments for Schizophrenia: A Critical Review of Pharmacology and Mechanisms of Action of Antipsychotic Drugs", Mol. Psychiatry, 2005, 10, 79-104.

Modafferi "Morphine withdrawal increases metabotropic glutamate 2/3 receptors expression in nucleus accumbens" Neurochemistry 2008, vol. 19(9), 911-914.

Moghaddam et al., "Activation of Glutamatergic Neurotransmission by Ketamine: A Novel Step in the Pathway from NMDA Receptor Blockade to Dopaminergic and Cognitive Disruptions Associated with the Prefrontal Cortex", J Neurosci. 1997, 17(8), 2921-2927.

Moghaddam et al., "From Revolution to Evolution: the Glutamate Hypothesis of Schizophrenia and Its Implication for Treatment", Neuropsychopharmacology, 2012, 37, 415.

Moghaddam et al., "Reversal of Phencyclidine Effects by a Group II Metabotropic Glutamate Receptor Agonist in Rats", Science, 1998, 281, 1349-1352.

Moldrich et al. Anti-epileptic activity of group II metabotropic glutamate receptor agonists (−)-2-oxa-4-aminobicyclo [3.1.0]hexane-4,6-dicarboxylate (LY379268) and (−)-2-thia-4-aminobicyclo[3.1.0]hexane-4,6-dicarboxylate (LY389795). Neuropharmacology 2001, vol. 41, pp. 8-18.

Moldrich et al., "Astrocyte Mglu(2/3)-Mediated Camp Potentiation is Calcium Sensitive: Studies in Murine Neuronal and Astrocyte Cultures", Neuropharmacology, 2002, 43(2), 189-203.

Moldrich et al., "Emerging Signalling and Protein Interactions Mediated via Metabotropic Glutamate Receptors", Curr. Drug Targets. CNS Neurol. Disord., 2003, 2(2), 109-122.

Moldrich et al., "Glutamate metabotropic receptors as targets for drug therapy in epilepsy", European Journal of Pharmacology, 2003, 476, 3-16.

Molina et al. "Polymorphic variation at the serotonin 1-A receptor gene is associated with comorbid depression and generalized anxiety" Psychiatry Genetics 2011, vol. 21, 195-201.

Molinaro et al., "Activation of Mg1u2/3 Metabotropic Glutamate Receptors Negatively Regulates the Stimulation of Inositol Phospholipid Hydrolysis Mediated by 5-Hydroxytryptamine2a Serotonin Receptors in the Frontal Cortex of Living Mice", Mol. Pharmacol., 2009, 76(2), 379-387.

Mondon et al. "Synthesis of Narciprimine and Related Compounds." Chem. Ber. vol. 105. 1972. 3726-47.

Mongin et al. "Advances in the directed metallation of azines and diazines (pyridines, pyrimidines, pyrazines, pyridazines, quinolines, benzodiazines and carbolines). Part 1: Metallation of Pyridines, quinolines and carbolines", Tetrahedron, 2001, 57(19), 4059-4090.

Monn et al. "Design, synthesis, and pharmacological characterization of (+)-2-aminobicyclo[3.1.0]hexane-2,6-dicarboxylic acid (LY354740): a potent, selective, and orally active group 2 metabotropic glutamate receptor agonist possessing anticonvulsant and anxiolytic properties" J Med Chem 1997, vol. 40, pp. 528-537.

Monn et al. "Synthesis and Metabotropic Glutamate Receptor Activity of S-Oxidized Variants of (−)-4-Amino-2-thiabicyclo-[3.1.0]hexane-4,6-dicarboxylate: Identification of Potent, Selective, and Orally Bioavailable Agonists for mGlu2/3 Receptors" J. Med. Chem. 2007, vol. 50, pp. 233-240.

Monn et al. "Synthesis, Pharmacological Characaterization, and Molecular Modeling of Heterobicyclic Amino Acids Related to (+)-2-Aminobicyclo[3.1.0]hexane-2,6-dicarboxylic Acid (LY354740): Identification of Two New Potent, Selective, and Systemically Active Agonists for Group II Metabotropic Glutamate Receptors." J. Med. Chem. vol. 42. 1999. 1027-40.

Monti et al., "Conventional and Power Spectrum Analysis of the Effects of Zolpidem on Sleep Eg in Patients with Chronic Primary Insomnia", Sleep, 2000, 23, 1075-1084.

Moore et al., "Cycloaddition of Cyanoketenes to Cinnamylideneamines and Benzylideneamines. Sythetic Scope, Stereochemistry, and Mechanism", J. Org. Chem, 1985, 50, 4231-4238, American Chemical Society.

Mora et al. "Role of 5-HT2A and 5-HT2C Receptor Subtypes in the Two Types of Fear Generated by the Elevated T-Maze" Pharmacology Biochemistry and Behavior 1997, vol. 58, pp. 1051-1057.

Moreno et al. "Group II Metabotropic Glutamate Receptors and Schizophrenia", Cell Mol. Life Sci., 2009, 66(23), 3777-3785.

Moreno et al. "Maternal Influenza Viral Infection Causes Schizophrenia-Like Alterations of 5-HT2A and mG1u2 Receptors in the Adult Offspring" The Journal of Neuroscience, 2011, vol. 31(5), pp. 1863-1872.

Moreno et al. "Pindolol Augmentation of Treatment-Resistant Depressed Patients" J Clin Psychiatry 1997, vol. 58, pp. 437-439.

Moreno et al., "Metabotropic Glutamate Mg1u2 Receptor is Necessary for the Pharmacological and Behavioral Effects Induced by Hallucinogenic 5-Ht2a Receptor Agonists", Neurosci. Lett., 2011, 493, 76-79.

Morgan et al., "Is Persistent Ketamine Use a Valid Model of the Cognitive and Oculomotor Deficits in Schizophrenia?", Biol. Psychiatry, 2009, 65(12), 1099-1102.

Morikawa et al., "Two Intracellular Pathways Mediate Metabotropic Glutamate Receptor-Induced Ca2+ Mobilization in Dopamine Neurons", Journal of Neuroscience, 2003, 23(1), 149-157.

Morishima et al. Enhanced cocaine responsiveness and impaired motor coordination in metabotropic glutamate receptor subtype 2 knockout mice. Proc. Natl. Acad. Sci. U. S. A 2005, 102 (11), 4170-4175.

Morishita "Clonazepam as a therapeutic adjunct to improve the management of depression: a brief review" Hum Psychopharmacol Clin Exp 2009, vol. 24, pp. 191-198.

Moroni et al. "Poly(ADP-ribose) polymerase inhibitors attenuate necrotic but not apoptotic neuronal death in experimental models of cerebral ischemia." Cell Death and Differentiation. vol. 8. 2001. 921-32.

Morpurgo et al., "Drug-Induced Modifications of Discriminated Avoidance Behavior in Rats", Psychopharmacol., 1965, 8, 91-99.

Morrill et al., "Synthesis of 4-Arylpiperidines from 1-Benzyl-4piperidone: Application of the Sharpiro Reaction and Alkenylsilane Cross-coupling," Organic Letters, 2007, vol. 9, pp. 1505-1508, The American Chem Society.

Morrison et al., "Schizophrenia: More Evidence for Less Glutamate", Expert Rev Neurother., 2007, 7 (1), 29-31.

Moussawi et al. "Group II metabotropic glutamate receptors (mG1u2/3) in drug addiction" European Journal of Pharmacology 2010, vol. 639, pp. 115-122.

(56) References Cited

OTHER PUBLICATIONS

Mudge et al. Genomic convergence analysis of schizophrenia: mRNA sequencing reveals altered synaptic vesicular transport in post-mortem cerebellum. PLoS ONE [Electronic Resource]. 3(11):e3625, pp. 1-24, 2008.
Mukhin et al., "Mglur Modulation of Post-Traumatic Neuronal Death: Role of NMDA Receptors", Neuroreport, 1997, 8(11), 2561-2566.
Muller, "Inflammation and the Glutamate System in Schizophrenia: Implications for Therapeutic Targets and Drug Development", Expert Opin. Ther. Targets, 2008, 12(12), 1497-1507.
Koh et al. "Deficits in social behavior and sensorimotor gating in mice lacking phospholipase Cb1" Genes, Brain and Behavior 2008, vol. 7, pp. 120-128.
Koh et al. "Treatment Strategies Targeting Excess Hippocampal Activity Benefit Aged Rats with Cognitive Impairment" Neuropsychopharmacology 2010, vol. 35, pp. 1016-1025.
Koh et al., "Non-NMDA Receptor-Mediated Neurotoxicity in Cortical Culture", J. Neurosci., 1990, 10(2), 693-705.
Komossa et al. "Second-generation antipsychotics for major depressive disorder and dysthymia (Review)" The Cochrane Collaboration, Published by John Wiley & Sons, Ltd. 2012.
Konarski et al. Volumetric neuroimaging investigations in mood disorders: bipolar disorder versus major depressive disorder. Bipolar Disord Feb. 2008; 10(1): 1-37.
Konieczny et al., "Ly354740, A Group II Metabotropic Glutamate Receptor Agonist with Potential Antiparkinsonian Properties in Rats", Naunyn Schmiedebergs Arch. Pharmacol., 1998, 358(4), 500-502.
Konstantakopoulos et al. Lamotrigine associated exacerbation of positive symptoms in paranoid schizophrenia. Schizophr Res. 2008; 98(1-3):325-326.
Koolschijn et al. Brain vol. abnormalities in major depressive disorder: a meta-analysis of magenetic resonance imaging studies. Hum Brain Mapp Nov. 2009; 30(11): 3719-3735.
Koroshetz et al. Emerging treatments for stroke in humans. [Review] [57 refs]. Trends in Pharmacological Sciences 1996, 17 (6), 227-233.
Kostrzewa et al., "Supersensitized D1 Receptors Mediate Enhanced Oral Activity After Neonatal 6-Ohda. Pharmacology", Biochemistry & Behavior, 1991, 39(3), 677-682.
Kotlinska et al., "The Role of Group I Mglu Receptors in the Expression of Ethanol-Induced Conditioned Place Preference and Ethanol Withdrawal Seizures in Rats", European Journal of Pharmacology, 2011, 670, 154-161.
Koulen et al., "Group II and Group III Metabotropic Glutamate Receptors in the Rat Retina: Distributions and Developmental Expression Patterns", European Journal of Neuroscience, 1996, 8(10), 2177-2187.
Kowal et al., "A [35s]Gtpgammas Binding Assessment of Metabotropic Glutamate Receptor Standards in Chinese Hamster Ovary Cell Lines Expressing the Human Metabotropic Receptor Subtypes 2 and 4", Neuropharmacology, 1998, 37(2), 179-187.
Kowal et al., "Functional Calcium Coupling with the Human Metabotropic Glutamate Receptor Subtypes 2 and 4 by Stable Co-Expression with a Calcium Pathway Facilitating G-Protein Chimera in Chinese Hamster Ovary Cells", Biochemical Pharmacology, 2003, 66(5), 785-790.
Kozari-Kova{hacek over (c)}i et al., "Lamotrigine Abolished Aggression in a Patient With Treatment-Resistant Posttraumatic Stress Disorder", Clinical Neuropharmacology, May/Jun. 2013, vol. 36, No. 3, 94-95.
Krieger "The Plasma Level of Cortisol as a Predictor of Suicide" Diseases of the nervous system 1974, vol. 35(5) pp. 237-240.
Krishnan et al. "The molecular neurobiology of depression" Nature 2008, vol. 455, pp. 894-902.
Krivoy et al. The possible involvement of metabotropic glutamate receptors in schizophrenia, European Neuropsychopharmacology (2007), epub, no page numbers, doi: 10.1016/j.euroneuro.2007.11.001.
Krohnke et al. "Methylketon-Addukte der Chinolinium-und Isochinolinium-Reihe." 211-28.
Krystal et al. "Preliminary evidence of attenuation of the disruptive effects of the NMDA glutamate receptor antagonist, ketamine, on working memory by pretreatment with the group II metabotropic glutamate receptor agonist, LY354740, in healthy human subjects" Psychopharmacology (Berl). 2005 vol. 179(1), pp. 303-309.
Krystal et al. "Subanesthetic effects of the noncompetitive NMDA antagonist, ketamine, in humans. Psychotomimetic, perceptual, cognitive, and neuroendocrine responses" Arch Gen Psychiatry. Mar. 1994; 51 (3):199-214.
Krystal et al. Comparative and interactive human psychopharmacologic effects of ketamine and amphetamine: implications for glutamatergic and dopaminergic model psychoses and cognitive function. Archives of General Psychiatry. 62(9):985-94, 2005.
Krystal et al. NMDA receptor antagonist effects, cortical glutamatergic function, and schizophrenia: toward a paradigm shift in medication development. [Review] [328 refs]. Psychopharmacology. 169(3-4):215-33, 2003.
Krystal et al., "Neuroplasticity as a Target for the Pharmacotherapy of Anxiety Disorders, Mood Disorders, and Schizophrenia", Drug Discov. Today, 2009, 14(13-14), 690-697.
Krystal et al., "Potential Psychiatric Applications of Metabotropic Glutamate Receptor Agonists and Antagonists", CNS Drugs, 2010, 24(8), 669-693.
Krystal, "N-methyl-D-aspartate glutamate receptors and alcoholism: reward, dependence, treatment, and vulnerability," Pharmacol. & Therapeutics 99: 79-94 (2003).
Kubo et al., "Structural Basis for a Ca2+-Sensing Function of the Metabotropic Glutamate Receptors", Science, 1998, 279(5357), 1722-1725.
Kubokawa et al., "Cloning and Characterization of a Bifunctional Metabotropic Receptor Activated by Both Extracellular Calcium and Glutamate", Febs Letters, 1996, 392(1), 71-76.
Kucukibrahimoglu et al. The change in plasma GABA, glutamine and glutamate levels in fluoxetine- or S-citalopram-treated female patients with major depression. Eur J Clin Pharmacol Jun. 2009; 65(6): 571-577.
Kufahl et al. "Enhanced Sensitivity to Attenuation of Conditioned Reinstatement by the mGluR2/3 Agonist LY379268 and Increased Functional Activity of mGluR2/3 in Rats with a History of Ethanol Dependence" Neuropsychopharmacology 2011, pp. 1-12.
Kugaya et al. "Beyond monoamines: glutamatergic function in mood disorders" CNS Spectr 2005, vol. 10, pp. 808-819.
Kullmann et al., "Extrasynaptic Glutamate Spillover in the Hippocampus: Evidence and Implications", Trends Neurosci., 1998, 21(1), 8-14.
Kunishima et al. "Structural basis of glutamate recognition by a dimeric metabotropic glutamate receptor" Nature 2000, vol. 407, pp. 971-977.
Kuo "Allosteric cofactor-mediated enzyme cooperativity: A theoretical treatment" Proc. Natl. Acad. Sci. USA, Sep. 1983, vol. 80, pp. 5243-5247.
Kurita et al., "Hdac2 Regulates Atypical Antipsychotic Responses through the Modulation of Mglu2 Promoter Activity", Nature Neuroscience, 2012, 15(9), 1245-1254.
Kurumaji et al. "Effects of MK-801 upon local cerebral glucose utilization in conscious rats and in rats anaesthetized with halothane "J Cereb Blood Flow Metab 1989, vol. 9, pp. 786-794.
Lahti et al. Ketamine activates psychosis and alters limbic blood flow in schizophrenia. Neuroreport. Apr. 19, 1995; 6(6):869-72.
Lam et al., "Effects of the Selective Metabotropic Glutamate Agonist Ly354740 in a Rat Model of Permanent Ischaemia", Neuroscience Letters, 1998, 254(2), 121-123.
Lambeng et al. "Selective mGLUR2 Negative Allosteric Modulators Reverse the Scopolamine-Induced Memory Deficit in the Novel Object Recognition Test," Society for Neuroscience 40th Annual Meeting, Nov. 16, 2010, San Diego, CA. (poster).
Lambert et al. Current issues in schizophrenia: overview of patient acceptability, functioning capacity and quality of life. CNS Drugs 2004;18 suppl 2:5-17.

(56) References Cited

OTHER PUBLICATIONS

Lamers et al. "Comorbidity Patterns of Anxiety and Depressive Disorders in a Large Cohort Study: the Netherlands Study of Depression and Anxiety (NESDA)" J Clin Psychiatry 2011, vol. 72(3), 341-348.
Lamotrigine Highlights of Prescribing Information, 2012.
Lan et al., Activation of Metabotropic Glutamate Receptor-1 Accelerates NMDA Receptor Trafficking, Abstracts/Neuropharmacology 43 (2002) 294.
Landen et al. "A randomized, double-blind, placebo-controlled trial of buspirone in combination with an SSRI in patients with treatment-refractory depression" J Clin Psychiatry 1998, vol. 59, pp. 664-668.
Landin et al. "The impact of restrictive entry criterion during the placebo lead-in period" Biometrics 2000, vol. 56, pp. 271-278.
Landmark, "Antiepileptic drugs in non-epilepsy disorders," CNS Drugs 22(1) 27-47 (2008).
Landwehrmeyer, "Riluzole in Huntington's Disease: A 3-Year, Randomized Controlled Study", Ann Neurol, 2007, 62, pp. 262-272.
Lane et al. "Bridging the gap: bitopic ligands of G-protein-coupled receptors" Trends in Pharmacological Sciences, Jan. 2013, vol. 34, No. 1, pp. 59-66.
Lang et al. "Molecular Mechanisms of Depression" Perspective on new treatment strategies Cell Physiol Biochem 2013, vol. 31, pp. 761-777.
Lang et al., "Molecular Mechanisms of Schizophrenia", Cell Physiol Biochem., 2007, 20(6), 687-702.
"Amelioration", definition from medical dictionary, 2014, p. 1.
"Disease control" fromask.com., 2014, p. 1-2.
"Neuroprotection as Initial Therapy in Acute Stroke", Third Report of an Ad Hoc Consensus Group Meeting, European Ad Hoc Consensus Group, Cerebrovascular Diseases 1998, 8(1), 59-72.
"Notification on the necessity to present additional materials", from the Eurasian Patent Organization dated Dec. 17, 2008.
"Structures", Chemical Abstracts, May 13, 2009, 23 pgs.
"Treatment", Definition from medical dictionary, 2014, p. 1-6.
A Dose-Ranging Study of JNJ-40411813 in Healthy Male Volunteers—Available from http://clinicaltrials.gov/show/NCT01358006, retrieved on Aug. 1, 2013.
A Study of [11C]JNJ-42491293, a Possible PET Ligand for the mGlu2 Receptor, in Healthy Adult Volunteers—Available from http://clinicaltrials.gov/show/NCT01359852, retrieved on Aug. 1, 2013.
A Study of JNJ-40411813 as Supplementary Treatment to an Antidepressant in Adults With Depression and Anxiety Symptoms—Available from: http://clinicaltrials.gov/show/NCT01582815, retrieved on Aug. 1, 2013.
Abi-Saab et al., "The NMDA Antagonist Model for Schizophrenia: Promise and Pitfalls", Pharmacopschiatry,1998, vol. 31, 104-109.
Abshire et al.,"Injection of L-allylglycine into the posterior hypothalamus in rats causes decreases in local GABA which correlate with increases in heart rate", Neuropharmacology, 1988, vol. 27(11), 1171-1177.
Acta Chimica Slovenica, 2005, vol. 52, No. 4, pp. 391-397.
Adam, "Symptomatic Treatment of Huntington Disease", Neurotherapeutics: The Journal of the American Society for Experimental Neurotherapeutics, Apr. 2008, vol. 5, 181-197.
Adams et al., "Effect of clozapine, haloperidol, or M100907 on phencyclidine-activated glutamate efflux in the prefrontal cortex", Biol. Psychiatry, 2001, 50(10), 750-757.
Adams, "A long-term, phase 2, multicenter, randomized, open-label, comparative safety study of pomaglumetad methionil (LY2140023 monohydrate) versus atypical antipsychotic standard of care in patients with schizophrenia", BMC Psychiatry, 2013, 13(143), 1-9.
Addex Partner Completes ADX71149 Phase I Program Press release Aug. 25, 2010 http://www.addextherapeutics.com/investors/press-releases/news-details/?tx ttnews%5Btt news%5D%20=103&cHash=91fade38b1d3dc85979989357b1a9281 retrieved on Aug. 22, 2013.
Addex Partner Doses First Patient in Phase 2 Clinical Study of ADX71149 for the Treatment of Major Depressive Disorder Patients with Anxiety Symptoms Press release Sep. 17, 2012 http://www.addextherapeutics.com/investors/press-releases/news-details/?tx ttnews%5Btt news%5D%20=214&cHash=12a9cc5ffefdb63c27d5b87a673f74eb retrieved on Aug. 22, 2013.
Addex Partner to Initiate Phase 2 Clinical Trial of ADX71149 for the Treatment of Major Depressive Disorder with Anxiety Symptoms Press release Jun. 5, 2012 http://www.addextherapeutics.com/investors/press-releases/news-details/?tx ttnews%5Btt news%5D%20=204&cHash=1865c3b31dOb9042f84c017bb2b5f32c retrieved on Aug. 22, 2013.
Addex Reports Top-line Data from a Successful Phase 2a Clinical Study with ADX71149 in Schizophrenia Patients Press release Nov. 5, 2012, http://www.addextherapeutics.com/investors/press-releases/news-details/?tx ttnews%5Btt_news%5D%20=225&cHash=9e5e13cb042971e6135f8ac786ce7453 retrieved on Aug. 22, 2013.
Addex, "Addex partner to initiate phase 2", 2013, p. 1.
Addington et al., "A depression rating scale for schizophrenics", Schizophr Res. 1990, vol. 3(4), 247-251.
Ader et al., "Effects of chlorpromazine on the acquisition and extinction of an avoidance response in the rat", J. Pharmacol. Exp. Ther., 1957, vol. 131, 144-148.
Agami et al., "An Efficient Synthesis of Polysubstituted 3-Halo-2(1 H)-Pyridinones", Synthesis, 2002, 1, 79-82.
Agari et al., "Intrapallidal metabotropic glutamate receptor activation in a rat model of Parkinson's disease: behavioral and histological analyses", Brain Res., 2008, 1203, 189-196.
Aghajanian et al., "Serotonin model of schizophrenia: emerging role of glutamate Mechanisms", Brain Research Reviews, 2000, vol. 31, 302-312.
Aghajanian et al., "Modeling "psychosis" in vitro by inducing disordered neuronal network activity in cortical brain slices", Psychopharmacology, 2009. 206, 575-585.
Agid et al., "How can drug discovery for psychiatric disorders be improved?" Nature Reviews Drug Discovery, 2007, vol. 6, 189-201.
Ago et al. "Activation of metabotropic glutamate 2/3 receptors attenuates methamphetamine-induced hyperlocomotion and increase in prefrontal serotonergic neurotransmission" Psychopharmacology 2011, vol. 217, pp. 443-452.
Ahnaou et al. "Modulation of group II metabotropic glutamate receptor (mGlu2) elicits common changes in rat and mice sleep-wake architecture" European Journal of Pharmacology 2009, vol. 603, pp. 62-72.
Ahnaou et al. "Modulation of group II metabotropic glutamate receptor (mGlu2) induces antidepressant-like suppression of rat and mice REM sleep" Soc. Neurosci. Abstr. 2007, p. 266.2/U14 San Diego, CA, USA.
Ainslie et al. "Practical Drug Evaluation Method" Arch Gen Psychiat 1965, vol. 12, pp. 368-373.
Al-Omran et al., "Studies with Polyfunctional Subsituted Heteroaromatics: New Routes for the Synthesis of Polyfunctionally Subsituted Pyridines and 1,2,4-Triazolo [1,5-a]pryidines", Heteroatom, 1995, vol. 6, 545-551, John Wiley & Sons, Inc.
Al-Shamma et al. "Nelotanserin, a novel selective human 5-hydroxytryptamine2A inverse agonist for the treatment of insomnia" J Pharmacol Exp Ther 2010, vol. 332, pp. 281-290.
Alagarsamy et al., "Coordinate Regulation of Metabotropic Glutamate Receptors", Current Opinion in Neurobiology, 2001, 11(3), 357-362.
Albasanz et al., "Internalization of metabotropic glutamate receptor in C6 cells through clathrin-coated vesicles", Molecular Brain Research, 2002, vol. 99, 54-66.
Alderson et al. Purification and Characterization of a Soluble Cyclic Nucleotide-Independent Ca2+-Calmodulin-Sensitive Protein Kinase from Rat Brain, J. Neurochem., 46:594-603 (1986).
Aleppo et al. Metabotropic glutamate receptors and neuronal toxicity. Advances in Experimental Medicine & Biology 1992, 318, 137-145.
Alexander et al. Metabotropic glutamate receptors as a strategic target for the treatment of epilepsy. Epilepsy Res. 2006, 71 (1), 1-22.
Allen et al., "Group II metabotropic glutamate receptor activation attenuates traumatic neuronal injury and improves neurological recovery after traumatic brain injury", J. Pharmacol. Exp. Ther., 1999, 290 (1), 112-120.

(56) References Cited

OTHER PUBLICATIONS

Alley et al. "Memantine lowers amyloid-beta peptide levels in neuronal cultures and in APP/PS1 transgenic mice" J Neurosci Res 2010, vol. 88, pp. 143-154.
Allosteric regulation, Wikipedia, p. 1-4 (2012).
Alper, R.H., "Agonist-Stimulated [35S]GTPyS Binding," Current Protocols in Pharmacology, 1998, Unit 2.6, 1-10.
Altamura et al., Designing outcome studies to determine efficacy and safety of antipsychotics for 'real world' treatment of schizophrenia. Int J Neuropsychopharmacol 2010; 13(7):971-973.
Altamura et al., Plasma and platelet exctitatory amino acids in psychiatric disorders. Am J Psychiatry Nov. 1993; 150(11): 1731-1733.
Altamura etal., Plasma concentrations of excitatory amino acids serine, glycine, taurine and histidine in major depression. Eur Neuropsychopharmacol 1995; 5 Suppl: 71-75.
Amiri et al. "A Role for Leu118 of Loop E in Agonist Binding to the a7 Nicotinic Acetylcholine Receptor" Mol Pharmacol 2008, vol. 73, pp. 1659-1667.
Amitai et al., "Effects of metabotropic glutamate receptor 2/3 agonism and antagonism on schizophrenia-like cognitive deficits induced by phencyclidine in rats", European Journal of Pharmacology, 2010, 67-80.
Andreescu et al. "Effect of comorbid anxiety on treatment response and relapse risk in late-life depression: controlled study" The British Journal of Psychiatry 2007, 190, 344-349.
Andreescu et al. "The Default Mode Network in Late-Life Anxious Depression" Am J Geriatr Psychiatry 19:11, Nov. 2011.
Andreescu et al., "Comorbid anxiety and depression: bete noire or quick fix?" British Journal of Psychiatry 2012, 200:179-181.
Lieberman Serotonergic basis of antipsychotic drug effects in schizophrenia. Biol. Psychiatry 1998, 44, 1099-1117.
Liebowitz et al Biological accompaniments of lactate-induced panic. Psychopharmacology bulletin 1984, vol. 20 (1), pp. 43-44.
Liebowitz et al Lactate provocation of panic attacks. I. Clinical and behavioral findings. Archives of general psychiatry 1984, vol. 41 (8), pp. 764-770.
Liechti et al. "Interactive effects of the mGlu5 receptor angatonist MPEP and the mGlu2/3 receptor antagonist LY341495 on nicotine self-administration and reward deficits associated with nicotine withdrawal in rats" European Journal of Pharmacology 2007, vol. 554, pp. 164-174.
Liechti et al. "Metabotropic Glutamate 2/3 Receptors in the Ventral Tegmental Area and the Nucleus Accumbens Shell Are Involved in Behaviors Relating to Nicotine Dependence" The Journal of Neuroscience 2007, vol. 27(34), pp. 9077-9085.
Liechti et al. "Role of the Glutamatergic System in Nicotine Dependence Implications for the Discovery and Development of New Pharmacological Smoking Cessation Therapies" CNS Drugs 2008, 22(9), pp. 705-724.
Liechti et al. "Metabotropic glutamate 2/3 receptor activation induced reward deficits but did not aggravate brain reward deficits associated with spontaneous nicotine withdrawal in rats" Biochemical Pharmacology 2007, vol. 74, pp. 1299-1307.
Lilly Stops Phase III Development of Pomaglumetad Methionil for the Treatment of Schizophrenia Based on Efficacy Results Press release Aug. 29, 2012 http://newsroom.lilly.com/releasedetail.cfm?ReleaseID=703018 retrieved on Aug. 7, 2013.
Lin et al. "A meta-analytic review of double-blind, placebo-controlled trials of antidepressant efficacy of omega-3 fatty acids" J Clin Psychiatry 2007, vol. 68(7), pp. 1056-1061.
Lindemann et al. "CTEP: a novel, potent, long-acting, and orally bioavailable metabotropic glutamate receptor 5 inhibitor" JPET 2011, vol. 339, pp. 474-486.
Linden et al. "Effects of mGlu2 or mGlu3 receptor deletions on mGlu2/3 receptor agonist (LY354740)-induced brain c-Fos expression: Specific roles for mGlu2 in the amygdala and subcortical nuclei, and mGlu3 in the hippocampus" Neuropharmacology 2006, 51:213-228.
Linden et al. "Anxiolytic Activity of the MGLU2/3 Receptor Agonist LY354740 on the Elevated Plus Maze is Associated with the Suppression of Stress-Induced c-Fos in the Hippocampus and Increases in c-Fos Induction in Several Other Stress-Sensitive Brain Regions" Neuropsychopharmacology (2004) 29, 502-513.
Linden et al. "Use of mGluR2 and mGluR3 knockout mice to explore in vivo receptor specificity of the mGluR2/3 selective agonist LY341495" Neuropharmacology 2009, vol. 57, pp. 172-182.
Linden et al. Comparison of c-Fos induction in the brain by the mGlu2/3 receptor antagonist LY341495 and agonist LY354740: evidence for widespread endogenous tone at brain mGlu2/3 receptors in vivo. Neuropharmacology 2005, 49 Suppl 1, 120-134.
Linden, "Anxiolytic-like activity of the mGLU2/3 receptor agonist LY354740 in the elevated plus maze test is disrupted in metabotropic glutamate receptor 2 and 3 knock-out mice," Psychopharmacol. 179: 284-291(2005).
Lindsley et al. "Progress Towards Validating the NMDA Receptor Hypofunction Hypothesis of Schizophrenia" Current Topics in Medicinal Chemistry, 2006, vol. 6, pp. 771-785.
Linn et al. Activation of metabotropic glutamate receptors modulates the voltage-gated sustained calcium current in a teleost horizontal cell. Journal of Neurophysiology 1999, 81 (2), 425-434.
Lipton, "Excitatory Amino Acids as a Final Common Pathway for Neurologic Disorders", Mechanisms of Disease, The New England Journal of Medicine, 1994, vol. 330 No. 9., pp. 613-622.
Lissin et al. An immunocytochemical assay for activity-dependent redistribution of glutamate receptors from the postsynaptic plasma membrane. Annals of the New York Academy of Sciences 1999, 868, 550-553.
Litman, "AZD8529, A positive allosteric modulator at the mGluR2 receptor, does not improve symptoms in schizophrenia: a proof of principle study" NCDEU: An Annual Meeting Sponsored by Am Soc. of Clin. Psychopharmacology, Poster and Abstract, 2013.
Liu et al. "A unified theory of two-stage adaptive designs" Theory and methods 2002, vol. 97, pp. 1034-1041.
Liu et al. "Doubly Randomized Delayed-Start Design for Enrichment Studies with Responders or Nonresponders" Journal of Biopharmaceutical Statistics 2012, vol. 22(4), pp. 737-757.
Liu et al. "Pharmacogenetic analysis of the mGlu2/3 agonist LY2140023 monohydrate in the treatment of schizophrenia" The Pharmacogenomics Journal 2010, pp. 1-9.
Liu et al., "Ischemic Insults Direct Glutamate Receptor Subunit 2-Lacking AMPA Receptors to Synaptic Sites", Journal of Neuroscience, May 17, 2006, 26(20), 5309-5319.
Lopez-Rodriguez et al. "Changes in extracellular glutamate levels in rat orbitofrontal cortext during sleep and wakefulness" Arch Med Res 2007, vol. 38, pp. 52-55.
Lorenzetti et al: Structural brain abnormalities in major depressive disorder: a selective review of recent MRI studies. J Affect Disord 2009, vol. 117(1-2), pp. 1-17.
Lorrain et al. "Group II mGlu Receptor Activation Suppresses Norepinephrine Release in the Ventral Hippocampus and Locomotor Responses to Acute Ketamine Challenge" Neuropsychopharmacology 2003, vol. 28, pp. 1622-1632.
Lou et al. "Allosteric modulation of the presynaptic Ca2+ sensor for vesicle fusion" Nature 2005, vol. 435, pp. 497-501.
Lowe et al. "Effects of a novel mGlu2/3 receptor agonist prodrug, LY2140023 monohydrate, on central monoamine turnover as determined in human and rat cerebrospinal fluid" Psychopharmacology 2011, EPUB, No Page Numbers, DOI 10.1007/s00213-011-2427-9.
Lowry et al. "Serotonergic Systems, Anxiety, and Affective Disorder: Focus on the Dorsomedial Part of the Dorsal Raphe Nucleus" Annals of the New York Academy of Sciences 2008, vol. 1148, pp. 86-94.
Lujan et al. "Glutamate and GABA receptor signalling in the developing brain" Neuroscience 2005, vol. 130, pp. 567-580.
Luscher et al. "Group I mGluR-dependent synaptic long-term depression: mechanisms and implications for circuitry and disease" Neuron 2010, vol. 65, pp. 445-459.
Lyon et al. "Altered Hippocampal Expression of Glutamate Receptors and Transporters in GRM2 and GRM3 Knockout Mice" Synapse 2008, vol. 62, pp. 842-850.

(56) References Cited

OTHER PUBLICATIONS

Lyon et al. "Fractionation of Spatial Memory in GRM2/3 (mGlu2/mGlu3) Double Knockout Mice Reveals a Role for Group II Metabotropic Glutamate Receptors at the Interface Between Arousal and Cognition" Neuropsychopharmacology 2011, pp. 1-13.
Macchiarulo et al. The role of electrostatic interaction in the molecular recognition of selective agonists to metabotropic glutamate receptors. Proteins. 50(4):609-19, 2003.
MacDonald "Positive Allosteric Modulation of mGluR2 Receptors in the treatment of CNS Disorders" Presentation slides, 3rd Symposium on GPCRs in Medicinal Chemistry, Oss, Netherlands, Sep. 2010.
MacDonald "The Design of Allosteric Modulators for the treatment of CNS disorders" 11th Advances and Progress in Drug Design, London, Feb. 21, 2012, Presentation slides.
MacDonald "The Design of mGluR Modulators for the treatment of CNS Disorders" Abstract, 2013 Anglo-Swedish Medicinal Chemistry Symposium, Stockholm.
MacDonald, "The Design of Mglur Modulators for the Treatment of CNS Disorders" Presentation Slides, 6.sup.th Anglo-Swedish Medicinal Chemistry Symposium, Stockholm, 19.sup.th Jun. 2013.
Macek et al. Differential involvement of group I and group III mGluRs as autoreceptors at lateral and medial perforant path synapses. J Neurophysiol. 1996, 76 (6), 3798-3806.
Macek et al., "Protein Kinase C and A3 Adenosine Receptor Activation Inhibit Presynaptic Metabotropic Glutamate Receptor (Mglur) Function and Uncouple Mglurs from Gtp-Binding Proteins", J. Neurosci., 1998, 18(16), 6138-6146.
Mackrill Protein-protein interactions in intracellular Ca2+-release channel function. [Review] [220 refs]. Biochemical Journal 1999, 337 (Pt 3), 345-361.
Maeda et al., "Different Roles of Group I and Group II Metabotropic Glutamate Receptors on Phencyclidine-Induced Dopamine Release in the Rat Prefrontal Cortex", Neuroscience Letters, 2003, 336 (3), 171-174.
Maeng, "Cellular mechanisms underlying the antidepressant effects of ketamine: role of alpha-amino-3-hydroxy-5-methylisoxazole-4-propionic acid receptors," Biol. Psychiatry 63: 349-352 (2008).
Malone et al., "Characterisation of Mglurs Which Modulate Nociception in the Pag of the Mouse", Neuropharmacology,1998, 37(12), 1475-1483.
Makoff et al., "Molecular Characterization and Localization of Human Metabotropic Glutamate Receptor Type 3", Molecular Brain Research, 1996, 40(1), 55-63.
Malames et al. "N-Substituted Spirosuccinimide, Spiropyridazine, Spiroazetidine, and Acetic Acid Aidose Reductase Inhibitiors Derived From Isoquinoline-1, 3-dinoes. 2", J Med Chem., 1994, 37(13), 2059-2070.
Malatynska et al. "Dominant-submissive behavior as models of mania and depression" Neuroscience and Biobehavioral Reviews 2005, vol. 29(4-5), pp. 715-737.
Malatynska et al. "Levels of mRNA for .alpha.-, .beta.-, and .gamma.-Synuclein in the brains of newborn, juvenile, and adult ratls" J Mol Neurosci. 2006, vol. 29(3), pp. 269-277.
Malatynska et al., "Assessing Activity Onset Time and Efficacy for Clinically Effective Antidepressant and Antimanic Drugs in Animal Models Based on Dominant-Submissive Relationships", Neuroscience and Biobehavioral Reviews, 2007, 31, 904-919.
Gonzalez-Maeso et al. Psychedelics and schizophrenia. Trends Neurosci. 2009, 32 (4), 225-232.
Gonzalez-Maeso Hallucinogens recruit specific cortical 5-HT2A receptor-mediated signaling pathways to affect behavior. Neuron 2007, 53, 439-452.
Gonzalez-Maeso Transcriptome fingerprints distinguish hallucinogenic and nonhallucinogenic 5-hydroxytryptamine 2A receptor agonist effects in mouse somatosensory cortex. J. Neurosci. 2003, 23, 8836-8843.
Goodman et al. The Yale-Brown Obsessive Compulsive Scale: I. Development, use, and reliability. Arch Gen Psychiatry. 1989;46(11):1006-1011.

Goodwin et al. Advantages and disadvantages of combination treatment with antipsychotics. ECNP Consensus Meeting, Mar. 2008. Nice. Eur Neuropsychoparmacol. 2009; 19(7):520-532.
Gorcs et al. Immunohistochemical visualization of a metabotropic glutamate receptor. Neuroreport 1993, 4 (3), 283-286.
Gorman "Comorbid Depression and Anxiety Spectrum Disorders" Depression and Anxiety 1996/1997, vol. 4, 160-168.
Gorman et al. "Anxiogenic effects of C02 and hyperventilation in patients with panic disorder" Am J Psychiatry 1994, vol. 151, pp. 547-553.
Gorman et al. A hypothesized role for dendritic remodeling in the etiology of mood and anxiety disorders. J Neuropsychiatry Clin Neurosci 2010 Summer; 22(3): 256-264.
Goudet et al. (2009) Metabotropic receptors for glutamate and GABA in pain. Brain Res. Rev.; 60 (1): 43-56.
Goudet et al. Asymmetric functioning of dimeric metabotropic glutamate receptors disclosed by positive allosteric modulators. J. Biol. Chem. 2005, 280 (26), 24380-24385.
Gouzoulis-Mayfrank Inhibition of return in the human 5HT2A agonist and NMDA antagonist model of psychosis. Neuropsychopharmacology 2006, 31, 431-441.
Gouzoulis-Mayfrank Psychological effects of (S)-ketamine and N,N-dimethyltryptamine (DMT): a double-blind, cross-over study in healthy volunteers. Pharmacopsychiatry 2005, 38, 301-311.
Govek et al. "Benzazoles as Allosteric Potentiators of Metabotropic Glutamate Receptor 2" 229th ACS National Meeting, San Diego, CA, United States, Mar. 13-17, 2005 (2005), MEDI-036.
Govek et al., "Benzazoles as allosteric potentiators of metabotropic glutamate receptor 2 (mGluR2): Efficacy in an animal model for schizophrenia", Bioorg. Med. Chem Lett., 2005, 15, 4068-4072.
Gozzi et al. "Differential Effects of Antipsychotic and Glutamatergic Agents on the phMRI Response to Phencyclidine" Neuropsychopharmacology 2008, vol. 33, pp. 1690-1703.
Gray et al. "Functionalisation of 2-Methoxy-6-Methylpyridine." Synthetic Communications. vol. 24 (10). 1994. 1367-79.
Gregory et al. "Allosteric modulation of metabotropic glutamate receptors: Structural insights and therapeutic potential" Neuropharmacology 2011, vol. 60, pp. 66-81.
Gregory et al. "Overview of Receptor allosterism" Current Protocols in Pharmacology 2010, 1.21.1-1.21.34.
Gregory et al. Prefrontal group II metabotropic glutamate receptor activation decreases performance on a working memory task. Ann N Y. Acad. Sci. 2003, 1003, 405-409.
Grillon et al., "Anxiolytic effects of a novel group II metabotropic glutamate receptor agonist (LY354740) in the fear-potentiated startle paradigm in humans", Psychopharmacology, 2003, 168, 446-454.
Groebe Screening for positive allosteric modulators of biological targets. Drug Discov. Today 2006, 11 (13-14), 632-639.
Grueter et al. Group II and III metabotropic glutamate receptors suppress excitatory synaptic transmission in the dorsolateral bed nucleus of the stria terminalis. Neuropsychopharmacology 2005, 30 (7), 1302-1311.
Gu et al. "Distribution of metabotropic glutamate 2 and 3 receptors in the rat forebrain: implications in emotional responses and central disinhibition" Brain Res 2008, vol. 1197, pp. 47-62.
Gu et al. Expression of functional metabotropic glutamate receptors in primary cultured rat osteoblasts. Cross-talk with N-methyl-D-aspartate receptors. J. Biol. Chem. 2000, 275 (44), 34252-34259.
Gueremy et al. 2-Amino-6-chloro-4-(N-methylpiperazino)pyrimidines, Inhibitors of Spiroperidol Binding. Journal of Medicinal Chemistry. vol. 25. 1982. 1459-65.
Guerineau et al. Activation of a nonselective cationic conductance by metabotropic glutamatergic and muscarinic agonists in CA3 pyramidal neurons of the rat hippocampus. J. Neurosci. 1995, 15 (6), 4395-4407.
Guerineau et al. G-protein-mediated desensitization of metabotropic glutamatergic and muscarinic responses in CA3 cells in rat hippocampus. Journal of Physiology 1997, 500 (Pt 2), 487-496.
Guimaraes et al. "Ritanserin facilitates anxiety in a simulated public-speaking paradigm" Journal of Psychopharmacology 1997, vol. 11 (3), pp. 225-231.

(56) References Cited

OTHER PUBLICATIONS

Gunduz-Bruce "The acute effects of NMDA antagonism: From the rodent to the human brain" Brain Res Rev 2009, vol. 60, pp. 279-286.
Gupta et al. Metabotropic glutamate receptor protein expression in the prefrontal cortex and striatum in schizophrenia. Synapse 2005, 57 (3), 123-131.
Gurevich et al. Alterations in the cortical serotonergic system in schizophrenia: a postmortem study. Biol. Psychiatry 1997, 42, 529-545.
Haak et al. Metabotropic glutamate receptor activation modulates kainate and serotonin calcium response in astrocytes. J. Neurosci. 1997, 17 (5), 1825-1837.
Hackler et al. Selective potentiation of the metabotropic glutamate receptor subtype 2 blocks phencyclidine-induced hyperlocomotion and brain activation. Neuroscience. 168(1):209-18, 2010.
Hamaguchi et al., "Effects of Hetero Atom Substituents in the decomposition of Pyrazolines: Abnormal Behavior of Methoxy Group Compared with Arylthio of Arylseleno Group.", Heterocycles, 986, vol. 24, 2111-2115.
Hamilton A rating scale for depression. J Neurol Neurosurg Psychiatry Feb. 1960; 23: 56-62.
Hamilton Diagnosis and rating of anxiety, in Studies of Anxiety , MM Lader, Ed., Meedley Bros., Kent, 1969, pp. 76-79.
Hamilton Standardised assessment and recording of depressive symptoms. Psychiatr Neurol Neurochir Mar.-Apr. 1969; 72(2): 201-205.
Hamilton The assessment of anxiety states by rating. Br J Med Psychol 1959; 32(1): 50-55.
Hampson et al. Characterization of two alternatively spliced forms of a metabotropic glutamate receptor in the central nervous system of the rat. Neuroscience. 1994, 60 (2), 325-336.
Handley et al. Effects of alpha-adrenoceptor agonists and antagonists in a maze-exploration model of fear-motivated behavior. Naunyn-Schmied. Arch. Pharmacol., 327, 1-5, 1984.
Hanfeld et al., "Synthese von 3-Cyan-6-methyl-4pyridyl-und 3-Cyan-4-methyl-6-pyridyl-pyrid-2(1FI)-onen und-thionen", 1988, 43, 762-764.
Hanna et al. "Differentiating the roles of mGlu2 and mGlu3 receptors using LY541850, an mGlu2 agonist/mGlu3 antagonist" Neuropharmacology 2012, epub, no page numbers, doi:10.1016 1j.neuropharm.2012.02.023.
Hannah et al. "Heterocomplex formation of 5-HT2A-mGlu2 and its relevance for cellular signaling Cascades" Neuropharmacology 2012, vol. 62, pp. 2184-2191.
Hansen et al. Glutamate joins the ranks of immunomodulators. Nature Medicine. 16(8):856-8, 2010.
Happe et al. "Agonist-stimulated [35S]GTPgammaS autoradiograph: optimization for high sensitivity" Eur J Pharmacol 2001, vol. 422, pp. 1-13.
Harald et al. "Meta-review of depressive subtyping models" Journal of Affective Disorders 2012, 139, 126-140.
Harich, "Stimulation of the metabotropic glutamate 2/3 receptor attenuates social novelty discrimination deficits induced by neonatal phencyclidine treatment", Psychopharmacology, 2007,192, pp. 511-519.
Hard et al. The Clinical Global Impression—Schizophrenia scale: a simple instrument to measure the diversity of symptoms present in schizophrenia. Acta Psychiatr Scand Suppl. 2003;(416):16-23.
Harper et al., "Agonist-Stimulated [35S]GTPyS Binding", Current Protocols in Pharmacology, 1998, 2.6.1-2.6.10, John Wiley & Sons.
European Patent Application No. 07726932.2: Office Action dated Sep. 8, 2009, 10 pages.
European Patent Application No. 08717514.7: Office Action dated Jun. 28, 2010, 6 pages.
European Patent Application No. 08717515.4: Official Communication dated May 3, 2010, 5 pages.
European Patent Application No. 11181481.1: Office Action dated Dec. 6, 2012, 6 pages.
European Patent Application No. EP 08166832: Search Report dated May 8, 2009, 5 pages.
Ezquerra et al. "Efficient Reagents for the synthesis of 5-, 7-, and 5,7-substituted indoles starting from aromatic amines: scopes and limitations" J Org Chem 1996, vol. 61, pp. 5804-5812.
Fagni et al. Identification and functional roles of metabotropic glutamate receptor-interacting proteins. [Review] [91 refs]. Seminars in Cell & Developmental Biology. 15(3):289-98, 2004.
Farabaugh et al. "Anxious Depression and early changes in the HAMD-17 anxietysomatization factor items and antidepressant treatment outcome" Int Clin Psychopharmacol. Jul. 2010; 25(4): 214-217.
Faries et al. "The double-blind variable placebo lead-in period: results from two antidepressant clinical trials" Journal of Clinical Psychopharmacology 2001, vol. 21, pp. 561-568.
Fava et al. "Difference in Treatment Outcome in Outpatients With Anxious Versus Nonanxious Depression: A Star D Report" Am J Psychiatry 2008; 165:342-351.
Fava et al. "The Efficacy and Tolerability of Duloxetine in the Treatment of Anxious Versus Non-Anxious Depression: A Post-Hoc Analysis of an Open-Label Outpatient Study" Annals of clinical Psychiatry 2007, vol. 19(3), 187-195.
Fava et al. "The problem of the placebo response in clinical trials for psychiatric disorders: culprits, possible remedies, and a novel study design approach" Psychother Psychosom 2003, vol. 72, pp. 115-127.
Fava et al. Data Supplement for "Difference in Treatment Outcome in Outpatients With Anxious Versus Nonanxious Depression: A STAR*D Report" American Journal of Psychiatry, Mar. 2008 (data supplement, no page numbers available).
Fava et al. Reliability and validity of the Massachusetts General Hospital Cognitive and Physical Functioning Questionnaire. Psychother Psychosom 2009; 78(2):91-97.
Fava et al. What clinical and symptom features and comorbid disorders characterize outpatients with anxious major depressive disorder a replication and extension. Can J Psychiatry Nov. 2006; 51(13): 823-835.
Fava et al., "Anxiety Disorders in Major Depression" Comprehensive Psychiatry 2000, 41(2), 97-102.
Fava et al., "Clinical Correlates and Symptom Patterns of Anxious Depression Among Patients with Major Depressive Disorder in Star*D", Psychological Medicine, 2004, 34, 1299-1308.
Fava et al., "Major Depressive Subtypes and Treatment Response", Biol. Psychiatry, 1997, 42, 568-576.
Fawcett "Treating Impulsivity and Anxiety in the Suicidal Patient" Ann N Y Acad Sci. Apr. 2001; 932:94-102; discussion 102-5.
Fawcett et al. Anxiety syndromes and their relationship to depressive illness. J Clin Psychiatry Aug. 1983; 44(8 pt 2): 8-11.
Fawcett et al., "The Detection and Consequences of Anxiety in Clinical Depression", J Clin Psychiatry, 1997, 58(Suppl 8), 35-40.
FDA Center for Drug Evaluation and Research, "Introduction and Drug History", 2003, NDA 21-487, Pharmacology Reviews, p. ix.
Feeley et al., "Mglurs: A Target for Pharmacotherapy in Parkinson Disease", Experimental Neurology, 2003, 184(Supp1-6), S30-S36.
Feenstra et al., "Local Activation of Metabotropic Glutamate Receptors Inhibits the Handling-Induced Increased Release of Dopamine in the Nucleus Accumbens but Not That of Dopamine or Noradrenaline in the Prefrontal Cortex: Comparison with Inhibition of Ionotropic Receptors", Journal of Neurochemistry, 1998, 70(3), 1104-1113.
Feinberg et al, "The selective group mGlu 2/3 receptor agonist LY379268 suppresses REM sleep and fast EEG in the rat," Pharmacology, Biochemistry and Behavior 73 (2002) 467-474.
Feinberg et al. "The Metabotropic Glutamate (mGLU)2/3 Receptor Antagonist LY341495 [25-2-Amino-2-(1S,2S-2-carboxycyclopropyl-I-yl)-3-(xanth-9-yl)pr- opanoic Acid] Stimulates Waking and Fast Electroencephalogram Power and Blocks the Effects of the mGLU2/3 Receptor Agonist LY379268 [(−)-2-Oxa-4-aminobicyclo[3.1.0]hexane-4,6-dicarboxylate] in Rats" JPET 2005, vol. 312, pp. 826-833.
Fell et al. "Activation of metabotropic glutamate (mGlu)2 receptors suppresses histamine release in limbic brain regions following acute ketamine challenge" Neuropharmacology 2010, vol. 58, pp. 632-639.

(56) References Cited

OTHER PUBLICATIONS

Fell et al. "Evidence for the role of mGlu2 not mGlu3 receptors in the preclinical antipsychotic pharmacology of the mGlu2/3 receptor agonist LY404039" Journal of Pharmacology & Experimental Therapeutics 2008, vol. 326, pp. 209-217.
Fell et al. "Group II metabotropic glutamate receptor agonists and positive allosteric modulators as novel treatments for schizophrenia" Neuropharmacology 2011, xxx, 1-11 epub, no page numbers, doi: doi:10.1016/j.neuropharm.2011.06.007.
Fell et al. "In Vitro and in Vivo Evidence for a Lack of Interaction with Dopamine D2 Receptors by the Metabotropic Glutamate 2/3 Receptor Agonists 1S,2S,5R,65-2-Aminobicyclo[3.1.0]hexane-2,6-bicaroxylate Monohydrate (LY354740) and (−)-2-Oxa-4-aminobicyclo[3.1.0] Hexane-4,6-dicarboxylic Acid (LY379268)" JPET 2009, vol. 331, pp. 1126-1136.
Fell et al. "N-(4-((2-(trifluoromethyl)-3-hydroxy-4-(isobutyryl)phenoxy)methyl)benzy1-)-1-methyl-1H-imidazole-4-carboxamide (THIIC), a Novel Metabotropic Glutamate 2 Potentiator with Potential Anxiolytic/Antidepressant Properties: In Vivo Profiling Suggests a Link between Behavioral and Central Nervous System Neurochemical Changes" JPET 2011, vol. 336, pp. 165-177.
Fell et al. "N-(44(2-(trifluoromethyl)-3-hydroxy-4-(isobutyryl)phenoxy)methyl)benzy1)-1-methyl-1H-imidazole-4-carboxamide (THIIC), a novel mGlu2 potentiator with potential anxiolytic/antidepressant properties: in vivo profiling suggests a link between behavioral and CNS neurochemical changes" JPET Fast Forward. Published on Oct. 14, 2010 as Epub, No Page Numbers, DOI:10.1124/jpet.110.172957.
Fendt et al., "Metabotropic Glutamate Receptors are Involved in Amygdaloid Plasticity", European Journal of Neuroscience, 2002, 15(9), 1535-1541.
Fenton et al. "The Role of a Prescription in Anxiety Medication Use, Abuse, and Dependence" Am J Psychiatry 2010, vol. 167, pp. 1247-1253.
Ferraguti et al. "Metabotropic Glutamate 1 Receptor: Current Concepts and Perspectives" Pharmacol Rev 2008, vol. 60, pp. 536-581.
Ferraguti et al. "Metabotropic glutamate receptors" Cell Tissue Res 2006, vol. 326, pp. 483-504.
Ferraguti et al., "Activation of the Extracellular Signal-Regulated Kinase 2 by Metabotropic Glutamate Receptors", European Journal of Neuroscience, 1999, 11(6), 2073-2082.
Ferris et al. "Interactions between LY354740, a group II metabotropic agonist and the GABAA-benzodiazepine receptor complex in the rat elevated plus-maze" J Psychopharmacol 2001, vol. 15, pp. 76-82.
Feyissa et al., "Elevated Level of Metabotropic Glutamate Receptor 2/3 in the Prefrontal Cortex in Major Depression", Prog. Neuropsychopharmacol. Biol. Psychiatry, 2010, 34(2), 279-283.
File "The use of social interaction as a method for detecting anxiolytic activity of chlordiazepoxide-like drugs" Journal of Neuroscience Methods (1980), 2(3), 219-38. CODEN: JNMEDT ISSN:0165-0270.
Filinger Effect of a Reserpine-like Agent on the Release and Metabolism of [3H]NA in Cell Bodies and Terminals, Gen. Pharmac., 25:1039-1043 (1994).
Fiorella et al. The role of the 5-HT2A and 5-HT2c receptors in the stimulus effects of hallucinogenic drugs I: Antagonist correlation analysis, Psychopharmacology, 121:347-356 (1995).
Fisher et al. "Non-Peptide RGD Surrogates Which Mimic a Gly-Asp B-Turn: Potent Antagonists of Platelet Glycoprotein IIb-IIIa." J. Med. Chem. 1997. vol. 40. 2085-101.
Fisher et al. "Antinociceptive effects following intrathecal pretreatment with selective metabotropic glutamate receptor compounds in a rat model of neuropathic pain" Pharmacology, Biochemistry and Behavior 2002, vol. 73, pp. 411-418.
Fisher et al. Intrathecal administration of the mGluR compound, (S)-4CPG, attenuates hyperalgesia and allodynia associated with sciatic nerve constriction injury in rats. Pain 1998, 77 (1), 59-66.

Fisher et al. The contribution of metabotropic glutamate receptors (mGluRs) to formalin-induced nociception. Pain 1996, 68 (2-3), 255-263.
Flint et al. Anxious depression in elderly patients: response to antidepressant treatment. Am J Geriatr Psychiatry 1997 Spring; 5(2): 107-115.
Flohr et al. "Poly(ADP-ribosyl)ation accelerates DNA repair in a pathway dependent on Cockayne syndrome B protein." Nucleic Acids Research. vol. 31 (18). 2003. 5332-7.
Flor et al. "Molecular cloning, functional expression and pharmacological characterization of the human metabotropic glutamate receptor type 2" Eur J Neurosci 1995, vol. 7, pp. 622-629.
Fonnum et al. Role of glutamate and glutamate receptors in memory function and Alzheimer's disease. Annals of the New York Academy of Sciences 1995, 757, 475-486.
Canadian Patent Application No. 2,581,144: Office Action dated May 13, 2009, 5 pages.
Caraci et al. "Targeting Group II Metabotropic Glutamate (mGlu) Receptors for the Treatment of Psychosis Associated with Alzheimer's Disease: Selective Activation of mGlu2 Receptors Amplifies p-Amyloid Toxicity in Cultured Neurons, Whereas Dual Activation of mGlu2 and mGlu3 Receptors Is Neuroprotective" Mol Pharmacol 2011, vol. 79, pp. 618-626.
Caraci et al. Metabotropic glutamate receptors in neurodegeneration/neuroprotection: still a hot topic?. [Review]. Neurochemistry International 2012, 61 (4), 559-565.
Carlsson et al. Neurotransmitter aberrations in schizophrenia: new perspectives and therapeutic implications. [Review] [67 refs]. Life Sciences 1997, 61 (2), 75-94.
Carlsson, "The Neurochemical Circuitry of Schizophrenia", Pharmacopsychiatry, 2006, 39, S10-314.
Carter, "Schizophrenia Susceptibility Genes Converge on Interlinked Pathways Related to Glutamatergic. Transmission and Long-Term Potentiation, Oxidative Stress and Oligodendrocyte Viability", Schizophr. Res., 2006, 86(1-3), 1-14.
Cartmell et al. "Attenuation of specific PCP-evoked behaviors by the potent mGlu213 receptor agonist, LY379268 and comparison with the atypical antipsychotic, clozapine" Psychopharmacology 2000, vol. 148, pp. 423-429.
Cartmell et al. "Characterization of [3H]-(2S,2'R,3'RO-2-(2,3,-dicarboxycyclopropyl)glycine ([3H]-DCG IV) binding to metabotropic mGlu2 receptor-transfected cell membranes." British Journal of Pharmacology. vol. 123. 1998. 497-504.
Cartmell et al. "The metabotropic glutamate 2/3 receptor agonists LY354740 and Ly379268 selectively attenuate phencyclidine versus d-amphetamine motor behavior in rats" J Pharmacol Exp Ther 1999, vol. 291, pp. 161-170.
Cartmell et al. Acute increases in monoamine release in the rat prefrontal cortex by the mG1u213 agonist LY379268 are similar in profile to risperidone, not locally mediated, and can be elicited in the presence of uptake blockade. Neuropharmacology 2001, 40 (7), 847-855.
Cartmell et al. The potent, selective mGlu213 receptor agonist LY379268 increases extracellular levels of dopamine, 3,4-dihydroxyphenylacetic acid, homovanillic acid, and 5-hydroxyindole-3-acetic acid in the medial prefrontal cortex of the freely moving rat. J Neurochem. 2000, 75 (3), 1147-1154.
Cartmell et al., "Dopamine and 5-Ht Turnover are Increased by the Mglu2/3 Receptor Agonist Ly379268 in Rat Medial Prefrontal Cortex, Nucleus Accumbens and Striatum", Brain Res., 2000, 887(2), 378-384.
Cartmell et al., "Effect of Metabotropic Glutamate Receptor Activation on Receptor-Mediated Cyclic Amp Responses in Primary Cultures of Rat Striatal Neurones", Brain Res., 1998, 791(1-2), 191-199.
Cartmell et al., "Regulation of Neurotransmitter Release by Metabotropic Glutamate Receptors", J. Neurochem., 2000, vol. 75, No. 3, 889-907.
Cartmell et al., "The Mglu(2/3) Receptor Agonist Ly379268 Selectively Blocks Amphetamine Ambulations and Rearing", Eur. J Pharmacol., 2000, 400(2-3), 221-224.
Cartmell et al., "Tolerance to the Motor Impairment, But Not the Reversal of PCP-Induced Motor Activities by Oral Administration

(56) References Cited

OTHER PUBLICATIONS of the Mglu2/3 Receptor Agonist, Ly379268", Naunyn Schmiedebergs Arch Pharmacol, 2000, 361, 39-46.
Casado et al. "GPCR homomers and heteromers: A better choice as targets for drug development than GPCR monomers?" Pharmacology & Therapeutics 2009, vol. 124, pp. 248-257.
Castagne et al., "Preclinical Behavioral Models for Predicting Antipsychotic Activity", Adv. Pharmacol., 2009, 57, 381-418.
Catania et al. Homologous desensitization of metabolotropic glutamate receptors in neuronal cultures. Pharmacological Research 1990, 22, Suppl 1, pp. 79-80.
Catania et al., "Desensitization of Metabotropic Glutamate Receptors in Neuronal Cultures", Journal of Neurochemistry, 1991, 56(4), 1329-1335.
Catania et al., "Group I Metabotropic Glutamate Receptors: A Role in Neurodevelopmental Disorders?", Mol Neurobiol, 2007, 35, 298-307.
Catania et al., "Metabotropic Glutamate Receptor Heterogeneity in Rat Brain", Molecular Pharmacology, 1994, 45(4), 626-636.
Catania et al., "Metabotropic Glutamate Receptors are Differentially Regulated During Development", Neuroscience, 1994, 61(3), 481-495.
Catterall Structure and function of neuronal Ca2+ channels and their role in neurotransmitter release. [Review] [151 refs]. Cell Calcium 1998, 24 (5-6), 307-323.
Cavalli et al. "Multi-target-Directed Ligands to Combat Neurodegenerative Diseases" J. Med. Chem. 2008, xxx, 000-000 Published on Web Jan. 9, 2008 (epub, no page numbers, doi: 10.1021/jm7009364).
Cavanni et al., "Pharmacological Analysis of Carboxyphenylglycines at Metabotropic Glutamate Receptors", European Journal of Pharmacology, 1994, 269(1), 9-15.
Celanire et al., "Recent Advances in the Drug Discovery of Metabotropic Glutamate Receptor 4 (mGluR4) Activators for the Treatment of CNS and Non-CNS Disorders", Expert Opin. Drug Discovery, 2012, 7(3), 261-280.
Celanire et al., Annual Reports in Medicinal Chemistry 2012, 47, 71-88.
Chaki "Group II metabotropic glutamate receptor agonists as a potential drug for schizophrenia" European Journal of Pharmacology 2010, vol. 639, pp. 59-66.
Chaki et al Anxiolytic- and antidepressant-like profile of a new CRF1 receptor antagonist, R278995/CRA0450. Eur J Pharmacol 485:145-158, 2004.
Chaki et al. "mGlu2/3 and mGlu5 receptors: Potential targets for novel antidepressants" Neuropharmacology 2013, vol. 66, pp. 40-52.
Chaki et al., "Targeting of Metabotropic Glutamate Receptors for the Treatment of Schizophrenia", Current Pharmaceutical Design, 2011, 17, 94-102.
Chakos et al. Baseline use of concomitant psychotropic medications to treat schizophrenia in the Catie trial. Psychiatr Serv. Aug. 2006; 57(8):1094-101.
Chakrabarty et al., "Glutamatergic Dysfunction in OCD", Neuropsychopharmacology, 2005, 30(9), 1735-1740.
Chakrasali et al. "Reaction of Acylketene S,N-Acetals with Malonyl Chloride: Synthesis of Novel 1,5-Substituted 4-Hydroxy-6-methylthio-2 (IH)-pyridones and 6,8-Substituted 4-Hydroxy-7-methylthio-2,5-dioxo-5,6-dihydro-2H-pyrano [3,2-c] pyridines." Jan. 1988. 87-9.
Charney et al. "Increased Anxiogenic effects of caffeine in panic disorders" Arch Gen Psychiatry 1985, vol. 42, pp. 233-243.
Charney et al. "Life Stress, Genes, and Depression: Multiple Pathways Lead to Increased Risk and New Opportunities for Intervention" Science's STKE: signal transduction knowledge environment 2004 (225), re5.
Charney et al. "Noradrenergic function in panic anxiety. Effects of Yohimbine in healthy subjects and patients with agoraphobia and panic disorder" Arch. Gen. Psychiatry 1984, vol. 41, pp. 751-763.
Chaudhari et al. "A metabotropic glutamate receptor variant functions as a taste receptor" Nature Neuroscience 2000, vol. 3, pp. 113-119.

Chavez-Noriega et al. Metabotropic glutamate receptors: potential drug targets for the treatment of schizophrenia. [Review] [267 refs]. Current Drug Targets—CNS & Neurological Disorders. 1(3):261-81, 2002.
Chavis et al., "Facilitatory Coupling Between a Glutamate Metabotropic Receptor and Dihydropyridine-Sensitive Calcium Channels in Cultured Cerebellar Granule Cells", J. Neurosci., 1995, 15(1), 135-143.
Chavis et al., "Modulation of Calcium Channels by Metabotropic Glutamate Receptors in Cerebellar Granule Cells", Neuropharmacology, 1995, 34(8), 929-937.
Chen et al., "Second-generation antipsychotics in major depressive disorder: update and clinical perspective", Curr Opin Psychiatry, 2011, vol. 24, 10-17.
Chen, "The chemical biology of clinically tolerated NMDA receptor antagonists", Journal of Neurochemistry, 2006, 97, 1611-1626.
Chiarugi et al. "Novel Isoquinolinone-Derived Inhibitors of Poly(ADP-ribose) Polymerase-1: Pharmacological Characterization and Neuroprotective Effects in an in Vitro Model of Cerebral Ischemia." Journal of Pharmacology and Experimental Therapeutics. vol. 305 (3). 2003. 943-9.
Chiechio et al. "Metabotropic glutamate receptors and the control of chronic pain" Curr Opin Pharmacol 2012, vol. 12, pp. 28-34.
Chiechio et al. Transcriptional regulation of type-2 metabotropic glutamate receptors: an epigenetic path to novel treatments for chronic pain. Trends in Pharmacological Sciences. 31(4):153-60, 2010.
Chiechio et al., "Epigenetic Modulation of Mglu2 Receptors by Histone Deacetylase Inhibitors in the Treatment of Inflammatory Pain", Mol. Pharmacol., 2009, 75(5), 1014-1020.
Chilean Patent Application No. 671-2008: Office Action dated Oct. 29, 2010, 9 pages.
Chilean Patent Application No. 681-2007: Office Action dated Jan. 11, 2011, 6 pages.
Chin et al. "Awake Rat Pharmacological Magnetic Resonance Imaging as a Translational Pharmacodynamic Biomarker: Metabotropic Glutamate 2/3 Agonist Modulation of Ketamine-Induced Blood Oxygenation Level Dependence Signals" JPET 2011, vol. 336, pp. 709-715.
Chin et al. "Awake Rat Pharmacological MRI as a Translational Pharmacodynamic Biomarker: mGluR2/3 Agonist Modulation of Ketamine-induced Bold Signals" JPET Fast Forward. Published on Dec. 20, 2010 as EPUB, No Page Numbers, DOI:10.1124/jpet.110.173880.
Chin et al., "Amyloid Beta Protein Modulates Glutamate-Mediated Neurotransmission in the Rat Basal Forebrain: Involvement of Presynaptic Neuronal Nicotinic Acetylcholine and Metabotropic Glutamate Receptors", J. Neurosci., 2007, 27(35), 9262-9269.
Chinese Patent Application No. 2007800092105: Office Action dated Jun. 19, 2012, 4 pages.
Chinese Patent Application No. 200880107135.0: Office Action dated Jul. 4, 2012, 4 pages.
Choi Methods for antagonizing glutamate neurotoxicity. [Review] [343 refs]. Cerebrovascular & Brain Metabolism Reviews 1990, 2 (2), 105-147.
Chojnacka-Wojcik et al. "Glutamate receptor ligands as anxiolytics" Current Opinion in Investigational Drugs 2001, vol. 2(8), pp. 1112-1119.
Christopolous et al. "G Protein-Coupled Receptor Allosterism and Complexing" Pharmacol Rev 2002, vol. 54, pp. 323-374.
Chrostopoulos., "Allosteric Binding Sites on Cell-Sturcture Receptors: Novel Targets for Drug Discovery", Nature Rev., Mar. 2002, 1, 198-210.
Cid "Discovery of a potent and orally bioavailable Positive Allosteric Modulator of mGluR2 for the treatment of CNS disorders" Presentation slides, 16th SCI/RSC Medicinal Chemistry Symposium, Cambridge, Sep. 2011.
Cid "JNJ-42153605: A Novel Positive Allosteric Modulator of mGluR2 for the Treatment of CNS disorders" Presentation slides, RICT 2012—48th International Conference on Medicinal Chemistry, Poitiers 2012.
Cid et al. "Discovery of 1,4-Disubstituted 3-Cyano-2-pyridones: A New Class of Positive Allosteric Modulators of the Metabotropic Glutamate 2 Receptor" J Med Chem 2012, vol. 55, pp. 2388-2405.

(56) References Cited

OTHER PUBLICATIONS

Cid et al. Discovery of 1,5-Distributed Pyridones: A New Class of Positive Allosteric Modulators of the Metabotropic Glutamate 2 Receptor' ACS Chem Neurosci 2010, vol. 1, pp. 788-795.
Cid et al. "Discovery of 3.cndot.Cyclopropylmethy1-7-(4-phenylpiperidin-1-y1)-8-trifluoromethyl[1,-2,4]triazolo[4,3.cndot.A]pyridine (JNJ-42153605): A Positive Allosteric Modulator of the Metabotropic Glutamate 2 Receptor" J Med Chem 2012, vol. 55, pp. 8770-8789.
Citrome "Adjunctive Aripiprazole, Olanzapine, or Quetiapine for Major Depressive Disorder: An Analysis of Number Needed to Treat, Number Needed to Harm, and Likelihood to be Helped or Harmed" Postgraduate Medicine 2010, vol. 122 (4), pp. 39-48.
Clark et al. Effects of the mGlu2/3 receptor agonist LY379268 on motor activity in phencyclidine-sensitized rats. Pharmacol. Biochem. Behay. 2002, 73 (2), 339-346.
Clark et al., "Synthesis of Thieno[2,3-dJpyrimidines from 4,6-Dichloropyrimidine-5-carbaldehydes", Journal Heterocyclic Chem, 1993, vol. 30, 1065-1072.
Clarke, "Tripartite model of anxiety and depression: psychometric evidence and taxonomic implications" J. Abnormal Psych. 100(3):316-336 (1991).
Clayton et al. "Follow-Up and Family Study of Anxious Depression" Am J Psychiatry 1991, vol. 148, pp. 1512-1517.
Cleary et al. "Factor Analysis of the Hamilton Depression Scale" Drugs Exptl Clin Res 1977, vol. 1 (1-2), pp. 115-120.
Clements et al., "The Time Course of Glutamate in the Synaptic Cleft", Science, 1992, 258(5087), 1498-1501.
Cleve et al., "Positive Allosteric Modulators of Type 5 Metabotropic Glutamate Receptors (mGluR5) and their Therapeutic Potential for the Treatment of CNS Disorders", Molecules, 2011, 16, 2097-2106.
Clinical Trials, "A Dose-Ranging Study of JNJ-40411813 in Healthy Male Volunteers", Available from http://clinicaltrials.gov/show/NCT01358006, retrieved on Aug. 1, 2013.
Clinical Trials, "A Study of JNJ-40411813 as Supplementary Treatment to an Antidepressant in Adults with Depression and Anxiety Symptoms", Available from: http://clinicaltrials.gov/show/NCT01582815, retrieved on Aug. 1, 2013.
Clinical Trials, "AZD8529 Single Ascending Dose Study (Sad)", Clinicaltrials.Gov. No. NCT00755378, Available From: Http://Clinicaltrials.Gov/Show/Nct00755378, retrieved on Aug. 22, 2013.
Clinical Trials, "First-In-Patient Study to Assess the Safety and Tolerability and to Explore the Potential Therapeutic Efficacy of a Novel Glutamate Modulator as Monotherapy and as Add-On Therapy in Patients with Schizophrenia", Available From: Https:/Www.Clinicaltrialsregister.Eu-Eudract No. 2010-023369-23, retrieved on Aug. 1, 2013.
Clinical Trials, "Investigation of the Safety, Tolerability and Potential Therapeutic Effects of JNJ-40411813 in Patients with Schizophrenia", Clinicaltrials Gov. No. NCT01323205, Available From: Http://Clinicaltrials.Gov/Show/NCT01323205, Retrieved Aug. 1, 2013.
Clinical Trials, "Ketamine Challenge Study with JNJ-40411813", Clinical Trials. Gov No. NCT01101659, Available From: Http://Clinicaltrials.Gov/Ct2/Show/Nct01101659, 2010, 3 pages.
Clinical Trials, "Study to Assess the Efficacy, Safety, and Tolerability of AZD8529 in Adult Schizophrenia Patients", Clinicaltrials.Gov. No. NCT00921804, Available From: Http://Clinicaltrials.Gov/Show/Nct00921804, Retrieved Aug. 23, 2013, 3 pages.
Clinical Trials, "The Effects Azd8529 on Cognition and Negative Symptoms in Schizophrenics", Clinicaltrials.Gov. No. NCT00986531, Available From: Http://Clinicaltrials.Gov/Show/Nct00986531, retrieved on Aug. 23, 2013, 2 pages.
Clinicaltrials.Gov.sub.—Nct00755378, "Azd8529 Single Ascending Dose Study (Sad)". Clinicaltrials.Gov. Available From: Http://Clinicaltrials.Gov/Show/Nct00755378, Retrieved Aug. 22, 2013.
Clinicaltrials.gov.sub.—NCT00921804, "Study to assess the efficacy, safety, and tolerability of AZD8529 in adult schizophrenia patients". ClinicalTrials.gov. Available from: http://clinicaltrials.gov/show/NCT00921804, retrieved Aug. 23, 2013.

Clinicaltrials.gov.sub.—NCT00986531, "The effects AZD8529 on cognition and negative symptoms in schizophrenics". Available from: http://clinicaltrials.gov/show/NCT00986531, retrieved Aug. 23, 2013.
Cloninger et al., "The Empirical Structure of Psychiatric Comorbidity and its Theoretical Significance", Comorbidity of Mood and Anxiety Disorders, 1990, 439-462.
Cohen et al. A global measure of perceived stress. J Health Soc Behav Dec. 1983; 24(4): 385-396.
Colangelo et al. "Differential effects of acute administration of clozapine or haloperidol on local cerebral glucose utilization in the rat" Brain Research 1997, vol. 768, pp. 273-278.
Collingridge et al. Excitatory amino acid receptors and synaptic plasticity. [Review] [38 refs]. Trends in Pharmacological Sciences 1990, 11 (7), 290-296.
Collins et al. From ligand binding to gene expression: new insights into the regulation of G-protein-coupled receptors. [Review] [25 refs]. Trends in Biochemical Sciences 1992, 17 (1), 37-39.
Collins et al., "Arachidonic Acid Metabolites and the Synaptic Potentiation Evoked by Activation of Metabotropic Glutamate Receptors", European Journal of Pharmacology, 1998, 342(2-3), 213-216.
Colpaert et al. A Critical Study on RO-4-1284 Antagonism in Mice, Arch. Int. Pharmacodyn., 215:40-90 (1975).
Colzi et al. Monoamine Oxidase—A Inhibitors and Dopamine Metabolism in Rat Caudatus: Evidence That an Increased Cytosolic Level of Dopamine Displaces Reversible Monoamine Oxidase-A Inhibitors in Vivo, J. Pharmacol. Exper. Therapeutics, 265:103-111 (1993).
Comins et al. "N-vs. O-Alkylation in the Mitsunobu Reaction of 2-Pyridone." Tetrahedron Letters. vol. 35 (18). 1994. 2819-22.
Committee for Proprietary Medicinal Products (CPMP), European Agency for the Evaluation of Medicinal Products; meeting Feb. 26, 1998, London (UK): Note for guidance on the clinical investigation of medicinal products in the treatment of schizophrenia, 10pp.
Conigrave et al. Allosteric activation of plasma membrane receptors—physiological implications and structural origins. [Review] [81 refs]. Progress in Biophysics & Molecular Biology. 81(3):219-40, 2003.
Conn et al. "Allosteric modulators of GPCRs: a novel approach for the treatment of CNS disorders" Nature Reviews Drug Discovery 2009, vol. 8, pp. 41-54.
Conn et al. "Metabotropic Glutamate Receptors in the Basal Ganglia Motor Circuit" Nature Reviews Neuroscience 2005, vol. 6, pp. 787-798.
Conn et al. "Pharmacology and Functions of Metabotropic Glutamate Receptors" Annu Rev Pharmacol Toxicol 1997, vol. 37, pp. 205-237.
Conn, P.J. "Activation of metabotropic glutamate receptors as a novel approach for the treatment of schizophrenia." Trends in Pharmacological Sciences 2008 vol. 30 No. 1 25-31.
Conn. Physiological roles and therapeutic potential of metabotropic glutamate receptors. [Review] [26 refs]. Annals of the New York Academy of Sciences. 1003:12-21, 2003.
Connoly et al. "If at First You Don't Succeed: A Review of the Evidence for Antidepressant Augmentation, Combination and Switching Strategies" Drugs 2011, vol. 71(1), 43-64.
Uher et al., "Melancholic, Atypical and Anxious Depression Subtypes and Outcome of Treatment with Escitalopram and Nortriptyline", Journal of Affective Disorders, 2011, 132, 112-120.
Um et al. "Alzheimer amyloid-.beta. oligomer bound to postsynaptic prion protein activates Fyn to impair neurons" Nature Neuroscience 2012, vol. 15(9), pp. 1227-1235.
Undine et al. "Molecular Mechanisms of Schizophrenia" Cell Physiol Biochem 2007, vol. 20, pp. 687-702.
Ung et al., "Synthesis and Biological Activities of Conformationally Restricted Cyclopentenyl-Glutamate Analogues", Journal of Organic Chemistry, 2002, 67(1), 227-233.
Upton, "Excitatory Amino Acids as a Final Common Pathway for Neurologic Disorders", Mechanisms of Disease, The New England Journal of Medicine, 1994, vol. 330 No. 9., pp. 613-622.

(56) References Cited

OTHER PUBLICATIONS

Urwyler "Allosteric modulation of family C G-protein-coupled receptors from molecular insights to therapeutic perspectives" Pharmacol Rev 2011, vol. 63, pp. 59-126.

Uslaner et al. Combined administration of an mGlu2/3 receptor agonist and a 5-HT 2A receptor antagonist markedly attenuate the psychomotor-activating and neurochemical effects of psychostimulants. Psychopharmacology (Berl) 2009, 206 (4), 641-651.

Uys et al. "Glutamate: The New Frontier in Pharmacotherapy for Cocaine Addiction" CNS & Neurological Disorders—Drug Targets, 2008, vol. 7, pp. 482-491.

Vaccarino et al., "Symptoms of Anxiety in Depression: Assessment of Item Performance of the Hamilton Anxiety Rating Scale in Patients with Depression", Depression and Anxiety, 2008, 25, 1006-1013.

Valentine et al., "Targeting Glial Physiology and Glutamate Cycling in the Treatment of Depression", Biochem. Pharmacol., 2009, 78(5), 431-439.

Vales et al. "The difference in effect of mG1u2/3 and mGlu5 receptor agonists on cognitive impairment induced by MK-801" European Journal of Pharmacology 2010, vol. 639, pp. 91-98.

Valproate Information available from http://www.fda.gov/Drugs/DrugSafety/PostmarketDrugSafetyInformationforPatientsandProviders/ucm192645.htm (2011).

Van Berckel et al. "Modulation of Amphetamine-Induced Dopamine Release by Group II Metabotropic Glutamate Receptor Agonist LY354740 in Non-Human Primates Studied with Positron Emission Tomography" Neuropsychopharmacology 2006, vol. 31, pp. 967-977.

Van Berckel et al. "The course of untreated anxiety and depression, and determinants of poor on-year outcome: a one-year cohort study" BMC Psychiatry 2010, vol. 10, 86.

Van Den Pol, "Presynaptic Metabotropic Glutamate Receptors in Adult and Developing Neurons: Autoexcitation in the Olfactory Bulb", Journal of Comparative Neurology, 1995, 359(2), 253-271.

Van Der Linden et al. In vitro Chracterization of the Binding of the mGlu2 Receptor Positive Allosteric Modulator [3H]JNJ-40068782 to Native and Recombinant mglu2 Receptors. 7th Int. Meeting on metabotropic Glutamate Receptors 2011, Taormina, Italy.

Van Tol et al. "Regional Brain Volume In Depression and Anxiety Disorders" Arch Gen Psychiatry. 2010; 67(10):1002-1011.

Van Valkenberg et al. "Anxious Depressions. Clinical, Family History, and Naturalistic Outcome—Comparisons with Panic and Major Depressive Disorders" Journal of affective disorders 1984, vol. 6(1), pp. 67-82.

Van Vliet et al., "Adaptive Changes in the No. of Gs- and Gi-Proteins Underlie Adenylyl Cyclase Sensitization in Morphine-Treated Rat Striatal Neurons", European Journal of Pharmacology, 1993, 245(1), 23-29.

VanAllan et al., "Reactions of Some 4-Methylene-4H-pyran Derivatives with Primary and Secondary Amines", Journal of Heterocyclic Chemistry, Jun. 1970, vol. 7, 495-507.

Vandergriff et al. "The selective mglu2/3 receptor agonist LY354740 attenuates morphine-withdrawal-induced activation of locus coeruleus neurons and behavioral signs of morphine withdrawal" Neuropharmacology 1999, vol. 38, pp. 217-222.

Vandesompele et al. "Accurate normalization of real-time quantitative RT-PCR data by geometric averaging of multiple internal control genes" Genome Biology 2002, 3(7):research0034.1-0034.11, epub only.

Varney et al . "Metabotropic Glutamate Receptor Involvement in Models of Acute and Persistent Pain: Prospects for the Development of Novel Analgesics" Current Drug Targets—CNS & Neurological Disorders 2002, vol. 1, pp. 283-296.

Vasilieva "Clinical-Dynamic Characteristics of Depressive Disorders Comorbid With Anxiety Disorders" Abstract P01-109 of 18th European Congress of Psychiatry. Feb. 27, Mar. 2, 2010—Munich, Germany.

Vaughan et al. "Reactivity of 3-Alkyl-4-arylazomethylene-3,4-dihydro-1,2,3-benzotriazines in Protic Solvents: 1,4-Addition Reactions and Dimroth Rearrangement." Journal of Heterocyclic Chemistry. vol. 28. Nov. 1991. 1709-13.

Verhagen et al. "Effect of the 5-HTTLPR polymorphism in the serotonin transporter gene on major depressive disorder and related comorbid disorders" Psychiatric Genetics 2009, vol. 19, pp. 39-44.

Verma et al., "Regulation of Striatal Dopamine Release by Metabotropic Glutamate Receptors", Synapse 1998, 28(3), 220-226.

Vernon et al. Additive neuroprotection by metabotropic glutamate receptor subtype-selective ligands in a rat Parkinson's model. Neuroreport 2008, 19 (4), 475-478.

Versiani et al. "Fluoxetine versus amitriptyline in the treatment of major depression with associated anxiety (anxious depression): a double-blind comparison" International Clinical Psychopharmacology 1999, vol. 14, pp. 321-327.

Vezina et al. Metabotropic glutamate receptors and the generation of locomotor activity: interactions with midbrain dopamine. [Review] [135 refs]. Neuroscience & Biobehavioral Reviews 1999, 23 (4), 577-589.

Vilsmaier et al., "Diastereoselective Syntheses of N-Protected Derivatives of 1a,5a,6fi-6-Amino-3-azabicyclo [3.101 hexane; A Route to Trovafloxacin 6fl-Diastereomer", Synthesis, 1998, pp. 739-744.

Vinson et al. "Metabotropic glutamate receptors as therapeutic targets for schizophrenia" Neuropharmacology 2012, vol. 62, pp. 1461-1472.

Vippagunta et al, "Crystalline Solids" Advanced Drug Delivery Reviews, vol. 48, pp. 3-26 (2001).

Vogel et al. Evidence for REM sleep deprivation as the mechanism of action of antidepressant drugs Prog Neuropsychopharmacol Biol Psychiatry. 1983;7(2-3):343-9.

Vogel et al., "Drug Effects on Rem Sleep and on Endogenous Depression", Neuroscience & Biobehavioral Reviews, 1990, 14, 49-63.

Vollenweider et al. "Differential psychopathology and patterns of cerebral glucose utilization produced by (S)- and (R)-ketamine in healthy volunteers using positron emission tomography (PET)" Eur Neuropsychopharmacol 1997, vol. 7, pp. 25-38.

Vollenweider et al. "Effect of clozapine and ketanserin on S-ketamine-induced brain activation and psychotic symptoms in healthy humans" Abstract, Symposia, Wednesday Jun. 6, 2012 28th CINP World Congress of Neuropsychopharmacology, Stockholm.

Vollenweider et al. "Metabolic hyperfrontality and psychopathology in the ketamine model of psychosis using positron emission tomography (PET) and [18F]fluorodeoxyglucose (FDG)" Eur Neuropsychopharmacol 1997, vol. 7, pp. 9-24.

Vollenweider et al., "A Systems Model of Altered Consciousness: Integrating Natural and Drug-Induced Psychoses", Brain Res. Bull., 2001, 56, 495-507.

Vollenweider et al., "Psilocybin Induces Schizophrenia-Like Psychosis in Humans via a Serotonin-2 Agonist Action", Neuroreport, 1998, 9, 3897-3902.

Wadenberg "Conditioned avoidance response in the development of new antipsychotics" Curr Pharm Des 2010, vol. 16, pp. 358-370.

Wakefield, Basil "Fluorinated Pharmaceuticals" Innovations in Pharmaceutical Technology 2003, 74, 76-78, Online http://web.archive.Org/web/20030905122408/http://www.iptonline.com/articles/public/IPTFOUR74NP.pdf. (accessed via Wayback machine Nov. 20, 2009 showing web availability as of Sep. 2003).

Walker et al. The role of amygdala glutamate receptors in fear learning, fear-potentiated startle, and extinction. Pharmacol. Biochem. Behav. 2002, 71 (3), 379-392.

Wang et al. "A simple and effcient automatable one step synthesis of triazolopyridines form carboxylic acids", Tetrahedron Letters, 2007, 48, 2237-2240.

Wang et al. "Allosteric modulators" J. PHarm. Exp. Terapeutics v. 331(2) 340-348 (2009).

Wang et al. "Radiosynthesis of PET radiotracer as a prodrug for imaging group II metabotropic glutamate receptors in vivo" Bioorganic & Medicinal Chemistry Letters 2012, vol. 22, pp. 1958-1962.

Wang et al., "Development of Metabotropic Glutamate Receptor Ligands for Neuroimaging", Curr Med Imaging Rev, 2007, 3, 186-205.

Wantanabe et al., "Pd/P(t-Bu).sub.3-Catalyzed Synthesis of Aromatic Amines," J TOSOH Res, 37-50 (1999).

(56) References Cited

OTHER PUBLICATIONS

Watkins "L-glutamate as a central neurotransmitter: looking back" Biochem Soc Trans 2000, vol. 28, pp. 297-310.
Weinberger The biological basis of schizophrenia: new directions. [Review] [47 refs]. Journal of Clinical Psychiatry 1997, 58, SuppMO, 22-27.
Bonanno et al. "Chronic antidepressants reduce depolarization-evoked glutamate release and protein interactions favoring formation of SNARE complex in hippocampus" J Neurosci 2005, vol. 25, pp. 3270-3279.
Bond et al. Neuroprotective effects of LY379268, a selective mGlu2/3 receptor agonist: investigations into possible mechanism of action in vivo. J Pharmacol. Exp. Ther. 2000, 294 (3), 800-809.
Bond et al. Pharmacology of metabotropic glutamate receptor-mediated enhancement of responses to excitatory and inhibitory amino acids on rat spinal neurones in vivo. Neuropharmacology. 1995, 34 (8), 1015-1023.
Bonnefous et al. Biphenyl-Indanones: Discovery of Positive Allosteric Potentiators of the Metabotropic Glutamate. Subtype 2 (mGlu2) Receptor 229th ACS National Meeting, San Diego, CA, United States, Mar. 13-17, 2005 (2005), MEDI-037.
Bonnefous et al. "Biphenyl-indanones: allosteric potentiators of metabotropic glutamate subtype 2 receptor" Bioorg Med Chem Lett 2005, vol. 15, pp. 4354-4358.
Boris-Moller et al. Changes in the extracellular levels of glutamate and aspartate during ischemia and hypoglycemia. Effects of hypothermia. Experimental Brain Research 1998, 121 (3), 277-284.
Borowitz et al. "Organophosphorus Chemistry. III. The Reactions of Triphenylphosphine with Secondary a-Bromo Ketones and with 2-Bromodimedone." Dec. 1966. 4031-7.
Bortolotto et al. Roles of metabotropic glutamate receptors in LTP and LTD in the hippocampus. [Review] [64 refs]. Current Opinion in Neurobiology 1999, 9 (3), 299-304.
Boules et al. "Neurotensin Agonists: Potential in the Treatment of Schizophrenia" CNS Drugs 2007, vol. 21(1), pp. 13-23.
Bouvrais-Veret et al. "Microtubule-associated STOP protein deletion triggers restricted changes in dopaminergic neurotransmission" J. Neurochem. (2008) 104, 745-756.
Boyette et al., "Factor structure of the Yale-Brown Obsessive-Compulsive Scale (Y-BOCS) in a large sample of patients with schizophrenia or related disorders and comorbid obsessive-compulsive symptoms", Psychiatry Res., 2011, 186, 409-413.
Brabet et al. "Comparative effect of L-CCG-I, DCG-IV and gamma-carboxy-I-glutamate on all cloned metabotropic glutamate receptor subtypes" Neuropharmacology 1998, vol. 37, pp. 1043-1051.
Bradley et al., "Activation of Group II Metabotropic Glutamate Receptors Inhibits Synaptic Excitation of the Subsantia Nigra Pars Reticulata," J. of Neuroscience, May 1, 2000, 20(9):3085-3094.
Braff et al., Human studies of prepulse inhibition of startle: normal subjects, patient groups, and pharmacological studies, Psychopharmacology, 156:234-258 (2001).
Braga et al. "Making Crystals from Crystals: A Green Route to Crystal Engineering and Polymorphism" Chem. Commun. 2005, 3635-3645.
Brauner-Osborne "Structure, Pharmacology and Therapeutic Prospects of Family C G-Protein Coupled Receptors" Current Drug Targets, 2007, vol. 8, pp. 169-184.
Brauner-Osborne et al. A new highly selective metabotropic excitatory amino acid agonist: 2-amino-4-(3-hydroxy-5-methylisoxazol-4-yl)butyric acid. Journal of Medicinal Chemistry 1996, 39 (16), 3188-3194.
Brauner-Osborne et al. Interaction of CPCCOEt with a chimeric mGlulb and calcium sensing receptor. Neuroreport 1999, 10 (18), 3923-3925.
Brauner-Osborne et al. Molecular pharmacology of 4-substituted glutamic acid analogues at ionotropic and metabotropic excitatory amino acid receptors. European Journal of Pharmacology 1997, 335 (2-3), R1-R3.

Brauner-Osborne et al. Pharmacology of (S)-homoquisqualic acid and (S)-2-amino-5-phosphonopentanoic acid [(S)-AP5] at cloned metabotropic glutamate receptors. British Journal of Pharmacology 1998, 123 (2), 269-274.
Breier et al. "Association of ketamine-induced psychosis with focal activation of the prefrontal cortex in healthy volunteers" Am J Psychiatry 1997, vol. 154, pp. 805-811.
Bremner et al. Development and preliminary psychometric properties of an instrument for the measurement of childhood trauma: The Early Trauma Inventory. Depress Anxiety 2000: 12(1): 1-12.
Briash etal, "Construction of the (Ia,5a,6a)-6-Amino-3-azabicyelo[3. LO]hexane Ring System", Syntlett, 1996, 11, 1100-1102.
Brighty et al., "Synthesis of (Ia,5a,6ct)-6-Amino-3-azabicyclo[3i. O]hexane, a Novel Achiral Diamine", Syntlett, 1996, 11, 1097-1099.
Brnardic et al. "3-Aryl-5-phenoxymethyl-1,3-oxazolidin-2-ones as positive allosteric modulators of mGluR2 for the treatment of schizophrenia: hit-to-lead efforts" Bioorg Med Chem Lett 2010, vol. 20, pp. 3129-3133.
Broekkamp et al. Major tranquillizers can be distinguished from minor tranquillizers on the basis of effects on marble burying and swim-induced grooming in mice. Eur. J. Pharmacol., 126, 223-229, 1986.
Bruno et al. Activation of class II or III metabotropic glutamate receptors protects cultured cortical neurons against excitotoxic degeneration. European Journal of Neuroscience 1995, 7 (9), 1906-1913.
Bruno et al. Activation of metabotropic glutamate receptors coupled to inositol phospholipid hydrolysis amplifies NMDA-induced neuronal degeneration in cultured cortical cells. Neuropharmacology. 1995, 34 (8), 1089-1098.
Bruno et al. Excitatory amino acids and neurotoxicity. [Review] [113 refs]. Functional Neurology 1993, 8 (4), 279-292.
Bruno et al. Metabotropic glutamate receptors and neurodegeneration. [Review] [98 refs]. Progress in Brain Research. 1998, 116, 209-221.
Bruno et al. Metabotropic glutamate receptors and neuronal degeneration in culture. [Review] [23 refs]. Advances in Neurology 1996, 71, 47-52.
Bruno et al. Molecular dynamics simulation of the heterodimeric mGluR2/5HT(2A) complex. An atomistic resolution study of a potential new target in psychiatric conditions. J. Chem. Inf. Model. 2009, 49 (6), 1602-1616.
Bruno et al. Neuroprotection by glial metabotropic glutamate receptors is mediated by transforming growth factor-beta. J. Neurosci. 1998, 18 (23), 9594-9600.
Bruno et al. The neuroprotective activity of group-II metabotropic glutamate receptors requires new protein synthesis and involves a glial-neuronal signaling. J. Neurosci. 1997, 17 (6), 1891-1897.
Bruno et al., "Lamotrigine augmentation of serotonin reuptake inhibitors in treatment-resistant obsessive-compulsive disorder: a double-blind, placebo-controlled study", Journal of Psychopharmacology, 2012, 26(11), 1456-1462.
Bruno, "Metabotropic Glutamate Receptor Subtypes as Targets for Neuroprotective Drugs", Journal of Cerebral Blood Flow and Metabolism, 2001, 21:1013-1033.
Buisson et al. The inhibitory mGluR agonist, S-4-carboxy-3-hydroxyphenylglycine selectively attenuates NMDA neurotoxicity and oxygen-glucose deprivation-induced neuronal death. Neuropharmacology. 1995, 34 (8), 1081-1087.
Bunch et al. "Excitatory amino acid transporters as potential drug targets" Expert Opin Ther Targets 2009, vol. 13(60, pp. 719-731.
Bunney et al. Norepinephrine in depression reactions. A review. Arch Gen Psychiatry Dec. 1965; 13(6): 483-494.
Burford et al. "Strategies for the identification of allosteric modulators of G-protein-coupled receptors", Biochem Pharmacol (2011), epub, no page numbers, doi:10.1016/tbcp.2010.12.012.
Bushell et al., "Pharmacological Antagonism of the Actions of Group II and III Mglur Agonists in the Lateral Perforant Path of Rat Hippocampal Slices", Br. J Pharmacol., 1996, 117(7), 1457-1462.
Bustillo et al. 1H-MRS at 4 tesla in minimally treated early schizophrenia. Mol Psychiatry. 2010; 15(6):629-636.

(56) References Cited

OTHER PUBLICATIONS

Butterfield et al. "The Glutamatergic System and Alzheimer's Disease: therapeutic implications" CNS Drugs 2003, vol. 17(9), pp. 641-652.
Byrnes et al., "Metabotropic Glutamate Receptors as Targets for Multipotential Treatment of Neurological Disorders", Neurotherapeutics, 2009, 6(1), 94-107.
CA Office Action dated Apr. 23, 2010.
Cacabelos et al. The glutamatergic system and neurodegeneration in dementia: preventive strategies in Alzheimer's disease. [Review] [228 refs]. International Journal of Geriatric Psychiatry 1999, 14 (1), 3-47.
Cai et al. "Local potentiation of excitatory synapses by serotonin and its alteration in rodent models of depression" Nature Neuroscience 2013, vol. 16(4), pp. 464-472.
Calabresi, "Antiepileptic drugs in migraine: from clinical aspects to cellular mechanisms," Trends in Pharmacological Sci. 28(4): 188-195 (2007).
Campbell et al. An update on regional brain vol. differences associated with mood disorders. Curr Opin Psychiatry Jan. 2006; 19(1): 25-33.
Canadian Patent Application No. 2,581,144: Office Action dated Dec. 4, 2012, 5 pages.
Kenakin, "Collateral Efficacy in Drug Discovery: Taking Advantage of the Good (Allosteric) Nature of 7tm Receptors", Trends Pharmacol. Sci., 2007, 28(8), 407-415.
Kendler et al. "Major Depression and Generalized Anxiety Disorder: Same Genes, (Partly) Different Environments?" Arch Gen Psychiatry 1992, vol. 49, pp. 716-722.
Kendler The Nosologic Validity of Paranoia (Simple Delusional Disorder) Arch Gen Psychiatry 1980, vol. 37, 699-706.
Kennett et al. "Evidence that 5-HT2C receptor antagonists are anxiolytic in the rat Geller-Seifter model of anxiety" Psychopharmacology 1994, vol. 114, pp. 90-96.
Kenny et al., "Group II Metabotropic and Alpha-Amino-3-Hydroxy-5-Methyl-4-Isoxazole Propionate (Ampa)/Kainate Glutamate Receptors Regulate the Deficit in Brain Reward Function Associated with Nicotine Withdrawal in Rats", J Pharmacol. Exp. Ther., 2003, 306(3), 1068-1076.
Kenny, "The ups and downs of addiction: role of metabotropic glutamate receptors", TRENDS in Pharmacological Sciences, 2004, vol. 25 No. 5, pp. 265-272.
Kent "Safety, tolerability and potential therapeutic efficacy of a novel glutamate modulator as adjunctive treatment in patients with schizophrenia" Abstract No. 3160, 2013 American Psychiatric Association Annual Meeting, San Francisco.
Kessler et al. "Comorbid Major Depression and Generalized Anxiety Disorders in the National Comorbidity Survey follow-up" Psychol Med. Mar. 2008 ; 38(3): 365-374.
Kessler et al. "Lifetime and 12-Month Prevalence of DSM-III-R Psychiatric Disorders in the United States: Results From the National Comorbidity Survey" Arch Gen Psych 1994, vol. 51, pp. 8-19.
Kessler et al. "Rethinking the duration requirement for generalized anxiety disorder: evidence from the National Comorbidity Survey Replication" Psychological Medicine 2005, Issue 7, pp. 1073-1082.
Kessler et al. "The Epidemiology of Co-ocurring Addictive and Mental Disorders: Implications for Prevention and Service Utilization" American Journal of Orthopsychiatry 1996, vol. 66(1), pp. 17-31.
Kessler et al. "The Epidemiology of Major Depressive Disorder: Results from the National Comorbidity Survey Replication (NCS-R)" JAMA 2003, vol. 289(23), pp. 3095-3105.
Kessler et al., "Epidemiology of Anxiety Disorders", Current Topics in Behavioral Neurosciences, 2010, 2, 21-35.
Kessler et al., "Impairment in Pure and Comorbid Generalized Anxiety Disorder and Major Depression at 12 Months in Two National Surveys", American Journal of Psychiatry, 1999, 156(12), 1915-1923.

Ketamine Challenge Study With JNJ-40411813 Available from: http://clinicaltrials.gov/ct2/show/NCT01101659; Clinical Trials. gov identifier. NCT01101659, retrieved on Aug. 1, 2013.
Kew "Positive and negative allosteric modulation of metabotropic glutamate receptors: emerging therapeutic potential" Pharmacology & Therapeutics 2004, vol. 104, pp. 233-244.
Kew et al. "Activity-dependent presynaptic autoinhibition by group II metabotropic glutamate receptors at the perforant path inputs to the dentate gyrus and CA1" Neuropharmacology 2001, vol. 40, pp. 20-27.
Kew et al. "Differential regulation of synaptic transmission by mGlu2 and mGlu3 at the perforant path inputs to the dentate gyms and CA1 revealed in mGlu2-/-mice" Neuropharmacology 2002, vol. 43, 215-221.
Kew et al. "Ionotropic and metabotropic glutamate receptor structure and pharmacology" Psychopharmacology 2005, vol. 179, pp. 4-29.
Khimia Geterotsiklicheskikh Soedinenii, 1985, vol. 5, PT 1985, 646-649.
Khimia Geterotsiklicheskikh Soedinenii, 1986, vol. 1986, PT 8, 1118-1123.
Kilama et al., "A new Synthetic Approach to the C-D Ring Portion of Streptonigrin Analogues", Journal of Heterocyclic Chemistry, Jul.-Aug. 1990, vol. 27, 1437-1440.
Kilbride et al. "Presynaptic Group II mGluR Inhibition of Short-Term Depression in the Medial Perforant Path of the Dentate Gyrus in Vitro" Neurophysiol 2001, vol. 85, pp. 2509-2515.
Kilbride et al. "Presynaptic inhibitory action of the group II metabotropic glutamate receptor agonists, LY354740 and DCG-IV" European Journal of Pharmacology 1998, vol. 356, pp. 149-157.
Kilts, "The Changing Roles and Targets for Animal Models of Schizophrenia", Biol. Psychiatr., 2001, 50, 845-855.
Kim et al. "Group II Metabotropic Glutamate Receptor Stimulation Triggers Production and Release of Alzheimer's Amyloid .beta.42 from Isolated Intact Nerve Terminals" The Journal of Neuroscience, Mar. 17, 2010 vol. 30(11), pp. 3870-3875.
Kim et al. "Metabotropic glutamate receptors" Phosphorylation and receptor signaling Journal of Neuroscience Research 2008, vol. 86, pp. 1-10.
Kim et al. "Neurofilament-M Interacts with the D1 Dopamine Receptor to Regulate Cell Surface Expression and Desensitization" The Journal of Neuroscience, Jul. 15, 2002, 22(14):5920-5930.
Kim et al. "Predictors of 12-week remission in a nationwide cohort of people with depressive disorders: the CRESCEND study" Hum. Psychopharmacol Clin Exp 2011; 26: 41-50.
Kim et al., "Activation of Metabotropic Glutamate Receptors in the Rat Nucleus Accumbens Increases Locomotor Activity in a Dopamine-Dependent Manner", Journal of Pharmacology & Experimental Therapeutics, 1997, 283(2), 962-968.
Kim et al., "Metabotropic Glutamate Receptors in the Rat Nucleus Accumbens Contribute to Amphetamine-Induced Locomotion", Journal of Pharmacology & Experimental Therapeutics, 1998, 284(1), 317-322.
Kingston et al. "LY341495 is a nanomolar potent and selective antagonist of group II metabotropic glutamate receptors" Neuropharmacology 1998, vol. 37, pp. 1-12.
Kingston et al. "Neuroprotection by metabotropic glutamate receptor agonists: LY354740, LY379268 and LY389795" European Journal of Pharmacology 1999, vol. 377, pp. 155-165.
Kingston et al. "Neuroprotective Actions of Novel and Potent Ligands of Group I and Group II Metabotropic Glutamate Receptors" Annals New York Academy of Sciences 1999, vol. 890, pp. 438-449.
Kinon, "A multicenter, inpatient, phase 2, double-blind, placebo-controlled dose-ranging study of LY2140023 monohydrate in patients with DSM-IV Schizophrenia" J. Clin. Psychopharmacology, 31 (3):349-355 (2011).
Kiselyov et al., "A one pot synthesis of polysubstituted inidazo[1,2-a]pyridines", Tetrahedron Letters, 2006, 47, 2941-2944, Elsevier.
Kishimoto et al., "Post-traumatic Stress Disorder Symptoms in a Female Patient Following Repeated Teasing: Treatment with Gabapentin and Lamotrigine and the Possible Role of Sensitization", Clinical Psychopharmacology and Neuroscience, 2014, 12(3), 240-242.

(56) References Cited

OTHER PUBLICATIONS

Kitano et al., "Synthesis and antifouling activity of 3-isocyanotheonellin and its analogues", Jour Chem Soc Perkin Trans, 2002, 2251-2255, The Royal Society of Chemistry.
Kitts: "The changing roles and targets for animal models of schizophrenia.", Biol. Psychiatr. 50: 845-855 (2001).
Klein "Mixed anxiety depression. For and against" L'Encephale 1993, vol. XIX, pp. 493-495.
Klein et al., "Glutamatergic Activation of Hippocampal Phospholipase D: Postnatal Fading and Receptor Desensitization", Journal of Neurochemistry, 1998, 70(4), 1679-1685.
Klemm et al. "Chemistry of Thienopyridines. VIII. Substitution Products Derived from Thieno[2,3-b] pyridine 7-Oxide (1)", Journal of Heterocyclic Chemistry, 1970, 7(1), 81-89.
Klodzinska et al. "Group II mGlu receptor agonists inhibit behavioural and electrophysiological effects of DOI in mice" Pharmacology, Biochemistry and Behavior 2002, vol. 73(2), pp. 327-332.
Klodzinska et al. "Roles of group II metabotropic glutamate receptors in modulation of seizure activity" Naunyn Schmiedebergs Arch Pharmacol 2000, vol. 361, pp. 283-288.
Klodzinska et al. "Selective group II glutamate metabotropic receptor agonist LY354740 attenuates pentetrazoleand picrotoxin-induced seizures" Pol J Pharmacol 1999, vol. 51, pp. 543-545.
Knesevich. Validity of Hamilton Rating-Scale for depression. Br J Psychiatry Jul. 1977; 131: 49-52.
Kniazeff et al. "Closed state of both binding domains of homodimeric mGlu receptors is required for full activity" Nat Struct Mol Biol 2004, vol. 11, pp. 706-713.
Knight et al. "Pharmacological characterization of the agonist radioligand binding site of 5-HT2A, 5-HT2B and 5-HT2C receptors" Naunyn-Schmiedeberg's Arch Pharmacol 2004, vol. 370, pp. 114-123.
Knoflach et al. "R1315, a potent orally active non-competitive group II metabotropic glutamate receptor antagonist with cognitive enhancing properties" 5th International Meeting on Metabotropic Glutamate Receptors, Taormina Sicily—Italy, Sep. 18-23, 2005.
Kodama et al. "Enhanced glutamate release during REM sleep in the rostromedial medulla as measured by in vivo microdialysis" Brain Res 1998, vol. 780, pp. 178-181.
Forstl, "Clinical Features of Alzheimer's disease", Eur Arch Psychiatry Clin Neurosci, 1999, 249: 288-290.
Foster "Metabotropic glutamate receptor ligands as potential therapeutics for addiction" Curr Drug Abuse Rev 2009, vol. 2, pp. 83-98.
Fraley "Positive allosteric modulators of the metabotropic glutamate receptor 2 for the treatment of schizophrenia" Expert Opin. Ther. Patents 2009, vol. 19(9), pp. 1259-1275.
Franco et al. "Novel pharmacological targets based on receptor heteromers" Brain Research Reviews 2008, vol. 58, pp. 475-482.
Franco et al. "The Two-State Dimer Receptor Model: A General Model for Receptor Dimers" Molecular Pharmacology 2006, vol. 69, pp. 1906-1912.
Frank et al. "Depression and health-related quality of life for low-income African-American women in the U.S." Quality of Life Research 2005, vol. 14, 2293-2301.
Frauli et al. Among the twenty classical L-amino acids, only glutamate directly activates metabotropic glutamate receptors. Neuropharmacology 2006, 50 (2), 245-253.
Freedman et al. Desensitization of G protein-coupled receptors. [Review] [109 refs]. Recent Progress in Hormone Research 1996, 51, 319-351.
Freedman Schizophrenia. N. Engl. J. Med. 2003, 349, 1738-1749.
French et al. Subfield-specific immediate early gene expression associated with hippocampal long-term potentiation in vivo. European Journal of Neuroscience 2001, 13 (5), 968-976.
Fribourg et al. "Decoding the Signaling of a GPCR heteromeric complex reveals a unifying mechanism of action of antipsychotic drugs" Cell 2011, vol. 147, pp. 1011-1023.
Fricker et al. Effects of N-acetylaspartylglutamate (NAAG) at group II mGluRs and NMDAR. Neuropharmacology 2009, 56 (6-7), 1060-1067.

Fuentes et al., "Synthesis of Heterocyclic Compounds; XL. Regioselective. synthesis of 4-subtituted 2-Amino-5-Cyano-6-methoxy-3-benzenesulfonylpyridines", Synthesis, 1984, pp. 768-770.
Fujii et al. "Lactams. IX. Generation of Latam Carbonyl Function in 1,3-Disubstituted Piperidines by Mercuric Acetate-EDTA Oxidation: Effects of Hydrocarbon Substituents at the 3-Postion." Chem. Pharm. Bull. vol. 25 (9). 1977. 2336-42.
Fujii et al. A chemical LTP induced by co-activation of metabotropic and N-methyl-D-aspartate glutamate receptors in hippocampal CA1 neurons. Brain Research. 999(1 ):20-8, 2004.
Fujimoto et al. Motor and cognitive function evaluation following experimental traumatic brain injury, Neurosci. And BiobehaV. Rev., 28:365-378 (2004).
Fujita et al. "Studies on 1-Alkyl-2(1 H)-pyridone Derivatives XXXII. The Friedel-Crafts Reaction of 1-Alkyl-2(1 H)-pyridone Derivatives with Acid Anhydride." Journal of the Pharmaceutical Society of Japan. vol. 110. 1990. 449-52.
Furukawa et al. "Antidepressants plus benzodiazepines for major depression" (Review) 2009 the Cochrane Collaboration. Published by JohnWiley & Sons, Ltd.
Fuxe et al. Integrated signaling in heterodimers and receptor mosaics of different types of GPCRs of the forebrain: relevance for schizophrenia. J Neural Transm. 2009, 116 (8), 923-939.
Galici et al., "A Selective Allosteric Potentiator of Metabotropic Glutamate (mGlu) 2 Receptors Has Effects Similar to an Orthosteric mGLu2/3 Receptor Agonist in Mouse Models Predictive of Antipsychotic Activity", J. of Pharmacology and Experimental Therapeutics, vol. 315, No. 3., p. 1181-1187.
Galici et al., "Biphenyl-indanone A, a Positive Allosteric Modulator of the Metabotropic Glutamate Receptor Subtype 2, Has Antipsychotic-and Anxiolytic-Like Effects in Mice", JPET, 2006, 318, 173-185.
Galimberti et al. "Long-Term Rearrangements of Hippocampal Mossy Fiber Terminal Connectivity in the Adult Regulated by Experience" Neuron 2006, vol. 50, pp. 749-763.
Gama et al. Heterodimerization of calcium sensing receptors with metabotropic glutamate receptors in neurons. J. Biol. Chem. 2001, 276 (42), 39053-39059.
Garbaccio et al. "Discovery of oxazolobenzimidazoles as positive allosteric modulators for the mGluR2 receptor" ACS Med Chem Lett 2010, vol. 1, pp. 406-410.
Garrido-Sanabria et al. Impaired expression and function of group II metabotropic glutamate receptors in pilocarpine-treated chronically epileptic rats. Brain Res. 2008, 1240, 165-176.
Garriock et al ."Genetic Studies of Drug Response and Side Effects in the STAR D Study, Part 1" J Clin Psychiatry 2009, vol. 70(8), 1186-1187.
Gasparini et al ."Allosteric modulators for mGlu receptors" Cuff Neuropharmacol 2007, vol. 5, pp. 187-194.
Gaudet et al., "Metabotropic Receptors for Glutamate and Gaba in Pain", Brain Res. Rev., 2009, 60(1), 43-56.
Gavezzotti, "Are Crystal Structures Predictable?" Accounts of Chemical Research, vol. 27, pp. 309-314 (1994).
Gerber et al. Metabotropic glutamate receptors: intracellular signaling pathways. [Review] [51 refs]. Current Opinion in Pharmacology. 7(1):56-61, 2007.
Gerwitz et al. "Behavioral evidence for interactions between a hallucinogenic drug and group II metabotropic glutamate receptors" Neuropsychopharmacology 2000, vol. 23, pp. 569-576.
Gewald et al. "Heterocyclen aus CH-aciden Nitrilen, VIII. 2-Aminothiophene aus methylenaktiven Nitrilen Carbonylverbindungen and Schwefel." Jahrg. vol. 99. 1966. 94-100.
Geyer Are cross-species measures of sensorimotor gating useful for the discovery of procognitive cotreatments for schizophrenia? Dialogues. Clin Neurosci. 2006, 8 (1), 9-16.
Ghammamy et al., "Cetyltrimethylammonium Bromochromate: A New and Efficient Oxidant for Organic Substrates", Synthetic Communications, 2007, 37, 599-605.
Ghose et al. "Differential Expression of Metabotropic Glutamate Receptors 2 and 3 in Schizophrenia: A Mechanism for Antipsychotic Drug Action?" Am J Psychiatry AJP in Advance. Published Jun. 1, 2009 (epub, no page numbers, doi: 10.1176/appi.ajp.2009. 08091445).

(56) References Cited

OTHER PUBLICATIONS

Gill et al. "Immunochemical localization of the metabotropic glutamate receptors in the rat heart" Brain Research Bulletin 1999, vol. 48(2), pp. 143-146.
Gilling et al. "Potency, voltage-dependency, agonist concentration-dependency, blocking kinetics and partial untrapping of the uncompetitive N-methyl-D-aspartate (NMDA) channel blocker memantine at human NMDA (GluN1/GluN2A) receptors" Neuropharmacology 2009, vol. 56, pp. 866-875.
Gilmour et al. "Diverse and often opposite behavioural effects of NMDA receptor antagonists in rats: implications for "NMDA antagonist modelling" of schizophrenia" Psychopharmacology 2009, vol. 205, pp. 203-216.
Giovannelli et al. "Comet Assay as a Novel Approach for Studying DNA Damage in Focal Cerebral Ischemia: Differential Effects of NMDA Receptor Antagonists and Poly(ADP-Ribose) Polymerase Inhibitors." Journal of Cerebral Blood Flow and Metabolism. vol. 22. 2002. 697-704.
Girardi et al. Differential expression of cerebellar metabotropic glutamate receptors mGLUR2/3 and mGLUR4a after the administration of a convulsant drug and the adenosine analogue cyclopentyladenosine. Neurochem. Res. 2007, 32 (7), 1120-1128.
Gjoni et al . "Receptor activation involving positive allosteric modulation, unlike full agonism, does not result in GABAB receptor desensitization" Neuropharmacology 2008, vol. 55, pp. 1293-1299.
Gleason et al. "Blockade of phencyclidine-induced hyperlocomotion by olanzapine, clozapine, and serotonin receptor subtype selective antagonists in mice." Psychopharmacology. vol. 129. 1997. 79-84.
Gleeson "Generation of a set of simple, interpretable ADMET rules of thumb" J Med Chem 2008, vol. 51, pp. 817-834.
Glick et al. A double-blind randomized trial of mood stabilizer augmentation using lamotrigine and valproate for patients with schizophrenia who are stabilized and partially responsive. J Clin Psychopharmacol 2009; 29(3):267-271.
Glick et al.: Concomitant medications may not improve outcome of antipsychotic monotherapy for stabilized patients with non-acute schizophrenia. J Clin Psychiatry 2006:67(8): 1261-1265.
Glin et al. "The Intermediate Stage of Sleep in Mice" Physiology & Behavior 1991, vol. 50, pp. 951-953.
Gnecco et al. "Oxidation of chiral non-racemic pyridinium salts to enantiopure 2-pyridine and 3-alkyl-2-pyridones." Tetrahedron: Asymmetry. vol. 9. 1998. 2027-9.
Goff et al. Lamotrigine as add-on therapy in schizophrenia: results of 2 placebo-controlled trials. J Clin Psychopharmacol. 2007;27(6):582-589 (abstract).
Goldberg et al. "Novel non-benzodiazepine anxiolytics" Neuropharmacology 1983, vol. 22, pp. 1499-1504.
Gonzalez-Maeso et al. "Identification of a serotonin/glutamate receptor complex implicated in psychosis" Nature 2008, vol. 452, pp. 93-97.
Harriman et al. "Synthesis of 4-Substituted 4-Arylpiperidines", Tetrahedron Letters, 2000, 41, 8853-8856, Pergamon.
Harrison "Metabotropic glutamate receptor agonists for schizophrenia" The British Journal of Psychiatry 2008 vol. 192, pp. 86-87.
Harrison et al. The group II metabotropic glutamate receptor 3 (mGluR3, mGlu3, GRM3): expression, function and involvement in schizophrenia. J. Psychopharmacol. 2008, 22 (3), 308-322.
Hartveit et al. Expression of the mRNA of seven metabotropic glutamate receptors (mGluRI to 7) in the rat retina. An in situ hybridization study on tissue sections and isolated cells. Eur. J Neurosci. 1995, 7 (7), 1472-1483.
Hascup et al. "An allosteric modulator of metabotropic glutamate receptors (mGluR2), (+)-TFMPIP, inhibits retraint stress-induced phasic glutamate release in rat prefrontal cortex" Journal of Neurochemistry 2012, vol. 122, pp. 619-627.
Hashimoto "Emerging role of glutamate in the pathophysiology of major depressive disorder" Brain Research Reviews 2009, vol. 61, pp. 105-123.

Hashimoto et al.: Increased levels of glutamate in brains from patients with mood disorders. Biol Psychiatry Dec. 2007; 62(11): 1310-1316.
Hasin et al. "Epidemiology of Major Depressive Disorder. Results From the National Epidemiologic Survey on Alcoholism and Related Conditions" Arch Gen Psychiatry 2005, vol. 62, pp. 1097-1106.
Hasler et al. Reduced prefrontal glutamate/glutamine and gamma-aminobutyric acid levels in major depression determined using proton magnetic resonance spectroscopy. Arch Gen Psychiatry Feb. 2007; 64(2): 193-200.
Hawgood et al. "Anxiety disorders and suicidal behavior: an update" Current Opinion in Psychiatry 2008, vol. 21, pp. 51-64.
He et al. "Conformational Color Polymorsphism and Control of Crystallization of 5-Methyl-2-[(4-methyl-2-mitrophenylOamino)-3-thiophenecarbonitrile." Journal of Pharmaceutical Sciences. vol. 90 (3). Mar. 2001. 371-88.
Heckler et al., "Selective Potentiation of the Metabotropic Glutamate Receptor Subtype 2 Blocks Phencyclidine-Induced Hyperlocomotion and Brain Activation", Neuroscience, 2010, 168(1), 209-218.
Helton et al,"Anxiolytic and Side-Effect Profile of LY354740: A Potent, Highly Selective, Orally Active Agonist for Group II Metabotropic Glutamate Receptors", Jour of Pharm and ExperTherap, 1998, vol. 284, pp. 651-660.
Helton et al. "LY354740: a Metabotropic Glutamate Receptor Agonist which Ameliorates Symptoms of Nicotine Withdrawal in Rats" Neuropharmacology, 1997, vol. 36, No. 11/12, pp. 1511-1516.
Hemstapat et al. "A Novel Family of Potent Negative Allosteric Modulators of Group II Metabotropic Glutamate Receptors" JPET 2007, vol. 322, pp. 254-264.
Henley et al. Characterization of the allosteric modulatory protein associated with non-NMDA receptors. [Review] [17 refs]. Biochemical Society Transactions 1993, 21 (1), 89-93.
Henry et al. The mGluR5 antagonist MPEP, but not the mGluR2/3 agonist LY314582, augments PCP effects on prepulse inhibition and locomotor activity. Neuropharmacology. 43(8):1199-209, 2002.
Herdeis et al. "[4+2] Cycloadducts of 5-Benzyloxy-2-Pyrindone with Electron Deficient Dienophiles. Regio- and Stereochemistry." Heterocycles. vol. 29 (2). 1989. 287-96.
Herdeis et al. "A Facile Entry to the 2-Azabicyclo[2.2.2]octane-6-one Skeleton via [4+2]-Cycloaddition." Jan. 1988. 76-8.
Herdeis et al. "A Three-Step Synthesis of b-Aminolaevulinic Acid." Arch. Pharm. vol. 317. 1984. 304-6.
Herdeis et al. "Stereochemistry and Reactivity of Phenylsulfonyl-substituted 2-Azabicyclo[2.2.2]octan-6-ones." Arch. Pharm. vol. 323. 1990. 937-42.
Heresco-Levy "Glutamatergic neurotransmission modulators as emerging new drugs for schizophrenia" Expert Opin Emerging Drugs 2005, vol. 10(4), pp. 827-844.
Hermann et al. "Human EEG gamma oscillations in neuropsychiatric disorders" Clinical Neurophysiology 2005, vol. 116, pp. 2719-2733.
Hermans et al. "Structural, signalling and regulatory properties of the group 1 metabotropic glutamate receptors : prototypic family C G-protein-coupled receptors" Biochem. J. 2001, vol. 359, pp. 465-484.
Herminghaus, "Brain metabolism in Alzheimer disease and vascular dementia assessed by in vivo proton magnetic resonance spectroscopy", Psychiatry Research: Neuroimaging 123, 2003, 183-190.
Hero et al., "The Clinical Global Impression—Schizophrenia Scale: A Simple Instrument to Measure the Diversity of Symptoms Present in Schizophrenia", Acta Psychiatr Scand Suppl., 2003, 416, 16-23.
Herrero et al. Functional switch from facilitation to inhibition in the control of glutamate release by metabotropic glutamate receptors. J. Biol. Chem. 1998, 273 (4), 1951-1958.
Herrero et al. Positive feedback of glutamate exocytosis by metabotropic presynaptic receptor stimulation [see comments]. Nature 1992, 360 (6400), 163-166.
Herrero et al. Rapid desensitization of the metabotropic glutamate receptor that facilitates glutamate release in rat cerebrocortical nerve terminals. European Journal of Neuroscience 1994, 6 (1), 115-120.

(56) References Cited

OTHER PUBLICATIONS

Hertzberg et al., "A Preliminary Study of Lamotrigine for the Treatment of Posttraumatic Stress Disorder", Biological Psychiatry, 1999, 45, 1226-1229.
Hettema "The Nosologic Relationship Between Generalized Anxiety Disorder and Major Depression" Depression and Anxiety 2008, vol. 25, 300-316.
Hetzenauer et al. "Individual contribution of metabotropic glutamate receptor (mGlu) 2 and 3 to c-Fos expression pattern evoked by mGlu2/3 antagonism" Psychopharmacology 2008, vol. 201, pp. 1-13.
Hickinbottom. "Reactions of organic compounds." 1939. 360-2.
Higashida et al. "Subtype-specific coupling with ADP-ribosyl cyclase of metabotropic glutamate receptors in retina, cervical superior ganglion and NG108-15 cells" Journal of Neurochemistry, 2003, vol. 85, pp. 1148-1158.
Higgins, "Pharmacological manipulation of mGlu2 receptors influences cognitive performance in the rodent", Neuropharmacology, 46, 2004, pp. 907-917.
Hijzen et al. Predictive validity of the potentiated startle response as a behavioral model for anxiolytic drugs, Psychopharmacology, 118:150-154 (1995).
Hirao et al. "Preparation of Optically Active 8,8'-Disubstituted 1,1'-Biisoquinoline." Heterocycles. vol. 42 (1). 1996. 415-22.
Hlavackova et al. "Evidence for a single heptahelical domain being turned on upon activation of a dimeric GPCR" EMBO 2005, vol. 24, pp. 499-509.
Hoang et al. "Expression of metabotropic glutamate receptors in nodose ganglia and the nucleus of the solitary tract" Am J Physiol Heart Circ Physiol 2001, vol. 281, pp. 457-462.
Hoeben et al. "Prediction of Serotonin 2A Receptor (5-HT2AR) Occupancy in Man From Nonclinical Pharmacology Data. Exposure vs. 5-HT2AR Occupancy Modeling Used to Help Design a Positron Emission Tomography (PET) Study in Healthy Male Subjects." Abstract, 2013 Annual Meeting of the Population Approach Group in Europe, Glasgow, Scotland.
Hoffman et al., "Human and Economic Burden of Generalized Anxiety Disorder", Depression and Anxiety, 2008, 25, 72-90.
Hofmeijer-Sevink et al., "Clinical Relevance of Comorbidity in Anxiety Disorders: A Report From the Netherlands Study of Depression and Anxiety (NESDA)", Journal of Affective Disorders, 2012, 137, 106-112.
Hohnadel et al. "Effect of repeated nicotine exposure on high-affinity nicotinic acetylcholine receptor density in spontaneously hypertensive rats" Neuroscience Letters 2005, vol. 382, pp. 158-163.
Holcomb et al. "Effects of Noncompetitive NMDA Receptor Blockade on Anterior Cingulate Cerebral Blood Flow in Volunteers with Schizophrenia" Neuropsychopharmacology 2005, vol. 30, pp. 2275-2282.
Holden, "Excited by Glutamate", Science, p. 1866-1868, vol. 300, Jun. 20, 2003.
Holloway et al., "Prenatal Stress Induces Schizophrenia-Like Alterations of Serotonin 2a and Metabotropic Glutamate 2 Receptors in the Adult Offspring: Role of Maternal Immune System", J. Neurosci., 2013, 33(3), 1088-1098.
Holscher et al. Metabotropic glutamate receptor activation and blockade: their role in long-term potentiation, learning and neurotoxicity. [Review] [125 refs]. Neuroscience & Biobehavioral Reviews 1999,23 (3), 399-410.
Homayoun et al. Orbitofrontal cortex neurons as a common target for classic and glutamatergic antipsychotic drugs. Proc. Natl. Acad. Sci. U. S. A. 2008, 105 (46), 18041-18046.
Homayoun et al., "Activation of Metabotropic Glutamate 2/3 Receptors Reverses the Effects of Nmda Receptor Hypofunction on Prefrontal Cortex Unit Activity in Awake Rats", J. Neurophysiol., 2005, 93(4), 1989-2001.
Homayoun et al., "Group 5 Metabotropic Glutamate Receptors: Role in Modulating Cortical Activity and Relevance to Cognition", European Journal of Pharmacology, 2010, 639, 33-39.

Cook et al. "Behavioral effects of some psychopharmacological agents.", Ann. NY Acad. S. 66: 740-752 (1957).
Cook et al. "Diethylaminoalkyl Ester Hydrochlorides of N-Alkyl-4-carbostyrilcarhoxylic Acids", J Am. Chem. Soc., 1952, 74, 543-554.
Cook et al., "Effects of Drugs on Avoidance and Escape Behavior", Fed. Proc. 23, 1964, 818-835.
Copani, "Activation of Metabotropic Glutamate Receptors Protects Cultured Neurons Against Apoptosis Induced by—Amyloid Peptide", Molecular Pharmacology, 1995, 47:890-897.
Copeland et al. "Positive allosteric modulation reveals a specific role for mGlu2 receptors in sensory processing in the thalamus" J Physiol 590.4 (2012) pp. 937-951.
Corlett at al., "Glutamatergic Model Psychoses: Prediction Error, Learning, and Inference", Neuropsychopharmacology, 2011, 36(1), 294-315.
Corti, "The use of knock-cut mice unravels distinct roles for mGlu2 and mGlu3 metabotropic glutamate receptors in mechanisms of neurodegeneration/neuroprotection," J. Neurosci. 27(31): 8297-8308 (2007).
Coryell et al. "Effects of anxiety on the long4erm course of depressive disorders" The British Journal of Psychiatry 2012, vol. 200, pp. 210-215.
Costantino et al. "Modeling of Poly (ADP-ribose) polymerase (PARP) Inhibitors. Docking of Ligands and Quantitative Structure-Activity Relationship Analysis." Journal of Medicinal Chemistry. vol. 44. 2001. 3785-94.
Coyle, "The Gaba-Glutamate Connection in Schizophrenia: Which is the Proximate Cause?", Biochem. Pharmacol., 2004, 68(8), 1507-1514.
Cozzi et al. Type 2 metabotropic glutamate (mGlu) receptors tonically inhibit transmitter release in rat caudate nucleus: in vivo studies with (2S,1'S,2'S,3'R)-2-(2'-carboxy-3'-phenylcydopropyl)glycine, a new potent and selective antagonist. European Journal of Neuroscience 1997, 9 (7), 1350-1355.
Craddock et al. "The genetics of schizophrenia and bipolar disorder: dissecting psychosis" J Med Genet 2005, vol. 42, pp. 193-204.
Cropley et al., "Molecular Imaging of the Dopaminergic System and its Association with Human Cognitive Function", Biol.Psychiatry, 2006, 59, 898-907.
Cube et al. "3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)" Bioorganic & Medicinal Chemistry Letters 15 (2005) 2389-2393.
Cummings, "Behavioral effects of memantine in Alzheimer disease patients receiving donepezil treatment" Neurology 2006;67:57-63.
Cymbalta (Registered) Highlights of Prescribing Information (2004).
Czapski et al. "Effect of poly (ADP-ribose) polymerase inhbitors on oxidative stress evoked hydroxyl radical level and macromolecules oxidation in cell free system of rat brain cortex." Neuroscience Letters. vol. 356. 2004. 45-8.
D'Alessandro et al. "The identification of structurally novel, selective, orally bioavailable positive allosteric modulators of mGluR2" Bioorg Med Chem Lett 2010, vol. 20, pp. 759-762.
D'Antoni et al., "Metabotropic Glutamate Receptors in Glial Cells", Neurochem. Res., 2008, 33(12), 2436-2443.
D'Ascenzo et al. mGluR5 stimulates gliotransmission in the nucleus accumbens. Proc. Natl. Acad. Sci. U. S. A 2007, 104 (6), 1995-2000.
D'Onofrio et al. Neuroprotection mediated by glial group-II metabotropic glutamate receptors requires the activation of the MAP kinase and the phosphatidylinositol-3-kinase pathways. Journal of Neurochemistry 2001, 78 (3), 435-445.
D'Onofrio et al., "Advances in the identification of g-secretase inhibitors for the treatment of Alzheimer's disease", Expert Opinion on Investigational Drugs, 2012, 7, 20-37.
Dale et al. "Mechanisms of metabotropic glutamate receptor desensitization: role in the patterning of effector enzyme activation" Neurochemistry International 2002, vol. 41, pp. 319-326.
Dale et al., "Spatial-Temporal Patterning of Metabotropic Glutamate Receptor-Mediated Inositol 1,4,5-Triphosphate, Calcium, and

(56) References Cited

OTHER PUBLICATIONS

Protein Kinase C Oscillations: Protein Kinase C-Dependent Receptor Phosphorylation is Not Required", J. Biol. Chem., 2001, 276(38), 35900-35908.

Danner et al. "Integrating patients' views into health technology assessment: Analytic hierarchy process (AHP) as a method to elicit patient preferences" International Journal of Technology Assessment in Health Care, 27:4 (2011), 369-375.

Dash et al. "Long-term homeostasis of extracellular glutamate in the rat cerebral cortex across sleep and waking states" J Neurosci 2009, vol. 29, pp. 620-629.

Datta et al, "Microinjection of glutamate into the pedunculopontine tegmentum induces REM sleep and wakefulness in the rat" Am J Physiol., Regul Integr Comp Physiol 2001, vol. 280, R752-R759.

Davidson et al. "Achieving Remission with Venlafaxine and Fluoxetine in Major Depression: Its Relationship to Anxiety Symptoms" Depression and Anxiety 2002, 16, 4-13.

Davidson et al.: "Differential effects of neuroleptic and other psychotropic agents on acquisition of avoidance in rats.", Life Sci. 18: 1279-1284 (1976).

Davis Diazepam and Flurazepam: Effects on Conditioned Fear as Measured with the Potentiated Startle Paradigm, Psychopharmacology, 62:1-7 (1979).

Davis et al. "2,1-Benzisothiazoles. XII. [1], The Use of N-Substituted-2,1-Benzisothiazolium Salts as Synthetic Equivalents of o-Aminobenzaldehydes. A Simple Synthesis of Some 2-Quinolones." Journal of Heterocyclic Chemistry. vol. 20. Nov.-Dec. 1983. 1707-8.

Davis Pharmacological and Anatomical Analysis of Fear Conditioning Using the Fear-Potentiated Startle Paradigm, Behavioral Neuroscience, 100:814-824 (1986).

Dawson et al. "Novel analysis for improved validity in semi-quantitative 2-deoxyglucose autoradiographic imaging" Journal of Neuroscience Methods 2008, vol. 175, pp. 25-35.

De Blasi et al. Molecular determinants of metabotropic glutamate receptor signaling. [Review] [77 refs]. Trends in Pharmacological Sciences. 2001, 22 (3), 114-120.

De Boer el al. "Characterization of the dinical effect of a positive allosteric modulator of the metabotropic glutamate receptor-2" Poster 2013 SOBP San Francisco http://www.addextherapeutics.com/fileadmin/user.sub.-upload/download/JNJ-POSTER.sub.-SOBP.sub.-2013.pdf retrieved on Aug. 22, 2013.

De Boer et al. "Characterization of the clinical effect of a positive allosteric modulator of the metabotropic glutamate receptor-2" Abstract, Society of Biological Psychiatry 67th Annual Scientific Convention May 3-5, 2012, Philadelphia, PA.

De Montis et al Selective adenylate cyclase increase in the limbic area of long-term imipramine-treated rats. European Journal of Pharmacology 1990, 180 (1), 169-174.

De Novellis et al. Type I and II metabotropic glutamate receptors modulate periaqueductal grey glycine release: interaction between mGlu2/3 and A1 adenosine receptors. Neuropharmacology 2002, 43(7):1061-9, 2002.

Dean the cortical serotonin2A receptor and the pathology of schizophrenia: a likely accomplice. J. Neurochem. 2003. 85, 1-13.

Dedeurwaerdere et al. "Memantine-induced brain activation as a model for the rapid screening of potential novel antipsychotic compounds: exemplified by activity of an mGlu2/3 receptor agonist" Psychophaimacology 2011, vol. 214, pp. 505-514.

Del Rio et al. Differential coupling of G-protein-linked receptors to Ca2+ mobilization through inositol(1,4,5) trisphosphale or ryanodine receptors in cerebelar granule cells in primary culture. European Journal of Neuroscience 1999, 11 (9), 3015-3022.

Del'Guidice et al. Messing up with traffic: different effects of antipsychotic agents on glutamate receptor complexes in vivo. Mol. Pharrnacol. 2008, 73 (5), 1339-1342.

Delille et al. "Heterocomplex formation of 5-HT2A-mGlu2 and its relevance for cellular signaling Cascades" Neuropharmacology 2012epub, no page numbers, doi:10.1016/j.neuropharm.2012.01.010.

Delille et al. "The two faces of the pharmacological interaction of mGlu2 and 5-HT2a—Relevance of receptor heterocomplexes and interaction through functional brain pathways" Neuropharmacology 2013, vol. 70, pp. 296-305.

Derks et al., "Kreapelin was right: a latent class analysis of symptom dimensions in patients and controls", Schizophrenia Bull. 2012, 495-505 [Epub ahead of print, no page numbers available].

Desseilles et al. Assessing the adequacy of past antidepressant trials: a clinician's guide to the antidepressant treatment response questionnaire. J Clin Psychiatry. Aug. 2011; 72(8): 1152-1154.

Dhal, P.N. et al., "Synthesis of thiohydantoins, thiazolidones and their derivatives from N.sup.1-(4'-aryl thiazole 2'-YL) thioureas", J. Indian Chem. Soc. 50(1):680-684, Oct. 1973.

Dhami et al. G Protein-coupled receptor kinase 2 regulator of G protein signaling homology domain binds to both metabotropic glutamate receptor 1a and Galphaq to attenuate signaling. Journal of Biological Chemistry. 279 (16):16614-20, 2004.

Dhami et al. Regulation of metabotropic glutamate receptor signaling, desensitization and endocytosis. Pharmacol. Ther. 2006, 111 (1), 260-271.

Dhanya et al. "Design and synthesis of an orally active metabotropic glutamate receptor subtype-2 (mCluR2) positive allosteric modulator (PAM) that decreases cocaine self-administration in rats" J Med Chem 2011, vol. 54, pp. 342-353.

\* cited by examiner

1',3'-DISUBSTITUTED-4-PHENYL-3,4,5,6-TETRAHYDRO-2H,1'H-[1,4']BIPYRIDINYL-2'-ONES

CROSS-REFERENCE TO RELATED APPLICATIONS

This application is a continuation of U.S. application Ser. No. 14/817,676, filed Aug. 4, 2015, which is a continuation application of U.S. application Ser. No. 13/803,267, filed on Mar. 14, 2013, now U.S. Pat. No. 9,132,122, issued Sep. 15, 2015, which is a continuation application of U.S. application Ser. No. 12/677,618, filed on Jun. 3, 2010, now U.S. Pat. No. 9,114,138, issued Aug. 25, 2015, which is a U.S. National Phase Application under 35 USC 371 of International Application PCT/EP2008/007551, filed Sep. 12, 2008, which claims priority to European Application No. 07116390.1, filed Sep. 14, 2007. Each application is hereby incorporated herein by reference in its entirety for all purposes.

FIELD OF THE INVENTION

The present invention relates to novel pyridinone-derivatives which are positive allosteric modulators of the metabotropic glutamate receptor subtype 2 ("mGluR2") and which are useful for the treatment or prevention of neurological and psychiatric disorders associated with glutamate dysfunction and diseases in which the mGluR2 subtype of metabotropic receptors is involved. The invention is also directed to pharmaceutical compositions comprising such compounds, to processes to prepare such compounds and compositions, and to the use of such compounds for the prevention or treatment of neurological and psychiatric disorders and diseases in which mGluR2 is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), and the NMDA, AMPA and kainate receptors which are responsible for fast excitatory transmission.

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signaling pathways.

The mGluR2 subtype is negatively coupled to adenylate cyclase via activation of Gαi-protein, and its activation leads to inhibition of glutamate release in the synapse. In the central nervous system (CNS), mGluR2 receptors are abundant mainly throughout cortex, thalamic regions, accessory olfactory bulb, hippocampus, amygdala, caudate-putamen and nucleus accumbens.

Activating mGluR2 was shown in clinical trials to be efficacious to treat anxiety disorders. In addition, activating mGluR2 in various animal models was shown to be efficacious, thus representing a potential novel therapeutic approach for the treatment of schizophrenia, epilepsy, addiction/drug dependence, Parkinson's disease, pain, sleep disorders and Huntington's disease.

To date, most of the available pharmacological tools targeting mGluRs are orthosteric ligands which activate several members of the family as they are structural analogs of glutamate.

A new avenue for developing selective compounds acting at mGluRs is to identify compounds that act through allosteric mechanisms, modulating the receptor by binding to a site different from the highly conserved orthosteric binding site.

Positive allosteric modulators of mGluRs have emerged recently as novel pharmacological entities offering this attractive alternative. Various compounds have been described as mGluR2 positive allosteric modulators. WO2004/092135 (NPS & Astra Zeneca), WO2004/018386, WO2006/014918 and WO2006/015158 (Merck), WO2001/56990 (Eli Lilly) and WO2006/030032 (Addex & Janssen Pharmaceutica) describe respectively phenyl sulfonamide, acetophenone, indanone, pyridylmethyl sulfonamide and pyridinone derivatives as mGluR2 positive allosteric modulators. None of the specifically disclosed compounds therein are structurally related to the compounds of the present invention.

It was demonstrated that such compounds do not activate the receptor by themselves. Rather, they enable the receptor to produce a maximal response to a concentration of glutamate which by itself induces a minimal response. Mutational analysis has demonstrated unequivocally that the binding of mGluR2 positive allosteric modulators does not occur at the orthosteric site, but instead at an allosteric site situated within the seven transmembrane region of the receptor.

Animal data are suggesting that positive allosteric modulators of mGluR2 have effects in anxiety and psychosis models similar to those obtained with orthosteric agonists. Allosteric modulators of mGluR2 were shown to be active in fear-potentiated startle, and in stress-induced hyperthermia models of anxiety. Furthermore, such compounds were shown to be active in reversal of ketamine- or amphetamine-induced hyperlocomotion, and in reversal of amphetamine-induced disruption of prepulse inhibition of the acoustic startle effect models of schizophrenia. (J. Pharmacol. Exp. Ther. 2006, 318, 173-185; Psychopharmacology 2005, 179, 271-283).

Recent animal studies further reveal that the selective positive allosteric modulator of metabotropic glutamate receptor subtype 2 biphenyl-indanone (BINA) blocks a hallucinogenic drug model of psychosis, supporting the strategy of targeting mGluR2 receptors for treating glutamatergic dysfunction in schizophrenia. (Mol. Pharmacol. 2007, 72, 477-484).

Positive allosteric modulators enable potentiation of the glutamate response, but they have also been shown to potentiate the response to orthosteric mGluR2 agonists such as LY379268 or DCG-IV. These data provide evidence for yet another novel therapeutic approach to treat above mentioned neurological and psychiatric diseases involving mGluR2, which would use a combination of a positive allosteric modulator of mGluR2 together with an orthosteric agonist of mGluR2.

DETAILED DESCRIPTION OF THE INVENTION

The present invention relates to compounds having metabotropic glutamate receptor 2 modulator activity, said compounds having the Formula (I)

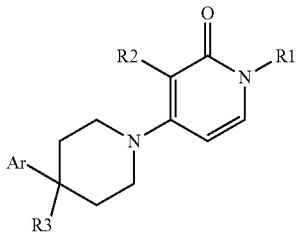

and the stereochemically isomeric forms thereof, wherein
$R^1$ is $C_{1-6}$alkyl; or $C_{1-3}$alkyl substituted with $C_{3-7}$cycloalkyl, phenyl, or phenyl substituted with halo, trifluoromethyl or trifluoromethoxy;
$R^2$ is halo, trifluoromethyl, $C_{1-3}$alkyl or cyclopropyl;
$R^3$ is hydrogen, fluoro, hydroxyl, hydroxy$C_{1-3}$alkyl, hydroxy$C_{1-3}$alkyloxy, fluoro$C_{1-3}$alkyl, fluoro$C_{1-3}$alkyloxy or cyano; and
Ar is unsubstituted phenyl; or phenyl substituted with n radicals $R^4$, wherein n is 1, 2 or 3;
$R^4$ is selected from the group consisting of hydrogen, halo, $C_{1-3}$alkyl, hydroxy$C_{1-3}$alkyl, polyhalo$C_{1-3}$alkyl, cyano, hydroxyl, amino, carboxyl, $C_{1-3}$alkyloxy$C_{1-3}$alkyl, $C_{1-3}$alkyloxy, polyhalo$C_{1-3}$alkyloxy, $C_{1-3}$alkylcarbonyl, mono- and di($C_{1-3}$alkyl)amino, and morpholinyl; or
two vicinal $R^4$ radicals taken together form a bivalent radical of formula —N=CH—NH— (a), —CH=CH—NH— (b), or —O—CH$_2$—CH$_2$—NH— (c); or $R^3$ and a $R^4$ radical in ortho position taken together form a bivalent radical of formula —CH$_2$—O— (d), or —O—CH$_2$— (e);

and the pharmaceutically acceptable salts and solvates thereof.

In one embodiment, the invention relates to a compound of Formula (I) or a stereochemically isomeric form thereof wherein
$R^1$ is $C_{1-6}$alkyl; or $C_{1-3}$alkyl substituted with $C_{3-7}$cycloalkyl, phenyl, or phenyl substituted with halo, trifluoromethyl or trifluoromethoxy;
$R^2$ is halo, trifluoromethyl, $C_{1-3}$alkyl or cyclopropyl;
$R^3$ is hydrogen, fluoro, hydroxyl, hydroxy$C_{1-3}$alkyl, hydroxy$C_{1-3}$alkyloxy, fluoro$C_{1-3}$alkyl, fluoro$C_{1-3}$alkyloxy or cyano; and
Ar is unsubstituted phenyl, or phenyl substituted with n radicals $R^4$, wherein n is 1, 2 or 3;
$R^4$ is selected from the group consisting of hydrogen, halo; $C_{1-3}$alkyl; hydroxy$C_{1-3}$alkyl, polyhalo$C_{1-3}$alkyl; cyano; hydroxy; amino; carboxyl; $C_{1-3}$alkyloxy$C_{1-3}$alkyl; $C_{1-3}$alkyloxy; polyhalo$C_{1-3}$alkyloxy; $C_{1-3}$alkylcarbonyl; mono- and di($C_{1-3}$alkyl)amino, and morpholinyl; or
two vicinal $R^4$ radicals taken together form a bivalent radical of formula —N=CH—NH— (a), —CH=CH—NH— (b), or —O—CH$_2$—CH$_2$—NH— (c);

and the pharmaceutically acceptable salts and solvates thereof.

In one embodiment, the invention relates to a compound according to Formula (I) or a stereochemically isomeric form thereof, wherein
$R^1$ is 1-butyl, 2-methyl-1-propyl, 3-methyl-1-butyl, (cyclopropyl)methyl or 2-(cyclopropyl)-1-ethyl;
$R^2$ is chloro, bromo, cyclopropyl or trifluoromethyl;
$R^3$ is hydrogen, fluoro or cyano; and
Ar is unsubstituted phenyl; or phenyl substituted with halo, trifluoromethyl, morpholinyl or hydroxy$C_{1-3}$alkyl;
or a pharmaceutically acceptable salt or solvate thereof.

In one embodiment, the invention relates to a compound according to Formula (I) or a stereochemically isomeric form thereof, wherein
$R^1$ is 1-butyl, 3-methyl-1-butyl, (cyclopropyl)methyl or 2-(cyclopropyl)-1-ethyl;
$R^2$ is chloro;
$R^3$ is hydrogen or fluoro; and
Ar is unsubstituted phenyl; or phenyl substituted with hydroxy$C_{1-3}$ alkyl;
or a pharmaceutically acceptable salt or solvate thereof.

In one embodiment the invention relates to the compound
3'-Chloro-1'-cyclopropylmethyl-4-phenyl-3,4,5,6-tetrahydro-2H,1'H-[1,4']bipyridinyl-2'-one (E1) or
1'-Butyl-3'-chloro-4-phenyl-3,4,5,6-tetrahydro-2H, 1'H-[1,4']bipyridinyl-2'-one (E2).

The notation $C_{1-3}$alkyl as a group or part of a group defines a saturated, straight or branched, hydrocarbon radical having from 1 to 3 carbon atoms, such as methyl, ethyl, 1-propyl and 1-methylethyl; e.g. hydroxy$C_{1-3}$alkyl for example defines hydroxymethyl, 2-hydroxyethyl, 3-hydroxypropyl and 1-hydroxy-1-methylethyl.

The notation $C_{1-6}$alkyl as a group or part of a group defines a saturated, straight or branched, hydrocarbon radical having from 1 to 6 carbon atoms such as methyl, ethyl, 1-propyl, 1-methylethyl, 1-butyl, 2-methyl-1-propyl, 3-methyl-1-butyl, 1-pentyl, 1-hexyl and the like.

The notation $C_{3-7}$cycloalkyl defines a saturated, cyclic hydrocarbon radical having from 3 to 7 carbon atoms, such as cyclopropyl, cyclobutyl, cyclopentyl, cyclohexyl and cycloheptyl.

The notation halo or halogen as a group or part of a group is generic for fluoro, chloro, bromo, iodo.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said salt forms can be converted into the free base form by treatment with an appropriate base.

The compounds according to Formula (I) containing acidic protons may also be converted into their therapeutically active non-toxic base salt forms by treatment with appropriate organic and inorganic bases. Appropriate base salt forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salt forms can be converted into the free acid forms by treatment with an appropriate acid.

The term solvate comprises the solvent addition forms as well as the salts thereof, which the compounds of formula (I) are able to form. Examples of such solvent addition forms are e.g. hydrates, alcoholates and the like.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. The invention also embraces each of the individual isomeric forms of the compounds of Formula (I) and their salts and solvates, substantially free, i.e. associated with less than 10%, preferably less than 5%, in particular less than 2% and most preferably less than 1% of the other isomers. Thus, when a compound of formula (I) is for instance specified as (R), this means that the compound is substantially free of the (S) isomer. Stereogenic centers may have the R- or S-configuration; substituents on bivalent cyclic (partially) saturated radicals may have either the cis- or trans-configuration.

Following CAS nomenclature conventions, when two stereogenic centers of known absolute configuration are present in a compound, an R or S descriptor is assigned (based on Cahn-Ingold-Prelog sequence rule) to the lowest-numbered chiral center, the reference center. The configuration of the second stereogenic center is indicated using relative descriptors [R*R*] or [R*,S*], where R* is always specified as the reference center and [R*,R*] indicates centers with the same chirality and [R*,S*] indicates centers of unlike chirality. For example, if the lowest-numbered chiral center in the compound has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

A. Preparation of the Final Compounds

Experimental Procedure 1

The compounds according to Formula (I), in the case of $R^2$ being halogen, can be prepared by reacting an intermediate of Formula (II) with an N-halosuccinimide reagent, such as N-chlorosuccinimide, N-bromosuccinimide or N-iodosuccinimide, according to reaction scheme (1). This reaction is performed in a suitable reaction-inert and aprotic solvent, such as, for example, dichloromethane or 1,2-dichloroethane, stirring the reaction mixture at a suitable temperature, typically at room temperature, for the required time to achieve completion of the reaction, usually 1 hour. In reaction scheme (1), $R^2$ is halogen and all other variables are defined as in Formula (I).

Reaction Scheme 1

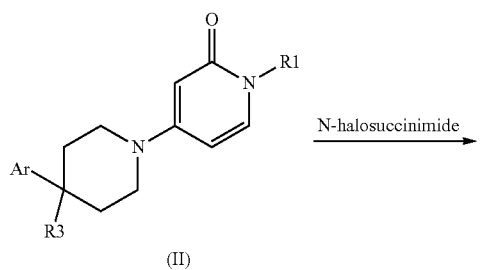

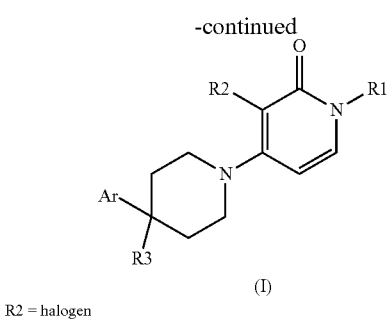

R2 = halogen

Experimental Procedure 2

Alternatively, compounds according to Formula (I) can be prepared by reacting an intermediate of Formula (III) with an intermediate of Formula (IV), which can be either commercially available or may be synthesized by procedures well known to anyone skilled in the art, according to reaction scheme (2). This reaction is performed in a suitable reaction-inert solvent such as, for example, toluene, in the presence of a suitable base such as, for example, sodium tert-butoxide, a metal-based catalyst, specifically a palladium catalyst, such as palladium(II) acetate, and a suitable ligand, such as for example [1,1'-binaphthalene]-2,2'-diylbis[diphenylphosphine] (BINAP), heating for a suitable period of time that allows the completion of the reaction, for example at 100° C. for 16 hours in a sealed tube. In reaction scheme (2), $Z^a$ is a group suitable for Pd mediated coupling with amines, such as, for example, a halogen or triflate. All other variables are defined as in Formula (I).

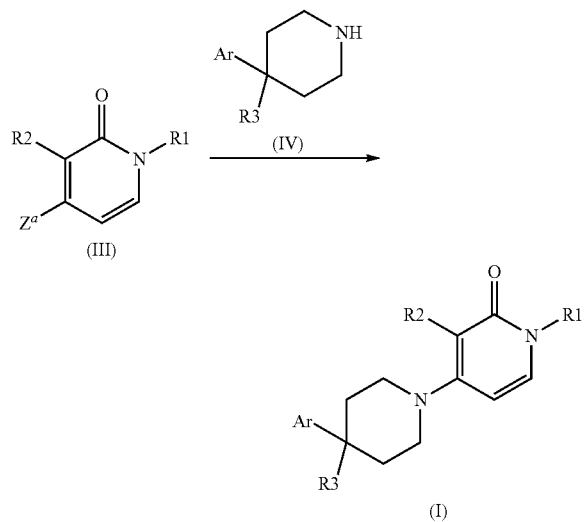

Reaction Scheme 2

Such intermediates of Formula (II) and Formula (III) may be prepared according to reaction schemes (3) to (11) (see below). The transformations of different functional groups present in the final compounds, into other functional groups according to Formula (I), can be performed by synthesis methods well known by the person skilled in the art.

Additionally, compounds according to Formula (I) can be prepared by a skilled person using art known procedures by further modifications of compounds of Formula (I):

Alkylation of compounds of Formula (I) that contain in their structure one or more hydroxy-substituents with a suitable alkylating agent such as for example 2-fluoroethyl tosylate under thermal conditions using a suitable base such as for example sodium hydride, in a suitable reaction-inert solvent such as, for example 1,2-dimethoxyethane or dimethylformamide.

Fluorination of compounds of Formula (I) that contain in their structure one or more hydroxy-substituents with a suitable fluorinating agent, such as for example (diethylamino)sulfur trifluoride. This reaction may be performed in a suitable reaction-inert solvent such as, for example, dichloromethane, under a moderately low temperature such as, for example, a temperature ranging from −78° C. to 30° C. during, for example, 0.5 to 12 hours.

Reaction of compounds of Formula (I) that contain in their structure one or more hydroxy-substituents with an alcohol derivative by using a suitable coupling system such as, for example, di-tert-butylazodicarboxylate/triphenylphosphine under thermal conditions.

B. Preparation of the Intermediates

Experimental Procedure 3

Intermediates of Formula (II) can be prepared by reacting an intermediate of Formula (V) with an intermediate of Formula (IV) according to reaction scheme (3). This reaction is performed in a suitable reaction-inert solvent such as, for example, toluene, in the presence of a suitable base such as, for example, sodium tert-butoxide, a metal-based catalyst, specifically a palladium catalyst, such as palladium(II) acetate, and a suitable ligand, such as for example [1,1'-binaphthalene]-2,2'-diylbis[diphenylphosphine] (BINAP), heating for a suitable period of time that allows the completion of the reaction, for example at 100° C. for 16 hours in a sealed tube. In reaction scheme (3), all variables are defined as in Formula (I).

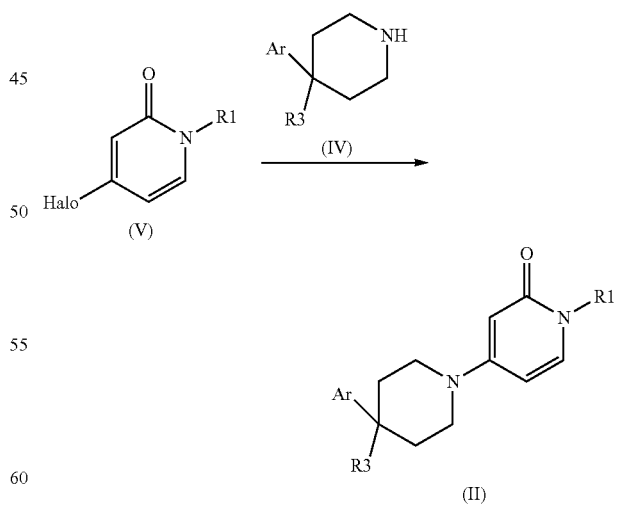

Reaction Scheme 3

Experimental Procedure 4

Intermediates of Formula (III-a) and (III-b) can be prepared by reacting an intermediate of Formula (VI), wherein Y is H or R² (as defined as in Formula I), with a suitable halogenating agent such as, for example, phosphorus oxybromide. This reaction may be performed in a suitable reaction-inert solvent such as, for example, DMF, at a moderately elevated temperature such as, for example, 110° C., for a suitable period of time that allows the completion of the reaction, for instance 1 hour. In reaction scheme (4), variable $R^1$ is defined as in Formula (I).

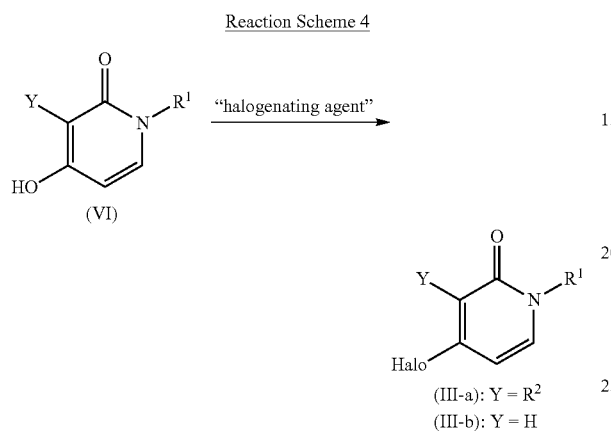

Experimental Procedure 5

Intermediates of Formula (III-c) can be prepared by reacting an intermediate of Formula (VI-a) with triflic anhydride (also called trifloromethanesulfonic anhydride). The reaction may be performed in a suitable reaction-inert solvent such as, for example, dichloromethane, in the presence of a base such as, for example, pyridine at a low temperature such as, for example, −78° C. In reaction scheme (5), all variables are defined as in Formula (I).

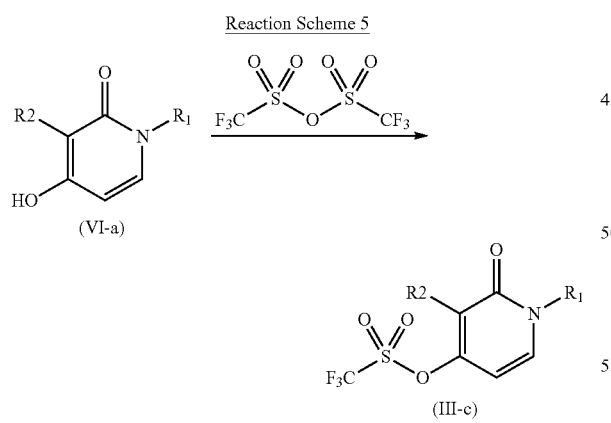

Experimental Procedure 6

Intermediates of Formula (VI) can be prepared by hydrogenolysis of intermediates of Formula (VII-a, VII-b or VII-c), in a suitable reaction-inert solvent such as, for example, ethanol, in the presence of a catalyst such as, for example, 10% palladium on activated carbon, for a period of time that ensures the completion of the reaction, typically at room temperature and 1 atmosphere of hydrogen for 2 hours. In reaction scheme (6), variable $R^1$ is defined as in Formula (I).

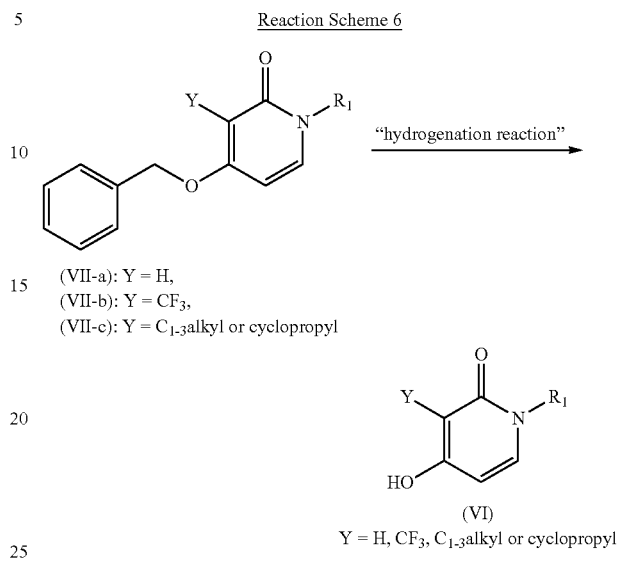

Experimental Procedure 7

Alternatively, intermediates of Formula (VI), wherein Y=halogen, can be prepared by reacting an intermediate of Formula (VII-d) in a mixture of acetic acid and hydrobromic acid, and heating the mixture at a temperature and for the time required to allow completion of the reaction, typically at 130° C. for 30 minutes under microwave irradiation. In reaction scheme (7), variable $R^1$ is defined as in Formula (I).

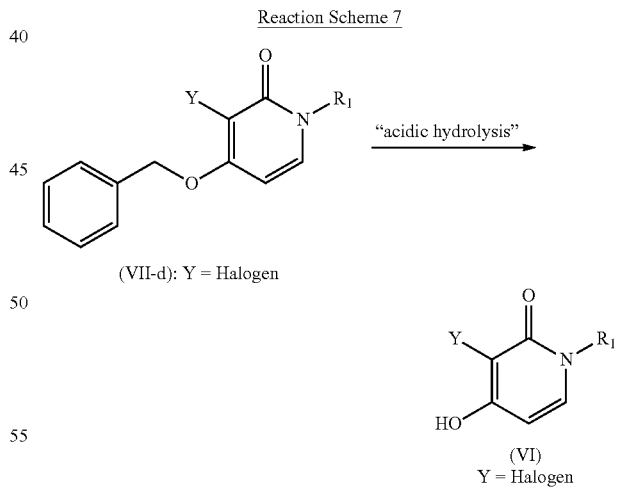

Experimental Procedure 8

Intermediates of Formula (VII-a) can be prepared by art known procedures by reacting commercially available 4-benzyloxy-1H-pyridin-2-one with a commercially available alkylating agent of Formula (VIII), in which $Z^b$ is a suitable leaving group, using a base such as, for example, $K_2CO_3$, and, optionally an iodine salt such as, for example, KI, in an inert solvent such as, for example, acetonitrile or DMF, at a moderately high temperature such as, for example, 80-120° C., for a suitable period of time that allows the completion of the reaction, for example 16 hours. In reaction scheme (8), variable $R^1$ is defined as in Formula (I) and $Z^b$ is a suitable leaving group such as, for example, halogen.

Experimental Procedure 10

Intermediates of Formula (VII-d) can be prepared by reacting an intermediate of Formula (VII-a) with a commercially available N-halosuccinimide, such as N-chloro- (NCS), N-bromo- (NBS) or N-iodosuccinimide (NIS), in a suitable reaction-inert solvent such as, for example, DMF, dichloromethane or acetic acid, typically at room temperature for 1 to 24 hours. In reaction scheme (10), variable $R^1$ is defined as in Formula (I).

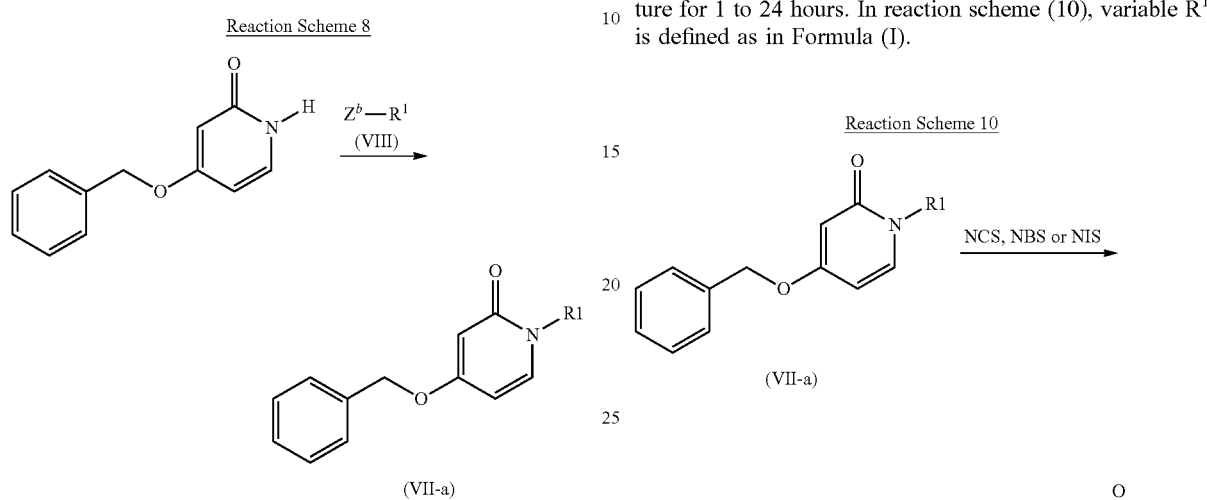

Reaction Scheme 8

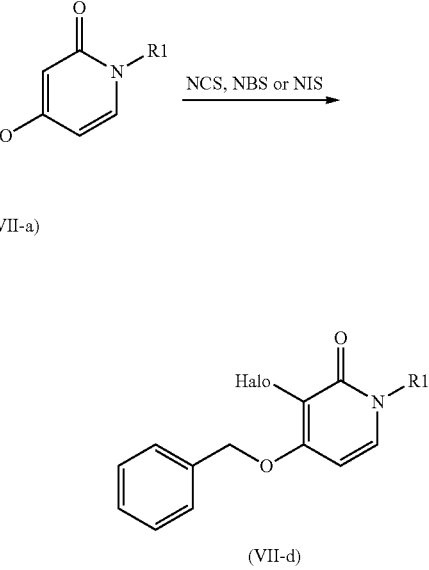

Reaction Scheme 10

Experimental Procedure 9

Intermediates of Formula (VII-b) can be prepared by reacting an intermediate of Formula (VII-e), wherein Y is iodine, with commercially available methyl 2,2-difluoro-2-(fluorosulfonyl)acetate, in a suitable reaction-inert solvent such as, for example, DMF, in presence of a suitable copper salt such as copper(I) iodide, heating for a suitable period of time that allows the completion of the reaction, for example at 100° C. for 5 hours. In reaction scheme (9), variable $R^1$ is defined as in Formula (I).

Experimental Procedure 11

Intermediates of Formula (VII-c) can be prepared by reacting an intermediate of Formula (VII-d) with a $C_{1-3}$alkyl- or cyclopropyl-boronic acid derivative, such as cyclopropyl-boronic acid or methyl-boronic acid, in a suitable reaction-inert solvent such as, for example, 1,4-dioxane, in the presence of a suitable palladium catalyst-complex such as, for example, [1,1'-bis(diphenylphosphino)-ferrocene]-dichloropalladium(II)—DCM complex, and in the presence of a suitable base such as sodium hydrogencarbonate, heating for a suitable period of time that allows the completion of the reaction, for example at 175° C. for 20 minutes under microwave irradiation. In reaction scheme (11), variable $R^1$ is defined as in Formula (I).

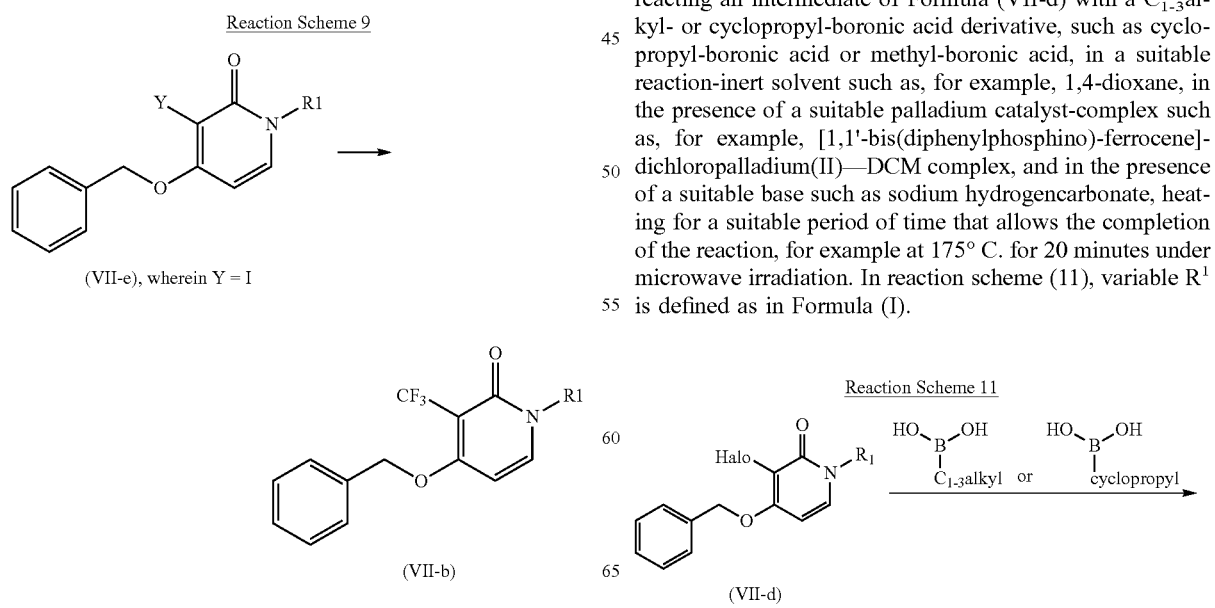

Reaction Scheme 9

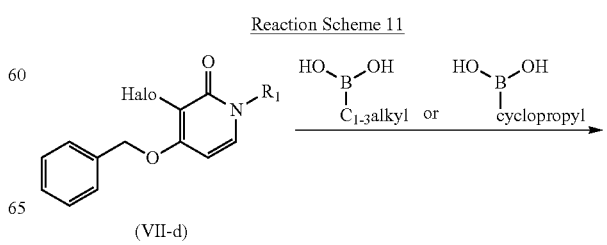

Reaction Scheme 11

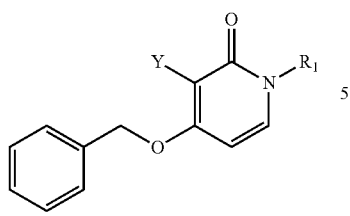

(VII-c): Y = C$_{1-3}$alkyl or cyclopropyl

Experimental Procedure 12

Intermediates of formula (IV) can be prepared by deprotection of the piperidine nitrogen in an intermediate of formula (IX) wherein L is a suitable protecting group for the nitrogen atom of a piperidine derivative, such as for example tert-butoxycarbonyl, ethoxycarbonyl, benzyloxycarbonyl, benzyl and methyl, applying art known procedures, according to reaction scheme (12). In reaction scheme (12), all variables are defined as in formula (I).

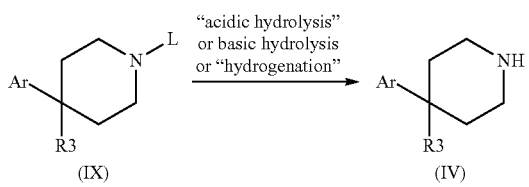

Experimental Procedure 13

Intermediates of formula (IV-a) can be prepared by hydrogenation of an intermediate of formula (X) applying art known procedures, according to reaction scheme (13). In reaction scheme (13), Ar is defined as in formula (I).

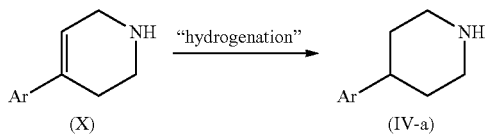

Experimental Procedure 14

Intermediates of formula (IX-a) can be prepared by hydrogenation of an intermediate of formula (XI) wherein L is a suitable protecting group for the nitrogen atom of a tetrahydropyridine derivative, such as for example tert-butoxycarbonyl, ethoxycarbonyl, benzyloxycarbonyl, benzyl and methyl, applying art known procedures, according to reaction scheme (14). In reaction scheme (14), Ar is defined as in Formula (I).

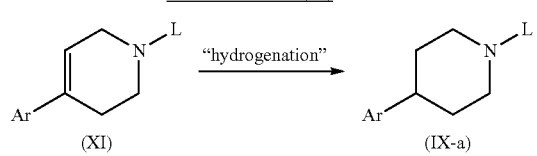

Experimental Procedure 15

Intermediates of formula (X) can be prepared by deprotection of the tetrahydropyridine nitrogen in an intermediate of formula (XI) wherein L is a suitable protecting group for the nitrogen atom of a tetrahydropyridine derivative, such as for example tert-butoxycarbonyl, ethoxycarbonyl, benzyloxycarbonyl, benzyl and methyl, applying art known procedures, according to reaction scheme (15). In reaction scheme (15), Ar is defined as in formula (I).

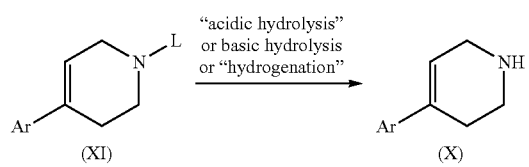

Experimental Procedure 16

Intermediates of formula (XI) can be prepared by reacting an intermediate of formula (XII) with an intermediate of formula (XIII) according to reaction scheme (16). The reaction may be performed in a suitable reaction-inert solvent, such as, for example, 1,4-dioxane, or mixtures of inert solvents such as, for example, 1,4-dioxane/DMF, in the presence of a suitable base, such as, for example, aqueous NaHCO$_3$ or Na$_2$CO$_3$, a suitable catalyst, such as for example a Pd-complex catalyst such as, for example, Pd(PPh$_3$)$_4$, under thermal conditions such as, for example, heating the reaction mixture at 150° C. under microwave irradiation, during, for example, 10 minutes. In reaction scheme (16), all variables are defined as in formula (I); $Z^c$ is a group suitable for Pd mediated coupling with boronic acids or boronic esters, such as, for example, a halo or triflate; L is a suitable protecting group for the nitrogen atom of a tetrahydropyridine derivative, such as for example tert-butoxycarbonyl, ethoxycarbonyl, benzyloxycarbonyl, benzyl and methyl and R$_4$ and R$_5$ are hydrogen or C$_{1-4}$alkyl, or may be taken together to form for example a bivalent radical of formula —CH$_2$CH$_2$—, —CH$_2$CH$_2$CH$_2$—, or —C(CH$_3$)$_2$C(CH$_3$)$_2$—.

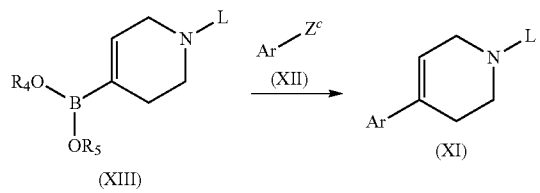

Experimental Procedure 17

Intermediates of formula (IV) wherein $R_3$ represents fluoro or $C_{1-3}$alkyl substituted with fluoro, said $R_3$ being represented by $-L_1-F$ wherein $L_1$ represents $C_{1-3}$alkyl or a covalent bond, and said intermediates being represented by formula (IV-b), can be prepared by art known procedures by reacting an intermediate of formula (IX-b) wherein L is a suitable protecting group for the nitrogen atom of the piperidine moiety, such as for example tert-butoxycarbonyl, ethoxycarbonyl, benzyloxycarbonyl, benzyl and methyl, with a suitable fluorinating agent such as for example (diethylamino)sulfur trifluoride, resulting in an intermediate of formula (IX-c) according to reaction scheme (17) step (a). The reaction may be performed in a suitable reaction-inert solvent, such as, for example, dichloromethane. The reaction may be performed under a moderately low temperature such as, for example, a temperature ranging from −78° C. to 30° C. during for example 0.5 to 12 hours. The resulting intermediate of formula (IX-c) can then be transformed according to reaction scheme (17) step (b), in an intermediate of Formula (IV-b) by deprotection of the piperidine nitrogen applying art known procedures, such as for example those described in experimental procedure 15 herein above. In reaction scheme (17), Ar is defined as in formula (I).

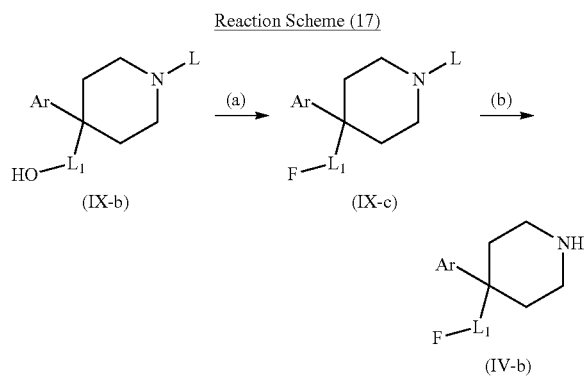

Reaction Scheme (17)

Experimental Procedure 18

Intermediates of formula (IV) wherein $R_3$ represents $C_{1-3}$alkyloxy substituted with fluoro, said $C_{1-3}$alkyloxy being represented by Q, said $R_3$ being represented by -Q-F, and said intermediates being represented by formula (IV-d), can be prepared by art known procedures by reacting a hydroxyl-substituted intermediate of formula (IX-d) wherein L is a suitable protecting group for the nitrogen atom of the piperidine moiety, such as for example tert-butoxycarbonyl, ethoxycarbonyl, benzyloxycarbonyl, benzyl and methyl, with a suitable fluorinating agent such as (diethylamino)sulfur trifluoride, resulting in an intermediate of formula (IX-e) according to reaction scheme (18) step (a). The reaction can be performed in a suitable reaction-inert solvent, such as, for example, dichloromethane, under a moderately low temperature such as, for example, a temperature ranging from −78° C. to 30° C. during for example 0.5 to 12 hours. The intermediate of Formula (IX-e) can then be transformed according to reaction scheme (18) step (b) in an intermediate of Formula (IV-d) by deprotection of the piperidine nitrogen applying art known procedures, such as for example those described in experimental procedure 17 hereinabove. In reaction scheme (18), Ar is defined as in formula (I).

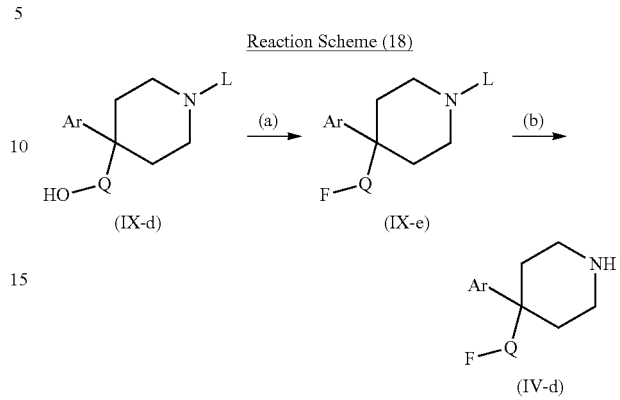

Reaction Scheme (18)

Experimental Procedure 19

Intermediates of formula (IX-b) wherein L1 represents $CH_2$, said intermediates being represented by formula (IX-f), can be prepared by reacting an intermediate of formula (XIV) wherein L is a suitable protecting group for the nitrogen atom of the piperidine moiety, such as for example tert-butoxycarbonyl, ethoxycarbonyl, benzyloxycarbonyl, benzyl and methyl, with a suitable reducing agent, such as for example, lithium aluminium hydride, according to reaction scheme (19). The reaction may be performed in a suitable solvent, such as for example tetrahydrofuran, at a moderately low temperature such as, for example from −20° C. In reaction scheme (19) Ar is defined as in formula (I)

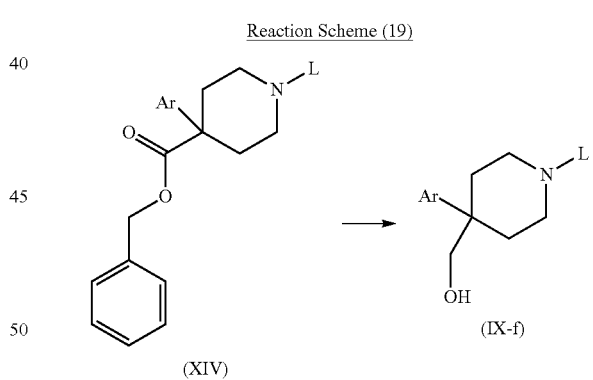

Reaction Scheme (19)

The starting materials according to Formulas (VIII), (IX-b), (IX-d), (XII), (XIII) and XIV are either commercially available or may be prepared according to conventional reaction procedures generally known by those skilled in the art.

Pharmacology

The compounds provided in this invention are positive allosteric modulators of metabotropic glutamate receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists, enhancing the response of the receptor. Hence, the present invention relates to a compound according to the present invention for use as a medicine, as well as to the use of a compound according to the invention or a pharmaceutical composition according to the invention for the manufacture of a medicament for treating or preventing, in particular treating, a condition in a mammal, including a human, the treatment or prevention of which is affected or facilitated by the neuromodulatory effect of allosteric modulators of mGluR2, in particular positive allosteric modulators thereof. The present invention also relates to a compound according to the present invention or a pharmaceutical composition according to the invention for use in the manufacture of a medicament for treating or preventing, in particular treating, a condition in a mammal, including a human, the treatment or prevention of which is affected or facilitated by the neuromodulatory effect of allosteric modulators of mGluR2, in particular positive allosteric modulators thereof. The present invention also relates to a compound according to the present invention or a pharmaceutical composition according to the invention for treating or preventing, in particular treating, a condition in a mammal, including a human, the treatment or prevention of which is affected or facilitated by the neuromodulatory effect of allosteric modulators of mGluR2, in particular positive allosteric modulators thereof.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR2.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of anxiety, schizophrenia, migraine, depression, and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Because such positive allosteric modulators of mGluR2, including compounds of Formula (I), enhance the response of mGluR2 to glutamate, it is an advantage that the present methods utilize endogenous glutamate.

Because positive allosteric modulators of mGluR2, including compounds of Formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of Formula (I), in combination with an mGluR2 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament. The present invention also relates to a combination of a compound according to the present invention and a mGluR2 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR2 orthosteric agonist, as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular positive mGluR2 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "THF" means tetrahydrofuran; "DMF" means N,N-dimethylformamide; "EtOAc" means ethyl acetate; "DCM" means dichloromethane; "DME" means 1,2-dimethoxyethane; "DCE" means 1,2-dichloroethane; "DIPE" means diisopropylether; "DMSO" means dimethylsulfoxide; "BINAP" means[1,1'-binaphthalene]-2,2'-diyl-bis[diphenylphosphine]; "DBU" means 1,8-diaza-7-bicyclo[5.4.0]undecene; Xantphos means (9,9-dimethyl-9H-xanthene-4,5-diyl)bis[diphenylphosphine]; MeOH means methanol; "q.s." means quantum sufficit; "M.P." means melting point;

Microwave assisted reactions were performed in a single-mode reactor: Initiator™ Sixty EXP microwave reactor (Biotage AB), or in a multimode reactor: MicroSYNTH Labstation (Milestone, Inc.).

Description 1

4-Benzyloxy-1-cyclopropylmethyl-1H-pyridin-2-one (D1)

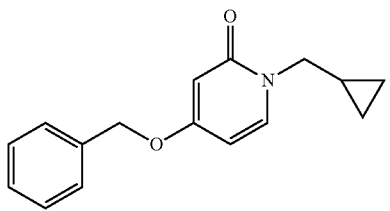 [SMILES: O=c1cc(OCc2ccccc2)ccn1CC1CC1]

Bromomethyl-cyclopropane (3.68 g, 27.33 mmol) and potassium carbonate (10.3 g, 74.52 mmol) were added to a solution of 4-benzyloxy-1H-pyridin-2-one (5.0 g, 24.84 mmol) in acetonitrile (200 ml) and the mixture was heated at reflux for 16 hours. The reaction mixture was filtered through diatomaceous earth and concentrated in vacuo. The crude residue was then triturated with diethylether to yield pure D1 (6.32 g, 98%) as a white solid.

Description 2

1-Cyclopropylmethyl-4-hydroxy-1H-pyridin-2-one (D2)

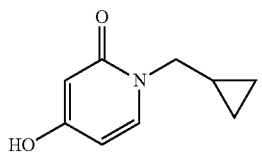 [SMILES: O=c1cc(O)ccn1CC1CC1]

A mixture of intermediate D1 (2.0 g, 7.83 mmol) and a catalytic amount of 10% palladium on activated carbon in ethanol (300 ml) was stirred under a hydrogen atmosphere for two hours. The mixture was filtered through diatomaceous earth and the solvent was evaporated in vacuo to yield intermediate D2 (1.3 g, 100%) that was used without further purification.

Description 3

4-Bromo-1-cyclopropylmethyl-1H-pyridin-2-one (D3)

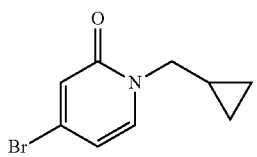 [SMILES: O=c1cc(Br)ccn1CC1CC1]

Phosphorus oxybromide (5.4 g, 18.9 mmol) was added to a solution of intermediate D2 (1.42 g, 8.6 mmol) in DMF (140 ml) and the mixture was heated at 110° C. for 1 hour. After cooling in an ice bath the solution was partitioned between water and EtOAc. After three extractions with EtOAc, the combined organic fractions were dried ($Na_2SO_4$) and the solvent was evaporated in vacuo. The crude product was purified by column chromatography (silica gel; DCM as eluent). The desired fractions were collected and evaporated in vacuo to yield intermediate D3 (1.82 g, 93%).

Description 7

4-Bromo-1-(3-methylbutyl)-1H-pyridin-2-one (D7)

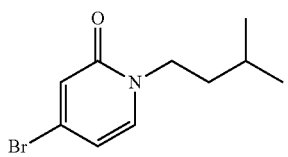

Intermediate D7 was prepared following the same procedure implemented for the synthesis of D3, using 4-hydroxy-1-(3-methylbutyl)-1H-pyridin-2-one as starting material, which was prepared by the same method used for the synthesis of intermediate D2, by reaction of 4-benzyloxy-1H-pyridin-2-one with 1-bromo-3-methylbutane.

Description 4

4-Benzyloxy-1-butyl-1H-pyridin-2-one (D4)

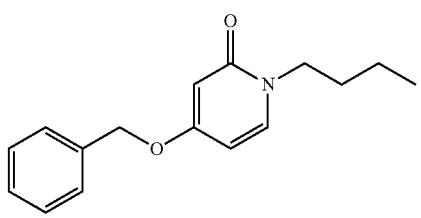 [SMILES: CCCCn1ccc(OCc2ccccc2)cc1=O]

1-Bromobutane (3.75 g, 27.33 mmol) and potassium carbonate (10.3 g, 74.52 mmol) were added to a solution of 4-benzyloxy-1H-pyridin-2-one (5.0 g, 24.84 mmol) in acetonitrile (200 ml) and the mixture was heated at reflux for 16 hours. The reaction mixture was filtered through diatomaceous earth and concentrated in vacuo. The crude residue was then triturated with diethylether to yield pure D4 (6.26 g, 98%) as a white solid.

Description 5

1-Butyl-4-hydroxy-1H-pyridin-2-one (D5)

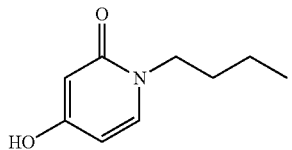

A mixture of intermediate D4 (2.01 g, 7.83 mmol) and a catalytic amount of 10% palladium on activated carbon in ethanol (300 ml) was stirred under a hydrogen atmosphere for two hours. The mixture was filtered through diatomaceous earth and the solvent was evaporated in vacuo to yield intermediate D5 (1.3 g, 100%) that was used without further purification.

Description 6

4-Bromo-1-butyl-1H-pyridin-2-one (D6)

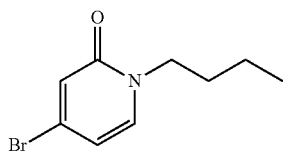

Phosphorus oxybromide (5.4 g, 18.9 mmol) was added to a solution of intermediate D5 (1.44 g, 8.6 mmol) in DMF (140 ml) and the mixture was heated at 110° C. for 1 hour. After cooling in an ice bath, the solution was partitioned between water and EtOAc. After three extractions with EtOAc, the combined organic fractions were dried (Na$_2$SO$_4$) and the solvent evaporated in vacuo. The crude product was purified by column chromatography (silica gel; DCM as eluent). The desired fractions were collected and evaporated in vacuo to yield intermediate D6 (1.82 g, 93%).

Description 8

1-Butyl-3-chloro-4-hydroxy-1H-pyridin-2-one (D8)

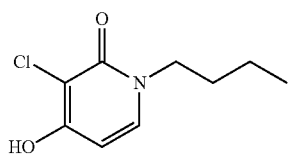

N-Chlorosuccinimide (1.6 g, 11.96 mmol) was added to a solution of intermediate D5 (2.0 g, 11.96 mmol) in DMF (30 ml). The reaction was stirred at room temperature overnight and then it was concentrated in vacuo. The crude product was purified by column chromatography (silica gel; 0-5% methanol/DCM as eluent) to yield intermediate D8 (2.0 g, 83%).

Description 9

Trifluoro-methanesulfonic acid 1-butyl-3-chloro-2-oxo-1,2-dihydropyridin-4-yl ester (D9)

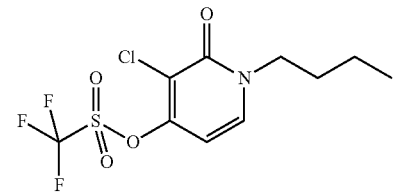 [SMILES: CCCCn1ccc(OS(=O)(=O)C(F)(F)F)c(Cl)c1=O]

Pyridine (1.60 ml, 19.8 mmol) was added to a cooled (−78° C.) solution of intermediate D8 (2.0 g, 9.92 mmol) in DCM (80 ml). The resulting solution was stirred for 10 minutes after which trifloromethanesulfonic anhydride (1.90 ml, 10.9 mmol) was added, and the resulting solution was stirred at −78° C. for 3 hours. Then the mixture was warmed to room temperature and was quenched by the addition of aqueous saturated ammonium chloride. The mixture was diluted with water, extracted with DCM, dried (Na$_2$SO$_4$) and the solvent evaporated in vacuo, yielding intermediate D9 (3.31 g, 100%) as a crude that was used without further purification.

Description 10

4-Benzyloxy-1-cyclopropylmethyl-3-iodo-1H-pyridin-2-one (D10)

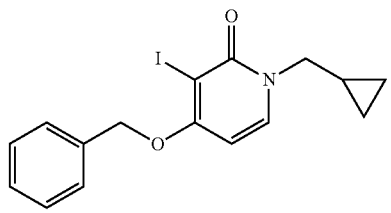 [SMILES: O=c1c(I)c(OCc2ccccc2)ccn1CC1CC1]

N-Iodosuccinimide (2.64 g, 11.74 mmol) was added to a solution of intermediate D1 (3.0 g, 11.74 mmol) in acetic acid (40 ml). The reaction mixture was stirred at room temperature for 1 hour, after which it was concentrated in vacuo, purified by flash chromatography (silica gel; 0-3% methanol/DCM as eluent) and finally recrystallized from diethyl ether to afford intermediate D10 (4.12 g, 92%) as a solid.

Description 11

4-Benzyloxy-1-cyclopropylmethyl-3-trifluoromethyl-1H-pyridin-2-one (D1)

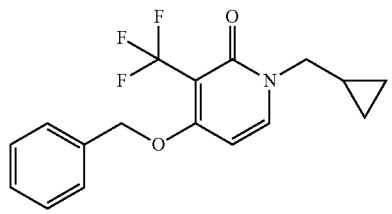 [SMILES: O=c1c(C(F)(F)F)c(OCc2ccccc2)ccn1CC1CC1]

Methyl 2,2-difluoro-2-(fluorosulfonyl)acetate (0.67 ml, 5.24 mmol) and intermediate D10 (1.0 g, 2.63 mmol) were added to a solution of copper(I) iodide (0.99 g, 5.24 mmol) in DMF (30 ml). The mixture was then heated at 100° C. for 5 hours, after which it was filtered through diatomaceous earth and the filtrate was concentrated in vacuo. The residue was purified by column chromatography (silica gel; DCM as eluent) to yield intermediate D11 (0.76 g, 89%).

Description 12

1-Cyclopropylmethyl-4-hydroxy-3-trifluoromethyl-1H-pyridin-2-one (D12)

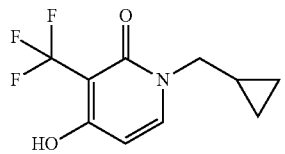 [SMILES: O=c1c(C(F)(F)F)c(O)ccn1CC1CC1]

A mixture of intermediate D11 (2.0 g, 6.19 mmol), a catalytic amount of 10% palladium on activated carbon and ethanol (60 ml) was stirred under hydrogen atmosphere for 2 hours. The mixture was filtered through diatomaceous earth and the solvent was evaporated in vacuo to yield crude intermediate D12 (1.45 g, 100%) that was used without further purification.

Description 13

4-Bromo-1-cyclopropylmethyl-3-trifluoromethyl-1H-pyridin-2-one (D13)

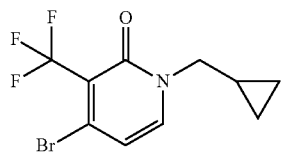

Phosphorus oxybromide (7.03 g, 24.5 mmol) was added to a solution of intermediate D12 (2.60 g, 11.1 mmol) in DMF (50 ml) and the mixture was heated at 110° C. for 1 hour. After cooling in an ice bath the solution was partitioned between water and EtOAc. After three extractions with EtOAc, the combined organic fractions were dried ($Na_2SO_4$) and the solvent evaporated in vacuo. The crude product was purified by column chromatography (silica gel; DCM as eluent). The desired fractions were collected and evaporated in vacuo to yield intermediate D13 (1.38 g, 42%).

Description 14

4-Benzyloxy-1-(4-trifluoromethoxy-benzyl)-1H-pyridin-2-one D14)

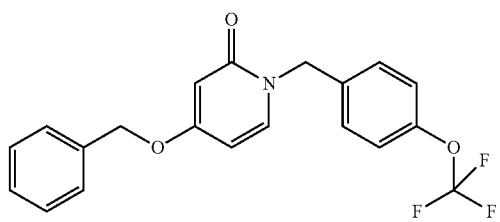 [SMILES: O=c1cc(OCc2ccccc2)ccn1Cc1ccc(OC(F)(F)F)cc1]

1-Bromomethyl-4-trifluoromethoxybenzene (3.32 g, 13.04 mmol) and potassium carbonate (3.51 g, 25.46 mmol) were added to a mixture of 4-benzyloxy-1H-pyridin-2-one (2.5 g, 12.42 mmol) in acetonitrile (10 ml). The reaction mixture was heated at reflux temperature for 24 hours. After cooling to room temperature, it was filtered through diatomaceous earth, the solid residues were washed with methanol and the combined organic extracts were evaporated in vacuo. The crude residue thus obtained was precipitated with DIPE to yield intermediate D14 (4.5 g, 96%) as a white solid.

Description 15

4-Benzyloxy-3-chloro-1-(4-trifluoromethoxy-benzyl)-1H-pyridin-2-one (D15)

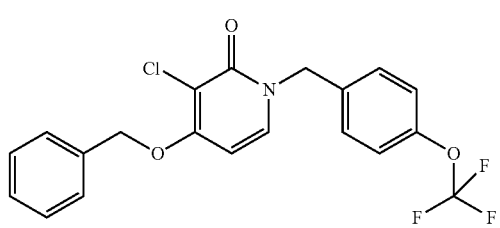 [SMILES: O=c1c(Cl)c(OCc2ccccc2)ccn1Cc1ccc(OC(F)(F)F)cc1]

N-Chlorosuccinimide (1.68 g, 12.61 mmol) was added to a solution of intermediate D14 (4.31 g, 11.47 mmol) in DMF (30 ml) and the mixture was stirred at room temperature for 24 hours. The solvent was evaporated and the solid residue was washed with water (4×25 ml). The crude solid was washed with DIPE to yield intermediate D15 (4.5 g, 95%) as a white solid.

Description 16

3-Chloro-4-hydroxy-1-(4-trifluoromethoxy-benzyl)-1H-pyridin-2-one (D16)

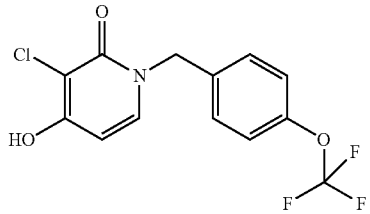 [SMILES: O=c1c(Cl)c(O)ccn1Cc1ccc(OC(F)(F)F)cc1]

Hydrobromic acid (0.1 ml) was added to a mixture of intermediate D15 (4.5 g, 10.98 mmol) in acetic acid (20 ml). The solution was heated at 130° C. for 30 minutes under microwave irradiation. After cooling to room temperature, the solvent was evaporated in vacuo and the residue was treated with an aqueous saturated solution of $NaHCO_3$ until the solution reached a pH of approximately 8. The white solid that precipitated was collected by filtration and washed with cold DIPE to yield intermediate D16 (1.1 g, 31%).

Description 17

4-Bromo-3-chloro-1-(4-trifluoromethoxy-benzyl)-1H-pyridin-2-one (D17)

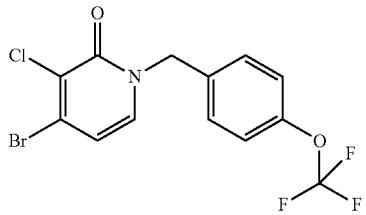 [SMILES: O=c1c(Cl)c(Br)ccn1Cc1ccc(OC(F)(F)F)cc1]

Phosphorus oxybromide (1.05 g, 3.75 mmol) was added to a solution of intermediate D16 (1.0 g, 3.13 mmol) in DMF (5 ml) and the mixture was heated at 115° C. for 4 hours. The solvent was evaporated in vacuo and the crude residue was treated with an aqueous saturated solution of $NaHCO_3$. The mixture was extracted with DCM (3×5 ml), the organic fractions were dried ($Na_2SO_4$) and the solvent was evaporated in vacuo. The crude product was purified by column chromatography (silica gel; diethyl ether as eluent). The desired fractions were collected and evaporated in vacuo to yield intermediate D17 (0.21 g, 18%) as a yellow oil.

Description 18

1'-Cyclopropylmethyl-4-phenyl-3,4,5,6-tetrahydro-2H,1'H-[1,4']bipyridinyl-2'-one (D18)

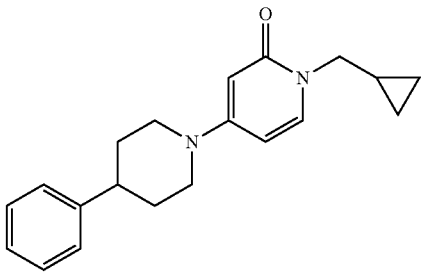 [SMILES: O=c1cc(N2CCC(c3ccccc3)CC2)ccn1CC1CC1]

4-Phenylpiperidine (0.45 g, 2.78 mmol), palladium(II) acetate (0.016 g, 0.069 mmol), sodium tert-butoxide (0.34 g, 3.5 mmol) and BINAP (0.065 g, 0.104 mmol) were added to a solution of intermediate D3 (0.32 g, 1.39 mmol) in toluene (5 ml). The reaction mixture was heated at 100° C. for 16 hours in a sealed tube, after which it was cooled to room temperature, diluted with water (5 ml) and then extracted with EtOAc (3×5 ml). The combined organic fractions were dried ($Na_2SO_4$) and the solvent evaporated in vacuo. The crude product was purified by column chromatography (silica gel; 0-4% methanol/DCM as eluent). The desired fractions were collected and evaporated in vacuo to yield intermediate D18 (0.33 g, 78%).

Description 19

1'-Butyl-4-phenyl-3,4,5,6-tetrahydro-2H,1'H-[1,4']bipyridinyl-2'-one (D19)

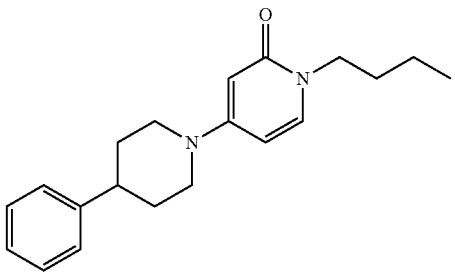 [SMILES: CCCCn1ccc(N2CCC(c3ccccc3)CC2)cc1=O]

4-Phenylpiperidine (0.45 g, 2.78 mmol), palladium(II) acetate (0.016 g, 0.069 mmol), sodium tert-butoxide (0.34 g, 3.5 mmol) and BINAP (0.065 g, 0.104 mmol) were added to a solution of intermediate D6 (0.32 g, 1.39 mmol) in toluene (5 ml). The reaction mixture was heated at 100° C. for 16 hours in a sealed tube, after which it was cooled to room temperature and then diluted with water (5 ml) and extracted with EtOAc (3×5 ml). The combined organic fractions were dried ($Na_2SO_4$) and the solvent evaporated in vacuo. The crude product was purified by column chromatography (silica gel; 0-4% methanol/DCM as eluent). The desired fractions were collected and evaporated in vacuo to yield intermediate D19 (0.38 g, 89%).

Description 20

1'-Cyclopropylmethyl-2'-oxo-4-phenyl-3,4,5,6,1',2'-hexahydro-2H-[1,4']bipyridinyl-4-carbonitrile (D20) JNJ-38818468

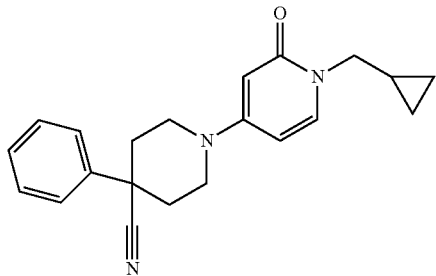 [SMILES: N#CC1(c2ccccc2)CCN(c2ccn(CC3CC3)c(=O)c2)CC1]

4-Cyano-4-phenylpiperidine hydrochloride (0.314 g, 1.41 mmol), palladium(II) acetate (0.013 g, 0.059 mmol) sodium tert-butoxide (0.347 g, 3.54 mmol) and BINAP (0.051 g, 0.08 mmol) were added to a stirred solution of intermediate D3 (0.27 g, 1.18 mmol) in toluene (5 ml). The reaction mixture was heated at 100° C. for 16 hours in a sealed tube. After cooling to room temperature the mixture was diluted with water and extracted with EtOAc. The combined organic phase was dried ($Na_2SO_4$) and the solvent evaporated in vacuo. The crude product was purified by column chromatography (silica gel; 10% ammonia in methanol (7M)/DCM as eluent). The desired fractions were collected and evaporated in vacuo to yield D20 (0.35 g, 87%) as a pale yellow oil.

Description 21

4-Hydroxy-4-phenylpiperidine-1-carboxilic acid tert-butyl ester (D21)

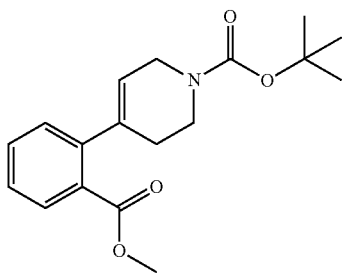 [SMILES: COC(=O)c1ccccc1C1=CCN(C(=O)OC(C)(C)C)CC1]

Methyl 2-bromobenzoate (1.816 ml, 12.936 mmol) [CAS 610-94-6] was added to a solution of 1,2,3,6-tetrahydro-4-(4,4,5,5-tetramethyl-1,3,2-dioxaborolan-2-yl)-pyridine (4 g, 12.936 mmol) [CAS 375853-82-0] (synthesis described in WO 2004072025 A2 20040826) in 1,4-dioxane (28 ml) and an aqueous saturated solution of $NaHCO_3$ (24 ml). The resulting solution was degassed using a stream of nitrogen and $Pd(PPh_3)_4$ (0.747 g, 0.647 mmol) was added to this solution. The reaction was then microwaved in a sealed tube at 140° C. for 5 minutes. The resulting cooled reaction mixture was then diluted with EtOAc and filtered through a pad of diatomaceous earth. The filtrate was collected, dried over $Na_2SO_4$ and concentrated in vacuo. The crude reaction mixture was then purified by column chromatography (silica gel; DCM to DCM/EtOAc up to 6% as eluent). The desired fractions were collected and evaporated in vacuo to yield D21 (4.04 g, 98%).

Description 22

4-(2-Fluoro-4-methoxycarbonyl-phenyl)-3,6-di-hydro-2H-pyridine-1-carboxylic acid tert-butyl ester (D22)

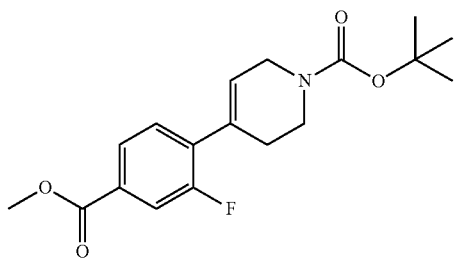 [SMILES: COC(=O)c1ccc(C2=CCN(C(=O)OC(C)(C)C)CC2)c(F)c1]

Methyl 4-bromo-3-fluorobenzoate (2.261 g, 9.702 mmol) [CAS 849758-12-9] was added to a solution of 1,2,3,6-tetrahydro-4-(4,4,5,5-tetramethyl-1,3,2-dioxaborolan-2-yl)-pyridine (3 g, 9.702 mmol) [CAS 375853-82-0] (synthesis described in WO 2004072025 A2 20040826) in 1,4-dioxane (21 ml) and an aqueous saturated solution of $NaHCO_3$ (18 ml). The resulting solution was degassed using a stream of nitrogen and $Pd(PPh_3)_4$ (0.561 g, 0.485 mmol) was added to this solution. The reaction was then microwaved in a sealed tube at 150° C. for 5 minutes. The resulting cooled reaction mixture was then diluted with EtOAc and filtered through a pad of diatomaceous earth. The filtrate was collected, dried over $Na_2SO_4$ and concentrated in vacuo. The crude reaction mixture was then purified by column chromatography (silica gel; DCM to DCM/EtOAc up to 6% as eluent). The desired fractions were collected and evaporated in vacuo to yield D22 (2.107 g, 65%).

Description 23

4-(2-Fluoro-4-methoxycarbonyl-phenyl)-piperidine-1-carboxylic acid tert-butyl ester (D23)

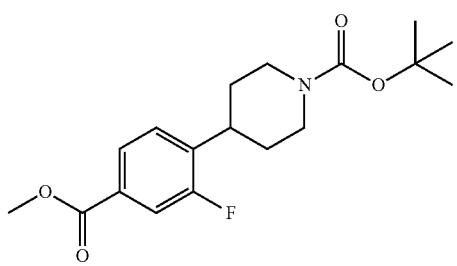 [SMILES: COC(=O)c1ccc(C2CCN(C(=O)OC(C)(C)C)CC2)c(F)c1]

A solution of intermediate D22 (2.81 g, 8.379 mmol) in methanol (120 ml) was hydrogenated at room temperature in the presence of palladium 10% on activated carbon (0.588 g) until the reaction was completed. The solids were filtered off and the filtrate was evaporated in vacuo to give D23 (2.73 g, 97%).

Description 24

4-[2-Fluoro-4-(1-hydroxy-1-methyl-ethyl)-phenyl]-piperidine-1-carboxylic acid tert-butyl ester (D24)

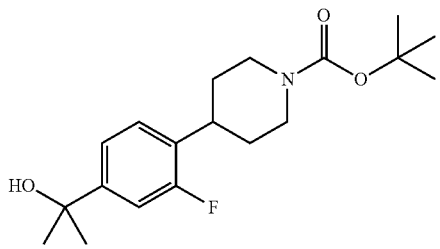 [SMILES: CC(C)(C)OC(=O)N1CCC(c2ccc(C(C)(C)O)cc2F)CC1]

A 1.4 M solution of methylmagnesium bromide in toluene/THF (17.339 ml, 24.274 mmol) was added dropwise to a cooled (0° C.) solution of intermediate D23 (2.73 g, 8.091 mmol) in diethylether (150 ml) under nitrogen atmosphere. The resulting reaction mixture was then stirred at 50° C. for 2 hours. After cooling in an ice bath the mixture was carefully quenched with a saturated aqueous solution of ammonium chloride, and then was extracted with EtOAc. The combined organic phase was dried ($Na_2SO_4$) and the solvent evaporated in vacuo to yield D24 (3.16 g, 100%).

Description 25

2-(3-Fluoro-4-piperidin-4-yl-phenyl)-propan-2-ol (D25)

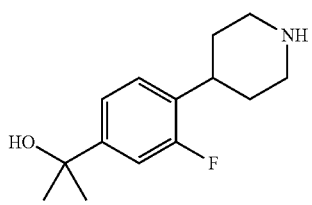 [SMILES: CC(C)(O)c1ccc(C2CCNCC2)c(F)c1]

A mixture of intermediate D24 (3.067 g, 7.852 mmol) and KOH (2.54 g, 45.268 mmol) in isopropyl alcohol (13.5 ml) and water (27 ml) was microwaved in a sealed tube at 180° C. for 60 minutes. The resulting cooled reaction mixture was then diluted with water and brine and extracted with dichloromethane. The combined organic extracts were dried ($Na_2SO_4$) and the solvent was evaporated in vacuo. The residue was treated with dichloromethane giving rise to a solid that was filtered off to yield 1.03 g intermediate D25. The filtrate was evaporated in vacuo and the residue thus obtained was then purified by column chromatography (silica gel; DCM/($NH_3$ 7N solution in MeOH) gradient up to 10% as eluent). The desired fractions were collected and evaporated in vacuo to yield a second batch of 0.5 g of D25 (total amount=1.53 g, 82%). M.P. 151° C.

Description 26

4-(2-Methoxycarbonyl-phenyl)-piperidine-1-carboxylic acid tert-butyl ester (D26)

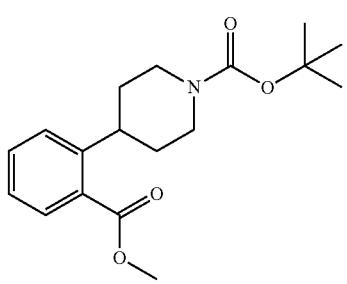 [SMILES: COC(=O)c1ccccc1C1CCN(C(=O)OC(C)(C)C)CC1]

A solution of intermediate D21 (4.04 g, 12.729 mmol) in methanol (120 ml) was hydrogenated at room temperature in the presence of palladium 10% on activated carbon (0.846 g) until the reaction was completed. The solids were filtered off and the filtrate was evaporated in vacuo to give D26 as white solid (3.67 g, 90%).

Description 27

4-[2-(1-Hydroxy-1-methyl-ethyl)-phenyl]-piperidine-1-carboxylic acid tert-butyl ester (D27)

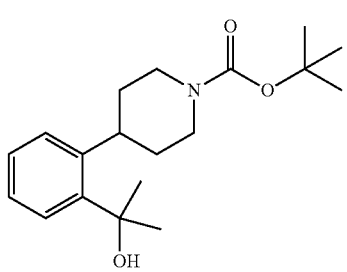 [SMILES: CC(C)(C)OC(=O)N1CCC(c2ccccc2C(C)(C)O)CC1]

A 1.4 M solution of methylmagnesium bromide in toluene/THF (17.443 ml, 24.421 mmol) was added dropwise to a cooled (0° C.) solution of intermediate D26 (2.6 g, 8.14 mmol) in diethylether (150 ml) under nitrogen atmosphere. The resulting reaction mixture was stirred at 45° C. for 2 hours. After cooling in an ice bath, the mixture was carefully quenched with a saturated aqueous solution of ammonium chloride, and then extracted with EtOAc. The combined organic phase was dried ($Na_2SO_4$) and the solvent evaporated in vacuo to yield D27 (2.77 g, 69%).

Description 28

2-(2-Piperidin-4-yl-phenyl)-propan-2-ol (D28)

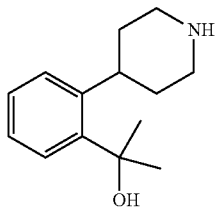 [SMILES: CC(C)(O)c1ccccc1C1CCNCC1]

A mixture of intermediate D27 (2.77 g, 5.636 mmol) and KOH (2.43 g, 43.357 mmol) in isopropyl alcohol (13.5 ml) and water (27 ml) was microwaved in a sealed tube at 180° C. for 60 minutes. The resulting cooled reaction mixture was then diluted with water and brine and extracted with dichloromethane. The residue was treated with dichloromethane giving rise to a solid that was filtered off. Yield: 0.737 g of intermediate D28. The filtrate was evaporated in vacuo and the residue was then purified by column chromatography (silica gel; DCM/(NH$_3$ 7N solution in MeOH) gradient up to 10% as eluent). The desired fractions were collected and evaporated in vacuo to yield a second batch of 0.306 g of intermediate D28 (total amount=1.04 g, 84%). M.P. 219.5° C.

Description 29

4-Hydroxy-4-phenylpiperidine-1-carboxilic acid tert-butyl ester (D29)

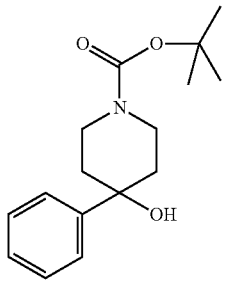 [SMILES: CC(C)(C)OC(=O)N1CCC(O)(c2ccccc2)CC1]

Di-tert-butyl dicarbonate (2.95 g, 13.53 mmol) was added to a solution of 4-hydroxy-4-phenylpiperidine (2 g, 11.28 mmol) in DCM (50 ml). The reaction was stirred at room temperature for 5 hours. The solvent was removed in vacuo, affording the desired intermediate D29 (3.12 g, 100%) as a crude that was used without further purification.

Description 30

4-fluoro-4-phenylpiperidin-1-carboxilic acid tert-butyl ester (D30)

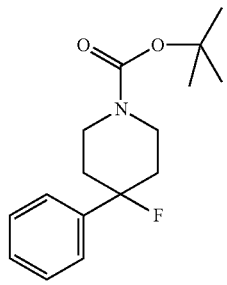 [SMILES: CC(C)(C)OC(=O)N1CCC(F)(c2ccccc2)CC1]

A solution of (diethylamino)sulfur trifluoride (0.74 ml, 5.67 mmol) in dry DCM (q.s.) was added to a cooled (−78° C.) solution of D29 (1.5 g, 5.4 mmol) in dry DCM (30 ml) under N$_2$ atmosphere. After the addition was complete, the reaction mixture was stirred at −78° C. for 1 hour and then allowed to reach room temperature and stirred for a further 30 minutes. An aqueous saturated NaHCO$_3$ solution (90 ml) was added and the mixture was stirred for 15 minutes, then the organic layer was separated. After this, 3-chloroperoxybenzoic acid (0.2 g, 1.18 mmol) was added and the reaction stirred at room temperature for 30 minutes. The reaction mixture was washed with aqueous saturated NaHCO$_3$, H$_2$O and brine, dried over Na$_2$SO$_4$, filtered and concentrated in vacuo affording the desired intermediate D30 (1.48 g, 98%) as a crude that was used without further purification.

Description 31

4-fluoro-4-phenylpiperidine hydrochloride (D31)

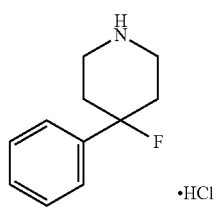 [SMILES: FC1(c2ccccc2)CCNCC1 ; Cl]

D30 (1.48 g, 5.29 mmol) was dissolved in 4N HCl in dioxane. The reaction was stirred at room temperature for 2 hours. The solvent was removed. The crude was triturated with diethyl ether and dried in vacuo to afford the desired intermediate D31 (1.10 g, 97%) as a chlorohydrate that was used without further purification.

Description 32

1'-Butyl-4-fluoro-4-phenyl-3,4,5,6-tetrahydro-2H,
1'H-[1,4']bipyridinyl-2-one (D32)

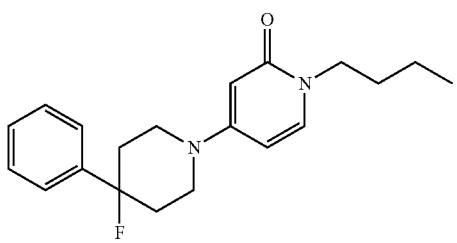 [SMILES: CCCCn1ccc(N2CCC(F)(c3ccccc3)CC2)cc1=O]

D31 (0.2 g, 0.94 mmol), palladium(II) acetate (0.009 g, 0.04 mmol) sodium tert-butoxide (0.25 g, 2.58 mmol) and BINAP (0.037 g, 0.06 mmol) were added to a stirred solution of intermediate D6 (0.20 g, 0.86 mmol) in toluene (5 ml). The reaction mixture was heated at 100° C. for 16 hours in a sealed tube. After cooling to room temperature the mixture was diluted with water and extracted with EtOAc. The combined organic phase was dried (Na$_2$SO$_4$) and the solvent evaporated in vacuo. The crude product was purified by column chromatography (silica gel; 10% ammonia in methanol (7N)/DCM as eluent). The desired fractions were collected and evaporated in vacuo to yield D32 (0.21 g, 87%) as a pale yellow oil.

Description 33

4-Benzyloxy-3-bromo-1-cyclopropylmethyl-1H-
pyridin-2-one (D33)

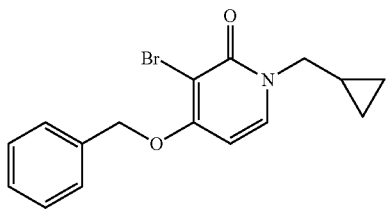 [SMILES: O=c1c(Br)c(OCc2ccccc2)ccn1CC1CC1]

A solution of intermediate D1 (3.0 g, 11.7 mmol) and N-bromosuccinimide (2.09 g, 11.7 mmol) in DCM (100 ml) was stirred at room temperature for 1 hour. The solvent was evaporated in vacuo and the crude residue was purified by column chromatography (silica gel; DCM as eluent). The desired fractions were collected and evaporated in vacuo yielding D33 (3.56 g, 91%).

Description 34

4-Benzyloxy-3-cyclopropyl-1-cyclopropylmethyl-
1H-pyridin-2-one (D34)

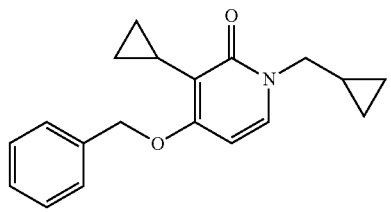 [SMILES: O=c1c(C2CC2)c(OCc2ccccc2)ccn1CC1CC1]

NaHCO$_3$ (1.0 g, excess), cyclopropylboronic acid (0.74 g, 8.93 mmol), potassium carbonate (1.23 g, 8.93 mmol) and [1,1'-bis(diphenylphosphino)ferrocene]dichloropalladium (II)—DCM complex (0.36 g, 0.45 mmol) were added to a solution of intermediate D10 (1.0 g, 2.98 mmol) in 1,4-dioxane (10 ml). The resulting mixture was heated at 175° C. for 20 minutes under microwave irradiation, after which it was filtered through diatomaceous earth and the solvent was evaporated in vacuo. The crude residue was purified by column chromatography (silica gel; 0-3% methanol/DCM as eluent). The desired fractions were collected and evaporated in vacuo yielding D34 (0.6 g, 69%).

Description 35

3-Cyclopropyl-1-cyclopropylmethyl-4-hydroxy-1H-
pyridin-2-one (D35)

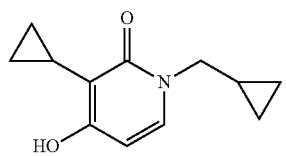 [SMILES: O=c1c(C2CC2)c(O)ccn1CC1CC1]

A mixture of intermediate D34 (1.0 g, 3.38 mmol) and a catalytic amount of 10% palladium on activated carbon in ethanol (150 ml) was stirred under a hydrogen atmosphere for 2 hours. The mixture was filtered through diatomaceous earth and the solvent was evaporated in vacuo to yield intermediate D35 (0.69 g, 100%) that was used without further purification.

Description 36

4-Bromo-3-cyclopropyl-1-cyclopropylmethyl-1H-
pyridin-2-one (D36)

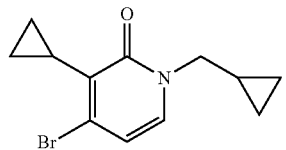 [SMILES: O=c1c(C2CC2)c(Br)ccn1CC1CC1]

Phosphorus oxybromide (2.4 g, 8.28 mmol) was added to a solution of intermediate D35 (0.85 g, 4.14 mmol) in DMF (60 ml), and the mixture was heated at 110° C. for 1 hour. After cooling in an ice bath, the solution was partitioned between water and EtOAc. The mixture was extracted with EtOAc (3×200 ml), the combined organic fractions were dried ($Na_2SO_4$) and the solvent evaporated in vacuo. The crude product was purified by column chromatography (silica gel; DCM as eluent). The desired fractions were collected and evaporated in vacuo to yield intermediate D36 (0.99 g, 89%).

Description 37

4-(1'-Cyclopropylmethyl-2'-oxo-3,4,5,6,1',2'-hexahydro-2H-[1,4']bipyridinyl-4-yl)-benzoic acid (D37)

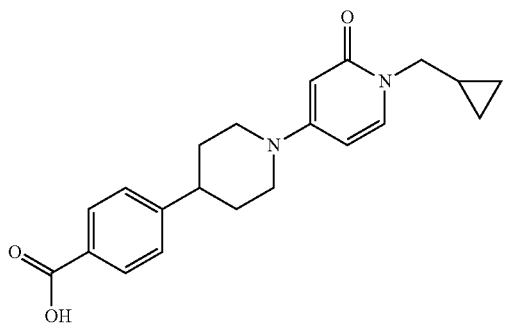 [SMILES: O=C(O)c1ccc(C2CCN(c3ccn(CC4CC4)c(=O)c3)CC2)cc1]

4-Piperidin-4-ylbenzoic acid methyl ester (0.40 g, 1.81 mmol), palladium(II) acetate (0.015 g, 0.069 mmol) sodium tert-butoxide (0.34 g, 3.44 mmol) and BINAP (0.06 g, 0.096 mmol) were added to a stirred solution of intermediate D3 (0.31 g, 1.37 mmol) in toluene (10 ml). The reaction mixture was heated at 100° C. for 16 hours in a sealed tube. After cooling to room temperature the mixture was diluted with EtOAc and then filtered through diatomaceous earth, after which the solvent was evaporated in vacuo. The crude residue was treated with a mixture of DCM/methanol and then filtered off. The filtrate was evaporated to dryness in vacuo to yield crude D37 (0.48 g, 100%) that was used without further purification.

Description 38

4-(1'-Cyclopropylmethyl-2'-oxo-3,4,5,6,1',2'-hexahydro-2H-[1,4']bipyridinyl-4-yl)-benzoic acid methyl ester (D38)

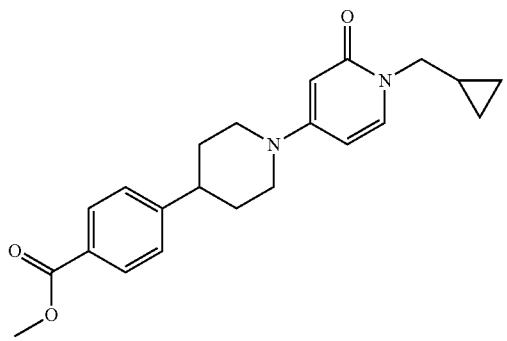 [SMILES: COC(=O)c1ccc(C2CCN(c3ccn(CC4CC4)c(=O)c3)CC2)cc1]

A mixture of intermediate D37 (0.43 g, 1.23 mmol), DBU (0.18 g, 1.23 mmol), dimethyl carbonate (4.5 ml, excess, 93 mmol), and acetonitrile (5 ml) was heated at 160° C. for 20 minutes under microwave irradiation. The cooled crude mixture was diluted with water and EtOAc was added, after which the organic layer was washed with an aqueous 10% citric acid solution, dried ($Na_2SO_4$) and the solvent evaporated in vacuo. The crude residue was purified by column chromatography (silica gel; 0-3% methanol/DCM as eluent). The desired fractions were collected and evaporated in vacuo to yield D38 (0.19 g, 38%).

Description 39

1'-Cyclopropylmethyl-4-[4-(1-hydroxy-1-methylethyl)-phenyl]-3,4,5,6-tetrahydro-2H,1'H-[1,4']bipyridinyl-2'-one (D39)

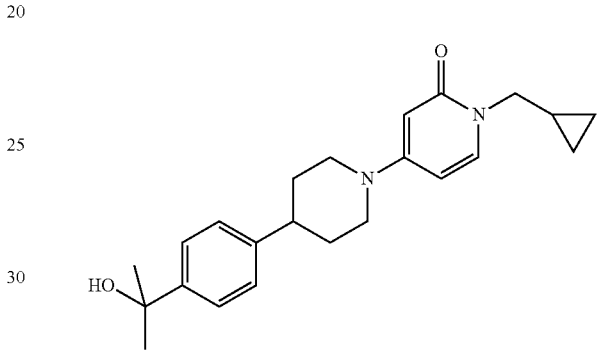

A 1.4 M solution of methylmagnesium bromide in toluene/THF (1.12 ml, 1.57 mmol) was added dropwise to a cooled (0° C.) solution of intermediate D38 (0.19 g, 0.52 mmol) in THF (20 ml) under nitrogen atmosphere. The resulting reaction mixture was stirred at 45° C. for 2 hours. After cooling in an ice bath the mixture was carefully quenched with a saturated aqueous solution of ammonium chloride, and then was extracted with EtOAc. The combined organic phase was dried ($Na_2SO_4$) and the solvent evaporated in vacuo. The residue was purified by column chromatography (silica gel; 0-5% methanol/DCM as eluent). The desired fractions were collected and evaporated in vacuo to yield D39 (0.077 g, 40%) as an oil.

Example 1

3'-Chloro-1'-cyclopropylmethyl-4-phenyl-3,4,5,6-tetrahydro-2H,1'H-[1,4']bipyridinyl-2'-one (E1)

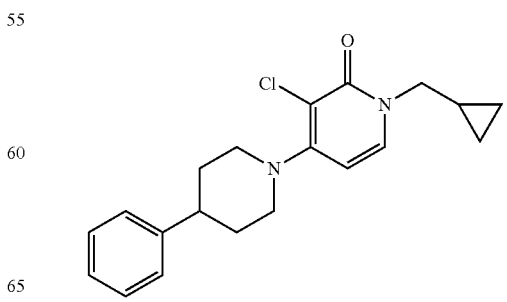

A solution of intermediate D18 (0.2 g, 0.65 mmol) and N-chlorosuccinimide (0.09 g, 0.65 mmol) in DCM (10 ml) was stirred at room temperature for 1 hour. The solvent was evaporated in vacuo and the crude product was purified by column chromatography (silica gel; 0-3% methanol/DCM as eluent). The desired fractions were collected and evaporated in vacuo and the resulting solid was recrystallized from diethyl ether to yield compound E1 (0.10 g, 47%) as a white solid.

Melting point: 170.8° C.

$^1$H NMR (400 MHz, CDCl$_3$) δ ppm 0.35-0.42 (m, 2H), 0.57-0.64 (m, 2H), 1.19-1.33 (m, 1H), 1.85-2.00 (m, 4H), 2.64-2.76 (m, 1H), 2.85-2.99 (m, 2H), 3.76-3.87 (m, 4H), 6.05 (d, J=7.6 Hz, 1H), 7.19-7.29 (m, 4H), 7.29-7.38 (m, 2H).

Example 2

1'-Butyl-3'-chloro-4-phenyl-3,4,5,6-tetrahydro-2H, 1'H-[1,4']bipyridinyl-2'-one (E2)

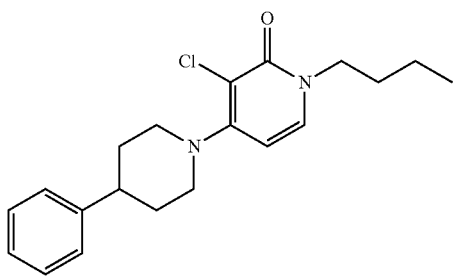 [SMILES: CCCCn1ccc(N2CCC(c3ccccc3)CC2)c(Cl)c1=O]

A solution of intermediate D19 (0.43 g, 1.40 mmol) and N-chlorosuccinimide (0.19 g, 1.40 mmol) in DCM (10 ml) was stirred at room temperature for 1 hour. The solvent was evaporated in vacuo and the crude product was purified by column chromatography (silica gel; 0-3% methanol/DCM as eluent). The desired fractions were collected and evaporated in vacuo and the resulting solid was recrystallized from diethyl ether to yield compound E2 (0.39 g, 82%) as a white solid.

Melting point: 149.4° C.

$^1$H NMR (400 MHz, CDCl$_3$) δ ppm 0.95 (t, J=7.3 Hz, 3H), 1.31-1.42 (m, 2H), 1.68-1.78 (m, 2H), 1.85-1.98 (m, 4H), 2.64-2.73 (m, 1H), 2.87-2.96 (m, 2H), 3.82 (br d, J=12.1 Hz, 2H), 3.93 (t, J=7.3 Hz, 2H), 6.03 (d, J=7.6 Hz, 1H), 7.10 (d, J=7.6 Hz, 1H), 7.19-7.28 (m, 3H), 7.29-7.37 (m, 2H).

Example 3

3'-Bromo-1'-cyclopropylmethyl-4-phenyl-3,4,5,6-tetrahydro-2H,1'H-[1,4']bipyridinyl-2'-one (E3)

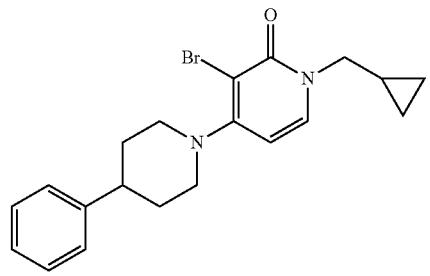 [SMILES: O=c1c(Br)c(N2CCC(c3ccccc3)CC2)ccn1CC1CC1]

N-Bromosuccinimide (0.145 g, 0.82 mmol) was added to a solution of intermediate D18 (0.25 g, 0.82 mmol) in DCM (10 ml). The reaction mixture was stirred at room temperature for 1 hour. Subsequently, the solvent was evaporated in vacuo and the crude residue was purified by column chromatography (silica gel; 0-3% methanol/DCM as eluent). The desired fractions were collected and evaporated in vacuo to yield compound E3 (0.20 g, 64%) as a white solid.

Melting point: 150° C.

$^1$H NMR (500 MHz, DMSO-d$_6$) δ ppm 0.34-0.40 (m, 2H), 0.44-0.50 (m, 2H), 1.16-1.26 (m, 1H), 1.77 (qd, J=12.38, 3.61 Hz, 2H), 1.88 (br d, J=12.1 Hz, 2H), 2.68-2.78 (m, 1H), 2.91 (br t, J=11.9 Hz, 2H) 3.69 (br d, J=12.1 Hz, 2H), 3.74 (d, J=7.2 Hz, 2H), 6.21 (d, J=7.5 Hz, 1H), 7.19-7.25 (m, 1H), 7.27-7.36 (m, 4H), 7.69 (d, J=7.5 Hz, 1H).

Example 4

1'-Cyclopropylmethyl-4-phenyl-3'-trifluoromethyl-3, 4,5,6-tetrahydro-2H,1'H-[1,4']bipyridinyl-2'-one (E4)

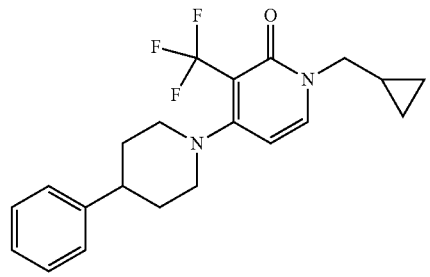 [SMILES: O=c1c(C(F)(F)F)c(N2CCC(c3ccccc3)CC2)ccn1CC1CC1]

4-Phenylpiperidine (0.33 g, 2.02 mmol), palladium(II) acetate (0.012 g, 0.05 mmol), sodium tert-butoxide (0.24 g, 2.52 mmol) and BINAP (0.05 g, 0.08 mmol) were added to a solution of intermediate D13 (0.3 g, 1.01 mmol) in toluene (7 ml). The reaction mixture was heated at 100° C. for 16 hours in a sealed tube, after which it was cooled to room temperature and then it was diluted with water (5 ml) and extracted with EtOAc (3×5 ml). The combined organic fractions were dried (Na$_2$SO$_4$) and the solvent evaporated in vacuo. The crude product was purified by column chromatography (silica gel; 0-4% methanol/DCM as eluent). The desired fractions were collected and evaporated in vacuo to yield compound E4 (0.11 g, 31%) as a white solid.

Melting point: 177.2° C.

$^1$H NMR (500 MHz, DMSO-$d_6$) δ ppm 0.33-0.38 (m, 2H), 0.45-0.50 (m, 2H), 1.13-1.22 (m, 1H), 1.64-1.75 (m, 2H), 1.84 (br d, J=11.0 Hz, 2H), 2.72-2.80 (m, 1H), 3.14 (br t, J=12.1 Hz, 2H), 3.59 (br d, J=13.0 Hz, 2H), 3.65 (d, J=7.2 Hz, 2H), 6.21 (d, J=7.8 Hz, 1H), 7.19-7.23 m, 1H), 7.24-7.29 (m, 2H), 7.29-7.34 (m, 2H), 7.73 (d, J=7.8 Hz, 1H).

Example 5

3'-Chloro-4-phenyl-1'-(4-trifluoromethoxybenzyl)-3,4,5,6-tetrahydro-2H,1'H-[1,4']bipyridinyl-2'-one (E5)

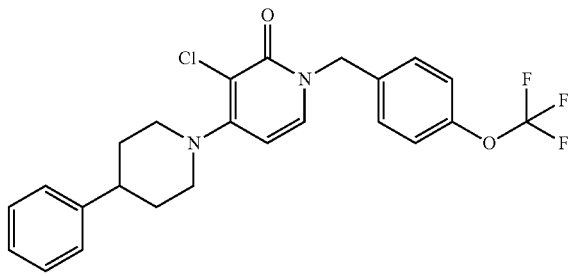 [SMILES: O=c1c(Cl)c(N2CCC(c3ccccc3)CC2)ccn1Cc1ccc(OC(F)(F)F)cc1]

A mixture of intermediate D17 (0.2 g, 0.52 mmol), 4-phenylpiperidine (0.1 g, 0.62 mmol), 2-(2'-Di-tert-butylphosphine)biphenylpalladium(II) acetate (0.01 g, 0.026 mmol) and potassium phosphate (0.23 g, 1.1 mmol) in 1,4-dioxane (3 ml) was stirred at 90° C. for 35 hours. The mixture was filtered through diatomaceous earth, and the filtrate was evaporated to dryness after washing with more 1,4-dioxane. The crude product was purified by column chromatography (silica gel; heptane/diethyl ether 1:1 as eluent). The desired fractions were collected and evaporated in vacuo to yield compound E5 (0.075 g, 31%) as a white solid.

Melting point: 168.6° C.

$^1$H NMR (400 MHz, CDCl$_3$) δ ppm 1.83-1.98 (m, 4H), 2.65-2.75 (m, 1H), 2.89-2.98 (m, 2H), 3.84 (br d, J=12.2 Hz, 2H), 5.12 (s, 2H), 6.06 (d, J=7.6 Hz, 1H), 7.14 (d, J=7.6 Hz, 2H), 7.15-7.28 (m, 5H), 7.29-7.40 (m, 4H).

Example 6

3'-Chloro-1'-cyclopropylmethyl-2'-oxo-4-phenyl-3,4,5,6,1',2'-hexahydro-2H-[1,4']bipyridinyl-4-carbonitrile (E6)

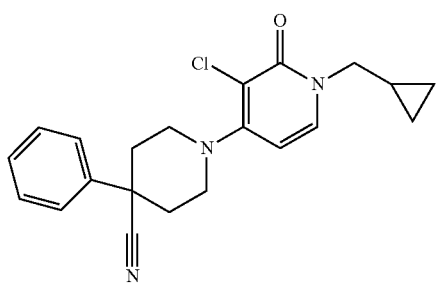 [SMILES: N#CC1(c2ccccc2)CCN(c2ccn(CC3CC3)c(=O)c2Cl)CC1]

A solution of intermediate D20 (0.35 g, 1.03 mmol) and N-chlorosuccinimide (0.14 g, 1.03 mmol) in DCM (25 ml) was stirred at room temperature for 1 hour. After addition of more DCM, the solution was washed with brine, dried (Na$_2$SO$_4$) and the solvent evaporated in vacuo. The crude product was purified by column chromatography (silica gel; 10% ammonia in methanol (7N)/DCM as eluent) and further purified by preparative HPLC. The desired fractions were collected and evaporated in vacuo to yield compound E6 (0.17 g, 47%) as a white solid.

Melting point: 173.7° C.

$^1$H NMR (400 MHz, DMSO-$d_6$) δ ppm 0.17-0.23 (m, 2H), 0.26-0.33 (m, 2H), 0.97-1.09 (m, 1H), 1.91-2.02 (m, 2H), 2.11 (br d, J=12.9 Hz, 2H) 2.98 (br t, J=12.4 Hz, 2H), 3.54-3.63 (m, 4H), 6.14 (d, J=7.4 Hz, 1H), 7.20-7.26 (m, 1H), 7.27-7.35 (m, 2H), 7.40-7.44 (m, 2H), 7.52 (d, J=7.4 Hz, 1H).

Example 7

1'-Butyl-3-chloro-4-fluoro-4-phenyl-3,4,5,6-tetrahydro-2H,1'H-[1,4']bipyridinyl-2-one (E7)

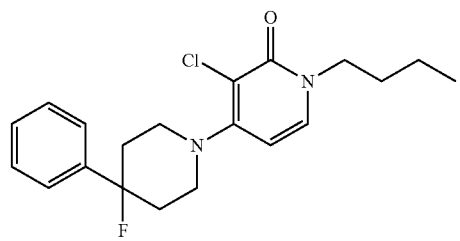 [SMILES: CCCCn1ccc(N2CCC(F)(c3ccccc3)CC2)c(Cl)c1=O]

A solution of intermediate D32 (0.21 g, 0.66 mmol) and N-chlorosuccinimide (0.08 g, 0.66 mmol) in DCM (30 ml) was stirred at room temperature for 10 minutes. After addition of more DCM the solution was washed with brine, dried (Na$_2$SO$_4$) and the solvent evaporated in vacuo. The crude product was purified by column chromatography (silica gel; 10% ammonia in methanol (7M)/DCM as eluent) and further purified by preparative HPLC. The desired fractions were collected and evaporated in vacuo to yield compound E7 (0.065 g, 27%) as a white solid.

Melting point: 136.7° C.

$^1$H NMR (400 MHz, DMSO-$d_6$) δ ppm 0.89 (t, J=7.4 Hz, 3H), 1.21-1.32 (m, 2H), 1.54-1.64 (m, 2H), 2.03 (t, J=11.8 Hz, 2H), 2.16 (td, J=13.9, 4.6 Hz, 1H), 2.26 (td, J=13.6, 4.6 Hz, 1H), 3.17 (dd, J=12.3, 11.1 Hz, 2H), 3.54-3.64 (m, 2H), 3.87 (t, J=7.2 Hz, 2H), 6.26 (d, J=7.6 Hz, 1H), 7.32-7.38 (m, 1H), 7.42 (t, J=7.4 Hz, 2H), 7.45-7.51 (m, 2H), 7.62 (d, J=7.4 Hz, 1H).

Example 8

3'-Cyclopropyl-1'-cyclopropylmethyl-4-phenyl-3,4,5,6-tetrahydro-2H,1'H-[1,4']bipyridinyl-2'-one (E8)

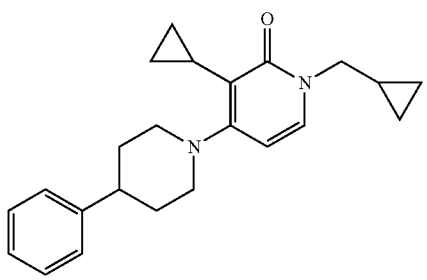 [SMILES: O=c1c(C2CC2)c(N2CCC(c3ccccc3)CC2)ccn1CC1CC1]

4-Phenylpiperidine (0.22 g, 1.34 mmol), palladium(II) acetate (0.008 g, 0.034 mmol), sodium tert-butoxide (0.16 g, 1.68 mmol) and BINAP (0.032 g, 0.05 mmol) were added to a solution of intermediate D36 (0.18 g, 0.67 mmol) in toluene (5 ml). The reaction mixture was heated at 100° C. for 16 hours in a sealed tube, after which it was cooled to room temperature and then diluted with water (5 ml) and extracted with EtOAc (3×5 ml). The combined organic fractions were dried (Na$_2$SO$_4$) and the solvent evaporated in vacuo. The crude product was purified by column chromatography (silica gel; 0-4% methanol/DCM as eluent). The desired fractions were collected and evaporated in vacuo to yield compound E8 (0.18 g, 77%) as a white solid.

Melting point: 201.9° C.

$^1$H NMR (500 MHz, DMSO-d$_6$) δ ppm 0.30-0.35 (m, 2H) 0.41-0.47 (m, 2H) 0.74-0.80 (m, 2H), 0.86-0.92 (m, 2H), 1.11-1.21 (m, 1H), 1.60-1.67 (m, 1H), 1.73-1.89 (m, 4H), 2.63-2.72 (m, 1H), 2.87 (br t, J=11.1 Hz, 2H), 3.57-3.65 (m, 4H), 6.07 (d, J=7.5 Hz, 1H), 7.19-7.24 (m, 1H), 7.26-7.37 (m, 4H), 7.46 (d, J=7.5 Hz, 1H).

Example 9

3'-Chloro-1'-cyclopropylmethyl-4-[4-(1-hydroxy-1-methyl-ethyl)-phenyl]-3,4,5,6-tetrahydro-2H,1'H-[1,4']bipyridinyl-2'-one (E9)

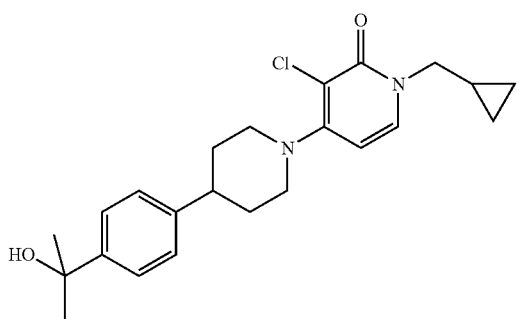 [SMILES: CC(C)(O)c1ccc(C2CCN(c3ccn(CC4CC4)c(=O)c3Cl)CC2)cc1]

A solution of intermediate D39 (0.077 g, 0.21 mmol) and N-chlorosuccinimide (0.03 g, 0.21 mmol) in DCM (8 ml) was stirred at room temperature for 5 minutes. The crude mixture was washed with a saturated NaHCO$_3$ solution, then it was extracted with DCM, the combined organic fractions were dried (Na$_2$SO$_4$) and the solvent evaporated in vacuo. The crude residue was purified by column chromatography (silica gel; 0-5% methanol/DCM as eluent). A second chromatography was performed (silica gel; DCM/EtOAc 1:1, and finally 100% EtOAc as eluents). The desired fractions were collected and evaporated in vacuo and the resulting solid was crystallized from diethyl ether to yield compound E9 (0.06 g, 71%) as a white solid.

$^1$H NMR (400 MHz, CDCl$_3$) δ ppm 0.35-0.41 (m, 2H), 0.56-0.64 (m, 2H), 1.19-1.30 (m, 1H), 1.59 (s, 6H), 1.73 (s, 1H), 1.85-1.99 (m, 4H), 2.65-2.76 (m, 1H), 2.87-2.97 (m, 2H), 3.78-3.87 (m, 4H), 6.05 (d, J=7.6 Hz, 1H), 7.21-7.26 (m, 3H), 7.45 (d, J=8.3 Hz, 2H).

Example 20

3'-Chloro-1'-cyclopropylmethyl-4-(2-fluoro-ethoxy)-4-phenyl-3,4,5,6-tetrahydro-2H,1'H-[1,4']bipyridinyl-2'-one (E20)

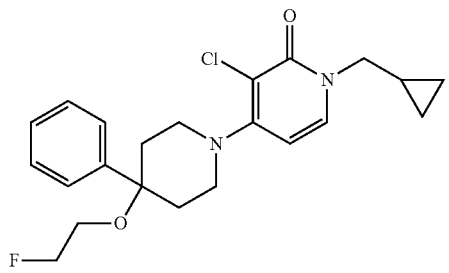 [SMILES: O=c1c(Cl)c(N2CCC(OCCF)(c3ccccc3)CC2)ccn1CC1CC1]

A solution of compound E31 (0.164 g, 0.46 mmol) in 1,2-dimethoxyethane (3 ml) was added dropwise to a mixture of sodium hydride (0.023 g, 0.58 mmol) in 1,2-dimethoxyethane (0.5 ml) at 0° C. The reaction mixture was stirred at room temperature for 15 minutes and subsequently a solution of 2-fluoroethyl tosylate [CAS: 383-50-6] (0.222 g, 1 mmol) in 1,2-dimethoxyethane (1 ml) was added. The reaction mixture was microwaved into a sealed tube at 180° C. for 20 minutes. The mixture was cooled to room temperature and an additional amount of sodium hydride (0.023 g, 0.58 mmol) was added. The mixture was the heated at 180° C. for 20 minutes under microwave irradiation. After cooling to room temperature, an aqueous saturated ammonium chloride solution was added and the mixture was extracted with EtOAc. The organic layer was separated, dried (Na$_2$SO$_4$) and the solvent was evaporated. The crude product was purified first by column chromatography (silica gel; eluent: DCM/EtOAc from 100/0 to 90/10). The desired fractions were collected and evaporated in vacuo to yield compound E20 (0.041 g, 18%).

$^1$H NMR (400 MHz, CDCl$_3$) δ ppm 0.36-0.40 (m, 2H), 0.58-0.62 (m, 2H), 1.22-1.28 (m, 1H), 2.12-2.21 (m, 4H), 3.27-3.36 (m, 4H), 3.57 (br d, J=12.1 Hz, 2H), 3.80 (d, J=7.2 Hz, 2H), 4.51 (dm, J=47.7 Hz, 2H), 6.08 (d, J=7.5 Hz, 1H), 7.23 (d, J=7.5 Hz, 1H), 7.29-7.32 (m, 1H), 7.37-7.41 (m, 2H), 7.44-7.46 (m, 2H).

Example 21

3'-Chloro-1'-cyclopropylmethyl-4-fluoromethyl-4-phenyl-3,4,5,6-tetrahydro-2H,1'H-[1,4']bipyridinyl-2'-one (E21)

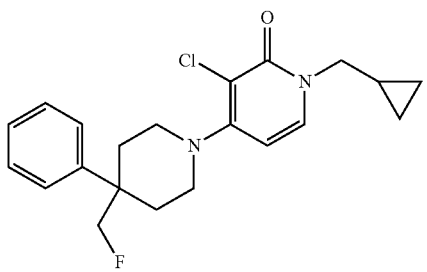 [SMILES: O=c1c(Cl)c(N2CCC(CF)(c3ccccc3)CC2)ccn1CC1CC1]

(Diethylamino)sulfur trifluoride (0.046 ml, 0.35 mmol) was added to a cooled (−78° C.) solution of compound E30 (0.119 g, 0.32 mmol) in DCM (1 ml). The reaction mixture was stirred at −78° C. for 3 hours and then additional for 2 hours at 0° C. Subsequently, additional (diethylamino)sulfur trifluoride (0.046 ml, 0.35 mmol) was added and the mixture was further stirred for 1 hour at room temperature. Na$_2$CO$_3$ (aqueous saturated solution) was added and the mixture was diluted with DCM. The organic layer was separated, dried (Na$_2$SO$_4$) and evaporated till dryness. The crude product was purified by column chromatography (silica gel; eluent: DCM/EtOAc from 100/0 to 80/20). The desired fractions were collected, evaporated in vacuo and finally freeze dried to yield compound E21 (0.019 g, 16%) as a white foam.

$^1$H NMR (400 MHz, CDCl$_3$) δ ppm 0.33-0.40 (m, 2H), 0.52-0.65 (m, 2H), 1.17-1.29 (m, 1H), 1.74-1.96 (m, 4H), 2.96 (d, J=22.7 Hz, 2H), 3.06 (dt, J=11.6, 3.7 Hz, 2H), 3.45-3.52 (m, 2H), 3.79 (d, J=7.2 Hz, 2H), 6.01 (d, J=7.6 Hz, 1H), 7.20-7.36 (m, 6H).

Example 22

1'-Butyl-3'-chloro-4-hydroxymethyl-4-phenyl-3,4,5,6-tetrahydro-2H,1'H-[1,4']bipyridinyl-2'-one (E22)

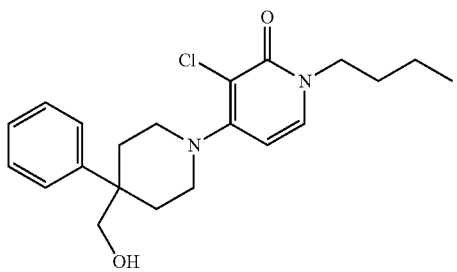 [SMILES: CCCCn1ccc(N2CCC(CO)(c3ccccc3)CC2)c(Cl)c1=O]

4-Hydroxymethyl-4-phenylpiperidine (0.172 g, 0.9 mmol), palladium(II) acetate (0.007 g, 0.03 mmol), cesium carbonate (0.391 g, 1.2 mmol) and Xantphos (0.035 g, 0.06 mmol) were added to a solution of intermediate D9 (0.2 g, 0.6 mmol) in trifluoromethylbenzene (2 ml). The reaction mixture was heated at 100° C. for 24 hours in a sealed tube, after which it was cooled to room temperature. Subsequently, it was diluted with DCM, H$_2$O (5 ml) and extracted with EtOAc (3×5 ml). The mixture was filtered through diatomaceous earth, and the filtrate was evaporated to dryness. The crude product was purified first by column chromatography (silica gel; eluent: DCM/EtOAc from 90/10 to 0/100) and then by reversed phase HPLC. The desired fractions were collected, evaporated in vacuo and finally freeze dried to yield compound E22 (0.041 g, 18%) as a white foam.

$^1$H NMR (400 MHz, CDCl$_3$) δ ppm 0.93 (t, J=7.3 Hz, 3H), 1.13 (br t, J=6.7 Hz, 1H), 1.28-1.40 (m, 2H), 1.64-1.75 (m, 2H), 1.98-2.08 (m, 2H), 2.31-2.40 (m, 2H), 2.98-3.10 (m, 2H), 3.41-3.51 (m, 2H), 3.63 (d, J=6.5 Hz, 2H), 3.90 (t, J=7.3 Hz, 2H), 5.92 (d, J=7.5 Hz, 1H), 7.04 (d, J=7.5 Hz, 1H), 7.27-7.33 (m, 1H), 7.36-7.46 (m, 4H).

Example 28

1'-Butyl-3'-chloro-4-[2-(1-hydroxy-1-methyl-ethyl)-phenyl]-3,4,5,6-tetrahydro-2H,1'H-[1,4']bipyridinyl-2'-one (E28)

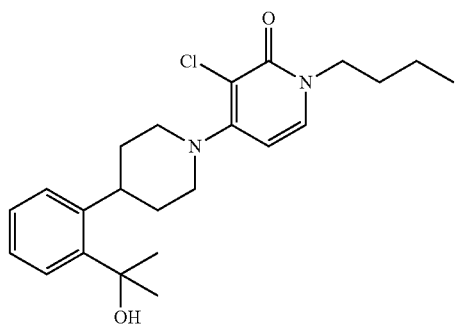 [SMILES: CCCCn1ccc(N2CCC(c3ccccc3C(C)(C)O)CC2)c(Cl)c1=O]

A mixture of intermediate D9 (0.254 g, 0.76 mmol), intermediate D28 (0.2 g, 0.912 mmol) and diisopropylethylamine (0.199 ml, 1.114 mmol) in acetonitrile (11 ml) was heated at 180° C. for 5 minutes under microwave irradiation. The cooled crude mixture was evaporated in vacuo. The crude residue was purified by column chromatography (silica gel; DCM/EtOAc/MeOH as eluent). The desired fractions were collected and evaporated in vacuo. The solid residue obtained was treated with diisopropylether. The solid was filtered to yield compound E28 (0.183 g, 61%).

M.P. 182° C.

$^1$H NMR (400 MHz, CDCl$_3$) δ ppm 0.95 (t, J=7.3 Hz, 3H), 1.32-1.42 (m, 2H), 1.70 (s, 6H), 1.71-1.77 (m, 2H), 1.79 (s, 1H), 1.82-1.90 (m, 2H), 1.91-2.05 (m, 2H), 2.88-2.98 (m, 2H), 3.76-3.87 (m, 3H), 3.93 (t, J=7.3 Hz, 2H), 6.03 (d, J=7.5 Hz, 1H), 7.11 (d, J=7.5 Hz, 1H), 7.16 (td, J=7.8, 1.4 Hz, 1H), 7.28 (td, J=7.4, 1.4 Hz, 1H), 7.41 (dd, J=7.7, 1.6 Hz, 1H), 7.42 (dd, J=7.6, 1.7 Hz, 1H).

Example 29

1'-Butyl-3'-chloro-4-[2-fluoro-4-(1-hydroxy-1-methyl-ethyl)-phenyl]-3,4,5,6-tetrahydro-2H,1'H-[1,4']bipyridinyl-2'-one (E29)

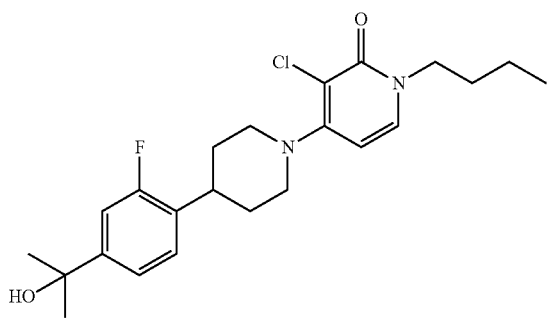 [SMILES: CCCCn1ccc(N2CCC(c3ccc(C(C)(C)O)cc3F)CC2)c(Cl)c1=O]

A mixture of intermediate D9 (0.261 g, 0.781 mmol), intermediate D25 (0.223 g, 0.938 mmol) and diisopropylethylamine (0.204 ml, 1.172 mmol) in acetonitrile (11 ml) was heated at 180° C. for 5 minutes under microwave irradiation. The cooled crude mixture was evaporated in vacuo. The crude residue was purified by column chromatography (silica gel; DCM/EtOAc/MeOH/NH$_3$ as eluent). The desired fractions were collected and evaporated in vacuo. The solid residue obtained was treated with diisopropylether. The solid was filtered to yield compound E29 (0.239 g, 73%). M.P. 150.5° C.

$^1$H NMR (400 MHz, CDCl$_3$) δ ppm 0.95 (t, J=7.3 Hz, 3H), 1.31-1.43 (m, 2H), 1.57 (s, 6H), 1.68-1.76 (m, 2H), 1.77 (s, 1H), 1.87-1.96 (m, 4H), 2.86-2.98 (m, 2H), 2.98-3.09 (m, 1H), 3.81 (br d, J=12.0 Hz, 2H), 3.93 (t, J=7.3 Hz, 2H), 6.03 (d, J=7.5 Hz, 1H), 7.11 (d, J=7.5 Hz, 1H), 7.16-7.25 (m, 3H).

Example 32

1-butyl-3-chloro-4-(1'H,3H-spiro[2-benzofuran-1,4'-piperidin]-1'-yl)pyridin-2(1H)-one (E32)

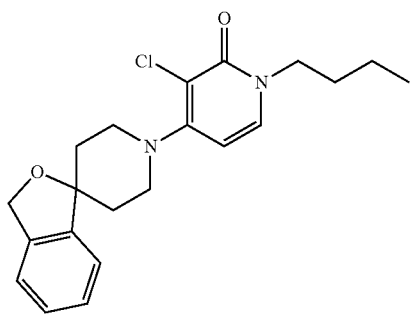 [SMILES: CCCCn1ccc(N2CCC3(CC2)OCc2ccccc23)c(Cl)c1=O]

A mixture of intermediate D9 (0.15 g, 0.45 mmol), 3H-spiro[2-benzofuran-1,4'-piperidine] (0.102 g, 0.54 mmol) and diisopropylethylamine (0.097 ml, 0.056 mmol) in acetonitrile (4 ml) was heated at 180° C. for 5 minutes under microwave irradiation. The cooled crude mixture was evaporated in vacuo. The crude residue was purified by column chromatography (silica gel; DCM/EtOAc/MeOH/NH$_3$ as eluent). The desired fractions were collected and evaporated in vacuo. The solid residue obtained was treated with diisopropylether. The solid was filtered to yield compound E32 (0.14 g, 84%).

$^1$H NMR (400 MHz, CDCl$_3$) δ ppm 0.95 (t, J=7.3 Hz, 3H), 1.30-1.43 (m, 2H), 1.67-1.79 (m, 2H), 1.85 (dd, J=13.8, 2.20 Hz, 2H), 2.12 (dt, J=13.0, 4.7 Hz, 2H), 3.25 (dt, J=12.4, 2.31 Hz, 2H), 3.57-3.68 (m, 2H), 3.94 (t, J=7.3 Hz, 2H), 6.06 (d, J=7.4 Hz, 1H), 7.12 (d, J=7.4 Hz, 1H), 7.16-7.34 (m, 7H).

Example 33

1-butyl-3-chloro-4-(1'H-spiro[1-benzofuran-3,4'-piperidin]-1'-yl)pyridin-2(1H)-one (E33)

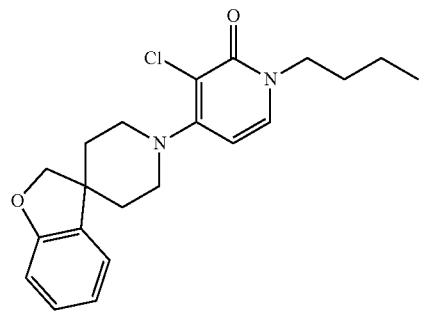 [SMILES: CCCCn1ccc(N2CCC3(CC2)COc2ccccc23)c(Cl)c1=O]

A mixture of intermediate D9 (0.15 g, 0.45 mmol), spiro[1-benzofuran-3,4'-piperidine](0.102 g, 0.54 mmol) and diisopropylethylamine (0.097 ml, 0.056 mmol) in acetonitrile (4 ml) was heated at 180° C. for 5 minutes under microwave irradiation. The cooled crude mixture was evaporated in vacuo. The crude residue was purified by column chromatography (silica gel; DCM/EtOAc/MeOH/NH$_3$ as eluent). The desired fractions were collected and evaporated in vacuo. The solid residue obtained was treated with diisopropylether. The solid was filtered to yield compound E33 (0.116 g, 84%).

$^1$H NMR (500 MHz, CDCl$_3$) δ ppm 0.95 (t, J=7.4 Hz, 3H), 1.30-1.43 (m, 2H), 1.66-1.79 (m, 2H), 1.86 (d, J=13.3 Hz, 2H), 2.05-2.19 (m, 2H), 2.84-2.97 (m, 2H), 3.68 (d, J=12.7 Hz, 2H), 3.94 (t, J=7.4 Hz, 2H), 4.44 (s, 2H), 6.01 (d, J=7.5 Hz, 1H), 6.83 (d, J=7.8 Hz, 1H), 6.92 (t, J=7.4 Hz, 1H), 7.07-7.24 (m, 3H).

Compounds E10, E11, E12, E13, E14, E15, E16, E17, E18, E19, E23, E24, E25 and E26 were prepared according to the reaction procedure described in Example 1. Compound E27 was prepared according to the reaction procedure described in Example 9.

Compound E30 and compound E31 were prepared according to the reaction procedure described in Example 22.

Physico-Chemical Data

LCMS—General Procedure

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS spectrometer. The MS detector was configured with an electrospray ionization source. Nitrogen was used as the nebulizer gas. The source temperature was maintained at 140° C. Data acquisition was performed with MassLynx-Openlynx software.

LCMS Method: For all Examples, Except for Examples E5, E18, E25, E27, E28, E29, E30 and E31, the Following Method was Used.

In addition to the general procedure: Reversed phase HPLC was carried out on an XDB-C18 cartridge (1.8 µm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol) to 50% B and 50% C in 6.5 minutes, to 100% B at 7 minutes and equilibrated to initial conditions at 7.5 minutes until 9.0 minutes. Injection volume 2 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

LCMS Method: This Method was Used for Examples E5 and E18.

In addition to the general procedure: Reversed phase HPLC was carried out on an ACE-C18 column (3.0 µm, 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

LCMS Method: This Method was Used for Example E25.

In addition to the general procedure: Reversed phase HPLC was carried out on a XDB-C18 cartridge (1.8 µm, 2.1×30 mm) from Agilent, with a flow rate of 0.8 ml/min, at 60° C. The gradient conditions used are: 90% A (0.5 g/l ammonium acetate solution), 10% B (mixture of Acetonitrile/Methanol, 1/1), to 100% B in 6.0 minutes, kept till 6.5 minutes and equilibrated to initial conditions at 7.0 minutes until 9.0 minutes. Injection volume 2 µl. Low-resolution mass spectra (SQD detector; quadrupole) were acquired only in positive ionization mode by scanning from 100 to 1000 in 0.1 seconds using an inter-channel delay of 0.08 second. The capillary needle voltage was 3 kV and the cone voltage was 20 V.

LCMS Method: This Method was Used for Example E27.

In addition to the general procedure: Reversed phase HPLC was carried out on a Sunfire-C18 column (2.5 µm, 2.1×30 mm) from Waters, with a flow rate of 1.0 ml/min, at 60° C. The gradient conditions used are: 95% A (0.5 g/l ammonium acetate solution+5% of acetonitrile), 2.5% B (acetonitrile), 2.5% C (methanol) to 50% B and 50% C in 6.5 minutes, kept till 7 minutes and equilibrated to initial conditions at 7.3 minutes until 9.0 minutes. Injection volume 2 µl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

LCMS Method: This Method was Used for Example E28, E29, E32 and E33.

In addition to the general procedure: Reversed phase HPLC was carried out on a BEH-C18 column (1.7 µm, 2.1×50 mm) from Waters, with a flow rate of 0.8 ml/min, at 60° C. without split to the MS detector. The gradient conditions used are: 95% A (0.5 g/l ammonium acetate solution+5% acetonitrile), 5% B (mixture of acetonitrile/methanol, 1/1), to 20% A, 80% B in 4.9 minutes, to 100% B in 5.3 minutes, kept till 5.8 minutes and equilibrated to initial conditions at 6.0 minutes until 7.0 minutes. Injection volume 0.5 µl. Low-resolution mass spectra (SQD detector; quadrupole) were acquired by scanning from 100 to 1000 in 0.1 seconds using an inter-channel delay of 0.08 second. The capillary needle voltage was 3 kV. The cone voltage was 20 V for positive ionization mode and 30 V for negative ionization mode.

LCMS Method: This Method was Used for Examples E30 and E31.

In addition to the general procedure: Reversed phase HPLC was carried out on an XDB-C18 cartridge (1.8 µm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol), kept 0.2 minutes, to 50% B, 50% C in 3.5 minutes, kept till 3.65 minutes and equilibrated to initial conditions at 3.8 minutes until 5.0 minutes. Injection volume 2 µl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Melting Points

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display and were obtained with experimental uncertainties that are commonly associated with this analytical method.

Nuclear Magnetic Resonance (NMR)

$^1$H NMR spectra were recorded either on Bruker DPX400 or Bruker AV-500 spectrometers operating at 400 and 500 MHz respectively. All reported chemical shifts (δ) are expressed in ppm relative to tetramethylsilane.

Table 1 lists compounds of Formula (I) that were prepared according to one of the above Examples.

TABLE 1
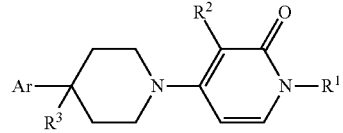
| Ex. | Ar | R¹ | R² | R³ | M.P. (° C.) | MH+ | RT (min) |
|---|---|---|---|---|---|---|---|
| E1 | Ph | 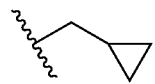 | Cl | H | 170.8 | 343 | 4.67 |
| E2 | Ph | 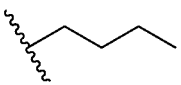 [SMILES: *CCCC] | Cl | H | 149.4 | 345 | 4.92 |
| E3 | Ph |  | Br | H | 150.2 | 387 | 4.81 |
| E4 | Ph | 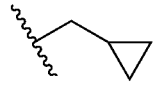 [SMILES: *CC1CC1] | CF₃ | H | 180.6 | 377 | 4.90 |
| E5 | Ph | 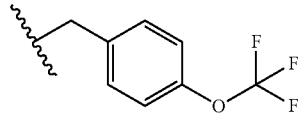 | Cl | H | 168.6 | 463 | 5.71 |
| E6 | Ph | 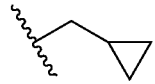 [SMILES: *CC1CC1] | Cl | CN | 173.7 | 368 | 4.01 |
| E7 | Ph | 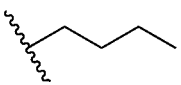 | Cl | F | 136.7 | 363 | 4.83 |
| E8 | Ph | 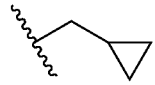 [SMILES: *CC1CC1] |  | H | 201.9 | 349 | 5.17 |
| E9 | 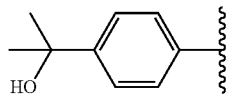 | 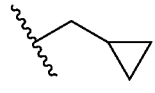 [SMILES: *CC1CC1] | Cl | H | 142.7 | 401 | 4.20 |
| E10 | Ph | 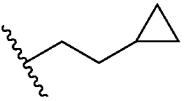 [SMILES: *CCC1CC1] | Cl | H | 244.6 | 357 | 4.97 |
| E11 | Ph | 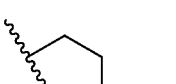 | Cl | H | nd | 359 | 5.29 |
| E12 | 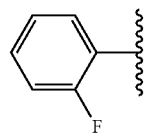 [SMILES: *c1ccccc1F] |  | Cl | H | nd | 361 | 4.76 |

TABLE 1-continued
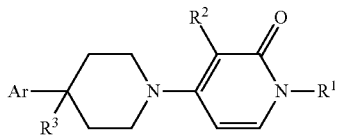
| Ex. | Ar | R¹ | R² | R³ | M.P. (° C.) | MH+ | RT (min) |
|---|---|---|---|---|---|---|---|
| E13 | 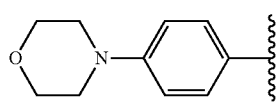 [SMILES: *c1ccc(N2CCOCC2)cc1] |  | Cl | H | nd | 428 | 4.47 |
| E14 | 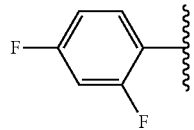 [SMILES: *c1ccc(F)cc1F] | 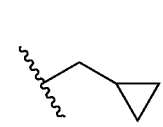 [SMILES: *CC1CC1] | Cl | H | 188.3 | 379 | 4.84 |
| E15 | 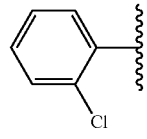 [SMILES: *c1ccccc1Cl] | 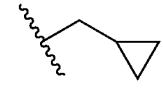 | Cl | H | 145.9 | 377 | 5.06 |
| E16 | 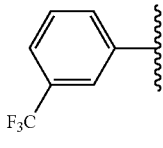 |  | Cl | H | 121.9 | 411 | 5.10 |
| E17 | Ph |  | Cl | F | 195.3 | 361 | 4.55 |
| E18 | Ph | 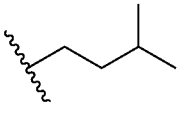 [SMILES: *CCC(C)C] | Cl | H | 147.3 | 359 | 5.41 |
| E19 | Ph | 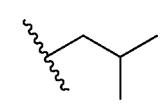 [SMILES: *CC(C)C] | Cl | H | nd | 345 | 4.87 |
| E20 | Ph |  | Cl | 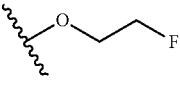 [SMILES: *OCCF] | nd | 405 | 4.51 |
| E21 | Ph |  | Cl | 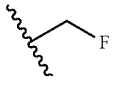 | nd | 375 | 4.68 |
| E22 | Ph | 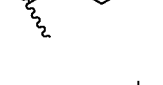 | Cl | 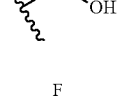 | nd | 375 | 3.88 |
| E23 | Ph | 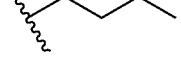 | Cl | F | 140.4 | 377 | 5.07 |

TABLE 1-continued

| Ex. | Ar | R¹ | R² | R³ | M.P. (° C.) | MH+ | RT (min) |
|---|---|---|---|---|---|---|---|
| E24 | 2,4-difluorophenyl | isopentyl | Cl | H | nd | 395 | 5.31 |
| E25 | 2,4-difluorophenyl | n-pentyl | Cl | H | nd | 381 | 5.10 |
| E26 | Ph | cyclopropylethyl | Cl | F | nd | 375 | 4.79 |
| E27 | 4-(2-hydroxypropan-2-yl)phenyl | n-butyl | Cl | H | 144.4 | 403 | 4.56 |
| E28 | 2-(2-hydroxypropan-2-yl)phenyl | n-butyl | Cl | H | 182.0 | 403 | 3.60 |
| E29 | 4-(2-hydroxypropan-2-yl)-3-fluorophenyl | n-butyl | Cl | H | 150.5 | 421 | 3.65 |
| E30 | Ph | cyclopropylmethyl | Cl | CH₂OH | nd | 373 | 2.82 |
| E31 | Ph | cyclopropylmethyl | Cl | OH | nd | 359 | 2.92 | nd: not determined

TABLE 2

| Ex. | R¹ | R² | Ar | M.P. (° C.) | MH+ | RT (min) |
|---|---|---|---|---|---|---|
| E32 | (pentyl) | Cl | (isobenzofuran-spiro-piperidine) | 133.1 | 373 | 3.68 |
| E33 | (butyl) | Cl | (isobenzofuran-spiro-piperidine) | 156.5 | 373 | 3.67 |

D. Pharmacological Examples

The compounds provided in the present invention are positive allosteric modulators of mGluR2. These compounds appear to potentiate glutamate responses by binding to an allosteric site other than the glutamate binding site. The response of mGluR2 to a concentration of glutamate is increased when compounds of Formula (I) are present. Compounds of Formula (I) are expected to have their effect substantially at mGluR2 by virtue of their ability to enhance the function of the receptor. The behaviour of positive allosteric modulators tested at mGluR2 using the [$^{35}$S]GTPγS binding assay method described below and which is suitable for the identification of such compounds, and more particularly the compounds according to Formula (I), are shown in Table 3.

[$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein at subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the agonist can be determined. MGluR2 receptors are shown to be preferentially coupled to Gαi-protein, a preferential coupling for this method, and hence it is widely used to study receptor activation of mGluR2 receptors both in recombinant cell lines and in tissues (Schaffhauser et al 2003, Pinkerton et al, 2004, Mutel et al (1998) Journal of Neurochemistry. 71:2558-64; Schaffhauser et al (1998) Molecular Pharmacology 53:228-33). Here we describe the use of the [$^{35}$S]GTPγS binding assay using membranes from cells transfected with the human mGluR2 receptor and adapted from Schaffhauser et al ((2003) Molecular Pharmacology 4:798-810) for the detection of the positive allosteric modulation (PAM) properties of the compounds of this invention.

Membrane Preparation

CHO-cells were cultured to pre-confluence and stimulated with 5 mM butyrate for 24 hours, prior to washing in PBS, and then collected by scraping in homogenisation buffer (50 mM Tris-HCl buffer, pH 7.4, 4° C.). Cell lysates were homogenized briefly (15 s) using an ultra-turrax homogenizer. The homogenate was centrifuged at 23 500×g for 10 minutes and the supernatant discarded. The pellet was resuspended in 5 mM Tris-HCl, pH 7.4 and centrifuged again (30 000×g, 20 min, 4° C.). The final pellet was resuspended in 50 mM HEPES, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulatory activity of test compounds in membranes containing human mGluR2 was performed using frozen membranes that were thawed and briefly homogenized prior to pre-incubation in 96-well microplates (15 μg/assay well, 30 minutes, 30° C.) in assay buffer (50 mM HEPES pH 7.4, 100 mM NaCl, 3 mM MgCl$_2$, 50 μM GDP, 10 μg/ml saponin,) with increasing concentrations of positive allosteric modulator (from 0.3 nM to 50 μM) and either a minimal pre-determined concentration of glutamate (PAM assay), or no added glutamate. For the PAM assay, membranes were pre-incubated with glutamate at EC$_{25}$ concentration, i.e. a concentration that gives 25% of the maximal response glutamate, and is in accordance to published data (Pin et al. (1999) Eur. J. Pharmacol. 375:277-294). After addition of [$^{35}$S]GTPγS (0.1 nM, f.c.) to achieve a total reaction volume of 200 µl, microplates were shaken briefly and further incubated to allow [$^{35}$S]GTPγS incorporation on activation (30 minutes, 30° C.). The reaction was stopped by rapid vacuum filtration over glass-fibre filter plates (Unifilter 96-well GF/B filter plates, Perkin-Elmer, Downers Grove, USA) microplate using a 96-well plate cell harvester (Filtermate, Perkin-Elmer, USA), and then by washing three times with 300 µl of ice-cold wash buffer ($Na_2PO_4.2H_2O$ 10 mM, $NaH_2PO_4.H_2O$ 10 mM, pH=7.4). Filters were then air-dried, and 40 µl of liquid scintillation cocktail (Microscint-O) was added to each well, and membrane-bound [$^{35}$S]GTPγS was measured in a 96-well scintillation plate reader (Top-Count, Perkin-Elmer, USA). Non-specific [$^{35}$S]GTPγS binding is determined in the presence of cold 10 µM GTP. Each curve was performed at least once using duplicate sample per data point and at 11 concentrations.

Data Analysis

The concentration-response curves of representative compounds of the present invention in the presence of added $EC_{25}$ of mGluR2 agonist glutamate to determine positive allosteric modulation (PAM), were generated using the Prism GraphPad software (Graph Pad Inc, San Diego, USA). The curves were fitted to a four-parameter logistic equation (Y=Bottom+(Top−Bottom)/(1+10^((Log $EC_{50}$−X) *Hill Slope) allowing determination of $EC_{50}$ values. The $EC_{50}$ is the concentration of a compound that causes a half-maximal potentiation of the glutamate response. This is calculated by subtracting the maximal responses of glutamate in presence of a fully saturating concentration of a positive allosteric modulator from the response of glutamate in absence of a positive allosteric modulator. The concentration producing the half-maximal effect is then calculated as $EC_{50}$.

TABLE 3

Pharmacological data for compounds according to the invention.

| Comp. No. | GTPgS - hR2 PAM $pEC_{50}$ |
|---|---|
| 1 | 6.53 |
| 2 | 6.74 |
| 3 | 6.88 |
| 4 | 6.45 |
| 5 | 6.90 |
| 6 | 6.34 |
| 7 | 6.62 |
| 8 | 6.04 |
| 9 | 6.57 |
| 10 | 6.88 |
| 11 | 7.11 |
| 12 | 7.03 |
| 13 | 6.64 |
| 14 | 6.92 |
| 15 | 7.00 |
| 16 | 7.12 |
| 17 | 6.57 |
| 18 | 7.20 |
| 19 | 6.71 |
| 20 | 6.91 |
| 21 | 6.25 |
| 22 | 6.05 |
| 23 | 6.58 |
| 24 | 6.91 |
| 25 | 6.83 |
| 26 | 6.41 |

TABLE 3-continued

Pharmacological data for compounds according to the invention.

| Comp. No. | GTPgS - hR2 PAM $pEC_{50}$ |
|---|---|
| 27 | 6.46 |
| 28 | 7.06 |
| 29 | 6.88 |
| 30 | nd |
| 31 | nd |
| 32 | nd |
| 33 | nd | nd = not determined

All compounds were tested in presence of mGluR2 agonist, glutamate at a predetermined $EC_{25}$ concentration, to determine positive allosteric modulation (GTPγS-PAM). Values shown are averages of duplicate values of 11-concentration response curves, from at least one experiment. All tested compounds showed a $pEC_{50}$ (−log $EC_{50}$) value of more than 5.0, from 6.05 to 7.20. The error of determination of a $pEC_{50}$ value for a single experiment is estimated to be about 0.3 log-units.

E. Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound having the formula:

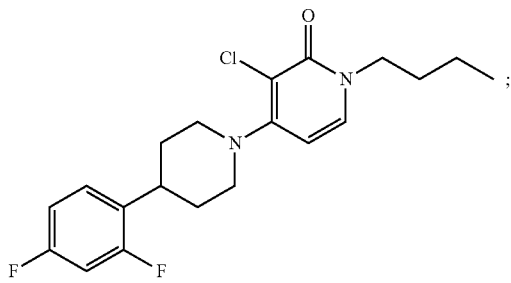 [SMILES: CCCCn1ccc(N2CCC(c3ccc(F)cc3F)CC2)c(Cl)c1=O]

a pharmaceutically acceptable salt or a solvate thereof.

2. The compound according to claim 1 wherein said compound is:

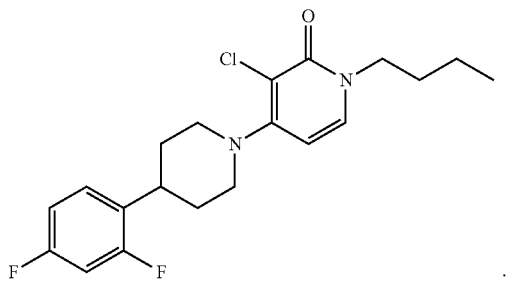 [SMILES: CCCCn1ccc(N2CCC(c3ccc(F)cc3F)CC2)c(Cl)c1=O]

3. A pharmaceutical composition comprising the compound of claim 1, or a pharmaceutically acceptable salt or a solvate thereof, and a pharmaceutically acceptable carrier or excipient.

4. The pharmaceutical composition of claim 3 comprising a therapeutically effective amount of a compound having the structure

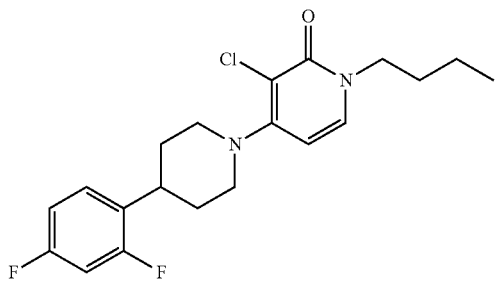 [SMILES: CCCCn1ccc(N2CCC(c3ccc(F)cc3F)CC2)c(Cl)c1=O]

and a pharmaceutically acceptable carrier or excipient.

5. A method for treating a central nervous system disorder in a human patient selected from the group of anxiety disorder, depression, psychotic disorder, or epilepsy or convulsive disorder, the method comprising administering to the patient in need thereof a compound of claim 1, or a pharmaceutically acceptable salt or a solvate thereof.

6. The method of claim 5, wherein the central nervous system disorder is an anxiety disorder, selected from the group of agoraphobia, generalized anxiety disorder (GAD), obsessive-compulsive disorder (OCD), panic disorder, post-traumatic stress disorder (PTSD), social phobia and other phobias.

7. The method of claim 6, wherein the anxiety disorder is generalized anxiety disorder (GAD).

8. The method of claim 5, wherein the central nervous system disorder is a psychotic disorder selected from the group of schizophrenia, schizoaffective disorder, and schizophreniform disorder.

9. The method of claim 8, wherein the psychotic disorder is schizophrenia.

10. The method of claim 5, wherein the central nervous system disorder is epilepsy or convulsive disorder.

11. The method of claim 10, wherein the epilepsy or a convulsive disorder is generalized nonconvulsive epilepsy, generalized convulsive epilepsy, petit mal status epilepticus, grand mal status epilepticus, partial epilepsy with or without impairment of consciousness, infantile spasms, or epilepsy partialis continua.

12. The method of claim 5, wherein the central nervous system disorder is depression.

13. A method for treating a central nervous system disorder in a human patient selected from the group of anxiety disorder, psychotic disorder, or epilepsy or convulsive disorder, the method comprising administering to the patient in need thereof a compound of claim 1, or a pharmaceutically acceptable salt or a solvate thereof.

14. The method of claim 13, wherein the central nervous system disorder is an anxiety disorder, selected from the group of agoraphobia, generalized anxiety disorder (GAD), obsessive-compulsive disorder (OCD), panic disorder, post-traumatic stress disorder (PTSD), social phobia and other phobias.

15. The method of claim 14, wherein the anxiety disorder is generalized anxiety disorder (GAD).

16. The method of claim 13, wherein the central nervous system disorder is a psychotic disorder selected from the group of schizophrenia, schizoaffective disorder, and schizophreniform disorder.

17. The method of claim 16, wherein the psychotic disorder is schizophrenia.

18. The method of claim 13, wherein the central nervous system disorder is epilepsy or convulsive disorder.

19. The method of claim 18, wherein the epilepsy or a convulsive disorder is generalized nonconvulsive epilepsy, generalized convulsive epilepsy, petit mal status epilepticus, grand mal status epilepticus, partial epilepsy with or without impairment of consciousness, infantile spasms, or epilepsy partialis continua.

20. The method of claim 13, wherein the central nervous system disorder is depression.

* * * * *